US010351526B2

(12) United States Patent
Ishiwata et al.

(10) Patent No.: US 10,351,526 B2
(45) Date of Patent: Jul. 16, 2019

(54) COLORING CURABLE RESIN COMPOSITION, CURED FILM, COLOR FILTER, METHOD FOR MANUFACTURING COLOR FILTER, SOLID-STATE IMAGING DEVICE, IMAGE DISPLAY DEVICE, COMPOUND, AND CATION

(71) Applicant: FUJIFILM Corporation, Tokyo (JP)

(72) Inventors: Yasuhiro Ishiwata, Fujinomiya (JP); Kazunari Yagi, Fujinomiya (JP); Akinori Fujita, Fujinomiya (JP); Koutaro Okabe, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/259,139

(22) Filed: Sep. 8, 2016

(65) Prior Publication Data
US 2016/0376234 A1     Dec. 29, 2016

Related U.S. Application Data

(63) Continuation of application No. PCT/JP2015/057123, filed on Mar. 11, 2015.

(30) Foreign Application Priority Data

Mar. 18, 2014  (JP) .................... 2014-054726
Aug. 14, 2014  (JP) .................... 2014-165308
Sep. 18, 2014  (JP) .................... 2014-190222

(51) Int. Cl.
| | | |
|---|---|---|
| G02B 5/20 | (2006.01) | |
| G03F 7/004 | (2006.01) | |
| C07D 209/14 | (2006.01) | |
| G03F 7/00 | (2006.01) | |
| G03F 7/027 | (2006.01) | |
| G03F 7/033 | (2006.01) | |
| G03F 7/105 | (2006.01) | |
| C09B 11/12 | (2006.01) | |
| C09B 69/10 | (2006.01) | |
| G02B 5/22 | (2006.01) | |
| C07C 211/58 | (2006.01) | |
| C07C 217/76 | (2006.01) | |
| C07C 229/36 | (2006.01) | |
| C07C 229/48 | (2006.01) | |
| C07C 317/32 | (2006.01) | |
| G03F 7/20 | (2006.01) | |
| G03F 7/32 | (2006.01) | |

(52) U.S. Cl.
CPC .......... *C07D 209/14* (2013.01); *C07C 211/58* (2013.01); *C07C 217/76* (2013.01); *C07C 229/36* (2013.01); *C07C 229/48* (2013.01); *C07C 317/32* (2013.01); *C09B 11/12* (2013.01); *C09B 69/103* (2013.01); *G02B 5/223* (2013.01); *G03F 7/0007* (2013.01); *G03F 7/027* (2013.01); *G03F 7/033* (2013.01); *G03F 7/105* (2013.01); *G03F 7/20* (2013.01); *G03F 7/32* (2013.01)

(58) Field of Classification Search
CPC ..... C09B 11/12; C09B 69/103; C07C 211/58; C07C 217/76; C07C 229/36; C07C 317/32; C07C 229/48; C07C 209/14; G02B 5/223; G03F 7/0007; G03F 7/027; G03F 7/028; G03F 7/031; G03F 7/033; G03F 7/105
USPC ...................... 430/7, 270.1, 281.1
See application file for complete search history.

(56) References Cited

U.S. PATENT DOCUMENTS

| | | | |
|---|---|---|---|
| 5,788,914 A | 8/1998 | Oi et al. | |
| 7,740,995 B2 | 6/2010 | Aizawa et al. | |
| 8,197,994 B2 | 6/2012 | Mizukawa et al. | |
| 8,367,282 B2 | 2/2013 | Mizukawa et al. | |
| 8,779,159 B2 | 7/2014 | Mizukawa et al. | |
| 9,605,154 B2 | 3/2017 | Fujita et al. | |
| 9,720,319 B2 * | 8/2017 | Fujita .................. | G03F 7/0007 |
| 2007/0037076 A1 | 2/2007 | Aizawa et al. | |
| 2008/0076044 A1 | 3/2008 | Mizukawa et al. | |
| 2010/0230647 A1 | 9/2010 | Mizukawa et al. | |
| 2012/0138877 A1 | 6/2012 | Mizukawa et al. | |
| 2012/0238752 A1 | 9/2012 | Mizukawa et al. | |
| 2015/0060744 A1 | 3/2015 | Park et al. | |
| 2016/0185969 A1 | 6/2016 | Fujita et al. | |

FOREIGN PATENT DOCUMENTS

| | | |
|---|---|---|
| CN | 105531327 A | 4/2016 |
| GB | 1188605 A | 4/1970 |

(Continued)

OTHER PUBLICATIONS

Computer-generated translation of WO 2015/080217 (Jun. 2015).*

(Continued)

*Primary Examiner* — John A McPherson
(74) *Attorney, Agent, or Firm* — Sughrue Mion, PLLC

(57) ABSTRACT

The present invention provides a colored curable resin composition that exhibits good heat resistance and durability in a sputtering process, a cured film, a color filter, a method for manufacturing a color filter, a solid-state image device, an image display device, a compound, and a cation. The colored curable resin composition contains a colorant represented by Formula (1), Formula (2), or Formula (3), a resin, a polymerizable compound, and a polymerization initiator. In Formula (1), $R^{101}$ and $R^{102}$ each independently represent a hydrogen atom or a substituent, $R^{103}$ to $R^{106}$ each independently represent a hydrogen atom, an alkyl group, an aryl group, or a heteroaryl group, $R^{107}$ to $R^{111}$ each independently represent a hydrogen atom or a substituent, n1 to n4 each independently represent an integer of 0 to 4, n5 represents an integer of 0 to 6, X represents an anion or is not present, and at least one of $R^{101}$, . . . , or $R^{111}$ includes an anion; and in the case where $R^{101}$ and $R^{102}$ represent hydrogen atoms, $R^{103}$ represents an aryl group having a substituent at at least the ortho-position.

29 Claims, 3 Drawing Sheets

(56) References Cited

FOREIGN PATENT DOCUMENTS

| JP | H06-75375 A | | 3/1994 |
|---|---|---|---|
| JP | H09-157536 A | | 6/1997 |
| JP | 2000-095805 A | | 4/2000 |
| JP | 2007-039478 A | | 2/2007 |
| JP | 2008-292970 A | | 12/2008 |
| JP | 2009-92924 A | | 4/2009 |
| JP | 2012-17425 A | | 1/2012 |
| JP | 2012-108469 A | | 6/2012 |
| JP | 2012-201694 A | | 10/2012 |
| JP | 2013-25194 A | | 2/2013 |
| JP | 2013-087248 A | * | 5/2013 |
| JP | 2013-119613 A | | 6/2013 |
| JP | 2013-148889 A | | 8/2013 |
| KR | 10-2013-0111024 A | | 10/2013 |
| WO | WO 2015/080217 A | * | 6/2015 |

OTHER PUBLICATIONS

Computer-generated translation of JP 2013-148889 (Aug. 2013) (Year: 2013).*
Computer-generated translation of JP 2013-087248 (May 2013) (Year: 2013).*
Office Action dated Feb. 7, 2017 from the Japanese Patent Office in counterpart Japanese Application No. 2014-190222.
Office Action dated May 17, 2017, from the State Intellectual Property Office of People's Republic of China in counterpart Chinese Application No. 201580012264.1.
Office Action dated Jun. 12, 2017 issued by the Korean Intellectual Property Office in corresponding Korean Application No. 10-2016-7023985.
International Preliminary Report on Patentability dated Sep. 29, 2016 from the International Bureau in counterpart International Application No. PCT/JP2015/057123.
International Search Report for PCT/JP2015/057123 dated Jun. 9, 2015.
Written Opinion for PCT/JP2015/057123 dated Jun. 9, 2015.
Office Action dated Feb. 27, 2018 from the State Intellectual Property Office of the P.R.C. in counterpart Chinese Application No. 201580012264.1.
Office Action dated Dec. 4, 2018 from the State Intellectual Property Office of the P.R.C. in counterpart Chinese Application No. 201580012264.1.
Office Action dated Jan. 24, 2019, from the Taiwanese Intellectual Property Office in counterpart Taiwanese application No. 104108396.

* cited by examiner

COLORING CURABLE RESIN COMPOSITION, CURED FILM, COLOR FILTER, METHOD FOR MANUFACTURING COLOR FILTER, SOLID-STATE IMAGING DEVICE, IMAGE DISPLAY DEVICE, COMPOUND, AND CATION

CROSS-REFERENCE TO RELATED APPLICATIONS

This application is a Continuation of PCT International Application No. PCT/JP2015/057123 filed on Mar. 11, 2015, which claims priority under 35 U.S.C. § 119(a) to Japanese Patent Application No. 2014-054726 filed on Mar. 18, 2014, Japanese Patent Application No. 2014-165308 filed on Aug. 14, 2014, and Japanese Patent Application No. 2014-190222 filed on Sep. 18, 2014. Each of the above application(s) is hereby expressly incorporated by reference, in its entirety, into the present application.

BACKGROUND OF THE INVENTION

1. Field of the Invention

The present invention relates to a coloring curable resin composition, a cured film, a color filter, a method for manufacturing a color filter, a solid-state imaging device, an image display device, a compound, and a cation.

2. Description of the Related Art

In the related art, color filters have been manufactured by producing a coloring curable resin composition containing a pigment dispersion composition obtained by dispersing an organic pigment or an inorganic pigment, a polyfunctional monomer, a polymerization initiator, an alkali-soluble resin, and as desired, other components, and forming a colored pattern using the coloring curable resin composition by photolithography, an ink jet method, or the like.

Recently, there is a trend toward more utilization of color filters not only in monitors but also in televisions (TVs) in the application to liquid crystal display devices (LCDs). With the trend of this expanding utilization, color filters are required to have high-grade color characteristics in terms of chromaticity, contrast, or the like. Further, with regard to color filters for use in image sensors (solid-state imaging devices), there has been a demand for further improvement in color characteristics such as reduction in color unevenness or improvement of chromatic resolving power.

However, color filters using pigment dispersion systems in the related art tend to cause problems such as occurrence of scattering due to coarse particles of a pigment or an increase in viscosity due to poor dispersion stability, and thus, it is often difficult to further improve contrast and brightness.

Therefore, not only the use of a pigment but also the use of a dye as a colorant has been studied from the related art (see, for example, JP1994-75375A (JP-H06-75375A)). It is considered that the use of a dye as a colorant is useful since the hue or brightness of the display image in displaying an image can be improved due to the color purity of the dye itself or the vividness of its hue, and also the contrast can be improved because of nonexistence of coarse particles.

As examples of the dye, compounds having various kinds of coloring bases such as a phthalocyanine dye, a dipyrromethene dye, a pyrimidine azo dye, a pyrazole azo dye, a xanthene dye, and a triarylmethane dye are known (see, for example, JP2008-292970A, JP2007-039478A, JP1997-157536A (JP-H09-157536A), JP2013-25194A, JP2012-201694A, JP2012-108469A, JP2000-095805A, JP2012-17425A, and JP2013-119613A).

SUMMARY OF THE INVENTION

Here, as a coloring curable composition resin for use in a color filter or the like, those having good heat resistance and durability in a sputtering process when they are used to produce cured films are required.

The present invention aims to solve such the problems and has an object to provide a coloring curable resin composition having good heat resistance and durability in a sputtering process. In particular, the present invention has an object to provide a coloring curable resin composition which is useful as a coloring curable resin composition for a blue filter. The present invention has another object to provide a cured film, a color filter, a method for manufacturing a color filter, a solid-state imaging device, and a liquid crystal display device, each using the coloring curable resin composition.

The present inventors have conducted extensive studies, and as a result, they have found that, a composition having high heat resistance and high durability in a sputtering process is obtained by using a triarylmethane dye having a specific structure, thereby completing the present invention.

Specifically, the problems were solved by the following means <1>, and preferably by <2> to <26>.

<1> A coloring curable resin composition comprising:
a colorant represented by Formula (1), Formula (2), or Formula (3);
a resin;
a polymerizable compound; and
a polymerization initiator:

Formula (1)

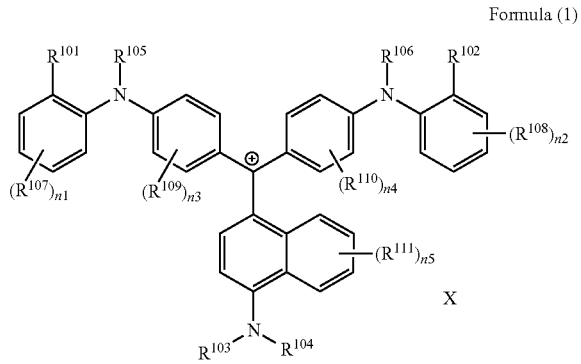

(in Formula (1), $R^{101}$ and $R^{102}$ each independently represent a hydrogen atom or a substituent, $R^{103}$ to $R^{106}$ each independently represent a hydrogen atom, an alkyl group, an aryl group, or a heteroaryl group, $R^{107}$ to $R^{111}$ each independently represent a hydrogen atom or a substituent, n1 to n4 each independently represent an integer of 1 to 4, n5 represents an integer of 0 to 6, X represents an anion or is not present, and at least one of $R^{101}$, ..., or $R^{111}$ includes an anion, provided that in the case where $R^{101}$ and $R^{102}$ represent hydrogen atoms, $R^{103}$ represents an aryl group having a substituent at at least the ortho-position),

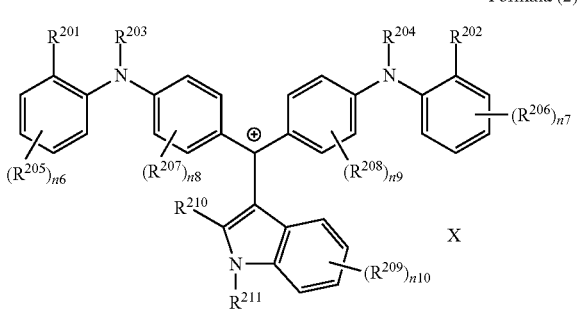

Formula (2)

(in Formula (2), $R^{201}$ and $R^{202}$ each independently represent a hydrogen atom or a substituent, at least one of $R^{201}$ or $R^{202}$ represents a substituent, $R^{203}$ to $R^{209}$ each independently represent a hydrogen atom or a substituent, $R^{210}$ and $R^{211}$ each independently represent an alkyl group, an aryl group, or a heteroaryl group, n6 to n10 each independently represent an integer of 1 to 4, X represents an anion or is not present, and at least one of $R^{201}$, ..., or $R^{211}$ includes an anion), and

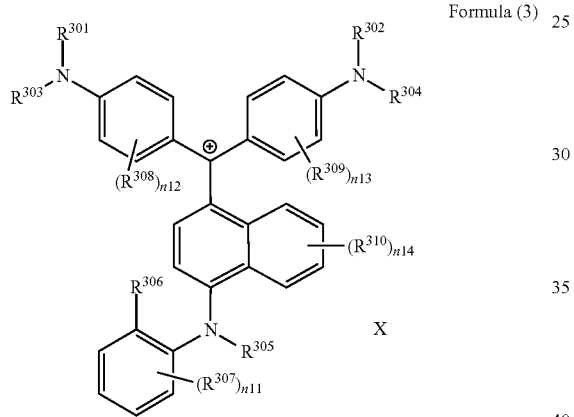

Formula (3)

(in Formula (3), $R^{301}$ and $R^{302}$ each independently represent a substituent, $R^{303}$ to $R^{305}$ each independently represent a hydrogen atom or a substituent, $R^{306}$ represents a substituent, $R^{307}$ to $R^{310}$ each independently represent a hydrogen atom, an alkyl group, or a halogen atom, n11 to n13 each independently represent an integer of 1 to 4, n14 represents an integer of 1 to 6, X represents an anion or is not present, and at least one of $R^{301}$, ..., or $R^{310}$ includes an anion).

<2> The coloring curable resin composition according to <1>, in which the colorant represented by Formula (1) is represented by Formula (1A):

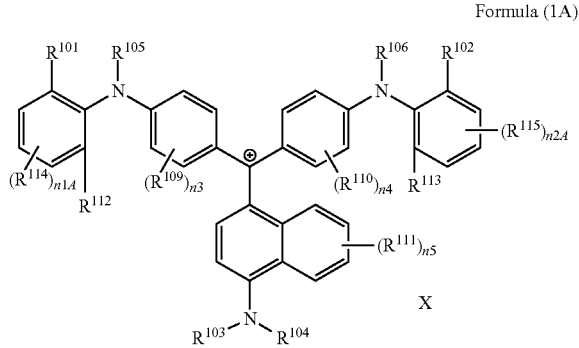

Formula (1A)

(in Formula (1A), $R^{101}$, $R^{102}$, $R^{112}$, and $R^{113}$ each independently represent a substituent, $R^{103}$ to $R^{106}$ each independently represent a hydrogen atom, an alkyl group, an aryl group, or a heteroaryl group, $R^{109}$ to $R^{111}$, $R^{114}$, and $R^{115}$ each independently represent a hydrogen atom or a substituent, n1A and n2A each independently represent an integer of 0 to 3, n3 and n4 each independently represent an integer of 0 to 4, n5 represents an integer of 0 to 6, X represents an anion or is not present, and at least one of $R^{101}$, ..., or $R^{115}$ includes an anion).

<3> The coloring curable resin composition according to <2>, in which in Formula (1A), $R^{101}$, $R^{102}$, $R^{112}$, and $R^{113}$ each independently represent an alkyl group.

<4> The coloring curable resin composition according to <2> or <3>, in which in Formula (1A), $R^{105}$ and $R^{106}$ represent a hydrogen atom.

<5> The coloring curable resin composition according to <1>, in which the colorant represented by Formula (1) is represented by Formula (1C):

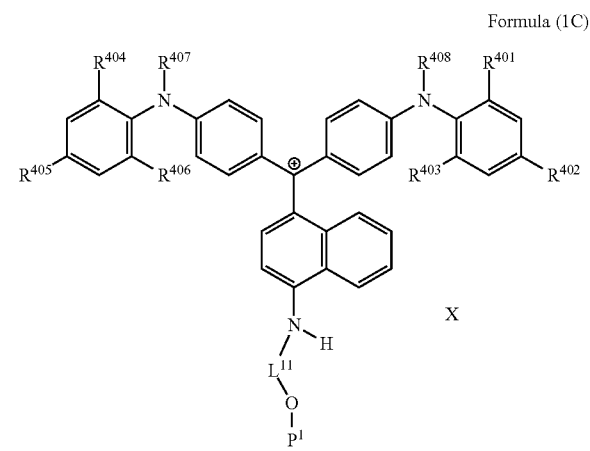

Formula (1C)

(in Formula (1C), $R^{401}$ to $R^{408}$ each independently represent a hydrogen atom or an alkyl group, $L^{11}$ represents a divalent linking group having 2 to 30 carbon atoms, $P^1$ represents a polymerizable group, and X represents an anion).

<6> The coloring curable resin composition according to <5>, in which in Formula (1C), $R^{401}$ to $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, and $P^1$ represents an acryloyl group, a methacryloyl group, or a —$CH_2C_6H_4CH=CH_2$ group.

<7> The coloring curable resin composition according to <1>, in which the colorant represented by Formula (1) is represented by Formula (1B):

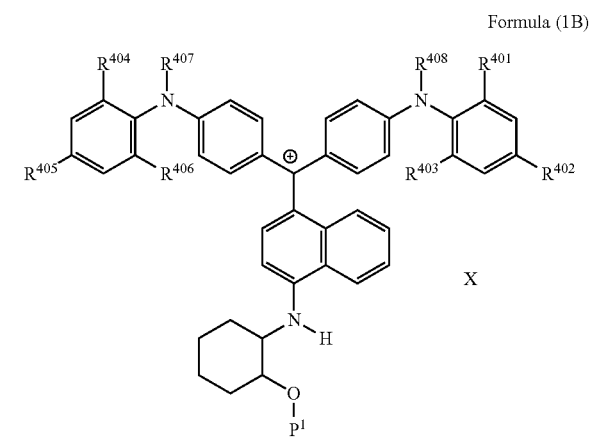

Formula (1B)

(in Formula (1B), $R^{401}$ to $R^{408}$ each independently represent a hydrogen atom or an alkyl group, $P^1$ represents a polymerizable group, and X represents an anion).

<8> The coloring curable resin composition according to <7>, in which in Formula (1B), $R^{407}$ and $R^{408}$ represent an alkyl group having 1 to 6 carbon atoms.

<9> The coloring curable resin composition according to <7> or <8>, in which in Formula (1B), $R^{401}$ to $R^{406}$ represent an alkyl group having 1 to 3 carbon atoms.

<10> The coloring curable resin composition according to any one of <7> to <9>, in which in Formula (1B), X represents a bistrifluoromethanesulfonylimide anion, a tristrifluoromethanesulfonylmethide anion, or a perfluoromethanesulfonic acid anion.

<11> The coloring curable resin composition according to <1>, in which the colorant represented by Formula (2) is represented by Formula (2A):

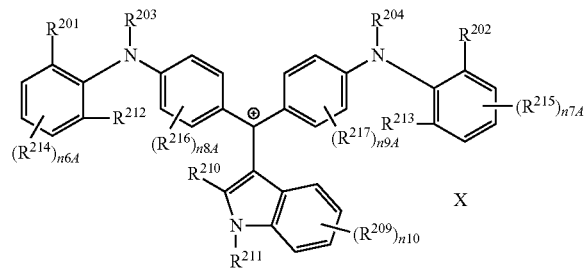

Formula (2A)

(in Formula (2A), $R^{201}$, $R^{202}$, $R^{212}$, and $R^{213}$ each independently represent a substituent, $R^{203}$, $R^{204}$, $R^{209}$, and $R^{214}$ to $R^{217}$ each independently represent a hydrogen atom or a substituent, $R^{210}$ and $R^{211}$ each independently represent an alkyl group, an aryl group, or a heteroaryl group, n6A and n7A each independently represent an integer of 1 to 3, n8A to n10 each independently represent an integer of 1 to 4, X represents an anion or is not present, and at least one of $R^{201}$, ..., or $R^{216}$ includes an anion).

<12> The coloring curable resin composition according to <11>, in which in Formula (2A), $R^{201}$, $R^{202}$, $R^{212}$, and $R^{213}$ each independently represent an alkyl group.

<13> The coloring curable resin composition according to <1>, in which the colorant represented by Formula (3) is represented by Formula (3A):

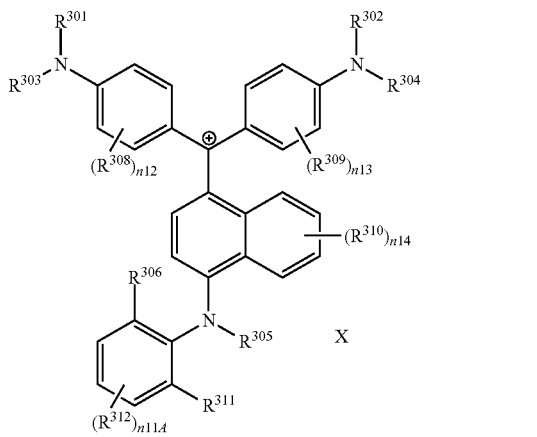

Formula (3A)

(in Formula (3A), $R^{301}$ and $R^{302}$ each independently represent a substituent, $R^{303}$ to $R^{305}$ each independently represent a hydrogen atom or a substituent, $R^{306}$ and $R^{311}$ each independently represent a substituent, $R^{308}$ to $R^{310}$, and $R^{312}$ each independently represent a hydrogen atom, an alkyl group, or a halogen atom, n11A represents an integer of 1 to 3, n12 and n13 each independently represent an integer of 1 to 4, n14 represents an integer of 1 to 6, X represents an anion or is not present, and at least one of $R^{301}$, ..., or $R^{312}$ includes an anion).

<14> The coloring curable resin composition according to <13>, in which in Formula (3A), $R^{306}$ and $R^{311}$ each independently represent an alkyl group.

<15> The coloring curable resin composition according to any one of <1> to <14>, further comprising at least one of a xanthene colorant or a dipyrromethene-based metal complex compound.

<16> The coloring curable resin composition according to any one of <1> to <15>, further comprising a pigment.

<17> The coloring curable resin composition according to any one of <1> to <16>, in which the colorant includes a polymerizable group and/or a multimer structure.

<18> The coloring curable resin composition according to any one of <1> to <17>, in which the coloring curable resin composition contains an oxime-based compound as a polymerization initiator.

<19> A colored cured film formed by curing the coloring curable resin composition according to any one of <1> to <18>.

<20> A color filter comprising the colored cured film according to <19>.

<21> A color filter using the coloring curable resin composition according to any one of <1> to <18>.

<22> A method for manufacturing a color filter, comprising:

a step of applying the coloring curable resin composition according to any one of <1> to <18> onto a support to form a coloring curable resin composition layer;

a step of patternwise exposing the coloring curable resin composition layer; and a step of removing an unexposed area by development to form a colored pattern.

<23> A solid-state imaging device comprising the color filter according to <20> or <21>, or a color filter obtained by the method for manufacturing a color filter according to <22>.

<24> An image display device comprising the color filter according to <20> or <21>, or a color filter obtained by the method for manufacturing a color filter according to <22>.

<25> An image display device comprising a color filter in at least three colors of red, green, and blue, in which the coloring curable resin composition according to any one of <1> to <18> is used in the color filter in blue.

<26> A compound represented by Formula (11), a compound represented by Formula (12), or a compound represented by Formula (13):

Formula (11)

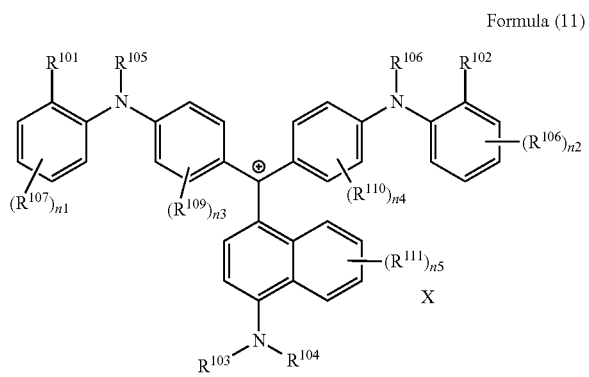

(in Formula (11), $R^{101}$ and $R^{102}$ each independently represent a hydrogen atom, a cyano group, —$SO_2N(C_2H_4OCH_3)_2$, or an alkyl group having 1 to 3 carbon atoms, $R^{103}$ to $R^{106}$ each independently represent a hydrogen atom, an alkyl group having 1 to 8 carbon atoms, or an aryl group, $R^{107}$ to $R^{111}$ each independently represent a hydrogen atom, a fluorine atom, a chlorine atom, a cyano group, a nitro group, —$NHCOCH_3$, —$SO_2NHC_2H_4OCH_3$, —$NHSO_2CH_3$, or an alkyl group having 1 to 3 carbon atoms, n1 to n4 each independently represent an integer of 1 to 4, n5 represents an integer of 0 to 6, X represents an anion or is not present, and at least one of $R^{101}$, . . . , or $R^{111}$ includes an anion, provided that in the case where $R^{101}$ and $R^{102}$ represent hydrogen atoms, $R^{103}$ represents an aryl group having a methyl group or an ester group as a substituent at at least the ortho-position), Formula (12)

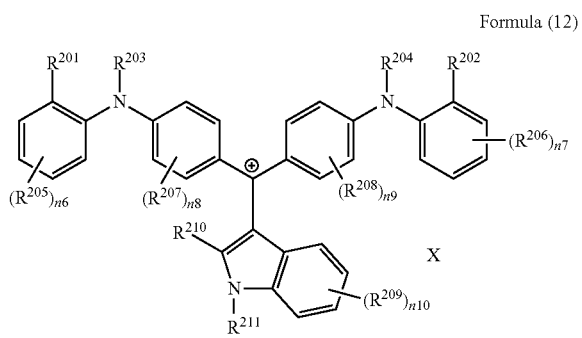

(in Formula (12), $R^{201}$ and $R^{202}$ each independently represent a hydrogen atom or a methyl group, at least one of $R^{201}$ or $R^{202}$ represents a methyl group, $R^{203}$ to $R^{209}$ each independently represent a hydrogen atom, a fluorine atom, —$SO_2N(C_2H_4OCH_3)_2$, or an alkyl group having 1 to 3 carbon atoms, $R^{210}$ and $R^{211}$ each independently represent a methyl group or a phenyl group, n6 to n10 each independently represent an integer of 1 to 4, X represents an anion or is not present, and at least one of $R^{201}$, . . . , or $R^{211}$ includes an anion), and Formula (13)

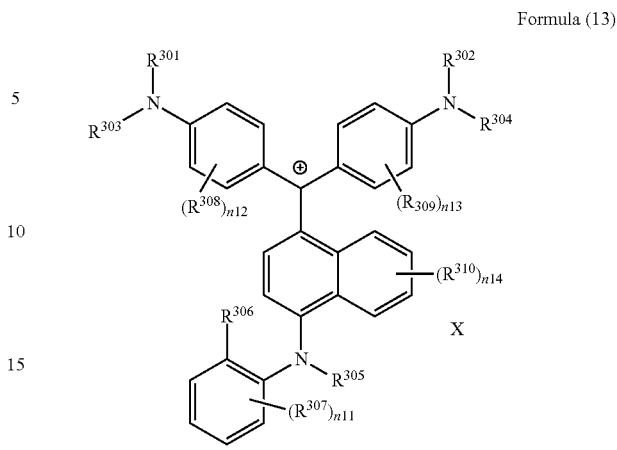

(in Formula (13), $R^{301}$ and $R^{302}$ each independently represent a methyl group or an ethyl group, $R^{303}$ to $R^{305}$ each independently represent a hydrogen atom or a methyl group, $R^{306}$ represents an ester group, $R^{307}$ to $R^{310}$ represents a hydrogen atom, n11 to n13 each independently represent an integer of 1 to 4, n14 represents an integer of 1 to 6, X represents an anion or is not present, and at least one of $R^{301}$, . . . , or $R^{310}$ includes an anion).

<27> The compound according to <26>, represented by Formula (14):

Formula (14)

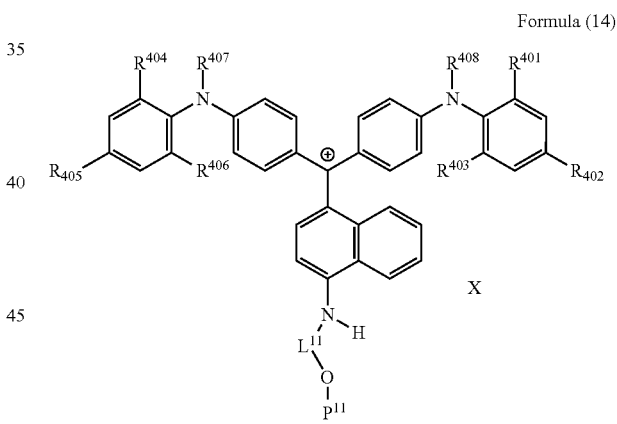

(in Formula (14), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, $P^{11}$ represents an acryloyl group, a methacryloyl group, or a —$CH_2C_6H_4CH$=$CH_2$ group, and X represents a bistrifluoromethanesulfonylimide anion, a tristrifluoromethanesulfonylmethide anion, or a perfluoromethanesulfonic acid anion).

<28> The compound according to <27>, in which in Formula (14), $L^{11}$ represents an alkylene group having 2 to 10 carbon atoms, and $P^{11}$ represents an acryloyl group or a methacryloyl group.

<29> The compound according to <26>, represented by Formula (15):

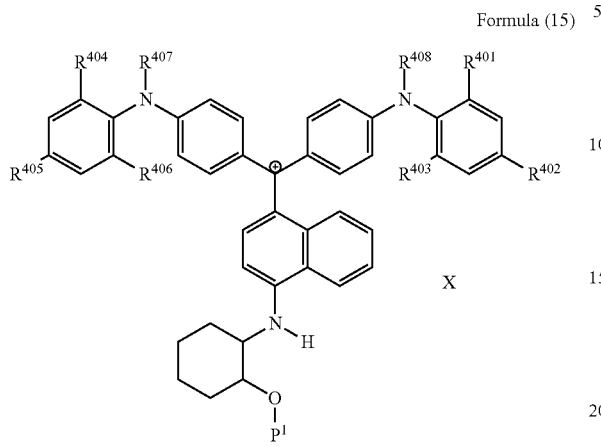

Formula (15)

(in Formula (15), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $P^1$ represents a polymerizable group, and X represents a bistrifluoromethanesulfonylimide anion, a tristrifluoromethanesulfonylmethide anion, or a perfluoromethanesulfonic acid anion).

<30> The compound according to <26>, represented by Formula (16):

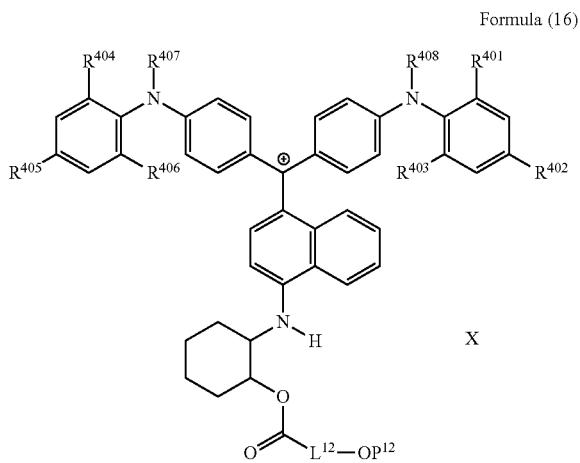

Formula (16)

(in Formula (16), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents an alkylene group having 2 to 12 carbon atoms, a cycloalkylene group, a phenylene group, or a group formed by combination of these groups, $P^{12}$ represents an acryloyl group or a methacryloyl group, and X represents a bistrifluoromethanesulfonylimide anion, a tristrifluoromethanesulfonylmethide anion, or a perfluoromethanesulfonic acid anion).

<31> The compound according to <26>, represented by Formula (17):

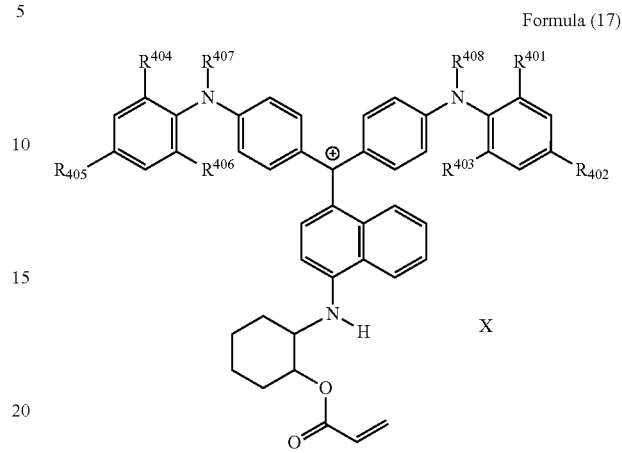

Formula (17)

(in Formula (17), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and X represents a bistrifluoromethanesulfonylimide anion, a tristrifluoromethanesulfonylmethide anion, or a perfluoromethanesulfonic acid anion).

<32> A cation represented by Formula (4):

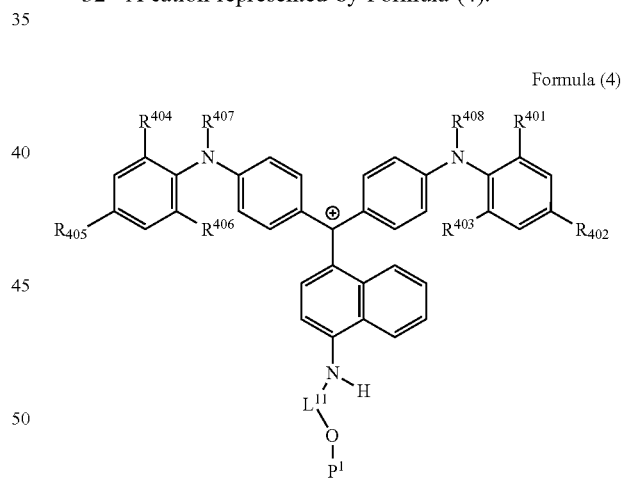

Formula (4)

(in Formula (4), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, and $P^1$ represents a polymerizable group).

<33> The cation according to <32>, in which in Formula (4), $P^1$ represents an acryloyl group, a methacryloyl group, or a —$CH_2C_6CH_4CH=CH_2$ group.

<34> The cation according to <32>, represented by Formula (5):

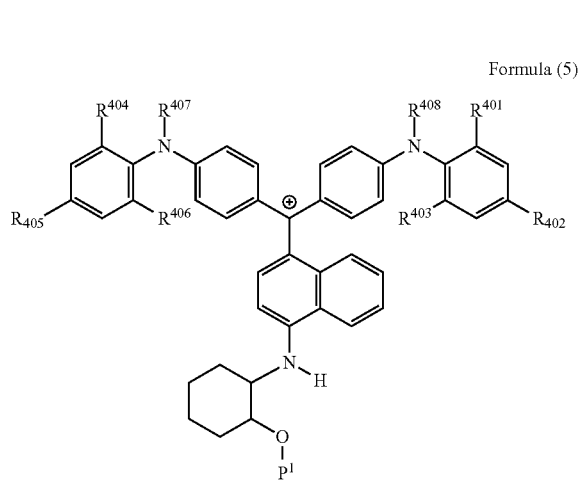

Formula (5)

(in Formula (5), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and $P^1$ represents a polymerizable group).

<35> The cation according to <32>, represented by Formula (6):

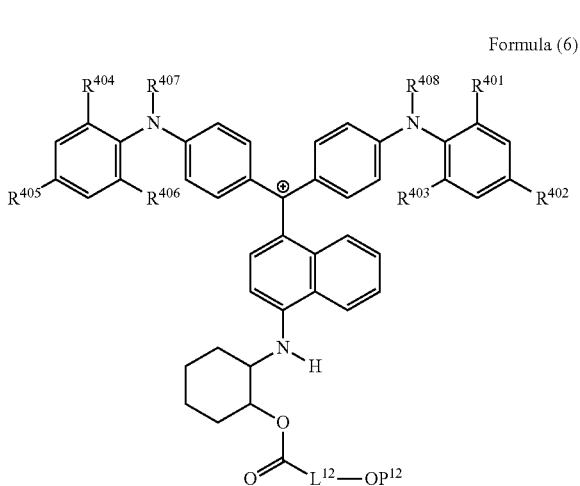

Formula (6)

(in Formula (6), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents an alkylene group having 2 to 12 carbon atoms, a cycloalkylene group, a phenylene group, or a group formed by combination of these groups, and $P^{12}$ represents an acryloyl group or a methacryloyl group).

<36> The cation according to <32>, represented by Formula (7):

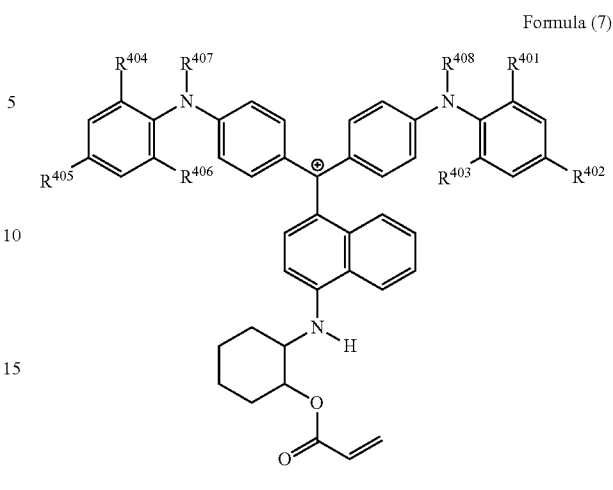

Formula (7)

(in Formula (7), $R^{401}$ to $R^{406}$ each independently represent a hydrogen atom or an alkyl group having 1 to 3 carbon atoms, and $R^{407}$ and $R^{408}$ each independently represent an alkyl group having 1 to 6 carbon atoms).

According to the present invention, it is possible to provide a coloring curable resin composition having good heat resistance and durability in a sputtering process. Further, it is also possible to provide a cured film, a color filter, a method for manufacturing a color filter, a solid-state imaging device, and a liquid crystal display device.

DESCRIPTION OF THE PREFERRED EMBODIMENTS

Figure 1:
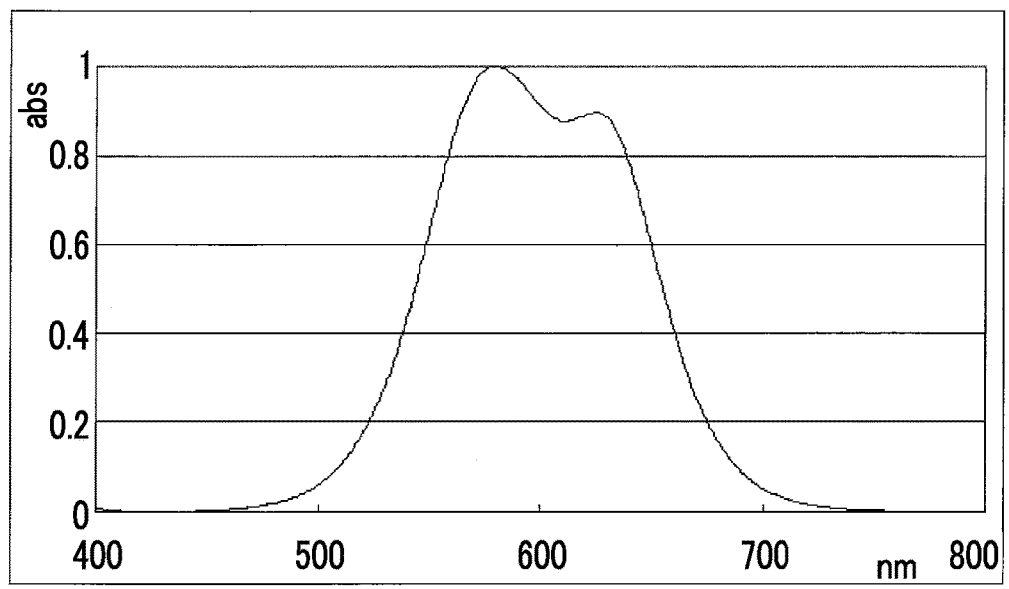
FIG. 1 is a view showing an absorption spectrum of a colorant TAM107.

Hereinafter, the contents of the present invention will be described in detail. Further, in the present specification, a numeral value range represented by "(a value) to (a value)" means a range including the numeral values represented before and after the range as a lower limit value and an upper limit value, respectively.

In the present specification, the total solid content refers to the total mass of the components remaining when a solvent is excluded from the entire composition of a coloring curable resin composition.

In citations for a group (atomic group) in the present specification, when the group is denoted without specifying whether it is substituted or unsubstituted, the group includes both a group (atomic group) having no substituent and a group (atomic group) having a substituent. For example, an "alkyl group" includes not only an alkyl group having no substituent (unsubstituted alkyl group), but also an alkyl group having a substituent (substituted alkyl group).

Furthermore, "radiation" in the present specification means, for example, a bright line spectrum of a mercury lamp, far ultraviolet rays represented by an excimer laser, extreme ultraviolet rays (EUV rays), X rays, electron beams, or the like. In addition, in the present invention, light means active light or radiation.

"Exposure" in the present specification includes, unless otherwise specified, not only exposure by bright line spectrum of a mercury lamp, far ultraviolet rays represented by an excimer laser, X-rays, EUV rays, or the like, but also writing by particle rays such as electron beams and ion beams.

Furthermore, in the present specification, "(meth)acrylate" represents either or both of acrylate and methacrylate, "(meth)acryl" represents either or both of acryl and methacryl, and "(meth)acryloyl" represents either or both of acryloyl and methacryloyl.

In addition, in the present specification, a "monomer material" and a "monomer" have the same definition.

The monomer in the present specification refers to a compound which is distinguished from an oligomer or a polymer and has a weight-average molecular weight of 2,000 or less.

In the present specification, a polymerizable compound refers to a compound having a polymerizable functional group, and may be a monomer or a polymer. The polymerizable functional group refers to a group involved in a polymerization reaction.

In the formulae in the present specification, Me represents a methyl group, Et represents an ethyl group, Pr represents a propyl group, Bu represents a butyl group, Ph represents a phenyl group, and Ac represents an acetyl group.

In the present specification, a term "step" includes not only an independent step, but also steps which are not clearly distinguished from other steps if an intended action of the steps is obtained.

The weight-average molecular weight in the present invention refers to a value as measured by gel permeation chromatography (GPC) unless otherwise specified. Measurement by GPC can be carried out by removing a solvent from a polymer obtained for isolation, diluting the isolated solid content to 0.1% by mass with tetrahydrofuran, and using three columns of TSKgel Super Multipore HZ-H (manufactured by Tosoh Corporation, 4.6 mm ID x 15 cm) connected in series in HLC-8020GPC (manufactured by Tosoh Corporation). The measurement can be carried out under the conditions of a sample concentration of 0.35% by mass, a flow rate of 0.35 mL/min, a sample injection amount of 10 μL, and a measurement temperature of 40° C., using an RI detector.

In the present specification, the total solid content refers to the total mass of the components remaining when a solvent is excluded from the entire composition of the composition. The solid content in the present invention is a solid content at 25° C.

[Coloring Curable Resin Composition]

The coloring curable resin composition of the present invention (hereinafter also referred to as the composition of the present invention) may contain a colorant represented by Formula (1), Formula (2), or Formula (3), a resin, a polymerizable compound, and a polymerization initiator.

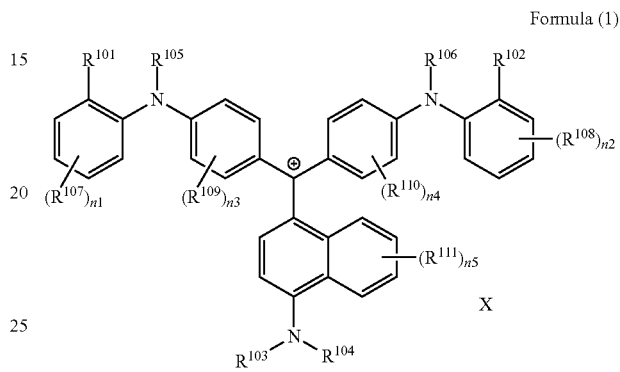

Formula (1)

(in Formula (1), $R^{101}$ and $R^{102}$ each independently represent a hydrogen atom or a substituent, $R^{103}$ to $R^{106}$ each independently represent a hydrogen atom, an alkyl group, an aryl group, or a heteroaryl group, $R^{107}$ to $R^{111}$ each independently represent a hydrogen atom or a substituent, n1 to n4 each independently represent an integer of 1 to 4, n5 represents an integer of 0 to 6, X represents an anion or is not present, and at least one of $R^{101}$, . . . , or $R^{111}$ includes an anion, provided that in the case where $R^{101}$ and $R^{102}$ represent hydrogen atoms, $R^{103}$ represents an aryl group having a substituent at at least the ortho-position)

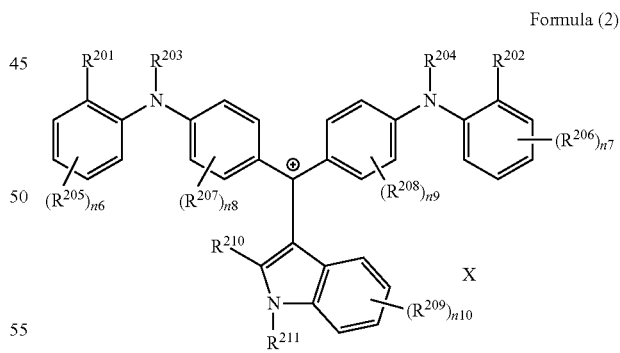

Formula (2)

(in Formula (2), $R^{201}$ and $R^{202}$ each independently represent a hydrogen atom or a substituent, at least one of $R^{201}$ or $R^{202}$ represents a substituent, $R^{203}$ to $R^{209}$ each independently represent a hydrogen atom or a substituent, $R^{210}$ and $R^{211}$ each independently represent an alkyl group, an aryl group, or a heteroaryl group, n6 to n10 each independently represent an integer of 0 to 4, X represents an anion or is not present, and at least one of $R^{201}$, . . . , or $R^{211}$ includes an anion):

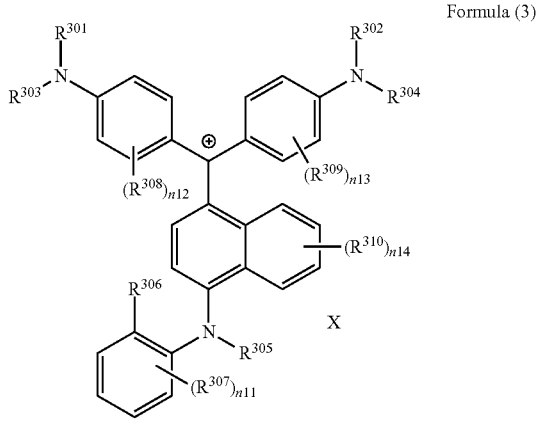

Formula (3)

(in Formula (3), $R^{301}$ and $R^{302}$ each independently represent an alkyl group, an aryl group, or a heteroaryl group, $R^{303}$ to $R^{305}$ each independently represent a hydrogen atom, an alkyl group, an aryl group, or a heteroaryl group, $R^{306}$ represents a substituent, $R^{307}$ to $R^{310}$ each independently represent a hydrogen atom, an alkyl group, or a halogen atom, n11 to n13 each independently represent an integer of 0 to 4, n14 represents an integer of 0 to 6, X represents an anion or is not present, and at least one of $R^{301}$, . . . , or $R^{310}$ includes an anion).

By having such a configuration, it is possible to form a cured film having good heat resistance and durability in a sputtering process. Although this mechanism is presumed, when at least one of nitrogen atoms in Formula (1), Formula (2), or in Formula (3) has an aryl group at the ortho-position, an aryl group is distorted from a plane formed of bonding arms of the nitrogen atoms, and the p orbit of the nitrogen atoms is effectively shielded by the substituents at the ortho position of the aryl group. As a result, a compound that undergoes an action with the p orbit of the nitrogen atom to promote the decomposition of the colorant is less likely to be close to the colorant represented by Formula (1), Formula (2), or Formula (3), and accordingly, the colorant is hardly decomposed, thereby improving heat resistance and durability in a sputtering process.

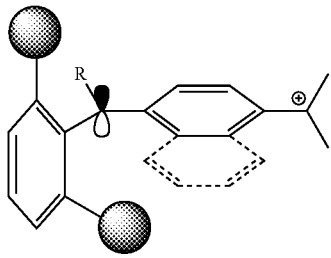

<Colorant Represented by Formula (1), Formula (2), or Formula (3)>

The colorant represented by Formula (1), Formula (2), or Formula (3) may be of a low-molecular type (for example, one having a molecular weight of less than 2,000) or may be of a high-molecular type (for example, one having a molecular weight of 2,000 or more), with the high-molecular type being preferable.

«Low-Molecular Type»
«<Colorant Represented by Formula (1)>»

In Formula (1), $R^{101}$ and $R^{102}$ each independently represent a hydrogen atom or a substituent, examples of the substituent include the substituents as defined in the substituent A group which will be described later, preferably the substituents having high volumes than that of a hydrogen atom, and more preferably an alkyl group, an aryl group, a heteroaryl group, and an ester group, and still more preferably an alkyl group. The alkyl group may be in any one of linear, branched, and cyclic forms, and is preferably in a linear or branched form, and more preferably a branched form. The number of carbon atoms of the alkyl group is preferably 1 to 12, more preferably 1 to 10, still more preferably 1 to 8, and particularly preferably 1 to 4. The alkyl group may have a substituent, but it is preferable that the alkyl group is not substituted. Examples of the substituent which may be contained in the alkyl group include the substituents as defined in the substituent A group which will be described later. Preferred examples of the substituent include an ester group, a carbamoyl group, a sulfamoyl group, a cyano group, an alkoxy group, and a halogen atom.

The number of carbon atoms of the aryl group is preferably 6 to 12, more preferably 6 to 10, and still more preferably 6. Examples of the aryl group include a phenyl group and a naphthyl group, and the aryl group is preferably a phenyl group. The aryl group may be monocyclic or a fused ring.

The number of carbon atoms of the heteroaryl group is preferably 1 to 12, more preferably 2 to 10, and still more preferably 3 to 5. Examples of the heteroaryl group include an imidazolyl group, a benzimidazolyl group, a triazole group, a diazole group, a thiazole group, a thiadiazole group, a benzoxazole group, a benzothiazole group, indole group, a furanyl group, a thiophenyl group, a benzofuranyl group, a benzothiophenyl group, a pyridinyl group, a pyrimidinyl group, a triazinyl group, a quinolinyl group, and a carbazoyl group.

$R^{103}$ represents a hydrogen atom, an alkyl group, an aryl group, or a heteroaryl group, and is preferably an alkyl group or an aryl group, and more preferably an aryl group.

The alkyl group may be in any one of linear, branched, and cyclic forms, and is preferably in a cyclic form. The number of carbon atoms of the alkyl group is preferably 1 to 12, more preferably 4 to 10, still more preferably 5 to 7, and particularly preferably 6. In the case where the alkyl group is cyclic, examples of the substituent which may be contained in the alkyl group include the substituents described in the substituent A group which will be described later, and the substituent is preferably a halogen atom, a (meth) acryloyl group, or the like.

The aryl group and the heteroaryl group have the same definitions as the aryl group and the heteroaryl group described in $R^{101}$ and $R^{102}$, and preferred ranges thereof are also the same. Examples of the substituent which may be contained in the aryl group include the substituents described in the substituent A group which will be described later, and the substituent is preferably an alkyl group having 1 to 3 carbon atoms.

Furthermore, in the case where $R^{101}$ and $R^{102}$ represent hydrogen atoms, $R^{103}$ represents an aryl group having a substituent at at least the ortho-position, and it is more preferably aryl having substituents at the 2 and 6 positions being, and still more preferably aryl having substituents at the 2, 4, and 6 positions. The substituent has the same definition as the substituents described in $R^{101}$ and $R^{102}$, and is preferably a methyl group.

$R^{104}$ represents a hydrogen atom, an alkyl group, an aryl group, or a heteroaryl group, and is preferably a hydrogen atom, and the alkyl group, the aryl group, and the heteroaryl group have the same definitions as $R^{103}$.

$R^{105}$ and $R^{106}$ each independently represent a hydrogen atom, an alkyl group, an aryl group, or a heteroaryl group, and are preferably a hydrogen atom or an alkyl group, and more preferably a hydrogen atom. The alkyl group may be in any one of linear, branched, and cyclic forms, and is preferably in a linear form. The number of carbon atoms of the alkyl group is preferably 1 to 12, more preferably 1 to 10, still more preferably 1 to 8, and particularly preferably 1 to 3. The aryl group and the heteroaryl group have the same definitions as $R^{103}$, and preferred ranges thereof are also the same.

In the case where $R^{105}$ and $R^{106}$ represent an alkyl group, an aryl group, or a heteroaryl group, examples of the substituent which may be contained in the groups include the substituents as defined in the substituent A group which will be described later. Preferred examples of the substituent include an epoxy group, a vinyl group, a (meth)acryloyl group, an alkoxy group, a halogen atom, and an ester group.

$R^{107}$ and $R^{108}$ each independently represent a hydrogen atom or a substituent. Examples of the substituent include the substituents as defined in the substituent A group which will be described later. In particular, as the substituent, an alkyl group, a halogen atom, a cyano group, a nitro group, —NHCOCH$_3$, —SO$_2$NHC$_2$H$_4$OCH$_3$ or —NHSO$_2$CH$_3$ is preferable, an alkyl group or a halogen atom is more preferable, and an alkyl group is still more preferable. The alkyl group has the same definition as the alkyl group described in $R^{101}$ and $R^{102}$, and preferred ranges thereof are also the same. The halogen atom has the same definition as the halogen atom as defined in the substituent A group which will be described later, and preferred ranges thereof are also the same.

$R^{109}$ to $R^{111}$ each independently represent a hydrogen atom or a substituent, and are preferably a hydrogen atom. Examples of the substituent include the substituents as defined in the substituent A group which will be described later. In particular, as the substituent, an alkyl group, a halogen atom, or —NHCOCH$_3$ is preferable. The alkyl group and the halogen atom have the same definitions as the alkyl group and the halogen atom described in $R^{107}$ and $R^{108}$, and preferred ranges thereof are also the same.

n1 and n2 each independently represent an integer of 1 to 4, and are preferably an integer of 1 to 3, and more preferably 1 or 2.

n3 and n4 each independently represent an integer of 1 to 4, and are preferably an integer of 1 to 3, and more preferably 1 or 2.

n5 represents an integer of 0 to 6, and is preferably an integer of 1 to 6, more preferably an integer of 1 to 4, and still more preferably 1 or 2.

X represents an anion or is not present, and at least one of $R^{101}$, . . . , or $R^{111}$ includes an anion. In the case where X is not present and at least one of $R^{101}$, . . . , or $R^{111}$ includes an anion, it is preferable that $R^{111}$ includes an anion.

<Substituent A Group>

The substituent group A represents a halogen atom (for example, a fluorine atom, a chlorine atom, and a bromine atom, preferably a chlorine atom and a fluorine atom, and more preferably a fluorine atom), an alkyl group (preferably a linear, branched, or cyclic alkyl group having 1 to 48 carbon atoms, more preferably a linear, branched, or cyclic alkyl group having 1 to 24 carbon atoms, and particularly preferably a linear, branched, or cyclic alkyl group having 1 to 8 carbon atoms, for example, a methyl group, an ethyl group, a propyl group, an isopropyl group, a butyl group, a t-butyl group, pentyl group, a hexyl group, a heptyl group, octyl group, a 2-ethylhexyl group, a dodecyl group, a hexadecyl group, a cyclopropyl group, a cyclopentyl group, a cyclohexyl group, a 1-norbonyl group, and a 1-adamantyl group), an alkenyl group (preferably an alkenyl group having 2 to 48 carbon atoms, and more preferably an alkenyl group having 2 to 18 carbon atoms, for example, a vinyl group, an allyl group, and a 3-buten-1-yl group), an aryl group (preferably an aryl group having 6 to 48 carbon atoms, and more preferably an aryl group having 6 to 24 carbon atoms, for example, a phenyl group and a naphthyl group), a heterocyclic group (preferably a heterocyclic group having 1 to 32 carbon atoms, and more preferably a heterocyclic group having 1 to 18 carbon atoms, for example, a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), a silyl group (preferably a silyl group having 3 to 38 carbon atoms, and more preferably a silyl group having 3 to 18 carbon atoms, for example, a trimethylsilyl group, a triethylsilyl group, a tributylsilyl group, a t-butyldimethylsilyl group, and a t-hexyldimethylsilyl group), a hydroxyl group, a cyano group, a nitro group, an alkoxy group (preferably an alkoxy group having 1 to 48 carbon atoms, and more preferably an alkoxy group having 1 to 24 carbon atoms, for example, a methoxy group, an ethoxy group, a 1-butoxy group, a 2-butoxy group, an isopropoxy group, a t-butoxy group, a dodecyloxy group, and a cycloalkyloxy group, for example, a cyclopentyloxy group and a cyclohexyloxy group), an aryloxy group (preferably an aryloxy group having 6 to 48 carbon atoms, and more preferably an aryloxy group having 6 to 24 carbon atoms, for example, a phenoxy group and a 1-naphthoxy group), a heterocyclic oxy group (preferably a heterocyclic oxy group having 1 to 32 carbon atoms, and more preferably a heterocyclic oxy group having 1 to 18 carbon atoms, for example, a 1-phenyltetrazol-5-oxy group and a 2-tetrahydropyranyloxy group), a silyloxy group (preferably a silyloxy group having 1 to 32 carbon atoms, and more preferably a silyloxy group having 1 to 18 carbon atoms, for example, a trimethylsilyloxy group, a t-butyldimethylsilyloxy group, and a diphenylmethylsilyloxy group), an acyloxy group (preferably an acyloxy group having 2 to 48 carbon atoms, and more preferably an acyloxy group having 2 to 24 carbon atoms, for example, an acetoxy group, a pivaloyloxy group, a benzoyloxy group, and a dodecanoyloxy group), an alkoxycarbonyloxy group (preferably an alkoxycarbonyloxy group having 2 to 48 carbon atoms, and more preferably an alkoxycarbonyloxy group having 2 to 24 carbon atoms, for example, an ethoxycarbonyloxy group, a t-butoxycarbonyloxy group, and a cycloalkyloxycarbonyloxy group, for example, a cyclohexyloxycarbonyloxy group), an aryloxycarbonyloxy group (preferably an aryloxycarbonyloxy group having 7 to 32 carbon atoms, and more preferably an aryloxycarbonyloxy group having 7 to 24 carbon atoms, for example, a phenoxycarbonyloxy group), a carbamoyloxy group (preferably a carbamoyloxy group having 1 to 48 carbon atoms, and more preferably a carbamoyloxy group having 1 to 24 carbon atoms, for example, an N,N-dimethylcarbamoyloxy group, an N-butylcarbamoyloxy group, an N-phenylcarbamoyloxy group, and an N-ethyl-N-phenylcarbamoyloxy group), a sulfamoyloxy group (preferably a sulfamoyloxy group having 1 to 32 carbon atoms, and more preferably a sulfamoyloxy group having 1 to 24 carbon atoms, for example, an N,N-diethylsulfamoyloxy group and an N-propylsulfamoyloxy group), an alkylsulfonyloxy group (preferably an alkylsulfonyloxy group having 1 to 38 carbon atoms, and more preferably an alkylsulfonyloxy group having 1 to 24 carbon atoms, for example, a methylsulfonyloxy group, a hexadecylsulfonyloxy group, and a cyclohexylsulfonyloxy group), an arylsulfonyloxy group (preferably an arylsulfonyloxy group having 6 to 32 carbon atoms, and more preferably an arylsulfonyloxy group having 6 to 24 carbon atoms, for example, a phenylsulfonyloxy group), an acyl group (preferably an acyl group having 1 to 48 carbon atoms, and more preferably an acyl group having 1 to 24 carbon atoms, for example, a formyl group, an acetyl group, a pivaloyl group, a benzoyl group, a tetradecanoyl group, and a cyclohexanoyl group), an alkoxycarbonyl group (preferably an alkoxycarbonyl group having 2 to 48 carbon atoms, and more preferably an alkoxycarbonyl group having 2 to 24 carbon atoms, for example, a methoxycarbonyl group, an ethoxycarbonyl group, an octadecyloxycarbonyl group, a cyclohexyloxycarbonyl group, and a 2,6-di-tert-butyl-4-methylcyclohexyloxycarbonyl group), an aryloxycarbonyl group (preferably an aryloxycarbonyl group having 7 to 32 carbon atoms, and more preferably an aryloxycarbonyl group having 7 to 24 carbon atoms, for example, a phenoxycarbonyl group), a carbamoyl group (preferably a carbamoyl group having 1 to 48 carbon atoms, and more preferably a carbamoyl group having 1 to 24 carbon atoms, for example, a carbamoyl group, an N,N-diethylcarbamoyl group, an N-ethyl-N-octylcarbamoyl group, an N,N-dibutylcarbamoyl group, an N-propylcarbamoyl group, an N-phenylcarbamoyl group, an N-methyl-N-phenylcarbamoyl group, and an N,N-dicyclohexylcarbamoyl group), an amino group (preferably an amino group having 32 or less carbon atoms, and more preferably an amino group having 24 or less carbon atoms, for example, amino group, a methylamino group, an N,N-dibutylamino group, a tetradecylamino group, a 2-ethylhexylamino group, and a cyclohexylamino group), an anilino group (preferably an anilino group having 6 to 32 carbon atoms, and more preferably an anilino group having 6 to 24 carbon atoms, for example, an anilino group and an N-methylanilino group), a heterocyclic amino group (preferably a heterocyclic amino group having 1 to 32 carbon atoms, and more preferably a heterocyclic amino group having 1 to 18 carbon atoms, for example, a 4-pyridylamino group), a carbonamide group (preferably a carbonamide group having 2 to 48 carbon atoms, and more preferably a carbonamide group having 2 to 24 carbon atoms, for example, an acetamide group, a benzamide group, a tetradecanamide group, a pivaloylamide group, and a cyclohexanamide group), a ureido group (preferably a ureido group having 1 to 32 carbon atoms, and more preferably a ureido group having 1 to 24 carbon atoms, for example, a ureido group, an N,N-dimethylureido group, and an N-phenylureido group), an imide group (preferably an imide group having 36 or less carbon atoms, and more preferably an imide group having 24 or less carbon atoms, for example, an N-succinimide group and an N-phthalimide group), an alkoxycarbonylamino group (preferably an alkoxycarbonylamino group having 2 to 48 carbon atoms, and more preferably an alkoxycarbonylamino group having 2 to 24 carbon atoms, for example, a methoxycarbonylamino group, an ethoxycarbonylamino group, a t-butoxycarbonylamino group, an octadecyloxycarbonylamino group, and a cyclohexyloxycarbonylamino group), an aryloxycarbonylamino group (preferably an aryloxycarbonylamino group having 7 to 32 carbon atoms, and more preferably an aryloxycarbonylamino group having 7 to 24 carbon atoms, for example, a phenoxycarbonylamino group), a sulfonamide group (preferably a sulfonamide group having 1 to 48 carbon atoms, and more preferably a sulfonamide group having 1 to 24 carbon atoms, for example, a methanesulfonamide group, a butanesulfonamide group, a benzenesulfonamide group, a hexadecanesulfonamide group, and a cyclohexanesulfonamide group), a sulfamoylamino group (preferably a sulfamoylamino group having 1 to 48 carbon atoms, and more preferably a sulfamoylamino group having 1 to 24 carbon atoms, for example, an N,N-dipropylsulfamoylamino group and an N-ethyl-N-dodecylsulfamoylamino group), an azo group (preferably an azo group having 1 to 32 carbon atoms, and more preferably an azo group having 1 to 24 carbon atoms, for example, a phenylazo group and a 3-pyrazolylazo group), an alkylthio group (preferably an alkylthio group having 1 to 48 carbon atoms, and more preferably an alkylthio group having 1 to 24 carbon atoms, for example, a methylthio group, an ethylthio group, an octylthio group, and a cyclohexylthio group), an arylthio group (preferably an arylthio group having 6 to 48 carbon atoms, and more preferably an arylthio group having 6 to 24 carbon atoms, for example, a phenylthio group), a heterocyclic thio group (preferably a heterocyclic thio group having 1 to 32 carbon atoms, and more preferably a heterocyclic thio group having 1 to 18 carbon atoms, for example, a 2-benzothiazolylthio group, a 2-pyridylthio group, and a 1-phenyltetrazolylthio group), an alkylsulfinyl group (preferably an alkylsulfinyl group having 1 to 32 carbon atoms, and more preferably an alkylsulfinyl group having 1 to 24 carbon atoms, for example, a dodecanesulfinyl group), an arylsulfinyl group (preferably an arylsulfinyl group having 6 to 32 carbon atoms, and more preferably an arylsulfinyl group having 6 to 24 carbon atoms, for example, a phenylsulfinyl group), an alkylsulfonyl group (preferably an alkylsulfonyl group having 1 to 48 carbon atoms, and more preferably an alkylsulfonyl group having 1 to 24 carbon atoms, for example, a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group, and a cyclohexylsulfonyl group), an arylsulfonyl group (preferably an arylsulfonyl group having 6 to 48 carbon atoms, and more preferably an arylsulfonyl group having 6 to 24 carbon atoms, for example, a phenylsulfonyl group and a 1-naphthylsulfonyl group), a sulfamoyl group (preferably a sulfamoyl group having 32 or less carbon atoms, and more preferably a sulfamoyl group having 24 or less carbon atoms, for example, a sulfamoyl group, an N,N-dipropylsulfamoyl group, an N-ethyl-N-dodecylsulfamoyl group, an N-ethyl-N-phenylsulfamoyl group, an N-cyclohexylsulfamoyl group, and an N-(2-ethylhexyl)sulfamoyl group), a phosphonyl group (preferably a phosphonyl group having 1 to 32 carbon atoms, and more preferably a phosphonyl group having 1 to 24 carbon atoms, for example, a phenoxyphosphonyl group, an octyloxyphosphonyl group, and a phenylphosphonyl group), a phosphinoylamino group (preferably a phosphinoylamino group having 1 to 32 carbon atoms, and more preferably a phosphinoylamino group having 1 to 24 carbon atoms, for example, a diethoxyphosphinoylamino group and a dioctyloxyphosphinoylamino group), an epoxy group, a (meth)acryloyl group, an ester group, —NHCOCH$_3$, —SO$_2$NHC$_2$H$_4$OCH$_3$, or —NHSO$_2$CH$_3$.

The colorant represented by Formula (1) is preferably represented by Formula (1A).

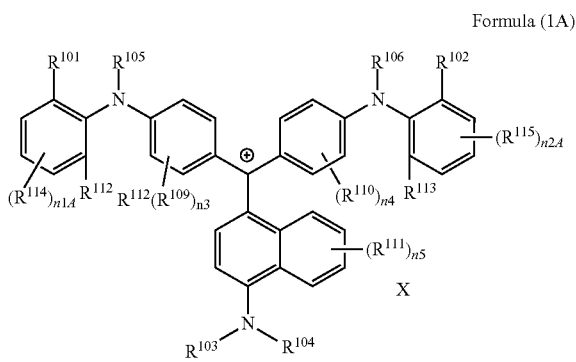

Formula (1A)

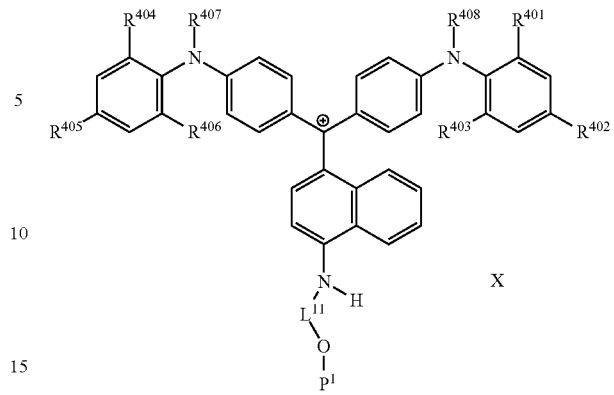

(in Formula (1A), $R^{101}$, $R^{102}$, $R^{112}$, and $R^{113}$ each independently represent a substituent, $R^{103}$ to $R^{106}$ each independently represent a hydrogen atom, an alkyl group, an aryl group, or a heteroaryl group, $R^{109}$ to $R^{111}$, $R^{114}$, and $R^{115}$ each independently represent a hydrogen atom or a substituent, n1A and n2A each independently represent an integer of 0 to 3, n3 and n4 each independently represent an integer of 1 to 4, n5 represents an integer of 0 to 6, X represents an anion or is not present, and at least one of $R^{101}$, ..., or $R^{115}$ includes an anion).

In Formula (1A), $R^{101}$, $R^{102}$, $R^{112}$, and $R^{113}$ have the same definitions as in the case where $R^{101}$ and $R^{102}$ in Formula (1) represent substituents, and preferred ranges thereof are also the same. Above all, it is preferable that $R^{101}$, $R^{102}$, $R^{112}$ and $R^{113}$ each independently represent an alkyl group.

$R^{103}$ to $R^{106}$ have the same definitions as $R^{103}$ to $R^{106}$ in Formula (1A), and preferred ranges thereof are also the same. It is preferable that $R^{105}$ and $R^{106}$ are hydrogen atoms.

$R^{109}$ and $R^{110}$ have the same definitions as $R^{109}$ and $R^{110}$ in Formula (1), and preferred ranges thereof are also the same.

$R^{111}$ has the same definition as $R^{111}$ in Formula (1), and preferred ranges thereof are also the same.

$R^{114}$ and $R^{115}$ each independently represent a hydrogen atom or a substituent. $R^{114}$ and $R^{115}$ have the same definitions as $R^{107}$ and $R^{108}$ in Formula (1), and preferred ranges thereof are also the same.

n1A and n2A each independently represent an integer of 1 to 3, and is preferably 1 or 2.

n3 and n4 each independently represent an integer of 1 to 4, and is preferably 1 or 2.

n5 represents an integer of 0 to 6, and is preferably an integer of 1 to 6, more preferably an integer of 1 to 4, and still more preferably 1 or 2.

X represents an anion or is not present, and at least one of $R^{101}$, ..., or $R^{115}$ includes an anion. In the case where X is not present and at least one of $R^{101}$, ..., or $R^{115}$ includes an anion, it is preferable that $R^{111}$ includes an anion. In the case where X represents an anion, it is preferable that X is a bistrifluoromethanesulfonylimide anion, a tristrifluoromethanesulfonylmethide anion, or a perfluoromethanesulfonic acid anion.

It is also preferable that the colorant represented by Formula (1) is represented by Formula (1C).

(in Formula (1C), $R^{401}$ to $R^{408}$ each independently represent a hydrogen atom or an alkyl group, $L^{11}$ represents a divalent linking group having 2 to 30 carbon atoms, $P^1$ represents a polymerizable group, and X represents an anion).

It is also preferable that the colorant represented by Formula (1) is represented by Formula (1B).

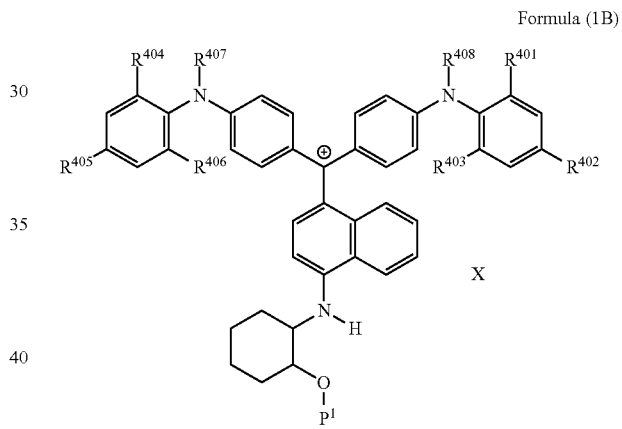

Formula (1B)

(in Formula (1B), $R^{401}$ to $R^{408}$ each independently represent a hydrogen atom or an alkyl group, $P^1$ represents a polymerizable group, and X represents an anion).

In Formulae (1C) and (1B), $R^{401}$ is preferably an alkyl group. The alkyl group may be in any one of linear, branched, and cyclic forms, and is preferably in a linear form. The number of carbon atoms of the alkyl group is preferably 1 to 6, more preferably 1 to 3, still more preferably 1 or 2, and particularly preferably 1.

$R^{402}$ to $R^{406}$ have the same definitions as $R^{401}$, and preferred ranges thereof are also the same.

$R^{407}$ is preferably an alkyl group. The alkyl group may be in any one of linear, branched, and cyclic forms, and is preferably in a linear form. The number of carbon atoms of the alkyl group is 1 to 6, more preferably 1 to 3, and still more preferably 1 or 2.

$R^{408}$ has the same definition as $R^{407}$, and preferred ranges thereof are also the same.

In Formula (1C), $L^{11}$ is preferably a divalent linking group having 2 to 30 carbon atoms, an alkylene group having 2 to 30 carbon atoms, cycloalkylene group, a phenylene group, or a group formed by combination of these groups. Further, in Formula (1C), $P^1$ is preferably a polymerizable group, an acryloyl group, a methacryloyl group, or a —CH$_2$C$_6$H$_4$CH=CH$_2$ group.

In Formula (1B), P$^1$ represents a polymerizable group. As the polymerizable group, known polymerizable groups which can be crosslinked by a radical, an acid, or heat can be used, and examples thereof include a group including an ethylenically unsaturated bond, a cyclic ether group (an epoxy group and an oxetane group), and a methylol group. Particularly, a group including an ethylenically unsaturated bond is preferable, a (meth)acryloyl group or a styrene group is more preferable, and a (meth)acryloyl group is still more preferable.

In Formulae (1C) and (1B), X represents an anion, in which the anion will be described later, and X is preferably a bistrifluoromethanesulfonylimide anion, a tristrifluoromethanesulfonylmethide anion, or a perfluoromethanesulfonic acid anion.

<Colorant Represented by Formula (2)>

In Formula (2), $R^{201}$ and $R^{202}$ each independently represent a hydrogen atom or a substituent, at least one of $R^{201}$ or $R^{202}$ represents a substituent. In the case where $R^{201}$ and $R^{202}$ represent a substituent, they have the same definitions as $R^{101}$ and $R^{102}$ in Formula (1), and preferred ranges thereof are also the same. In the case where $R^{201}$ and $R^{202}$ are substituents, examples of the substituent which may further be included in the group include the substituents as defined in the substituent A group as described above. Preferred examples of the substituent include an ester group, a carbamoyl group, a sulfamoyl group, a cyano group, an alkoxy group, and a halogen atom.

$R^{203}$ and $R^{204}$ each independently represent a hydrogen atom or a substituent. Examples of the substituent include the substituents as defined in the substituent A group which will be described later. In particular, as the substituent, an alkyl group or a halogen atom is preferable. In the case where the substituent is an alkyl group, it has the same definition as in the case where $R^{105}$ and $R^{106}$ in Formula (1) represent an alkyl group, and preferred ranges thereof are also the same. In the case where the substituent is a halogen atom, it has the same definition as halogen atom as defined in the substituent A group which will be described later, and preferred ranges thereof are also the same.

$R^{205}$ and $R^{206}$ each independently represent a hydrogen atom or a substituent. Examples of the substituent include the substituents as defined in the substituent A group which will be described later. In particular, as the substituent, an alkyl group, —SO$_2$N(C$_2$H$_4$OCH$_3$)$_2$, or a halogen atom is preferable. In the case where the substituent is an alkyl group, it has the same definition as in the case where $R^{107}$ and $R^{108}$ in Formula (1) represent an alkyl group, and preferred ranges thereof are also the same. In the case where the substituent is a halogen atom, it has the same definition as halogen atom as defined in the substituent A group which will be described later, and preferred ranges thereof are also the same.

In the case where $R^{203}$ to $R^{206}$ are an alkyl group, examples of the substituent which may be contained in the group include the substituents as defined in the substituent A group as described above. Preferred examples of the substituent include an ester group, a carbamoyl group, a sulfamoyl group, a cyano group, an alkoxy group, and a halogen atom.

$R^{207}$ to $R^{209}$ each independently represent a hydrogen atom or a substituent, and are preferably a hydrogen atom. The substituent has the same definitions as $R^{109}$ to $R^{111}$ in Formula (1), and preferred ranges thereof are also the same. In the case where $R^{207}$ to $R^{209}$ are a substituent, they may further have a substituent.

$R^{210}$ and $R^{211}$ each independently represent an alkyl group, an aryl group, or a heteroaryl group, and have the same definitions as the alkyl group, the aryl group, and the heteroaryl group described as $R^{103}$ in Formula (1). In particular, $R^{210}$ is preferably an alkyl group or an aryl group, and more preferably an alkyl group having 1 to 3 carbon atoms (particularly a methyl group) or a phenyl group. Further, $R^{211}$ is preferably an alkyl group or an aryl group, and more preferably an alkyl group having 1 to 3 carbon atoms (particularly a methyl group) or a phenyl group. Examples of the substituent which may be contained in $R^{210}$ and $R^{211}$ include the substituents as defined in the substituent A group as described above. Preferred examples of the substituent include an ester group, a carbamoyl group, a sulfamoyl group, a cyano group, an alkoxy group, a halogen atom, and a (meth)acryloyl group.

n6 to n10 each independently represent an integer of 1 to 4, and is preferably an integer of 1 to 3, and more preferably 1 or 2.

X represents an anion or is not present, and at least one of $R^{201}$, . . . , or $R^{211}$ includes an anion. In the case where X is not present and at least one of $R^{201}$, . . . , or $R^{211}$ includes an anion, it is preferable that $R^{211}$ includes an anion.

It is preferable that the colorant represented by Formula (2) is represented by Formula (2A).

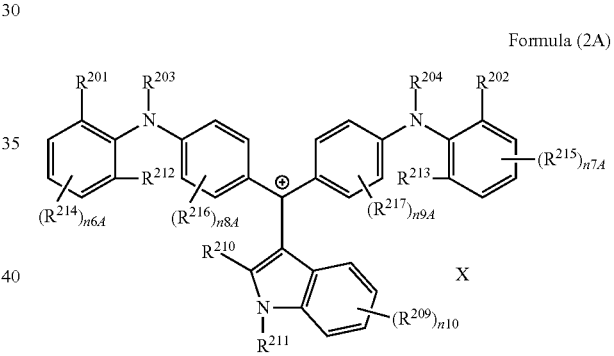

Formula (2A)

(in Formula (2A), $R^{201}$, $R^{202}$, $R^{212}$, and $R^{213}$ each independently represent a substituent, $R^{203}$, $R^{204}$, $R^{209}$, $R^{214}$ to $R^{217}$ each independently represent a hydrogen atom or a substituent, $R^{210}$ and $R^{211}$ each independently represent an alkyl group, an aryl group, or a heteroaryl group, n6A and n7A each independently represent an integer of 1 to 3, n8A to n10 each independently represent an integer of 1 to 4, X represents an anion or is not present, and at least one of $R^{201}$, . . . , or $R^{216}$ includes an anion).

In Formula (2A), $R^{201}$, $R^{202}$, $R^{212}$, and $R^{213}$ have the same definitions as in the case where $R^{201}$ and $R^{202}$ in Formula (2) represent a substituent, and preferred ranges thereof are also the same. Above all, it is preferable that $R^{201}$, $R^{202}$, $R^{212}$, and $R^{213}$ each independently represent an alkyl group.

$R^{203}$, $R^{204}$, and $R^{209}$ to $R^{211}$ have the same definitions as $R^{203}$, $R^{204}$ and $R^{209}$ to $R^{211}$ in Formula (2), and preferred ranges thereof are also the same.

$R^{214}$ and $R^{215}$ have the same definitions as $R^{205}$ in Formula (2), and preferred ranges thereof are also the same.

$R^{216}$ and $R^{217}$ have the same definitions as $R^{207}$ and $R^{208}$ in Formula (2), and preferred ranges thereof are also the same.

n6A and n7A each independently represent an integer of 1 to 3, and is preferably 1 or 2.

n8A to n10 each independently represent an integer of 1 to 4, and is preferably 1 or 2.

X represents an anion or is not present, and at least one of $R^{201}, \ldots,$ or $R^{216}$ includes an anion. In the case where X is not present and at least one of $R^{201}, \ldots,$ or $R^{216}$ includes an anion, it is preferable that $R^{211}$ includes an anion. In the case where X represents an anion, it is preferable that X is a bistrifluoromethanesulfonylimide anion, a tristrifluoromethanesulfonylmethide anion, or a perfluoromethanesulfonic acid anion.

<Colorant Represented by Formula (3)>

In Formula (3), $R^{301}$ and $R^{302}$ are each independently preferably a substituent, alkyl group, an aryl group, or a heteroaryl group, and more preferably an alkyl group.

The alkyl group may be in any one of linear, branched, and cyclic forms, but is preferably in a linear or branched form, and more preferably in a linear form. The number of carbon atoms of the alkyl group is preferably 1 to 12, more preferably 1 to 8, still more preferably 1 to 6, and particularly preferably 1 or 2.

The aryl group and the heteroaryl group have the same definitions as $R^{101}$ in Formula (1), and preferred ranges thereof are also the same. In the case where $R^{301}$ and $R^{302}$ have a substituent, examples of the substituent include the substituents as defined in the substituent A group as described above. Preferred examples of the substituent include an ester group, a carbamoyl group, a sulfamoyl group, a cyano group, an alkoxy group, and a halogen atom.

$R^{303}$ and $R^{304}$ each independently represent a hydrogen atom, an alkyl group, an aryl group, or a heteroaryl group, and is preferably an alkyl group. The alkyl group has the same definition as the alkyl group described as $R^{301}$ and $R^{302}$, and preferred ranges thereof are also the same.

$R^{305}$ represents a hydrogen atom, an alkyl group, an aryl group, or a heteroaryl group, and is preferably a hydrogen atom. The alkyl group, the aryl group, and the heteroaryl group have the same definitions as the alkyl group, the aryl group, and the heteroaryl group described as $R^{301}$ and $R^{302}$, and preferred ranges thereof are also the same.

$R^{306}$ represents a substituent, has the same definition as $R^{101}$ in Formula (1), and is preferably an ester group.

$R^{307}$ to $R^{310}$ each independently represent a hydrogen atom, an alkyl group, or a halogen atom, and are preferably a hydrogen atom. The alkyl group or the halogen atom has the same definition as the alkyl group or the halogen atom described as $R^{107}$ and $R^{108}$ in Formula (1), and preferred ranges thereof are also the same. Further, it is more preferable that $R^{307}$ is substituted at at least the 6-position.

n11 to n13 each independently represent an integer of 1 to 4, and is preferably 1 or 2.

n14 represents an integer of 1 to 6, preferably integer of 1 to 4, and more preferably 1 or 2.

X represents an anion or is not present, and at least one of $R^{301}, \ldots,$ or $R^{310}$ includes an anion. In the case where X is not present and at least one of $R^{301}, \ldots,$ or $R^{310}$ includes an anion, it is preferable that $R^{307}$ includes an anion.

It is preferable that the colorant represented by Formula (3) is represented by Formula (3A).

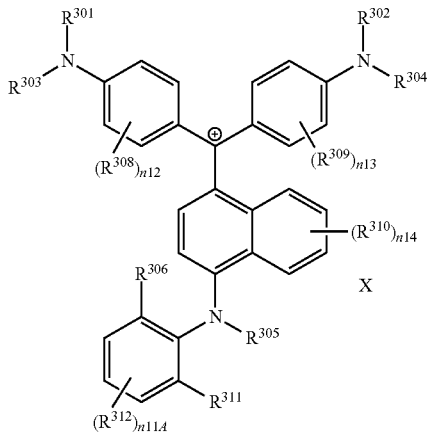

Formula (3A)

(in Formula (3A), $R^{301}$ and $R^{302}$ each independently represent a substituent, $R^{303}$ to $R^{305}$ each independently represent a hydrogen atom or a substituent, $R^{306}$ and $R^{311}$ each independently represent a substituent, $R^{308}$ to $R^{310}$, and $R^{312}$ each independently represent a hydrogen atom, an alkyl group, or a halogen atom, n11A represents an integer of 1 to 3, n12 and n13 each independently represent an integer of 1 to 4, n14 represents an integer of 1 to 6, X represents an anion or is not present, and at least one of $R^{301}, \ldots,$ or $R^{312}$ includes an anion).

In Formula (3A), $R^{301}$ to $R^{306}$ and $R^{308}$ to $R^{310}$ have the same definitions as $R^{301}$ to $R^{306}$ and $R^{308}$ to $R^{310}$ in Formula (3), and preferred ranges thereof are also the same. Above all, it is preferable that $R^{306}$ and $R^{311}$ each independently represent an alkyl group.

$R^{311}$ represents a substituent and has the same definition as $R^{101}$ in Formula (1), and preferred ranges thereof are also the same.

$R^{312}$ each independently represent a hydrogen atom, an alkyl group, or a halogen atom, and is preferably a hydrogen atom.

n11A represents an integer of 1 to 3, and is preferably 1 or 2.

n12 and n13 each independently represent an integer of 1 to 4, and is preferably 1 or 2.

n14 represents an integer of 1 to 6, and is preferably an integer of 1 to 4, and more preferably 1 or 2.

X represents an anion or is not present, and at least one of $R^{301}, \ldots,$ or $R^{312}$ includes an anion. In the case where X is not present and at least one of $R^{301}, \ldots,$ or $R^{312}$ includes an anion, it is preferable that $R^{312}$ includes an anion. In the case where X represents an anion, it is preferable that X is a bistrifluoromethanesulfonylimide anion, a tristrifluoromethanesulfonylmethide anion, or a perfluoromethanesulfonic acid anion.

The colorants represented by Formula (1) to Formula (3) may include a polymerizable group and/or a multimer structure. The polymerizable group and the multimer structure may have a triarylmethane structure, and may have an anion X. As the polymerizable group, known polymerizable groups which can be crosslinked by a radical, an acid, or heat can be used, and examples thereof include a group having an ethylenically unsaturated bond, a cyclic ether group (an epoxy group and an oxetane group), and a methylol group. Particularly, a group having an ethylenically unsaturated bond is preferable, a (meth)acryloyl group is more preferable, and (meth)acryloyl groups derived from glycidyl (meth)acrylate and 3,4-epoxycyclohexyl methyl (meth)acrylate are still more preferable.

The multimer structure represents the skeleton structure of the repeating unit which will be described later.

In the colorants represented by Formula (1) to Formula (3), cations are present in the delocalized state as shown below. For example, in the colorant represented by Formula (1), the following structures have the same definitions, all of which are intended to be included in the present invention. Further, the cation site may be at any position in the molecule.

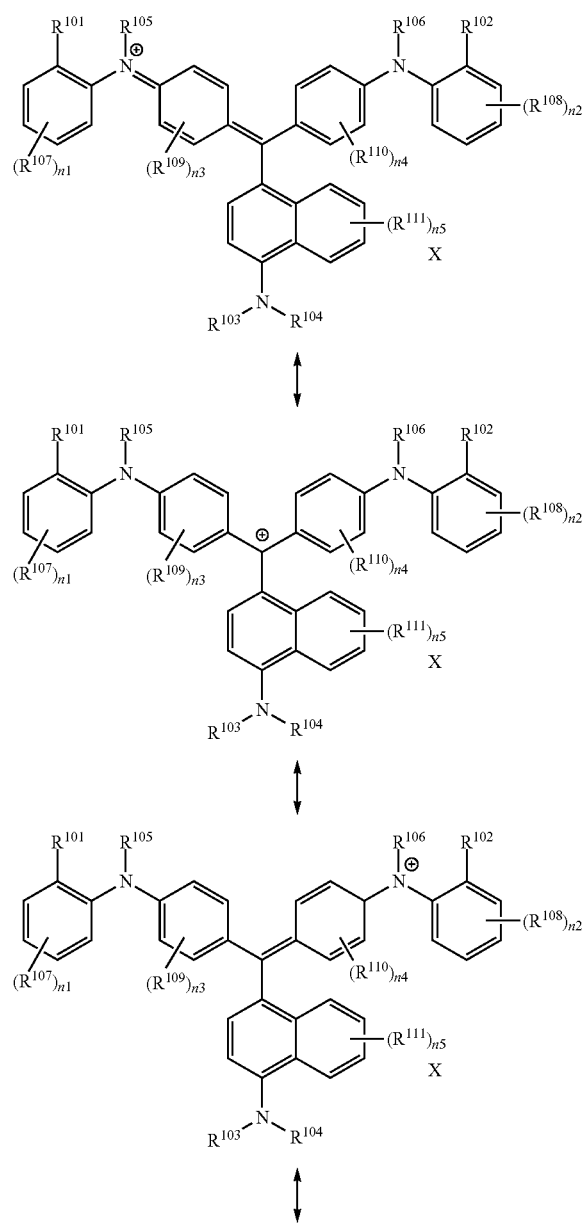

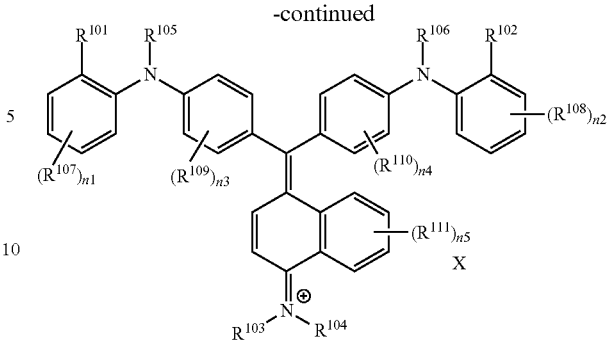

«<Anion X>»

The colorant represented by Formula (1) has an anion X inside the molecule and/or outside the molecule. Further, in the following description, the colorant represented by Formula (1) can be used as an examples for description, which will also be applied to the colorant represented by Formula (2) and the colorant represented by Formula (3).

The anion X is included according to the valency of the cation included in the colorant represented by Formula (1). The cation is usually preferably monovalent or divalent, and preferably monovalent. Inclusion of the anion X inside the molecule refers to presence of an anion site and a cation site inside the colorant represented by Formula (1) via one or more covalent bonds. Inclusion of the anion X outside the molecule refers to the other cases.

In addition, the anion X in the present invention is not particularly limited, but is preferably an anion with low nucleophilicity. The anion with low nucleophilicity represents an anion structure in which organic acids having a lower pKa than the pKa of sulfuric acid are dissociated.

Case where Anion X is Inside Molecule

A first embodiment of the anion X is a case where the anion X is inside the same molecule as that of the colorant represented by Formula (1), specifically the case where a cation and an anion are bonded to each other via a covalent bond inside the repeating unit having a colorant structure.

The anion portion in this case is preferably at least one selected from $—SO_3^-$, $—COO^-$, $—PO_3^-$, a structure represented by the following General Formula (A1), or a structure represented by the following General Formula (A2).

General Formula (A1)

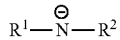

(in General Formula (A1), $R^1$ and $R^2$ each independently represent $—SO_2—$ or $—CO—$)

In General Formula (A1), it is preferable that at least one of $R^1$ or $R^2$ represents $—SO_2—$, and it is more preferable that both of $R^1$ and $R^2$ represent $—SO_2—$.

General Formula (A1) is more preferably represented by the following General Formula (A1-1).

General Formula (A1-1)

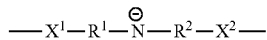

(in General Formula (A1-1), $R^1$ and $R^2$ each independently represent $—SO_2—$ or $—CO—$, and $X^1$ and $X^2$ each independently represent an alkylene group or an arylene group)

In General Formula (A1-1), $R^1$ and $R^2$ have the same definitions as $R^1$ and $R^2$ in General Formula (A1), and preferred ranges thereof are also the same.

In the case where $X^1$ represents an alkylene group, the number of carbon atoms of the alkylene group is preferably 1 to 8, and more preferably 1 to 6. In the case where $X^1$ represents an arylene group, the number of carbon atoms of the arylene group is preferably 6 to 18, more preferably 6 to 12, and still more preferably 6. In the case where $X^1$ has a substituent, it is preferably substituted with a fluorine atom.

$X^2$ represents an alkyl group or an aryl group, and is preferably an alkyl group. The number of carbon atoms of the alkyl group is preferably 1 to 8, more preferably 1 to 6, still more preferably 1 to 3, and particularly preferably 1. In the case where $X^2$ has a substituent, it is preferably substituted with a fluorine atom.

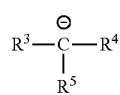

General Formula (A2)

(in General Formula (A2), $R^3$ represents —SO$_2$— or —CO—, and $R^4$ and $R^5$ each independently represent —SO$_2$—, —CO—, or —CN)

In General Formula (A2), it is preferable that at least one of $R^3$, . . . , or $R^5$ represents —SO$_2$—, and it is more preferable that at least two of $R^3$, . . . , or $R^5$ represent —SO$_2$—.

Case where Anion X is Separate Molecule

A second embodiment of the anion X is a case where the anion X is outside the same repeating unit and the cation and the anion are not bonded to each other via a covalent bond but present as separate molecules.

Examples of the anion X in this case include a fluorine anion, a chlorine anion, a bromine anion, an iodine anion, a cyanide ion, and a perchloric acid anion, as well as anions with low nucleophilicity, with the anions with low nucleophilicity being preferable.

The anion with low nucleophilicity may be an organic anion or an inorganic anion, but is preferably an organic anion. Examples of the anion used in the present invention include known anion with low nucleophilicity described in paragraph No. 0075 of JP2007-310315A, the disclosure of which is incorporated herein by reference.

Preferably, examples of the anion include a bis(sulfonyl) imide anion, a tris(sulfonyl)methide anion, a tetraarylborate anion, B$^-$(CN)$_{n1}$(OR)$_{4-n1}$ (in which R$^a$ represents an alkyl group having 1 to 10 carbon atoms or an aryl group having 6 to 10 carbon atoms, and n1 represents 1 to 4), PF$_{n2}$ R$^P_{(6-n2)}$$^-$ (in which R$^P$ represents a fluoroalkyl group having 1 to 10 carbon atoms, and n2 represents an integer of 1 to 6), and the anion is more preferably one selected from a bis(sulfonyl)imide anion, a tris(sulfonyl)methyl anion, a perfluorosulfonate anion, and a tetraaryl borate anion, and still more preferably a bis(sulfonyl)imide anion.

The bis(sulfonyl)imide anion as the anion with low nucleophilicity is preferably a structure represented by the following General Formula (AN-1), and more preferably a bistrifluoromethanesulfonylimide anion.

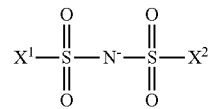

General Formula (AN-1)

(in Formula (AN-1), $X^1$ and $X^2$ each independently represent a fluorine atom or a fluorine atom-containing alkyl group having 1 to 10 carbon atoms. $X^1$ and $X^2$ may be bonded to each other to form a ring)

$X^1$ and $X^2$ each independently represent a fluorine atom or a fluorine atom-containing alkyl group having 1 to 10 carbon atoms, preferably a fluorine atom or a fluorine atom-containing alkyl group having 1 to 10 carbon atoms, more preferably a fluorine atom-containing alkyl group having 1 to 10 carbon atoms, still more preferably a perfluoroalkyl group having 1 to 4 carbon atoms, and particularly preferably a trifluoromethyl group.

The tris(sulfonyl) methide anion as the anion with low nucleophilicity is preferably a structure represented by the following General Formula (AN-2), and more preferably a tristrifluoromethanesulfonylmethide anion.

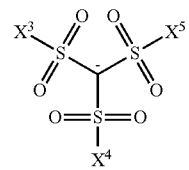

General Formula (AN-2)

(in Formula (AN-2), $X^3$, $X^4$, and $X^5$ each independently represent a fluorine atom or a fluorine atom-containing alkyl group having 1 to 10 carbon atoms)

$X^3$, $X^4$, and $X^5$ each independently have the same definitions as $X^1$ and $X^2$, and preferred ranges thereof are also the same.

The perfluorosulfonic acid anion is preferably a compound represented by the following General Formula (AN3), and more preferably a perfluoromethanesulfonic acid anion.

General Formula (AN3)

(In Formula (AN3), R represents a perfluoroalkyl group or perfluoroaryl group. In the case where R represents a perfluoroalkyl group, the number of carbon atoms thereof is preferably 1 to 6, and more preferably 1 to 3. In the case where R represents a perfluoroaryl group, the number of carbon atoms thereof is preferably 6 to 18, and more preferably 6 to 12).

As the tetraarylborate anion which is an anion with low nucleophilicity, a compound represented by the following General Formula (AN-5) is preferable.

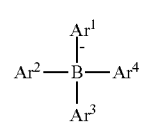

General Formula (AN-5)

(in Formula (AN-5), Ar$^1$, Ar$^2$, Ar$^3$, and Ar$^4$ each independently represent an aryl group)

Ar¹, Ar², Ar³, and Ar⁴ are each independently preferably an aryl group having 6 to 20 carbon atoms, more preferably an aryl group having 6 to 14 carbon atoms, and still more preferably an aryl group having 6 to 10 carbon atoms.

The aryl group represented by $Ar^1$, $Ar^2$, $Ar^3$, and $Ar^4$ may have a substituent. In the case where it has a substituent, examples of the substituent include a halogen atom, an alkyl group, an aryl group, an alkoxy group, a carbonyl group, a carbonyloxy group, a carbamoyl group, a sulfo group, a sulfonamide group, and a nitro group, preferably a halogen atom and an alkyl group, more preferably a fluorine atom and an alkyl group, and still more preferably a fluorine atom and a perfluoroalkyl group having 1 to 4 carbon atoms.

$Ar^1$, $Ar^2$, $Ar^3$, and $Ar^4$ are each independently more preferably a phenyl group having a halogen atom and/or an alkyl group having a halogen atom, and still more preferably a phenyl group having a fluorine atom and/or an alkyl group having fluorine atom.

The anion with low nucleophilicity is preferably —B$(CN)_{n1}(OR^a)_{4-n1}$ (in which $R^a$ represents an alkyl group having 1 to 10 carbon atoms or an aryl group having 6 to 10 carbon atoms, and n1 represents an integer of 1 to 4). $R^a$ as the alkyl group having 1 to 10 carbon atoms is preferably an alkyl group having 1 to 6 carbon atoms, more preferably an alkyl group having 1 to 4 carbon atoms. $R^a$ as the aryl group having 6 to 10 carbon atoms is preferably a phenyl group or a naphthyl group.

n1 is preferably 1 to 3, and more preferably 1 to 2.

The anion with low nucleophilicity is preferably —PF$_6$ $R^P_{(6-n2)}$ (in which $R^P$ represents a fluorinated alkyl group having 1 to 10 carbon atoms, and n2 represents an integer of 1 to 6). $R^P$ is preferably a fluorine atom-containing alkyl group having 1 to 6 carbon atoms, more preferably a fluorine-containing alkyl group having 1 to 4 carbon atoms, and still more preferably a perfluoroalkyl group having 1 to 3 carbon atoms.

n2 is preferably an integer of 1 to 4, and more preferably 1 or 2.

The anion with low nucleophilicity used in the present invention preferably has a mass of 100 to 1,000 per molecule, and more preferably has a mass of 200 to 500 per molecule.

The colorant of the present invention may include one kind or two or more kinds of anion with low nucleophilicity.

Specific examples of the anion with low nucleophilicity are shown below, but the present invention is not limited thereto.

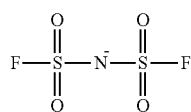
(IM-1)

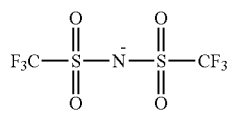
(IM-2)

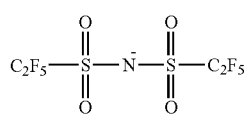
(IM-3)

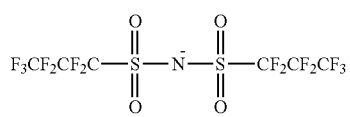
(IM-4)

-continued

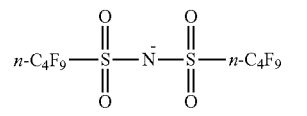
(IM-5)

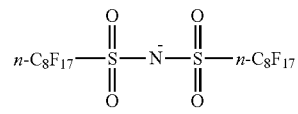
(IM-6)

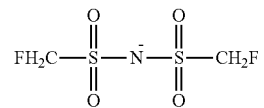
(IM-7)

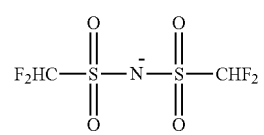
(IM-8)

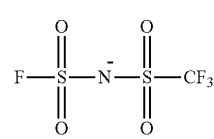
(IM-9)

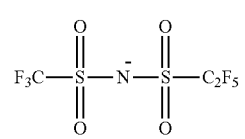
(IM-10)

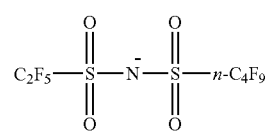
(IM-11)

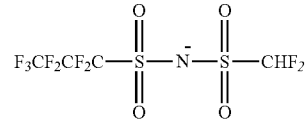
(IM-12)

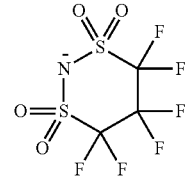
(IM-13)

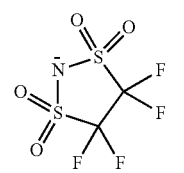
(IM-14)

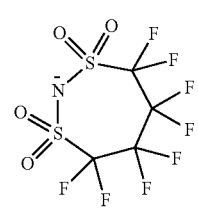
(IM-15)

-continued
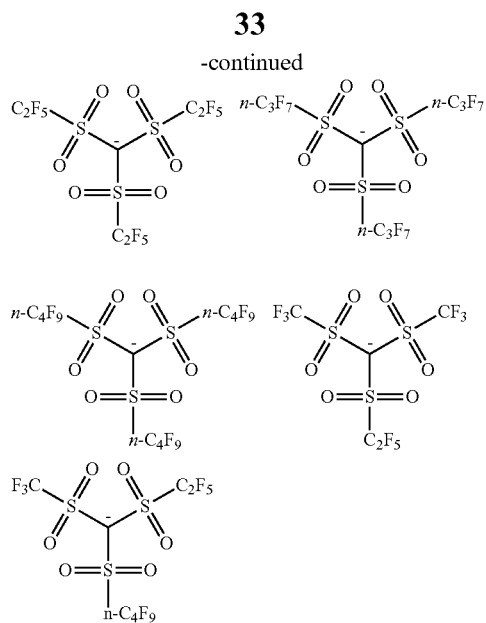
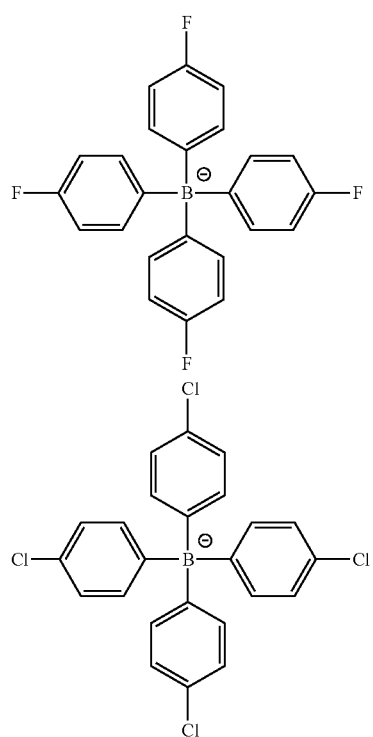
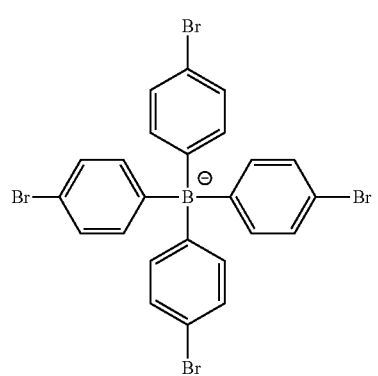
-continued
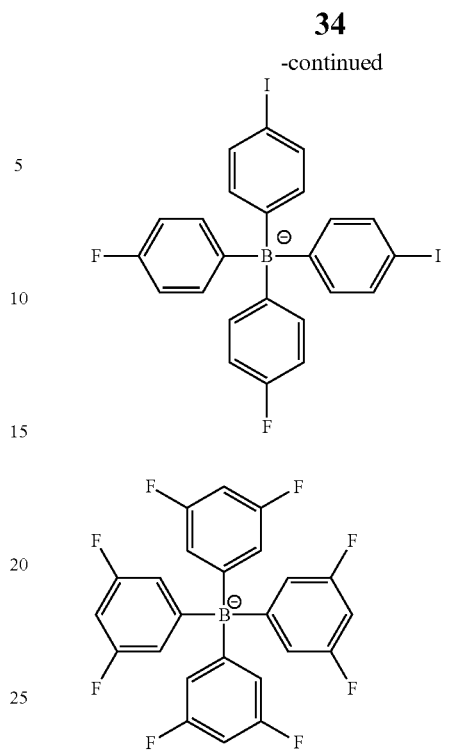
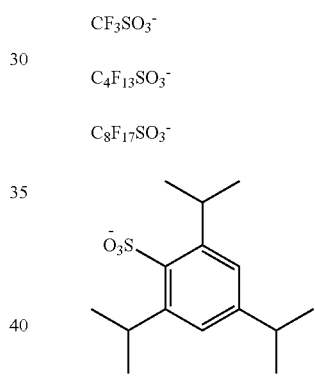
| | |
|---|---|
| $CF_3SO_3^-$ | (a-1) |
| $C_4F_{13}SO_3^-$ | (a-2) |
| $C_8F_{17}SO_3^-$ | (a-3) |
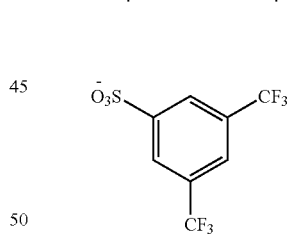 (a-4)
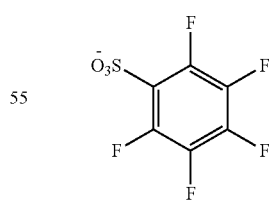 (a-5)
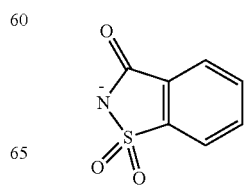 (a-6)
(a-7)

-continued
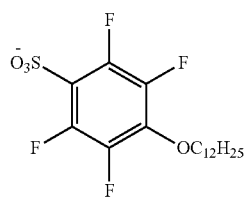 (a-8)
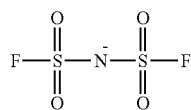 (a-9)
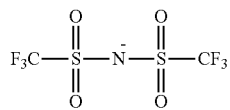 (a-10)
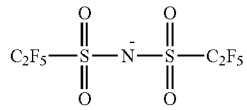 (a-11)
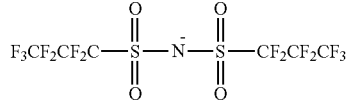 (a-12)
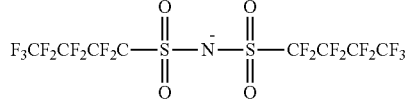 (a-13)
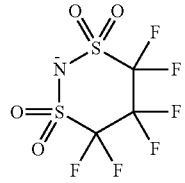 (a-14)
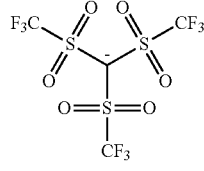 (a-15)
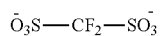 (a-16)
 (a-17)
 (a-18)
 (a-19)
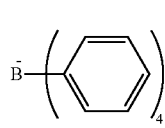 (a-20)
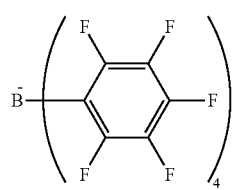 (a-21)
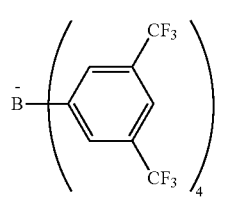 (a-22)
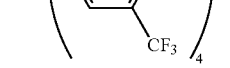 (a-23)
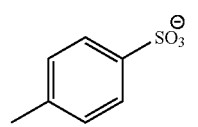 (a-24)
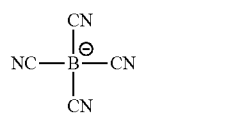 (a-25)
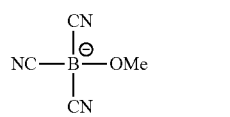 (a-27)
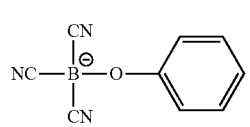 (a-28)
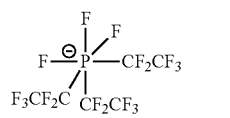
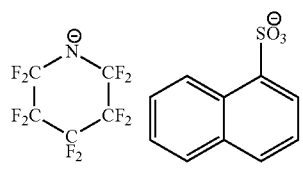
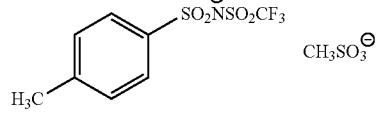
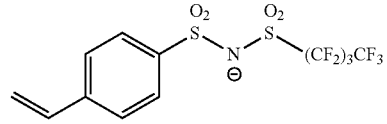
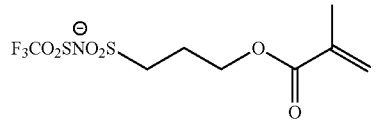

-continued

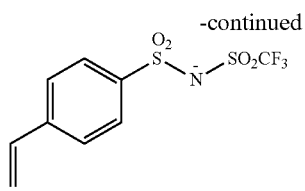

Moreover, in the second embodiment, the anion X may be a multimer. Examples of the multimer in this case include a multimer including a repeating unit including an anion and a multimer not including a repeating unit derived from a colorant structure including a cation. Here, preferred examples of the repeating unit including an anion include repeating units including anions which will be described later in a third embodiment. Further, the multimer including an anion may have a repeating unit other than the repeating unit including an anion. Preferred examples of such a repeating unit include those which will be described later as other repeating units that may be included in the colorant multimer.

Examples of the compound represented by Formula (1), Formula (2), or Formula (3), of a low-molecular type, which can be used in the present invention, are shown below, but are not limited thereto.

TAM001

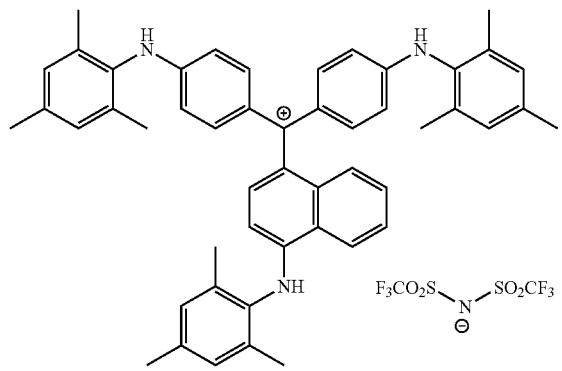

TAM002

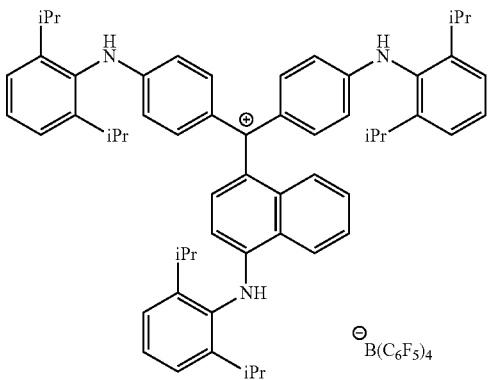

TAM003

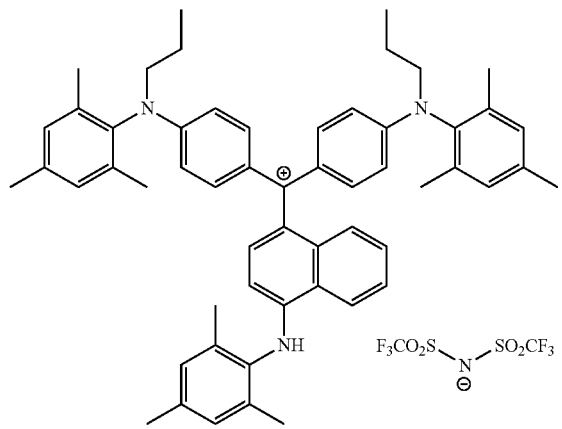

TAM004

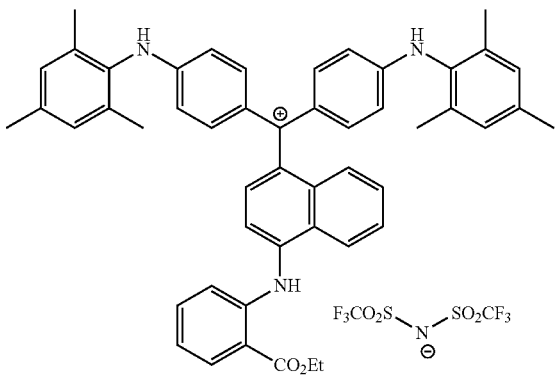

TAM005

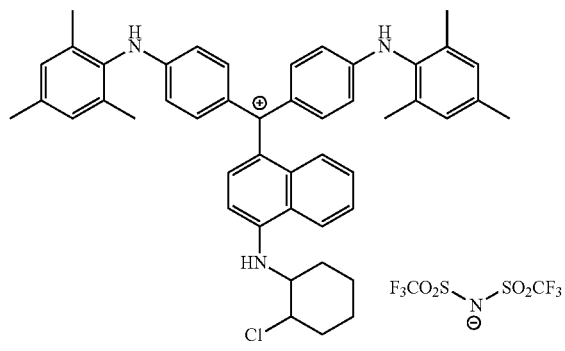

TAM006

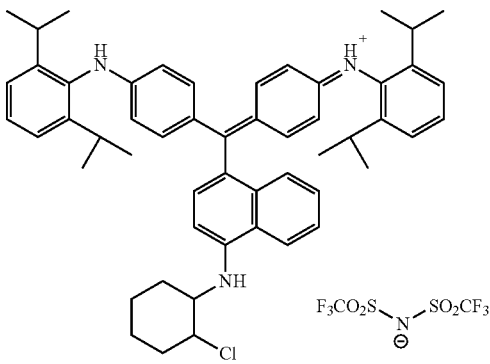

-continued
TAM007
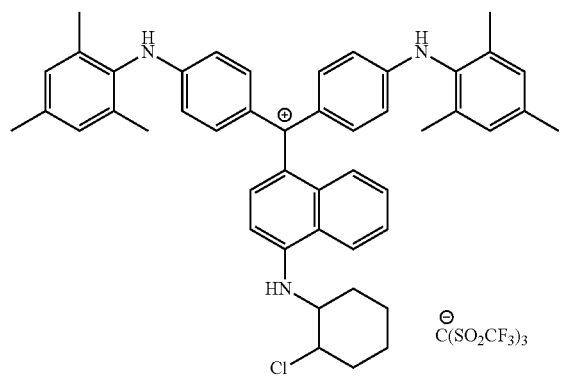
TAM008
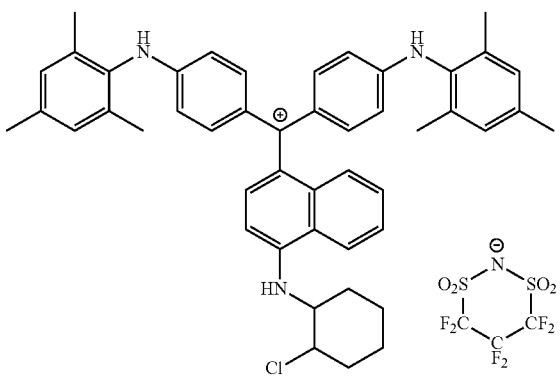
TAM009
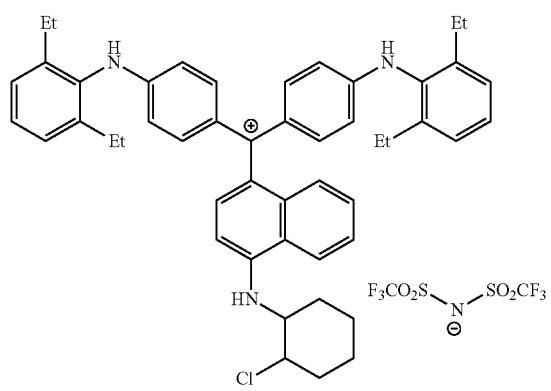
TAM010
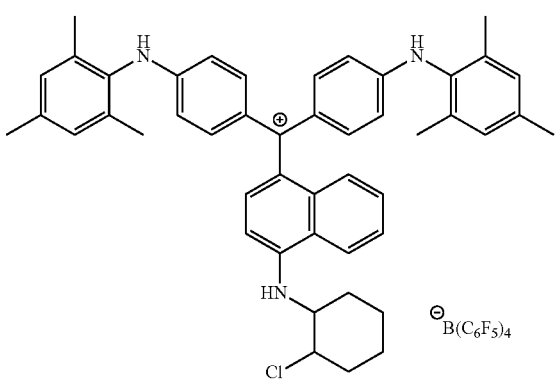
TAM011
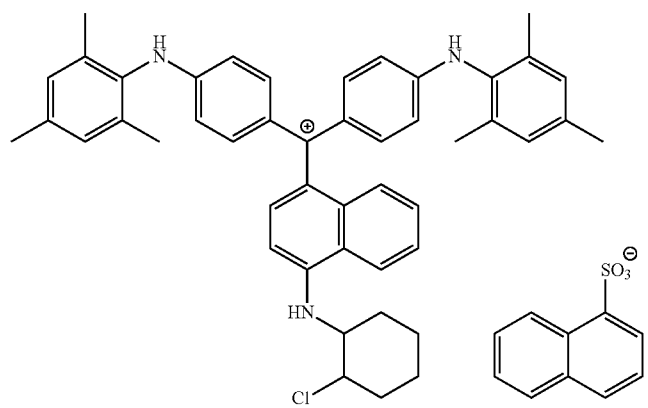
TAM012
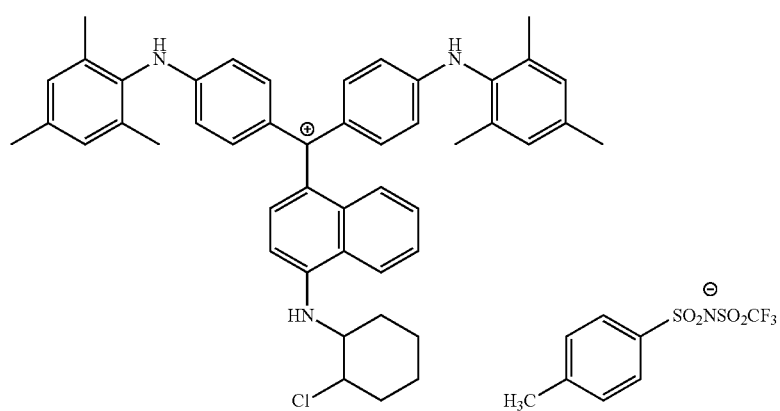

-continued
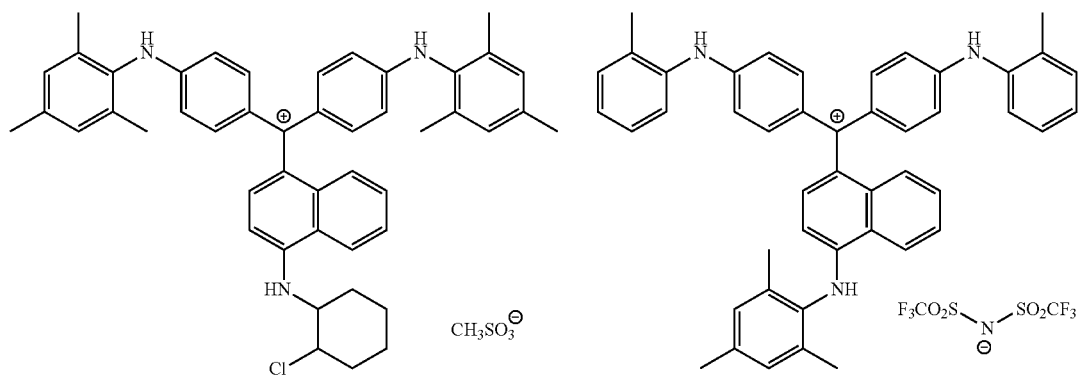
TAM013
TAM014
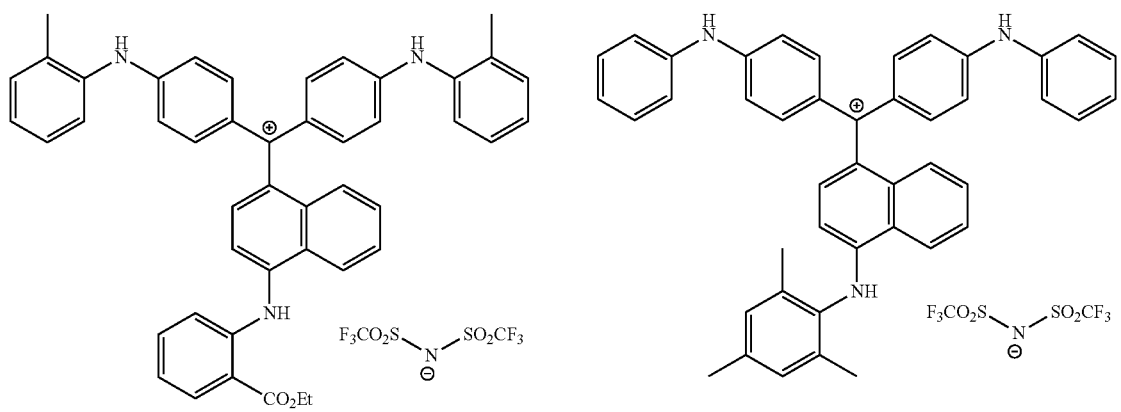
TAM015
TAM016
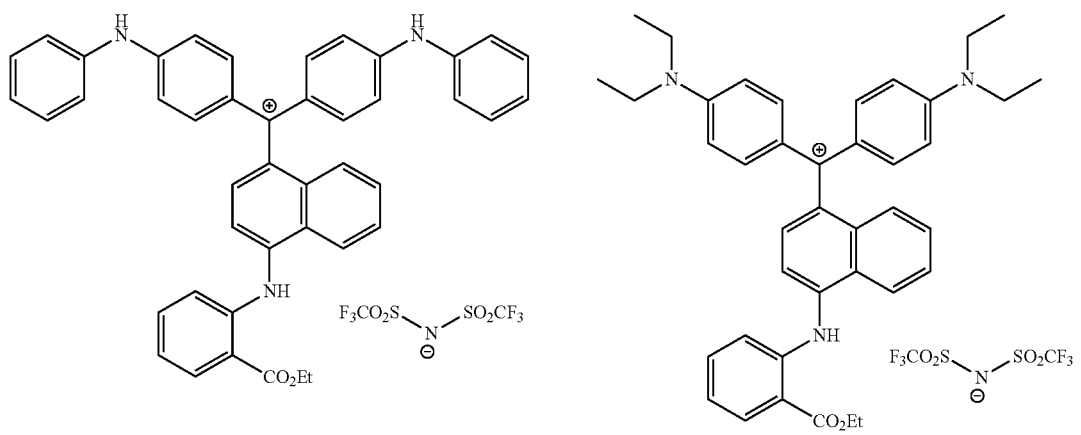
TAM017
TAM018
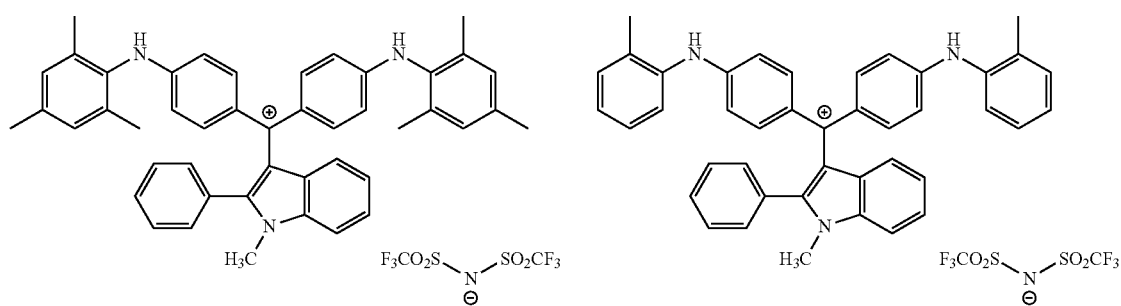
TAM019
TAM020

-continued
TAM101
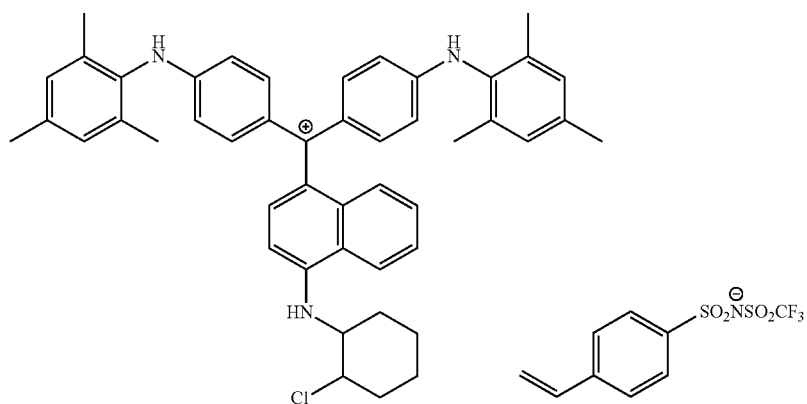
TAM102
TAM103
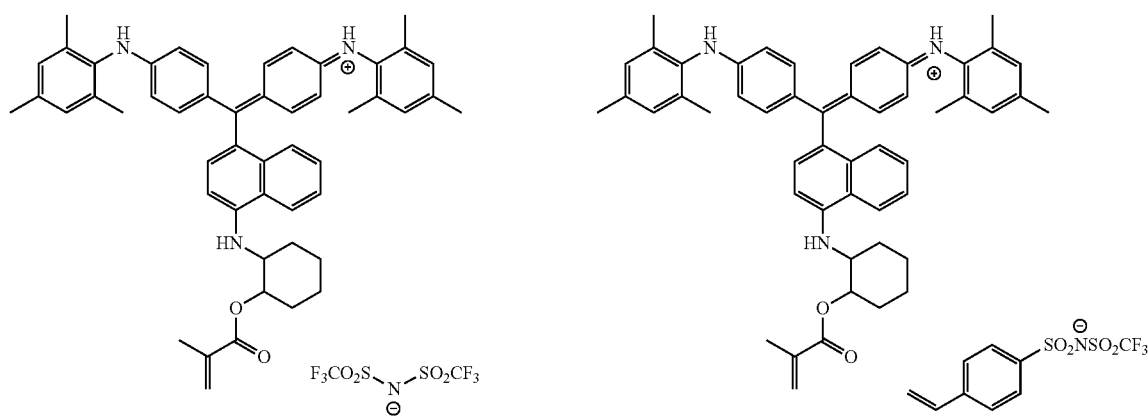
TAM104
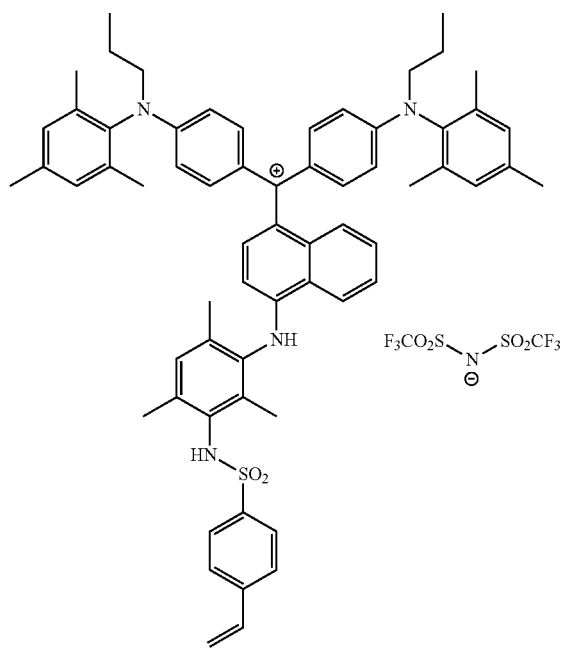

TAM105
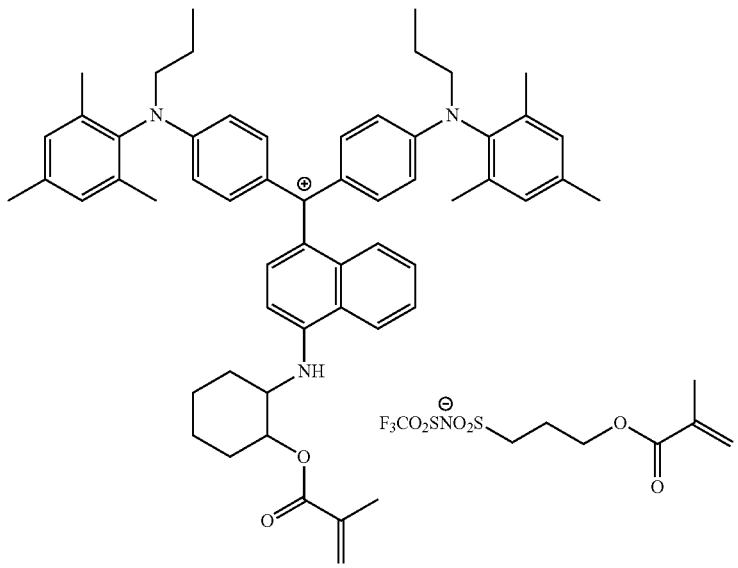
TAM106
TAM107
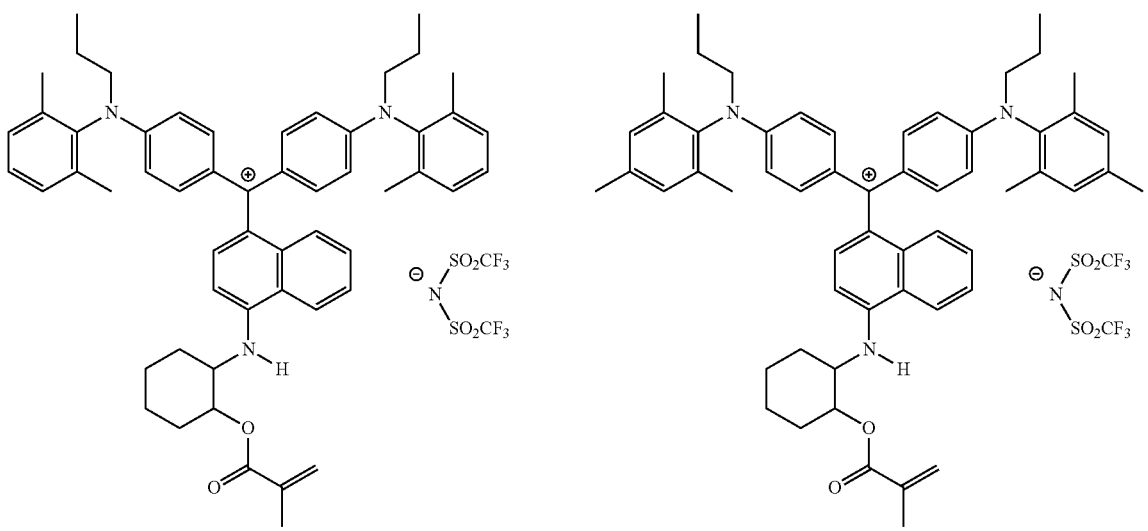
TAM108
TAM109
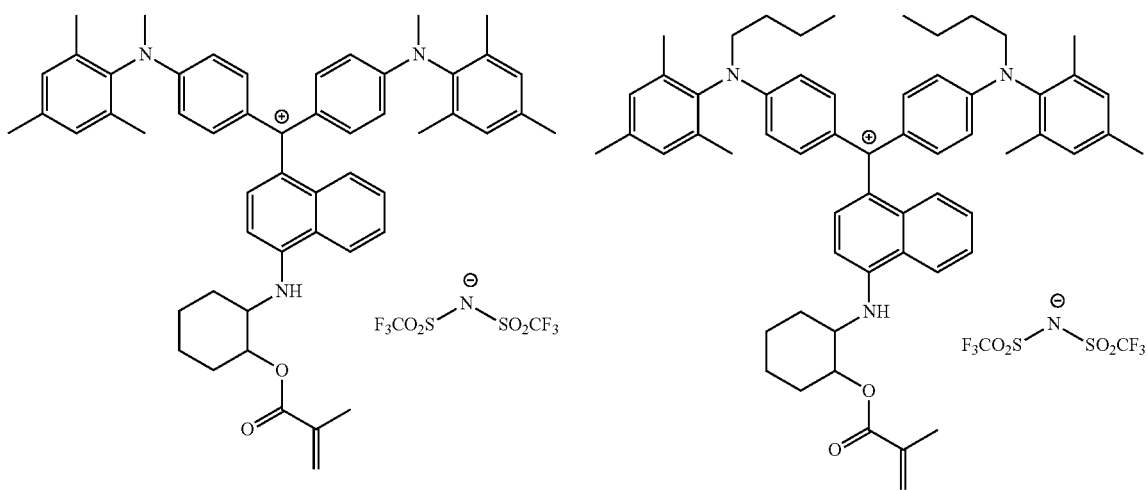

-continued
TAM110
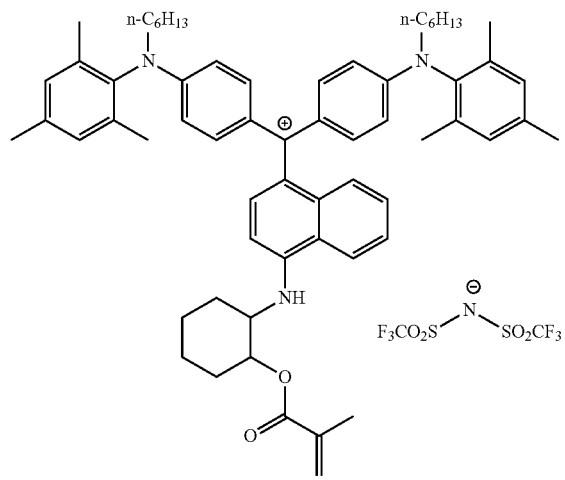
TAM111
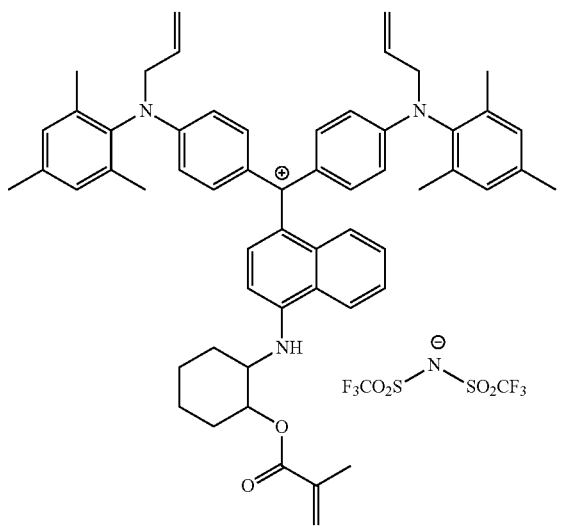
TAM112
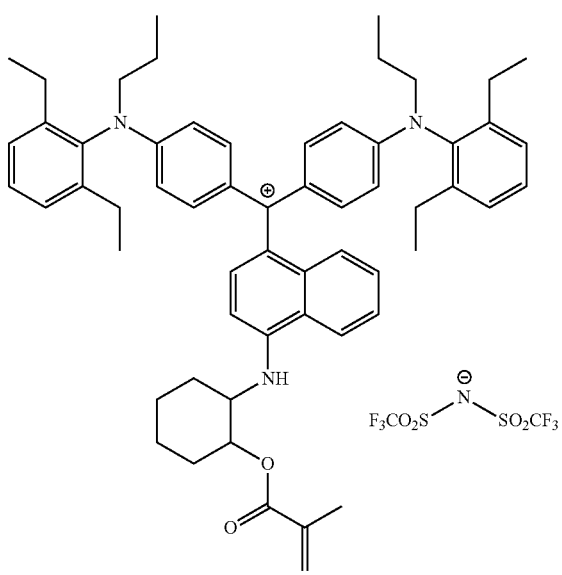
TAM113
TAM114
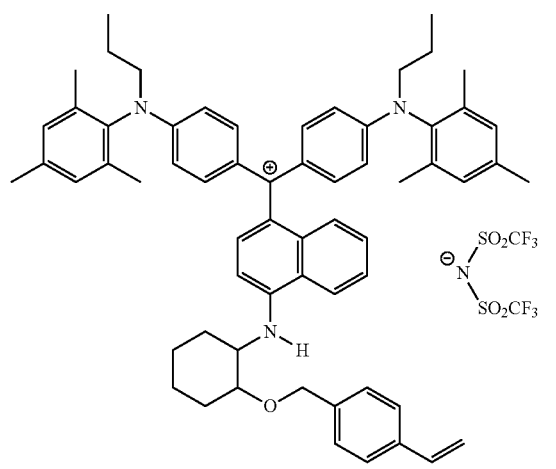
TAM115
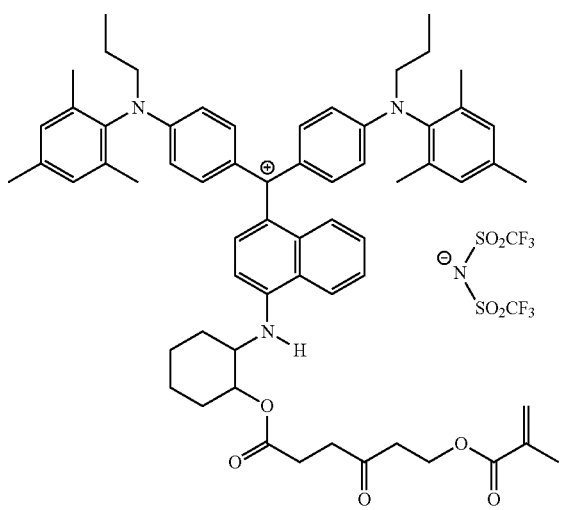

TAM116
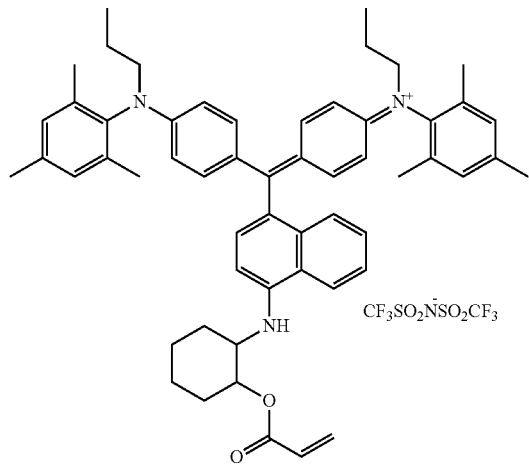
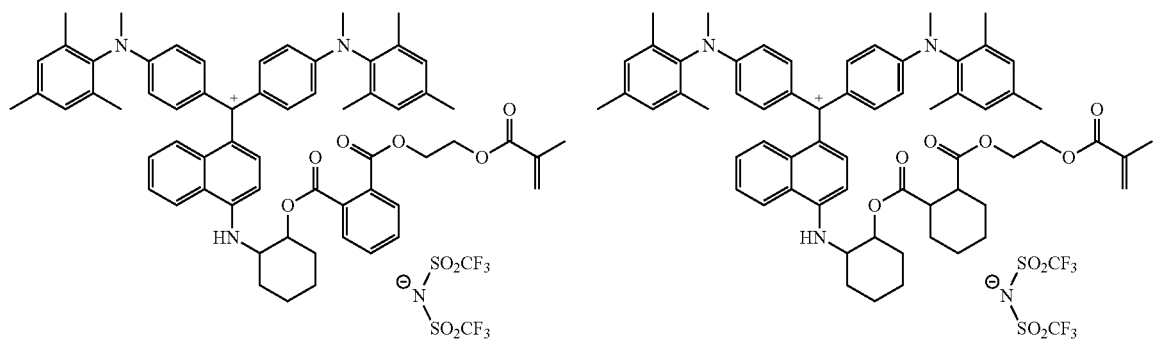
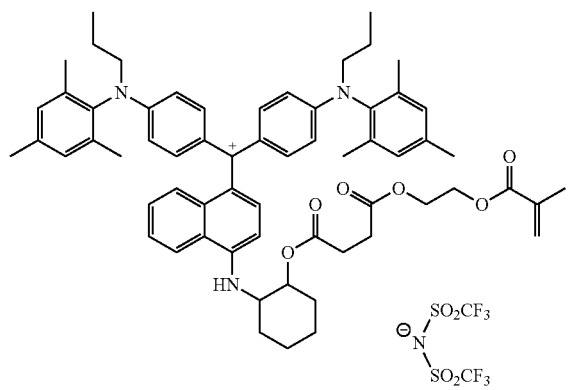
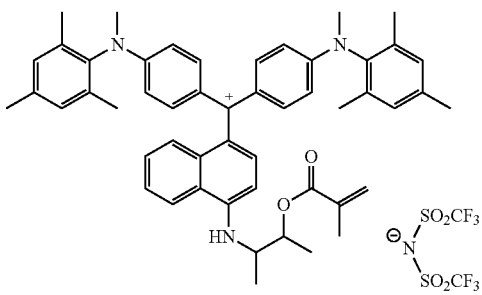
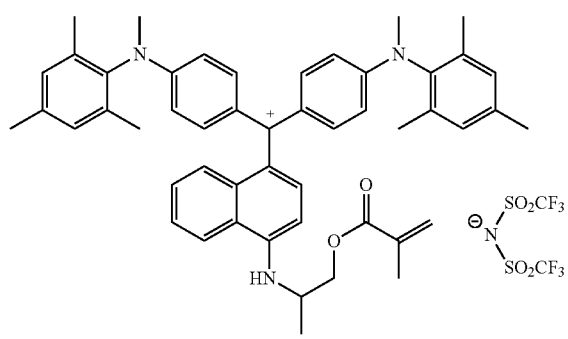
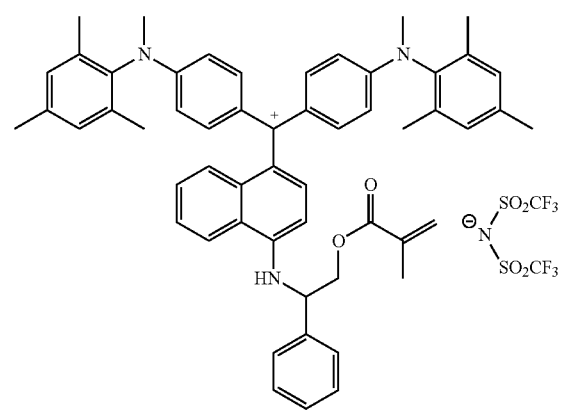

51 52
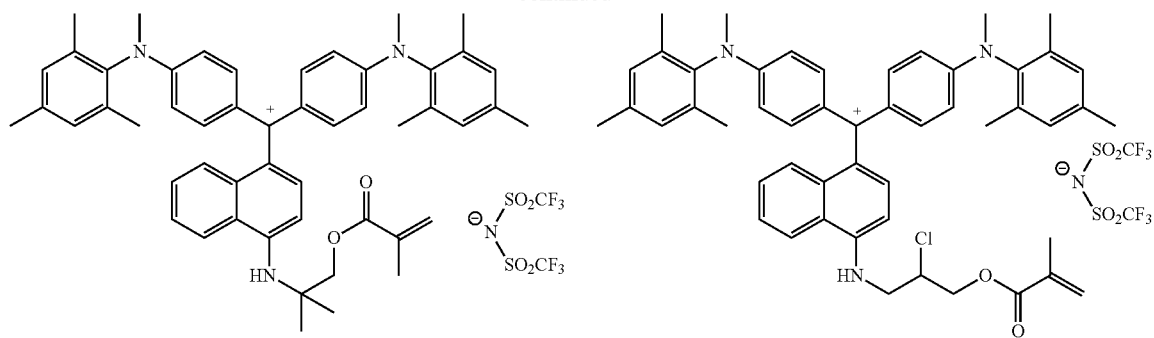
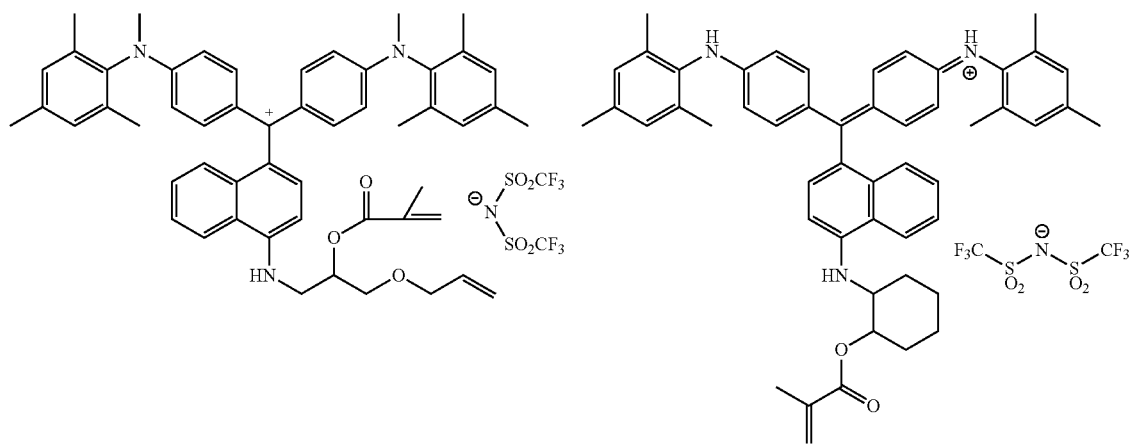
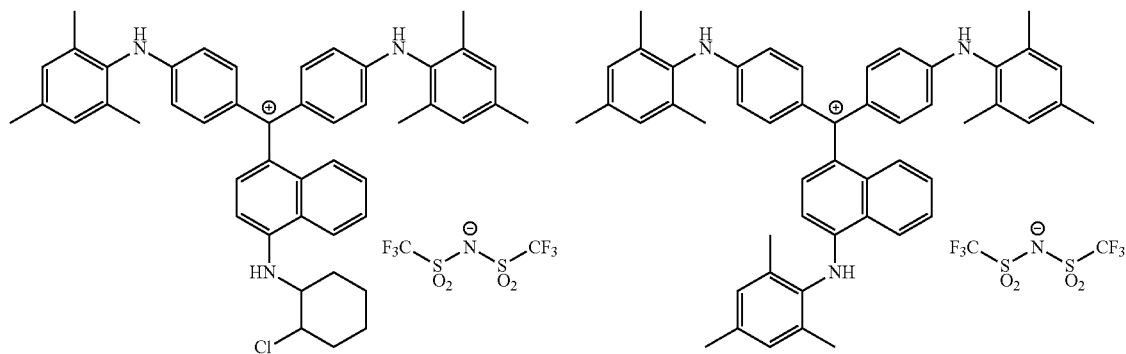
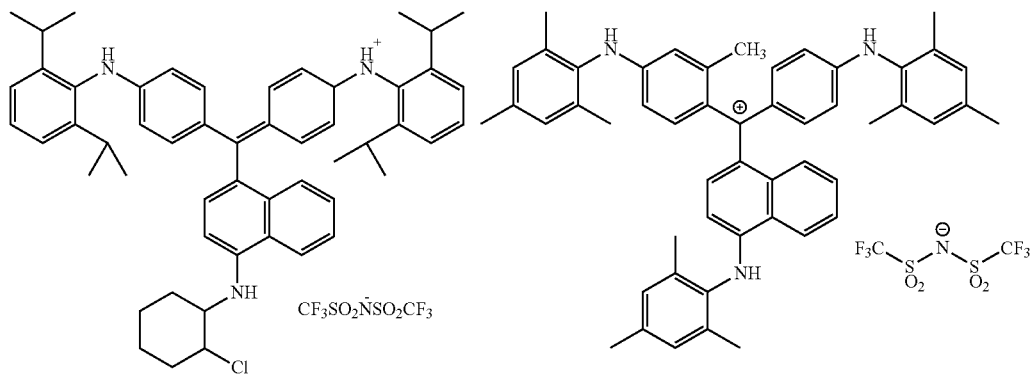

53
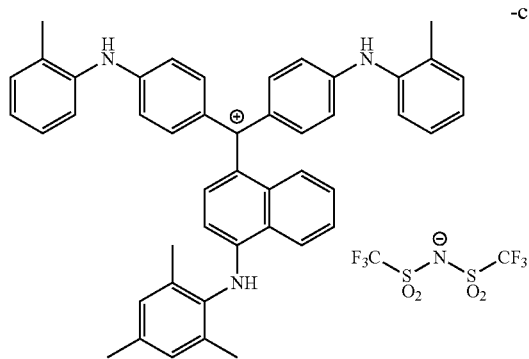
54
-continued
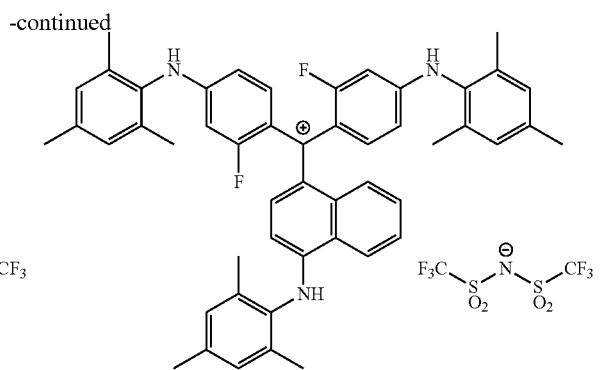
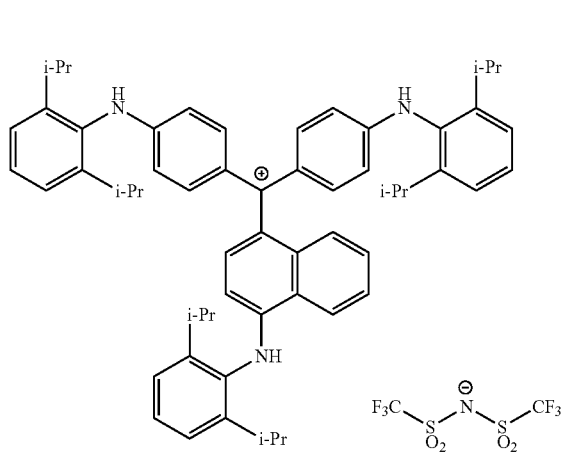
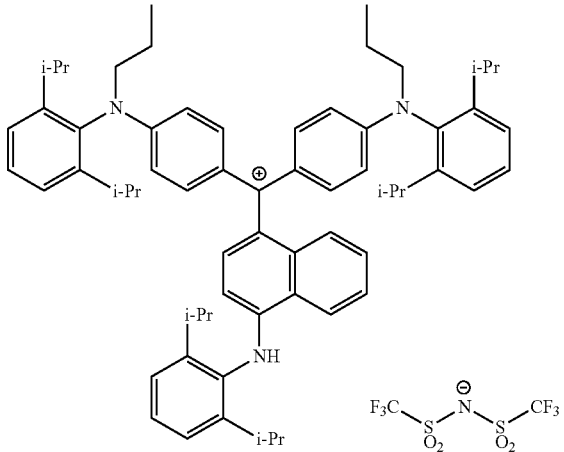
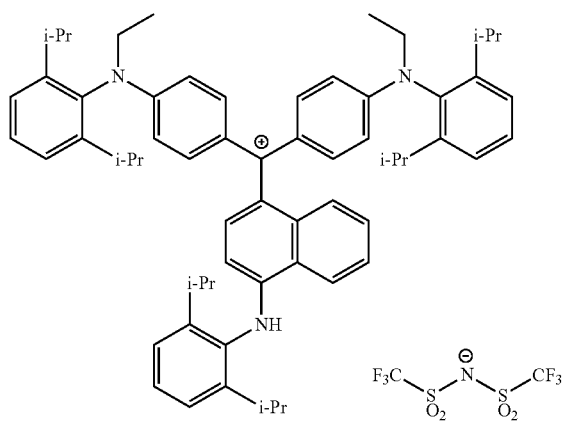
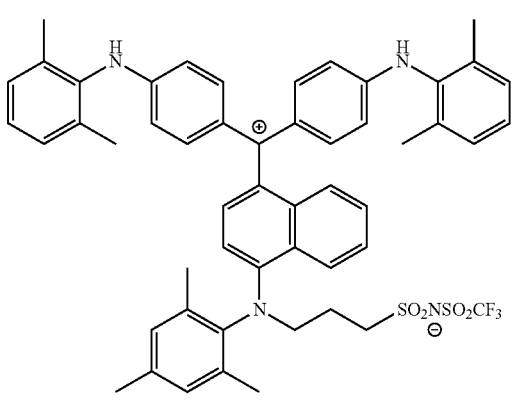
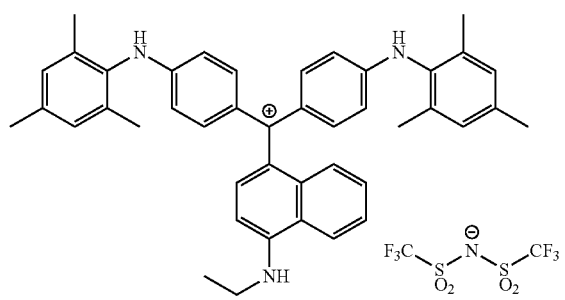
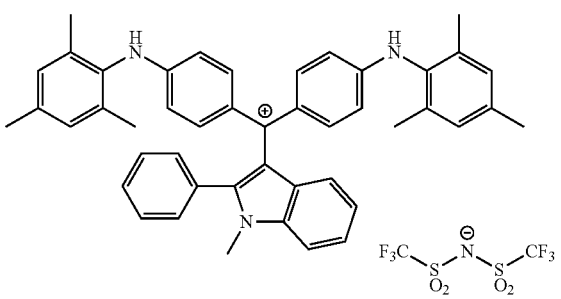

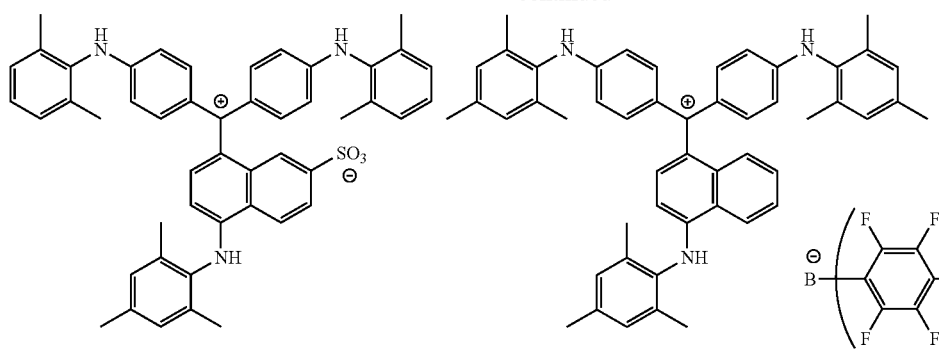
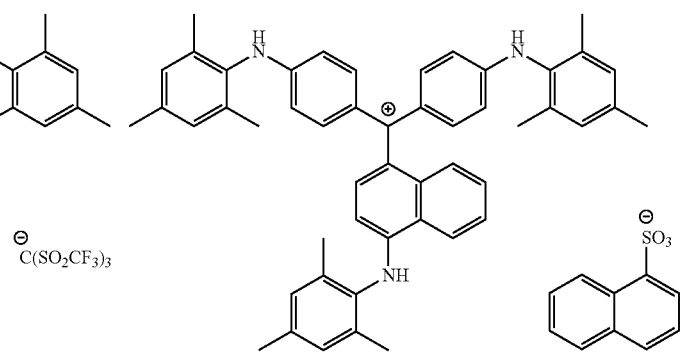
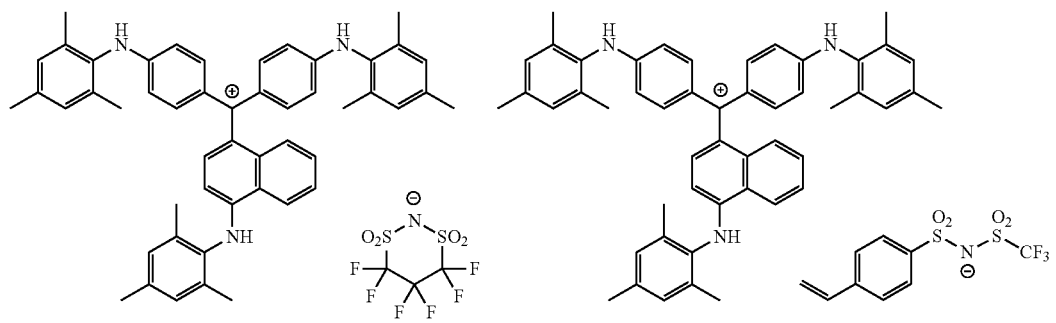
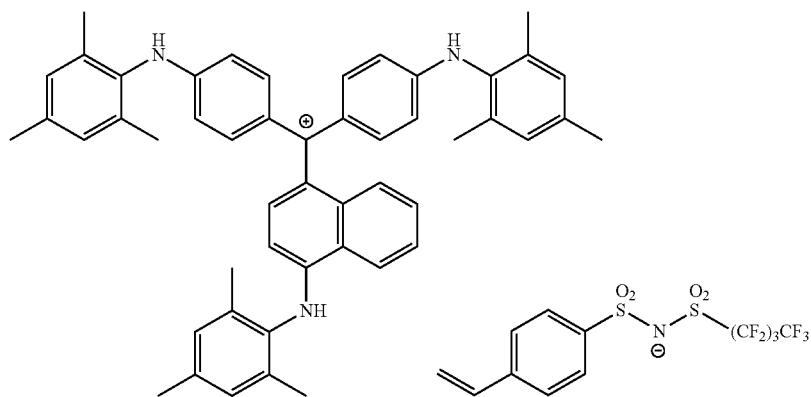

-continued
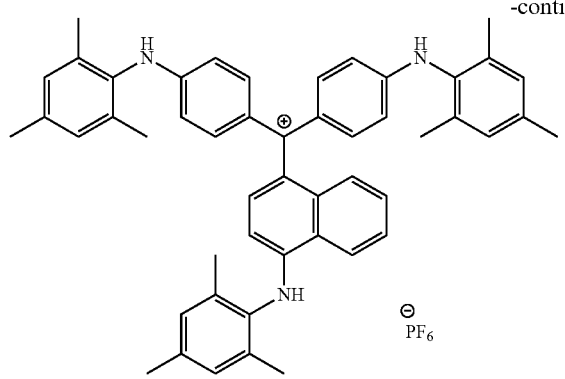
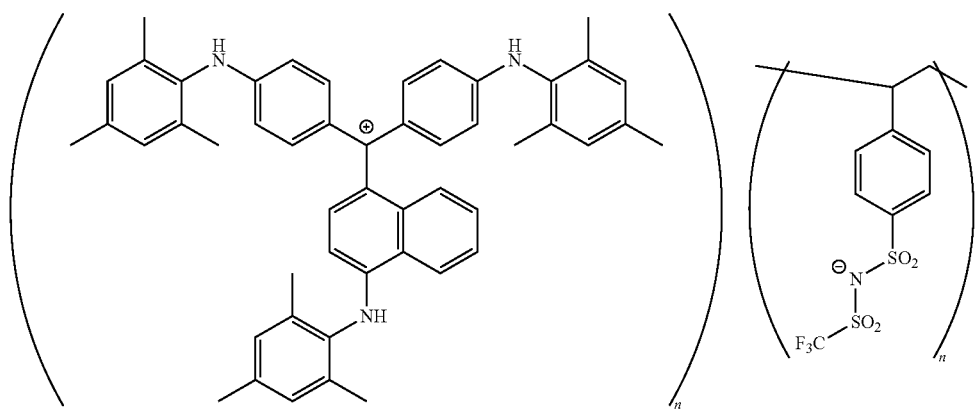
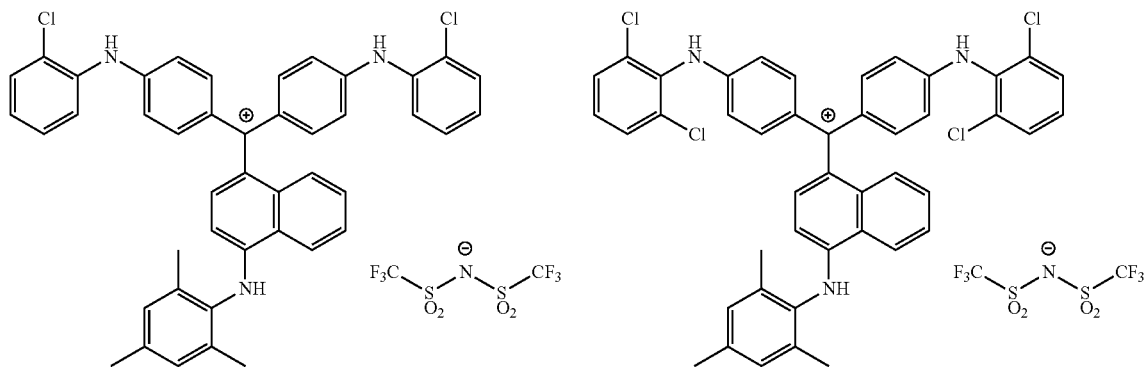
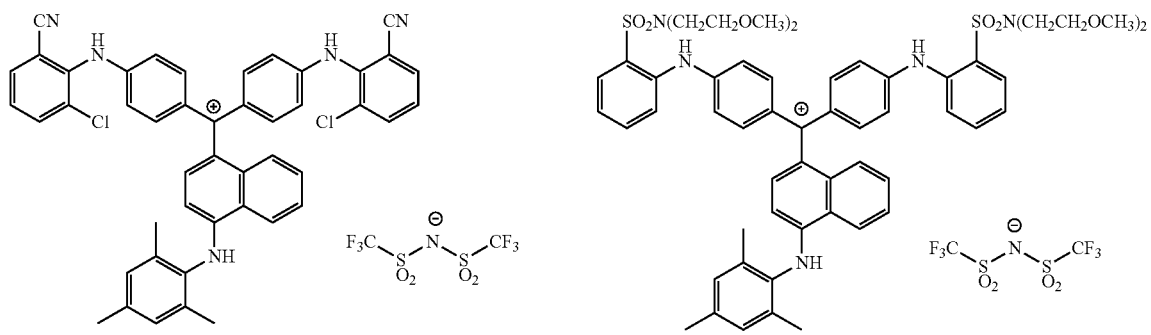

-continued
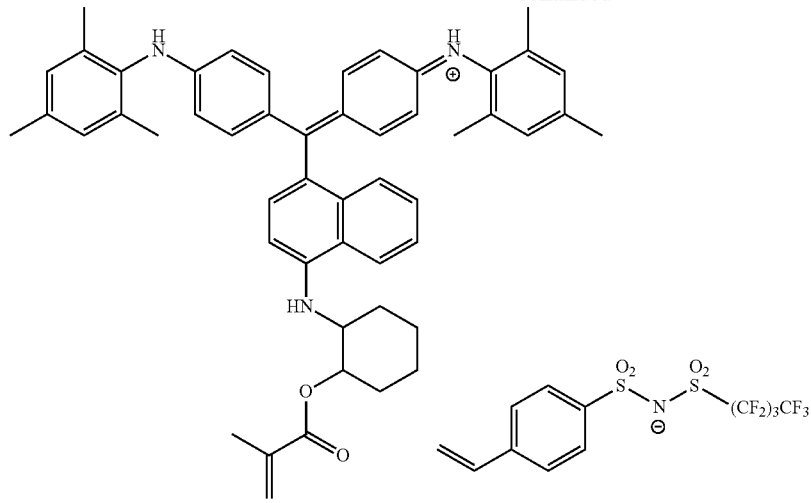
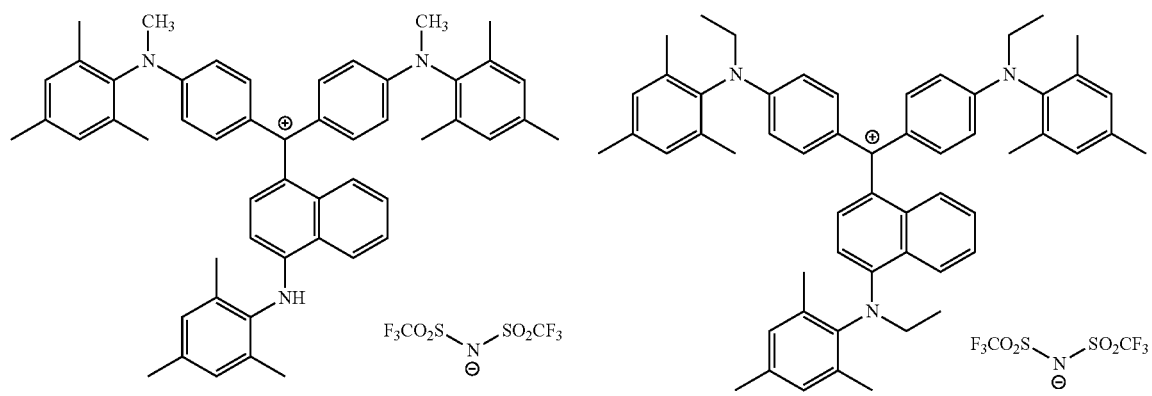
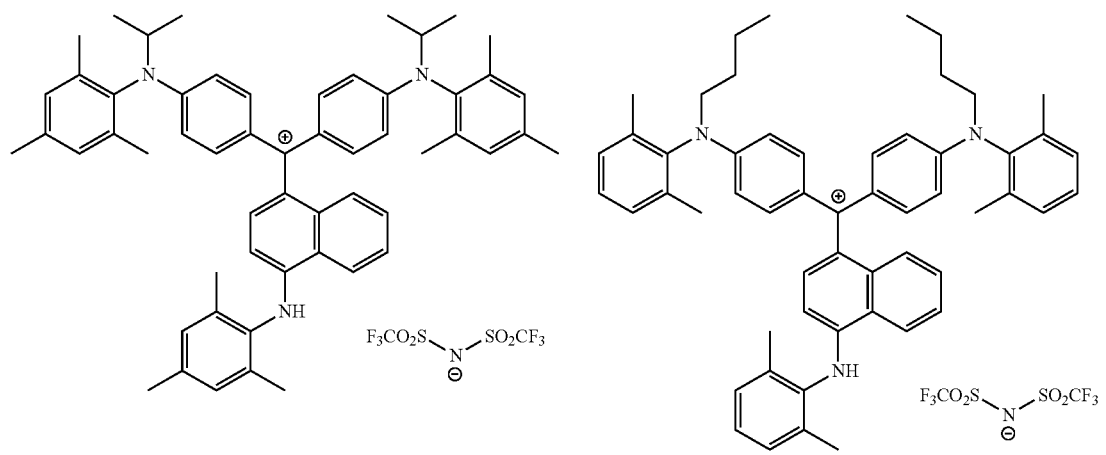

61
62
-continued
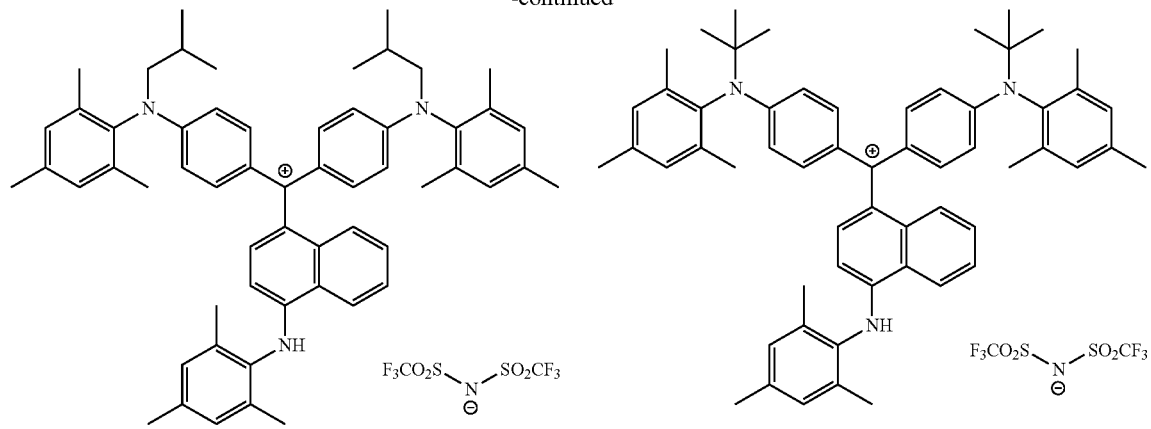
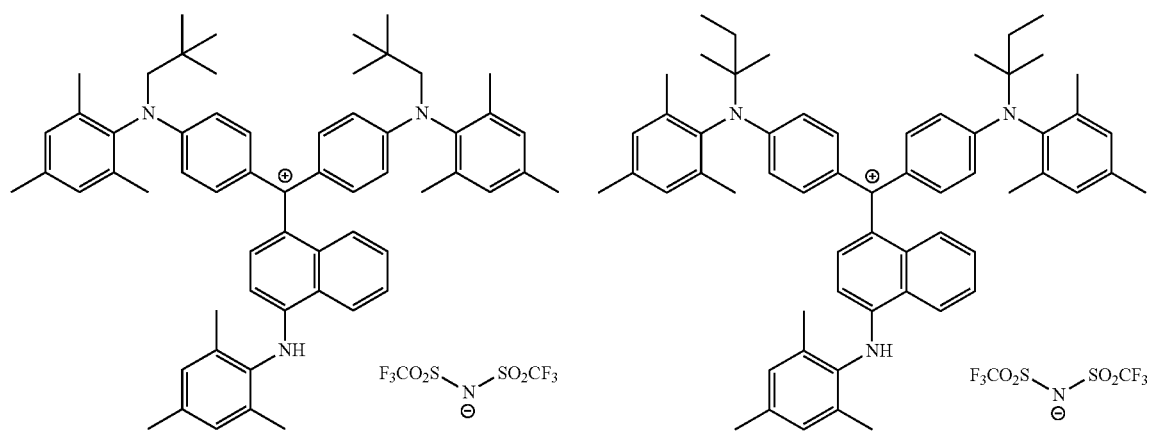
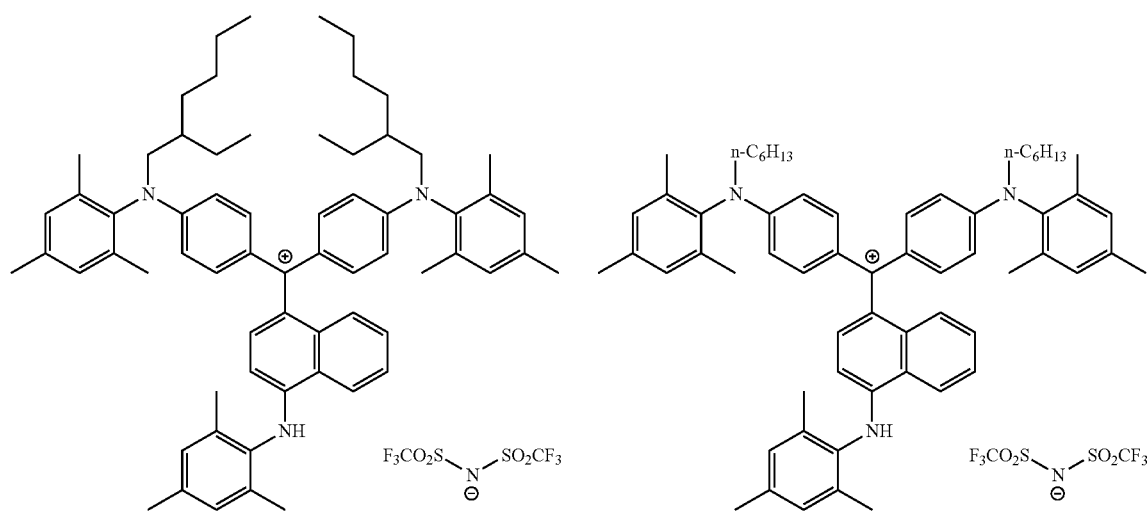

63 64
-continued
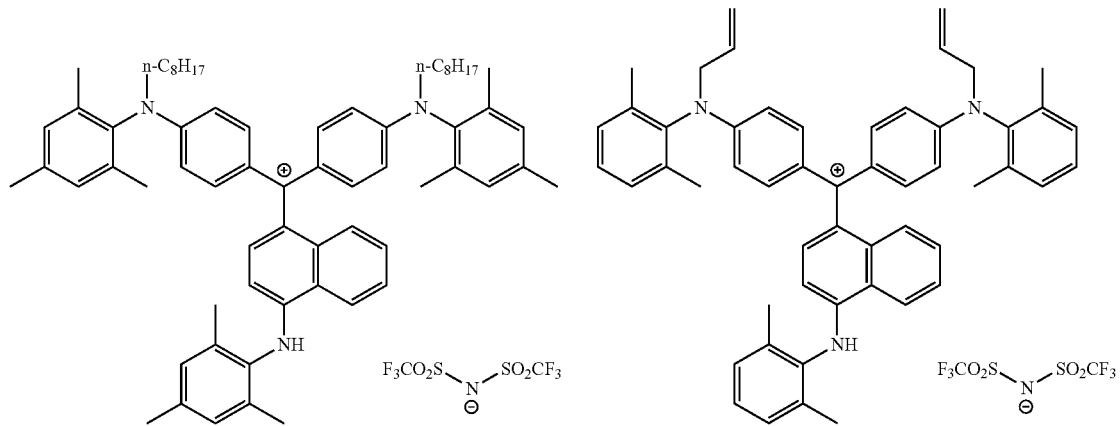
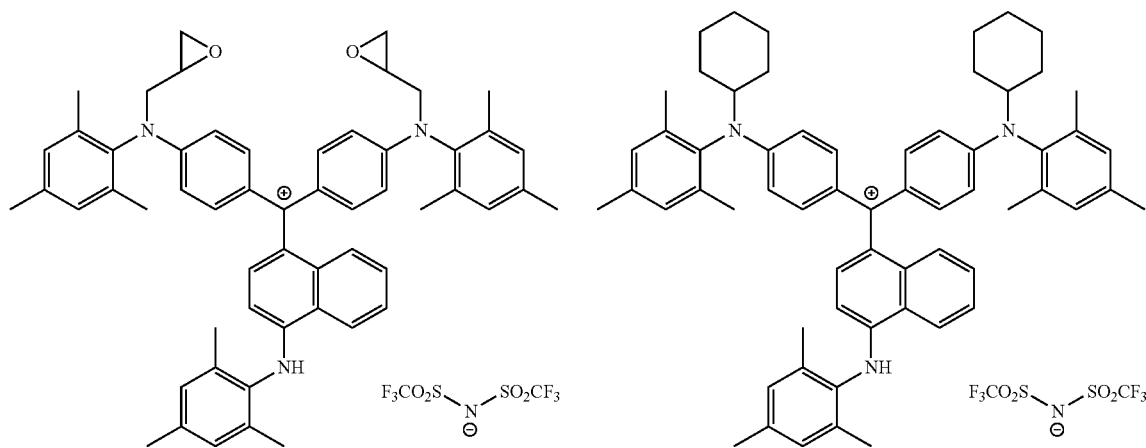
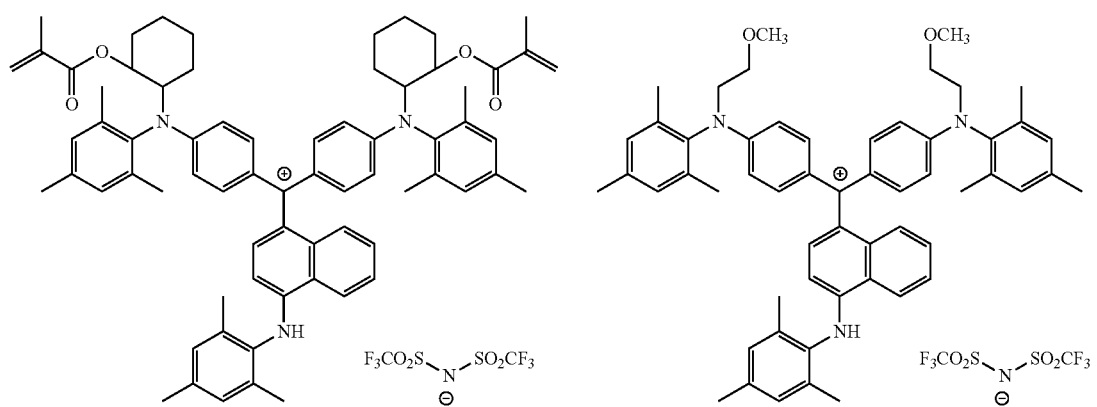

65 66
-continued
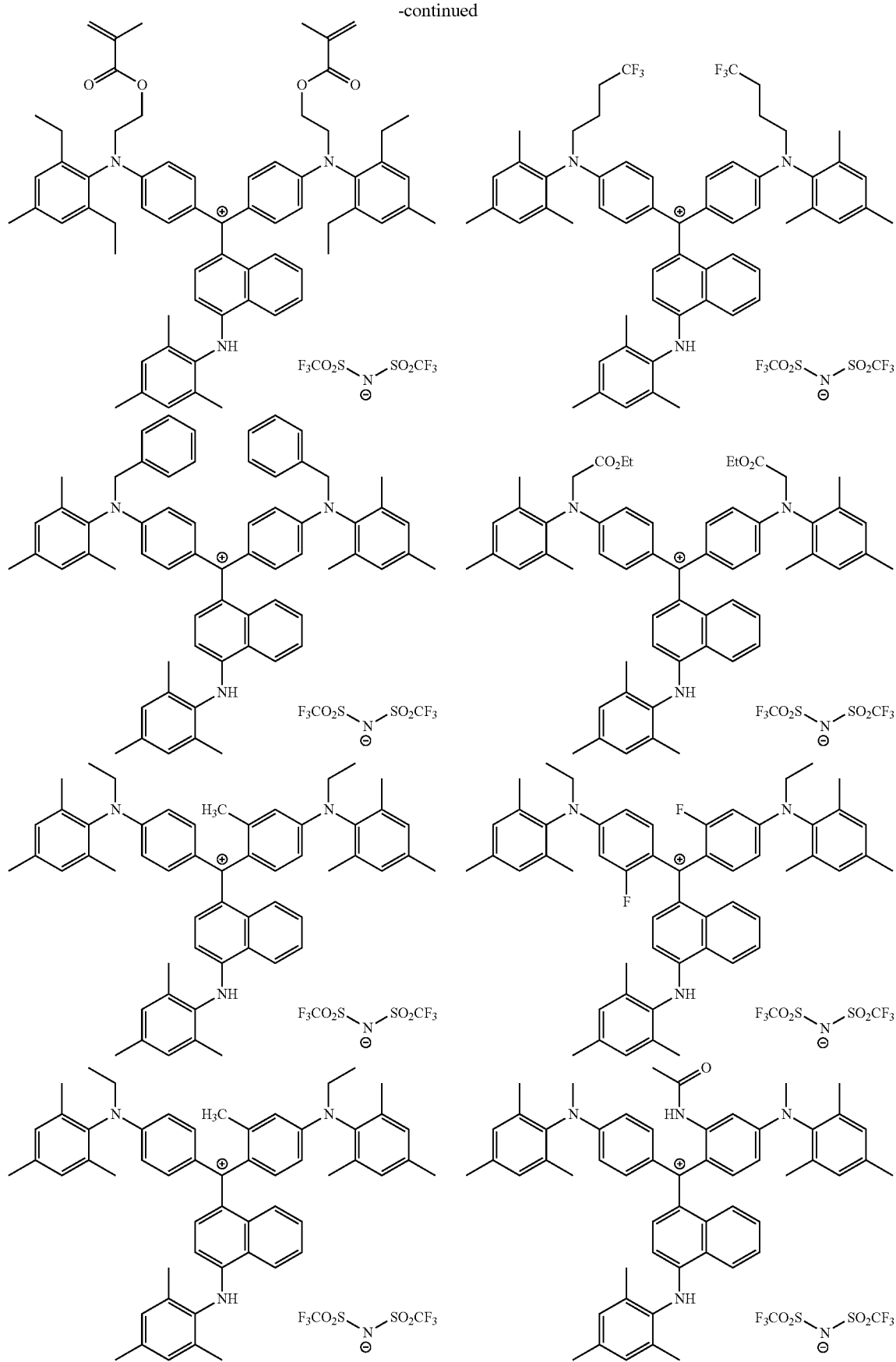

-continued
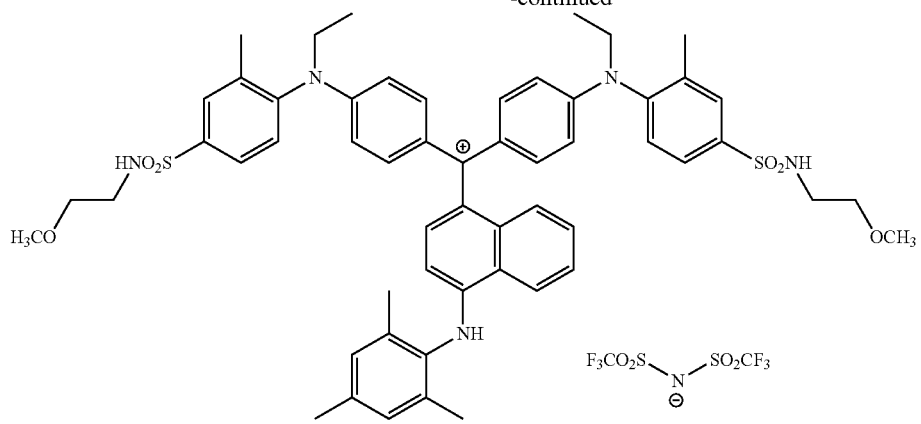
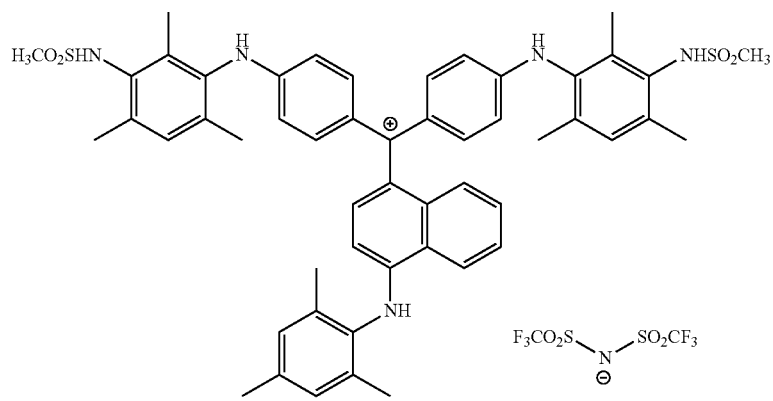
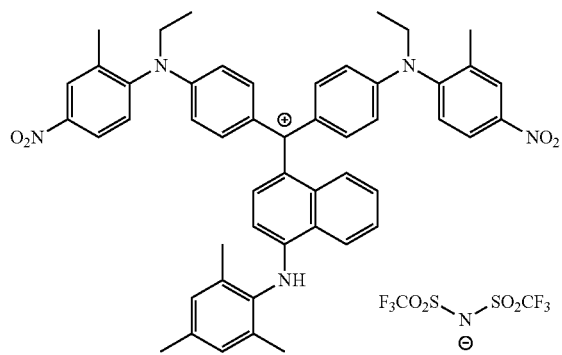
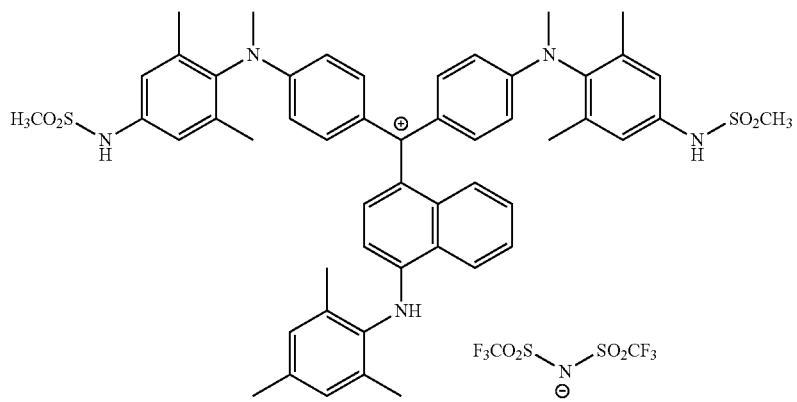

-continued
69
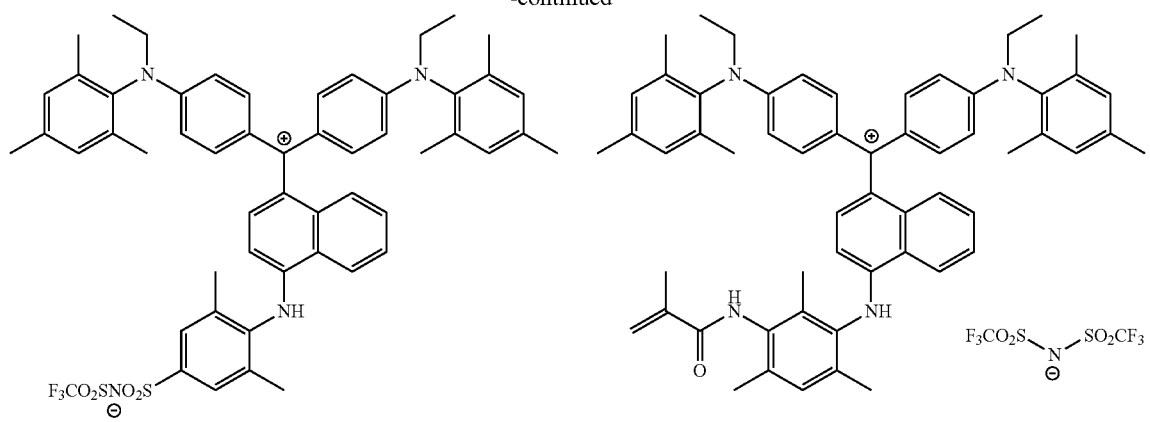
70
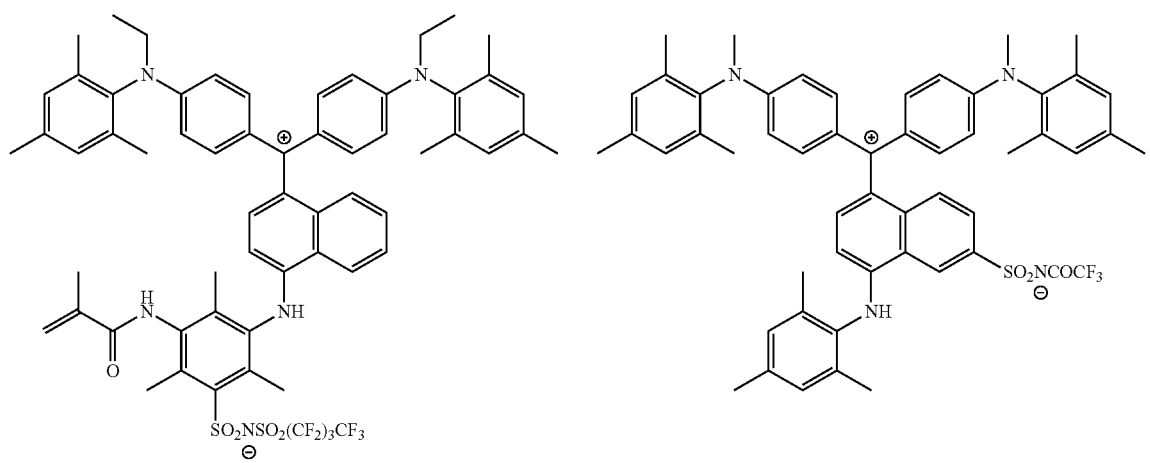
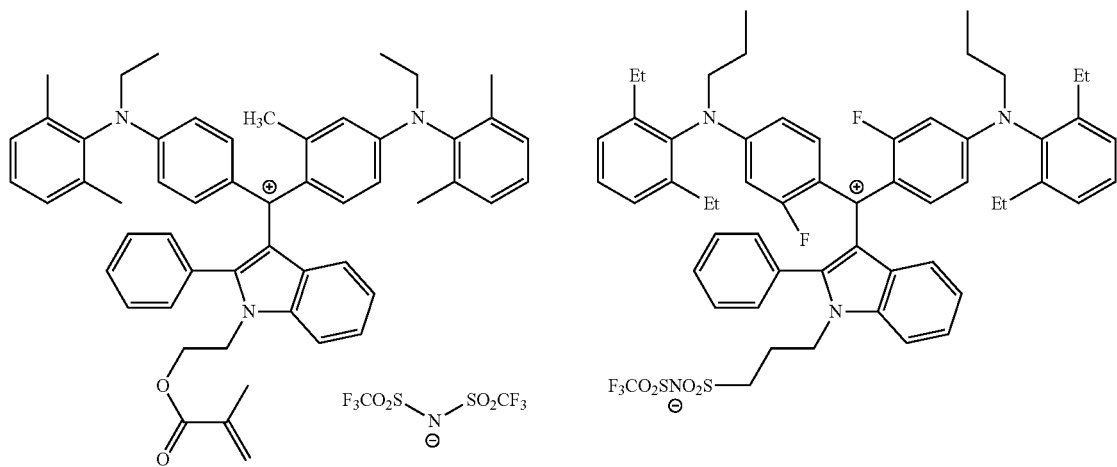

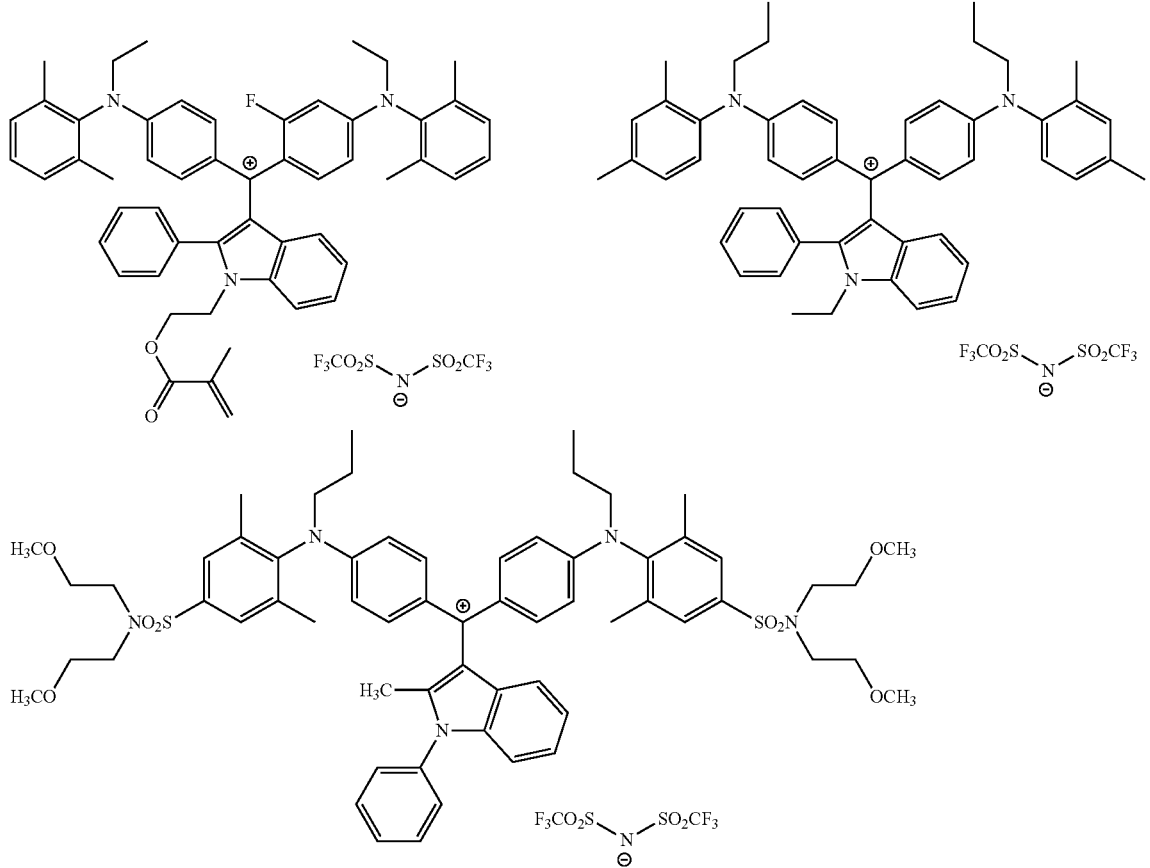

«High-Molecular Type»

Next, a case where the colorant represented by Formula (1) is of a high-molecular type will be described. Further, in the present specification, in the case where the colorant represented by Formula (1) is of a high-molecular type, it may be referred to as a colorant multimer in some cases. In addition, the colorant represented by Formula (1) will be used as an example for description, which will also be applied to the colorant represented by Formula (2) and the colorant represented by Formula (3).

In the case of the high-molecular type, it is preferable that any one site in the colorant represented by Formula (1) is bonded to a polymer and at least one group in Formula (1) is a repeating unit of the polymer. The respective substituents in Formula (1) other than groups bonded to the repeating unit of the polymer have the same definitions as those of a low-molecular type, and preferred ranges thereof are also the same.

Specifically, in the colorant represented by Formula (1), it is preferable that at least one of $R^{101}$, . . . , or $R^{111}$ is the repeating unit of the polymer, and it is more preferable that at least one of $R^{103}$ or $R^{104}$ is a repeating unit of the polymer.

Furthermore, in the colorant represented by Formula (2), it is preferable that at least one of $R^{201}$, . . . , or $R^{211}$ is the repeating unit of the polymer, and it is more preferable that $R^{211}$ is a repeating unit of the polymer.

In addition, in the colorant represented by Formula (3), it is preferable that at least one of $R^{301}$, . . . , or $R^{310}$ is the repeating unit of the polymer, and it is more preferable that $R^{307}$ is a repeating unit of the polymer.

In the case where the colorant represented by Formula (1) or the like is a polymer, the skeleton structure of the repeating unit is not particularly limited, but preferably has at least one of the structural unit represented by General Formula (A), General Formula (B), or General Formula (C), described in paragraph Nos. 0276 to 0304 of JP2013-28764A as a skeleton, and the colorant represented by Formula (1) is preferably a colorant multimer represented by General Formula (D). The description in paragraph Nos. 0276 to 0304 of JP2013-28764A are incorporated herein by reference.

In the present invention, a colorant multimer represented by the following General Formula (A) is preferably included.

«<Structural Unit Represented by General Formula (A)>»

General Formula (A)

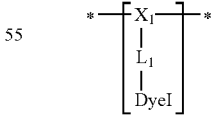

(In General Formula (A), $X_1$ represents a linking group formed by polymerization, and $L_1$ represents a single bond or a divalent linking group. DyeI is a site for bonding with any one of $R^{101}$ to $R^{111}$ in Formula (1), any one of $R^{201}$ to $R^{211}$ in Formula (2), or any one of $R^{301}$ to $R^{310}$ in Formula (3).)

Hereinafter, General Formula (A) will be described in detail.

In General Formula (A), $X_1$ represents a linking group formed by polymerization. That is, $X_1$ represents a portion which forms a repeating unit corresponding to a main chain formed by a polymerization reaction. Moreover, the sites represented by two *'s are repeating units. $X_1$ is not particularly limited as long as it is a linking group formed of a known polymerizable monomer. In particular, as $X_1$, linking groups represented by the following (XX-1) to (XX-24) are preferable; (meth)acryl-based linking chains represented by (XX-1) and (XX-2) are more preferable; linking groups selected from styrene-based linking chains represented by (XX-10) to (XX-17) and vinyl-based linking chains represented by (XX-18) and (XX-19), and (XX-24) are still more preferable; (meth)acryl-based linking chains represented by (XX-1) and (XX-2), styrene-based linking chains represented by (XX-10) to (XX-17), and vinyl-based linking chains represented by (XX-24) are even more preferable; and (meth)acryl-based linking chains represented by (XX-1) and (XX-2), and styrene-based linking chains represented by (XX-11) are even more preferable.

In (XX-1) to (XX-24), * represents a site for linking to $L_1$. Me represents a methyl group. Further, R in (XX-18) and (XX-19) represents a hydrogen atom, an alkyl group having 1 to 5 carbon atoms, or a phenyl group.

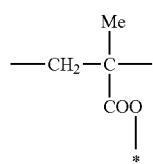

(XX-1)

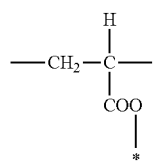

(XX-2)

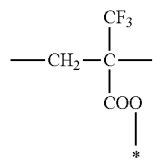

(XX-3)

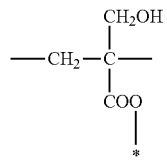

(XX-4)

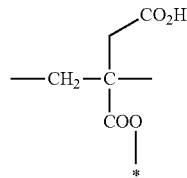

(XX-5)

-continued

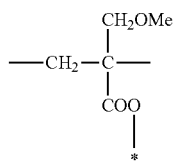

(XX-6)

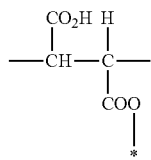

(XX-7)

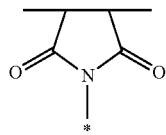

(XX-8)

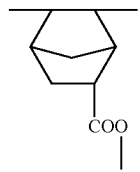

(XX-9)

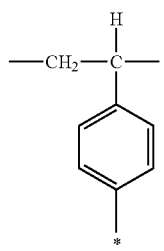

(XX-10)

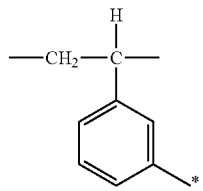

(XX-11)

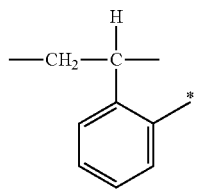

(XX-12)

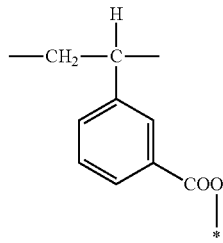

(XX-13)

(XX-14) 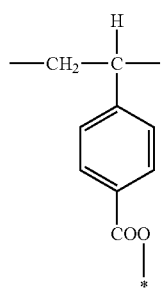
(XX-15) 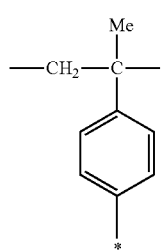
(XX-16) 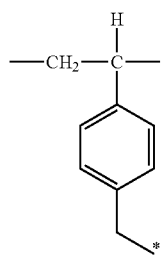
(XX-17) 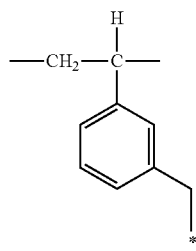
(XX-18) 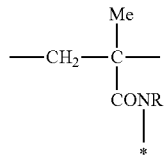
(XX-19) 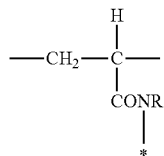
(XX-20) 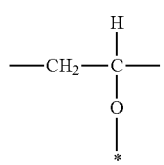
(XX-21) 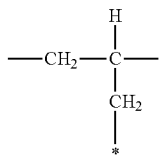
(XX-22) 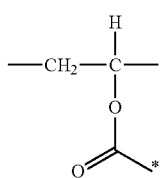
(XX-23) 
(XX-24) 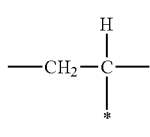
(XX-25) 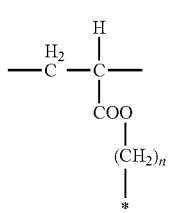
(XX-26) 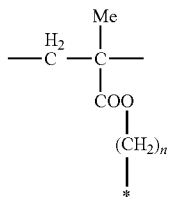
(XX-27) 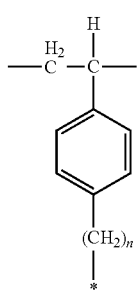

-continued

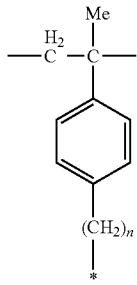
(XX-28)

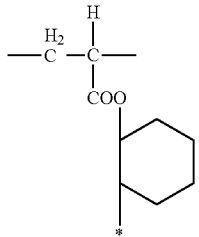
(XX-29)

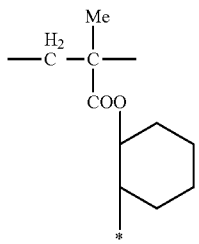
(XX-30)

In General Formula (A), $L_1$ represents a single bond or a divalent linking group. In the case where $L^1$ represents a divalent linking group, the divalent linking group represents a substituted or unsubstituted alkylene group having 1 to 30 carbon atoms (for example, a methylene group, an ethylene group, a trimethylene group, a propylene group, and a butylene group), a substituted or unsubstituted arylene group having 6 to 30 carbon atoms (for example, a phenylene group and a naphthalene group), a substituted or unsubstituted heterocyclic linking group, —CH═CH—, —O—, —S—, —C(═O)—, —CO$_2$—, —NR—, —CONR—, —O$_2$C—, —SO—, —SO—$_2$ and a linking group formed by combination of two or more of these groups are preferable. Further, a configuration in which $L_1$ includes an anion is preferable. $L_1$ is more preferably a single bond or an alkylene group, and still more preferably a single bond or —(CH$_2$)n- (in which n is an integer of 1 to 5). Here, R's each independently represent a hydrogen atom, an alkyl group, an aryl group, or a heterocyclic group. Examples of the case where $L_1$ includes an anion will be described later.

In General Formula (A), DyeI is a site for bonding with any one of $R^{101}$ to $R^{111}$ in Formula (1), any one of $R^{201}$ to $R^{211}$ in Formula (2), or any one of $R^{301}$ to $R^{310}$ in Formula (3).

The colorant multimer having the structural unit represented by General Formula (A) can be synthesized by (1) a method of synthesizing the multimer by means of addition polymerization using a monomer having a colorant residue, or (2) a method of synthesizing the multimer by causing a reaction between a polymer, which has a highly reactive functional group such as an isocyanate group, an acid anhydride group, or an epoxy group, and a colorant which has a functional group (a hydroxyl group, a primary or secondary amino group, a carboxyl group, or the like) that can react with the highly reactive group.

For the addition polymerization, known addition polymerization (radical polymerization, anionic polymerization, or cationic polymerization) is applicable, but among these, it is particularly preferable for the multimer to be synthesized by radical polymerization, since the reaction condition can be set to be mild conditions, and the colorant structure is not decomposed. For the radical polymerization, known reaction conditions can be applied. That is, the colorant multimer used in the present invention is preferably an addition polymer.

Among these, from the viewpoint of heat resistance, the colorant multimer having the structural unit represented by General Formula (A) in the present invention is preferably a radical polymer that is obtained by radical polymerization using a colorant monomer having an ethylenically unsaturated bond.

«<Other Functional Groups and Repeating Units>»

The colorant multimer of the present invention may have other functional groups in the colorant structure portions of the colorant multimer as described above. Examples of such other functional groups include a polymerizable group and an alkali-soluble group (preferably an acid group).

Furthermore, the colorant multimer of the present invention may include other repeating units than the repeating units including the colorant structure as described above. Such other repeating units may have functional groups.

Moreover, examples of such other repeating units include repeating units including at least one of a polymerizable group or an alkali-soluble group (preferably an acid group).

That is, the colorant multimer of the present invention may have other repeating units than the repeating units represented by General Formulae (A) to (C). One kind or two or more kinds of other repeating units may be included in one colorant multimer.

In addition, the colorant multimer of the present invention may have other functional groups inside the colorant multimers represented by General Formulae (A) to (D). Hereinafter, the details thereof will be described.

«« Polymerizable Group Contained in Colorant Multimer»»

The colorant multimer of the present invention may include a polymerizable group. One kind or two or more kinds of polymerizable group may be included.

With regard to the polymerizable group, the colorant structure may include a polymerizable group or other portions may include the polymerizable group. In the present invention, it is preferable that the colorant structure includes a polymerizable group. By adopting such a configuration, heat resistance tends to be improved.

In addition, in the present invention, in another preferable aspect, other portions than the colorant structure include a polymerizable group.

The polymerizable group has the same definition as the polymerizable group which may be contained represented by Formula (1) to Formula (3), and preferred ranges thereof are also the same.

The polymerizable group is preferably included as a repeating unit having a polymerizable group inside the colorant multimer, and more preferably included as a repeating unit having an ethylenically unsaturated bond. That is, one of preferred exemplary embodiments of the colorant multimer of the present invention is an aspect in which the colorant multimer contains a repeating unit including a colorant monomer and a repeating unit having a polymerizable group, and more preferably contains a repeating unit including a colorant monomer and a repeating unit having an ethylenically unsaturated bond.

Examples of the method of introducing the polymerizable group include (1) a method of introducing the polymerizable group by modifying the colorant multimer with a polymerizable group-containing compound, and (2) a method of introducing the polymerizable group by copolymerizing the colorant multimer with a polymerizable group-containing compound. Hereinafter, the methods will be described in detail.

(1) Method of Introducing Polymerizable Group by Modifying Colorant Multimer with Polymerizable Group-Containing Compound:

As the method of introducing a polymerizable group by modifying a colorant multimer with a polymerizable group-containing compound, known methods can be used without particular limitation. For example, (a) a method of causing a reaction between a carboxylic acid contained in the colorant multimer and an unsaturated bond-containing epoxy compound, (b) a method of causing a reaction between a hydroxyl group or an amino group contained in the colorant multimer and an unsaturated bond-containing isocyanate compound, and (c) a method of causing a reaction between an epoxy compound contained in the colorant multimer and an unsaturated bond-containing carboxylic acid compound are preferable from the viewpoint of production.

Examples of the unsaturated bond-containing epoxy compound in the (a) method of causing a reaction between a carboxylic acid contained in the colorant multimer and an unsaturated bond-containing epoxy compound include glycidyl methacrylate, glycidyl acrylate, allylglycidyl ether, 3,4-epoxy-cyclohexylmethyl acrylate, and 3,4-epoxy-cyclohexylmethyl methacrylate. Particularly, glycidyl methacrylate, and 3,4-epoxy-cyclohexylmethyl methacrylate are preferable since these compounds have crosslinking properties and storage stability. Known conditions can be used as the reaction conditions.

Examples of the unsaturated bond-containing isocyanate compound in the (b) method of causing a reaction between a hydroxyl group or an amino group contained in the colorant multimer and an unsaturated bond-containing isocyanate compound include 2-isocyanatoethyl methacrylate, 2-isocyanatoethyl acrylate, and 1,1-bis(acryloyloxymethyl) ethyl isocyanate. Among these, 2-isocyanatoethyl methacrylate is preferable since this compound has excellent crosslinking properties and storage stability. Known conditions can be used as the reaction conditions.

As the unsaturated bond-containing carboxylic acid compound in the (c) method of causing a reaction between an epoxy compound contained in the colorant multimer and an unsaturated bond-containing carboxylic acid compound, any carboxylic acid compounds can be used without particular limitation as long as the compound has a known (meth) acryloyloxy group. Among these, methacrylic acid and acrylic acid are preferable, and methacrylic acid is particularly preferable since this acid has excellent crosslinking properties and storage stability. Known conditions can be used as the reaction conditions.

(2) Method of Introducing Polymerizable Group by Copolymerizing Colorant Monomer and Polymerizable Group-Containing Compound:

As (2) the method of introducing a polymerizable group by copolymerizing a colorant monomer and a polymerizable group-containing compound, any known methods can be used without particular limitation. Among these, (d) a method of copolymerizing a radically polymerizable colorant monomer with a polymerizable group-containing compound that can be radically polymerized, and (e) a method of copolymerizing a colorant monomer that can be subjected to polyaddition with a polymerizable group-containing compound that can be subjected to polyaddition are preferable.

Examples of the polymerizable group-containing compound that can be radically polymerized in the (d) method of copolymerizing a radically polymerizable colorant monomer with a polymerizable group-containing compound that can be radically polymerized particularly include an allyl group-containing compound (for example, allyl (meth)acrylate), an epoxy group-containing compound (for example, glycidyl (meth)acrylate and 3,4-epoxy-cyclohexyl methyl (meth)acrylate), an oxetane group-containing compound (for example, 3-methyl-3-oxetanyl methyl (meth)acrylate), and a methylol group-containing compound (for example, N-(hydroxymethyl)acrylamide). Among these, an epoxy compound and an oxetane compound are particularly preferable. Known conditions can be used as the reaction conditions.

Examples of the polymerizable group-containing compound that can be subjected to polyaddition in the (e) method of copolymerizing a colorant monomer that can be subjected to polyaddition with a polymerizable group-containing compound that can be subjected to polyaddition include an unsaturated bond-containing diol compound (for example, 2,3-dihydroxypropyl (meth)acrylate). Known conditions can be used as the reaction conditions.

As the method of introducing a polymerizable group, a method of causing a reaction between a carboxylic acid contained in the colorant multimer and an unsaturated bond-containing epoxy compound is particularly preferable.

The amount of the polymerizable groups contained in the colorant multimer is preferably 0.1 mmol to 2.0 mmol, more preferably 0.2 mmol to 1.5 mmol, and particularly preferably 0.3 mmol to 1.0 mmol, with respect to 1 g of the colorant multimer.

In addition, when the colorant multimer contains repeating units having a polymerizable group, the proportion of the repeating units is preferably, for example, 5 moles to 50 moles, and more preferably 10 moles to 20 moles, with respect to 100 moles of all the repeating units.

Specific examples of repeating units having a polymerizable group will be shown below, but the present invention is not limited thereto.

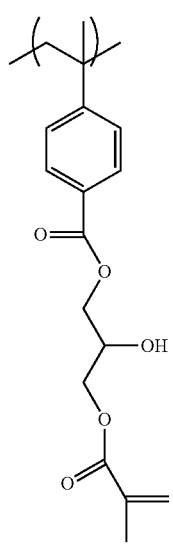

(G-3)

(G-4) 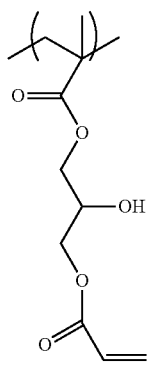
(G-5) 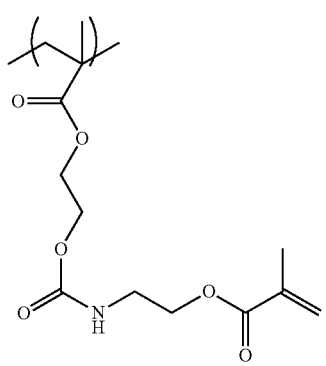
(G-6) 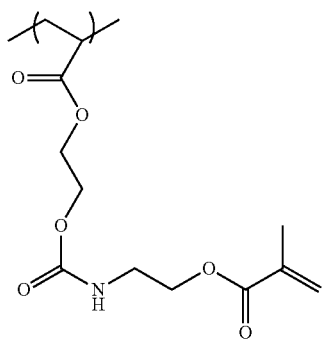
(G-7) 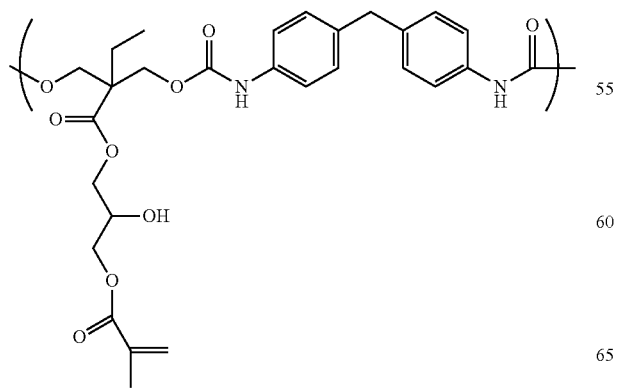
(G-8) 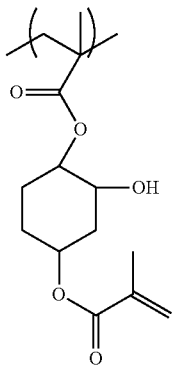
(G-9) 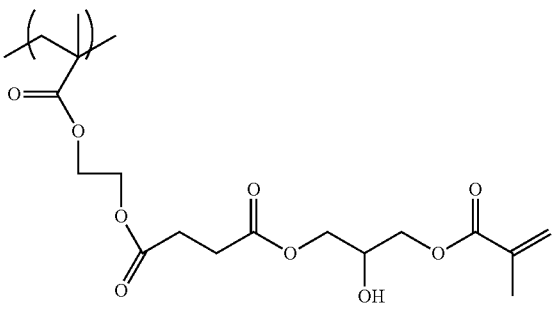
(G-10) 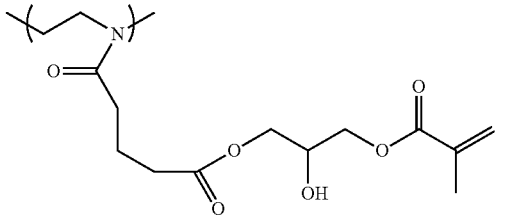
(G-11) (G-12) 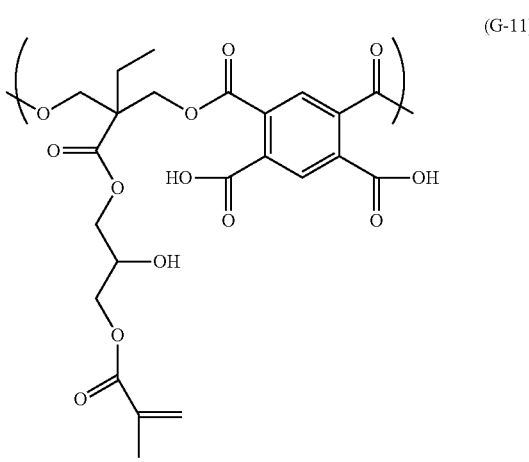

(G-13)
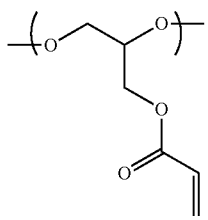

(G-14)
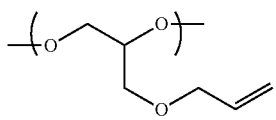

(G-15)
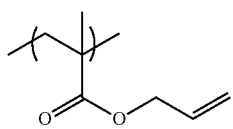

(G-16)
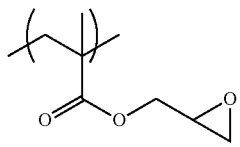

(G-17)
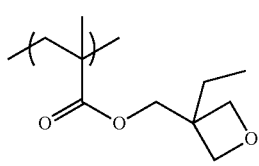

«<Alkali-Soluble Group Contained in Colorant Multimer>»

Examples of the acid group which may be contained in the colorant multimer in the present invention include a carboxylic acid group, a sulfonic acid group, and a phosphoric acid group.

In the present invention, it is preferable that an alkali-soluble group (preferably an acid group) is included in the colorant multimer as a structural unit having an alkali-soluble group (an acid group).

Examples of the method for introducing the alkali-soluble group into the colorant multimer include a method in which an alkali-soluble group is introduced into a colorant monomer in advance and a method of copolymerizing monomers (a caprolactone-modified derivative of acrylic acids and (meth)acrylic acids, a succinic anhydride-modified derivative of 2-hydroxyethyl (meth)acrylate, a phthalic anhydride-modified derivative of 2-hydroxyethyl (meth)acrylate, a 1,2-cyclohexane dicarboxylic acid anhydride-modified derivative of 2-hydroxyethyl (meth)acrylate, carboxylic acid-containing monomers such as styrenecarboxylic acid, itaconic acid, maleic acid, and norbornene carboxylic acid, phosphoric acid-containing monomers such as acid phosphoxyethyl methacrylate, and vinyl phosphonic acid, and sulfonic acid-containing monomers such as vinyl sulfonic acid and 2-acrylamide-2-methylsulfonic acid) other than a colorant monomer having an alkali-soluble group. It is more preferable to use both of the methods.

The amount of the alkali-soluble groups contained in the colorant multimer is preferably 0.3 mmol to 2.0 mmol, more preferably 0.4 mmol to 1.5 mmol, and particularly preferably 0.5 mmol to 1.0 mmol, with respect to 1 g of the colorant multimer.

Furthermore, in the case where the colorant multimer contains a repeating unit including a colorant monomer and a repeating unit having an acid group, the proportion of the repeating units containing the repeating unit having an acid group is preferably, for example, 5 moles to 70 moles, and more preferably 10 moles to 50 moles, with respect to 100 moles of all the repeating units.

Examples of other functional groups contained in the colorant multimer include development accelerators such as lactone, acid anhydride, amide, —COCH$_2$CO—, and a cyano group, and hydrophobicity or hydrophilicity-regulating groups such as a long chained alkyl group, a cyclic alkyl group, an aralkyl group, an aryl group, a polyalkylene oxide group, a hydroxyl group, a maleimide group, and an amino group, and these can be appropriately introduced into the colorant multimer.

Examples of the method of introducing the functional group include a method of introducing the functional group in advance to a colorant monomer, and a method of copolymerizing a monomer having the functional group.

Specific examples of the repeating unit having other functional groups than the alkali-soluble groups which may be contained in the colorant multimer are shown below, but the present invention is not limited thereto.

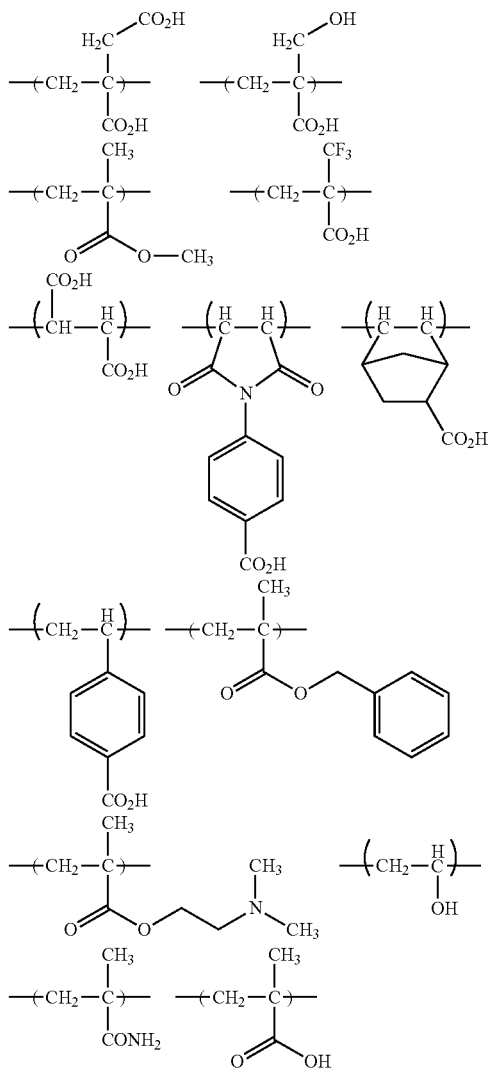

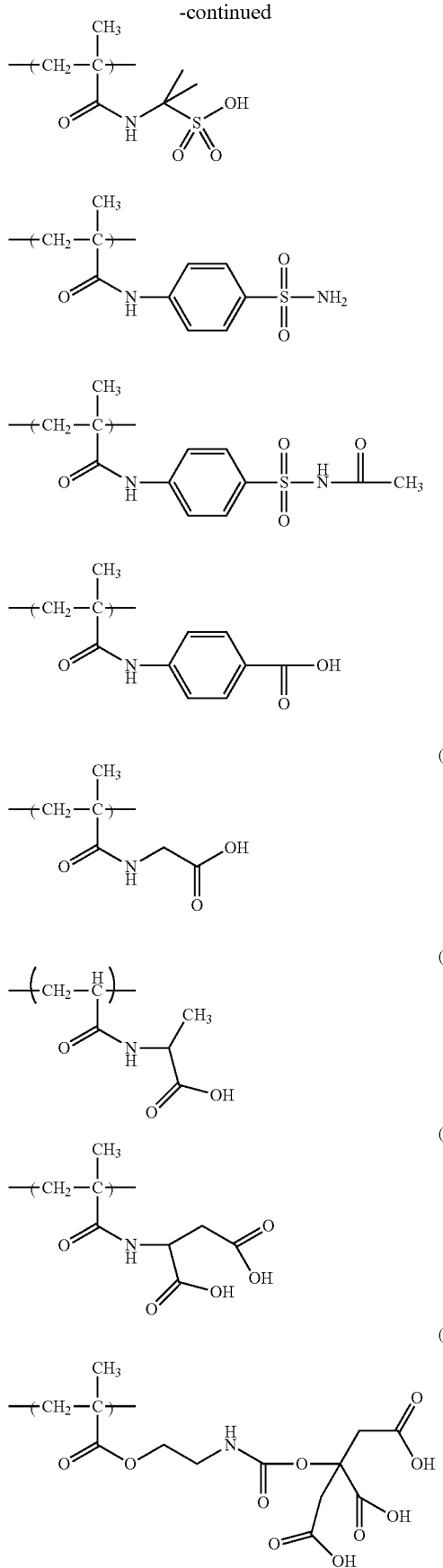
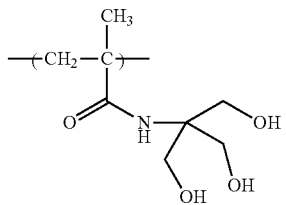 (H-26)
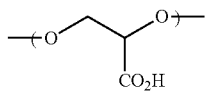 (H-27)
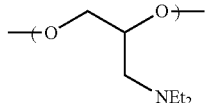 (H-28)
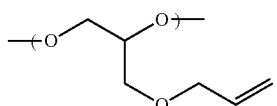 (H-29)
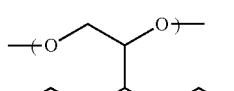 (H-30)
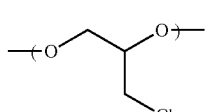 (H-31)
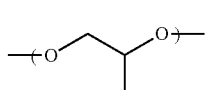 (H-32)
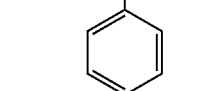
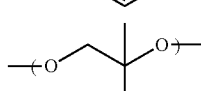
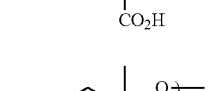
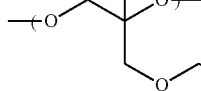

-continued

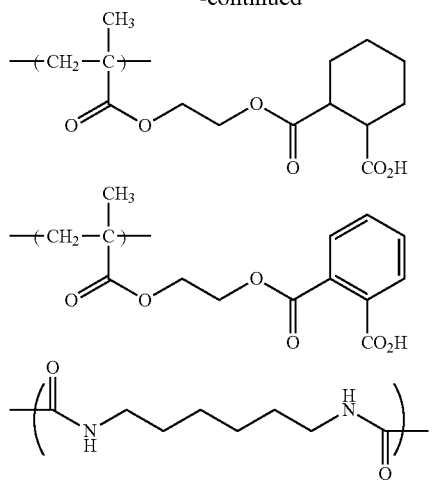

Specific examples of the repeating unit which may be contained in the colorant of the present invention include repeating units derived from at least one of (meth)acrylic acid, (meth)acrylic acid ester, or (meth)acrylic acid amide.

The weight-average molecular weight (Mw) of the colorant multimer is preferably 2,000 to 50,000, more preferably 3,000 to 30,000, and particularly preferably 6,000 to 20,000.

Moreover, the ratio [(Mw)/(Mn)] of the weight-average molecular weight (Mw) to the number-average molecular weight (Mn) of the colorant multimer is preferably 1.0 to 2.0, more preferably 1.1 to 1.8, and particularly preferably 1.1 to 1.5.

The glass transition temperature (Tg) of the colorant multimer according to the present invention is preferably 50° C. or higher, and more preferably 100° C. or higher. Further, a 5%-by-weight reduction temperature measured by thermogravimetric analysis (TGA measurement) is preferably 120° C. or higher, more preferably 150° C. or higher, and still more preferably 200° C. or higher. Within this region, when the coloring curable composition of the present invention is applied to the manufacture of a color filter and the like, the change in concentration due to a heating process can be decreased.

In the case where the colorant multimer used in the present invention includes other repeating units than the repeating unit having a colorant structure, a random polymer of a polymerizable compound including a colorant and other polymerizable compounds is preferable. By using the random polymer, the colorant structure is randomly present in the colorant multimer, and thus, the effects of the present invention will be more effectively exerted.

«<Anion X>»

Even in the case where a colorant represented by Formula (1) or the like is of a high-molecular type, it has an anion X inside the molecule and/or outside the molecule. The anion X is included according to the valency of the cation included in the colorant represented by Formula (1) or the like. The cation is usually monovalent or divalent, and preferably monovalent.

In the present embodiment, inclusion of the anion X inside the molecule refers to presence of the anion X inside the same repeating unit of the colorant multimer. That is, it refers to a case where a cation and an anion are bonded to each other via a covalent bond.

On the other hand, inclusion of the anion X outside the molecule refers to cases other than the above case, such as a case where a cation and an anion are not bonded to each other via a covalent bond and the anion X is present as a separate compound, or a case where a cation and an anion are respectively included as an independent repeating unit of the colorant multimer.

Case where Anion X is Inside the Same Repeating Unit

The anion moiety in the case where the anion X is inside the same repeating unit is the same as in the first embodiment of the anion of a low-molecular type, and preferred ranges thereof are also the same.

Case where Anion X is Separate Molecule

The anion in the case where the anion X is a separate molecule is the same as in the second embodiment of the anion of a low-molecular type, and preferred ranges thereof are also the same.

Case where Cation and Anion are Included in Separate Repeating Units of Colorant Multimer A third embodiment of the present invention refers to a case where a cation and an anion are respectively included in independent repeating units of the colorant multimer.

In the case of the present embodiment, the anion may be present in the side chain or the main chain of the colorant multimer, or the anion may be present in both of the main chain and the side chain. Preferably, it is present in the side chain.

Preferred examples of the repeating unit including the anion X include a repeating unit represented by General Formula (C) and a repeating unit represented by General Formula (D).

General Formula (C)

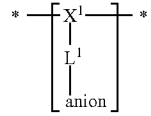

(in General Formula (C), $X^1$ represents the main chain of the repeating unit, $L^1$ represents a single bond or a divalent linking group, and the anion represents the above anion)

In General Formula (C), $X^1$ is preferably the main chain of the repeating unit, and usually represents a linking group formed by a polymerization reaction, and examples thereof include a (meth)acryl-based linking group, a styrene-based linking group, and a vinyl-based linking group and a (meth) acryl-based linking group is more preferably. Further, two sites represented by * form a repeating unit.

In the case where $L^1$ is a divalent linking group, an alkylene group having 1 to 30 carbon atoms (a methylene group, an ethylene group, a trimethylene group, a propylene group, and a butylene group), an arylene group having 6 to 30 carbon atoms (a phenylene group, a naphthalene group, or the like), a heterocyclic linking group, —CH=CH—, —O—, —S—, —C(=O)—, —CO—, —NR—, —CONR—, —OC—, —SO—, —SO$_2$—, and a linking group formed by combination of two or more of these groups are preferable. Here, R's each independently represent a hydrogen atom, an alkyl group, an aryl group, or a heterocyclic group.

In particular, $L^1$ is preferably a single bond or a divalent linking group formed by combination of two or more groups of an alkylene group having 1 to 10 carbon atoms (preferably —(CH$_2$)n- (in which n an integer of 5 to 10)), an arylene group having 6 to 12 carbon atoms (preferably a phenylene group or a naphthalene group), —NH—, —CO$_2$—, —O—, and —SO$_2$—.

Specific preferred examples of $X^1$ include the preferred examples of $X^1$ in General Formula (A).

General Formula (D)

(in General Formula (D), $L^2$ and $L^3$ each independently represent a single bond or a divalent linking group, and the anion represents the anion X)

In General Formula (D), in the case where $L^2$ and $L^3$ represent a divalent linking group, an alkylene group having 1 to 30 carbon atoms, an arylene group having 6 to 30 carbon atoms, a heterocyclic linking group, —CH=CH—, —O—, —S—, —C(=O)—, —CO$_2$—, —NR—, —CONR—, —O$_2$C—, —SO—, —SO$_2$—, and a linking group formed by combination of two or more of these groups are preferable. Here, R's each independently represent a hydrogen atom, an alkyl group, an aryl group, or a heterocyclic group.

$L^2$ is preferably an arylene group having 6 to 12 carbon atoms (particularly a phenylene group). The arylene group having 6 to 30 carbon atoms is preferably substituted with a fluorine atom.

$L^3$ is preferably a group formed by combination of an arylene group having 6 to 12 carbon atoms (particularly a phenylene group) and —O—, and at least one kind of arylene group having 6 to 12 carbon atoms is preferably substituted with a fluorine atom.

As a polymer which forms an anion multimer, a homopolymer constituted with only a dye compound component having a crosslinkable group or a copolymer of the dye compound component with other polymerizable compounds can be preferably used, but the homopolymer is more preferable.

With regard to the molecular weight of the anion multimer, it is preferable that the weight-average molecular weight is 3,000 to 30,000 and the Mw/Mn as a molecular weight distribution is 0.8 to 3.0, and it is more preferable that the weight-average molecular weight is 5,000 to 20,000 and the Mw/Mn in terms of a molecular weight distribution is 1 to 2.5.

In the case where the anion multimer is formed, a chain transfer agent may be added. As the chain transfer agent, an alkylmercaptan is preferable. The chain transfer agent is preferably an alkylmercaptan having 10 or less carbon atoms or an alkylmercaptan substituted with an ether group or an ester group, and more preferably an alkylmercaptan having a logP value of 5 or less.

The amount of the anion monomer having a polymerizable group which is a raw material for the anion multimer included in the anion multimer is preferably 5% or less, and more preferably 1% or less.

The content of the halogen ions included in the anion multimer is preferably 10 ppm to 3,000 ppm or less, more preferably 10 ppm to 2,000 ppm, and still more preferably 10 ppm to 1,000 ppm.

Specific examples of the repeating unit including the anion X are shown below, but the present invention is not limited thereto.

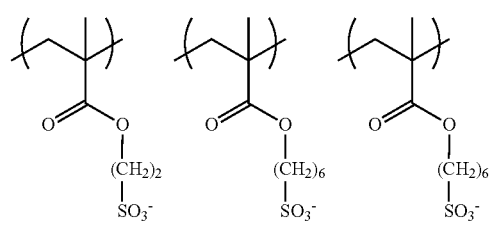

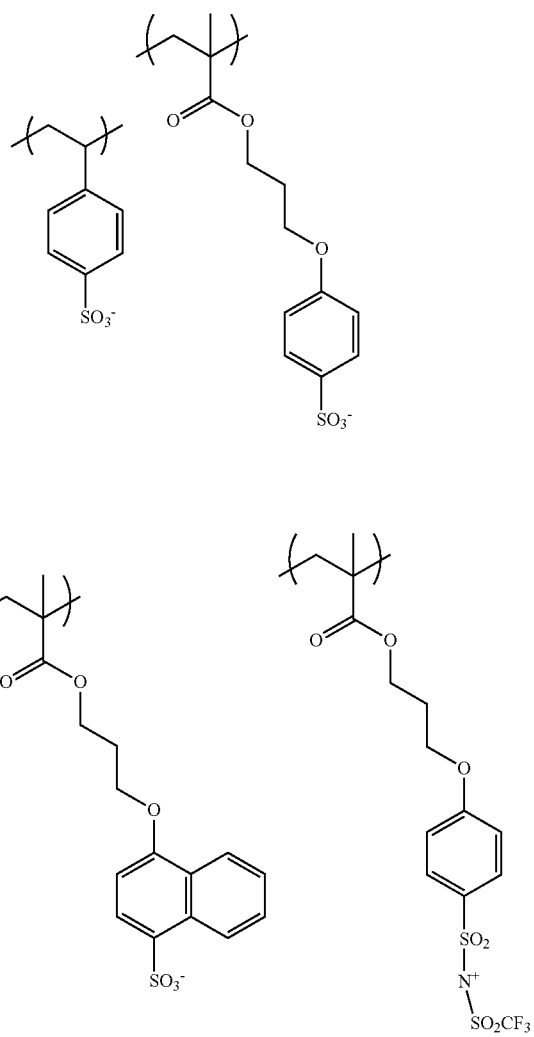

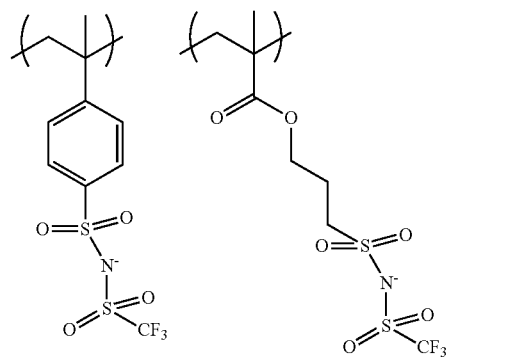

91
-continued
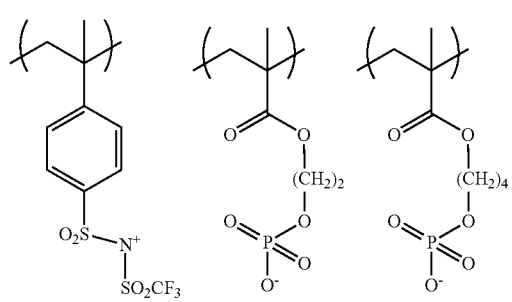
92
-continued
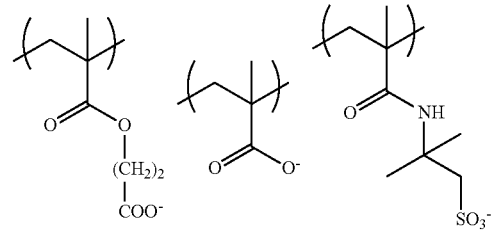
The following specific examples show a state where the anion structures are not dissociated, but it is certain that the state where the anion structures are dissociated is also included in the scope of the present invention.
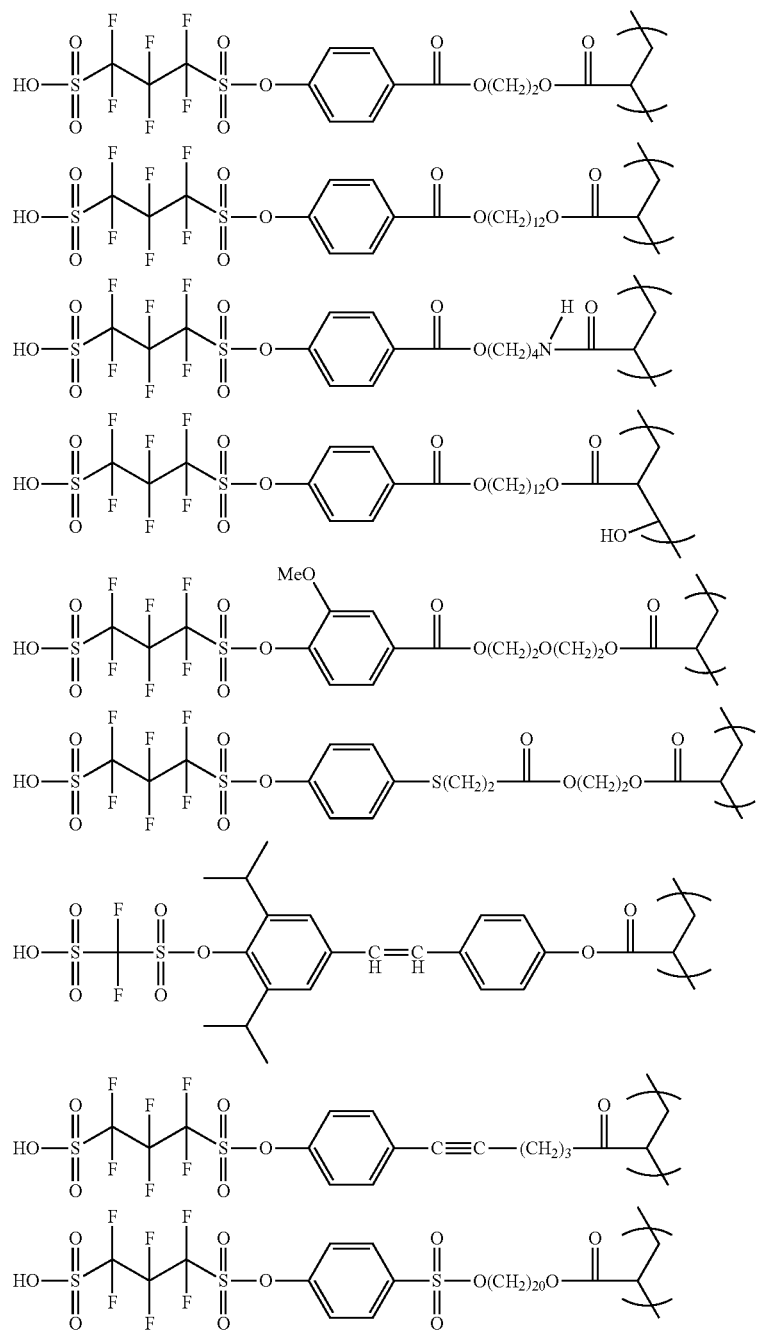

-continued
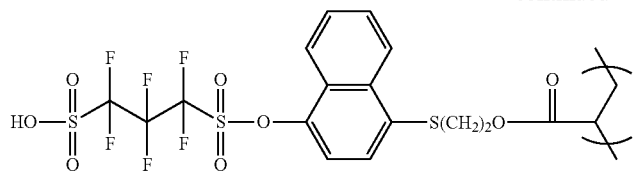
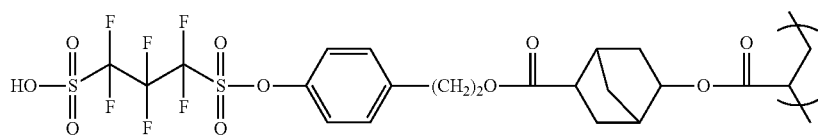
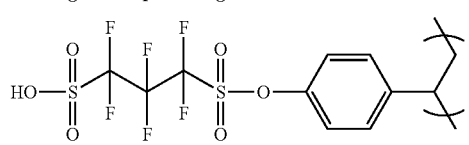
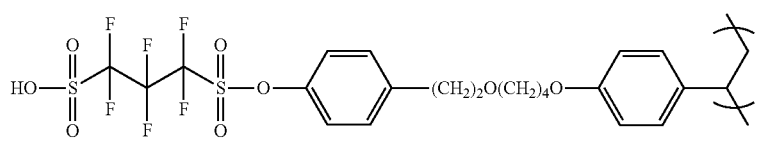
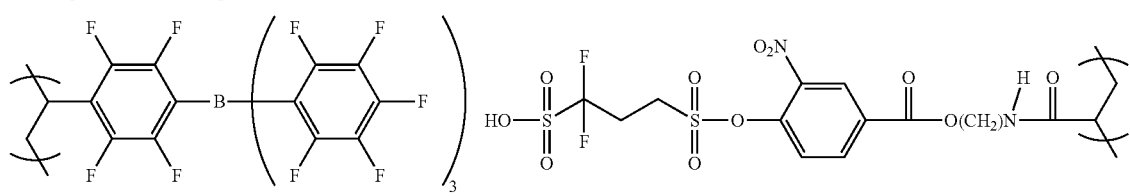
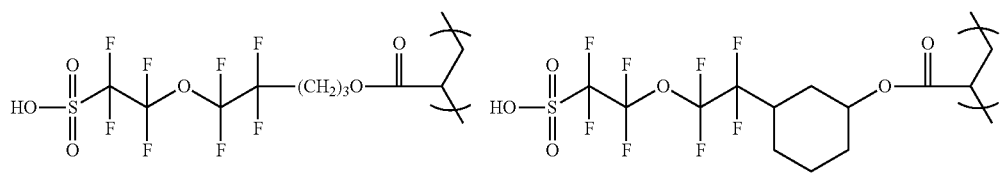
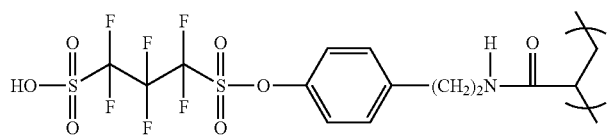
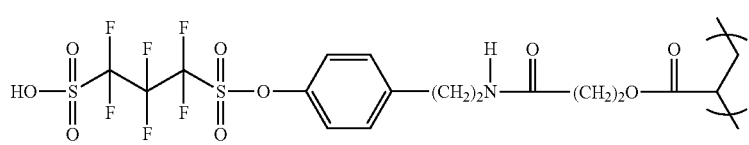
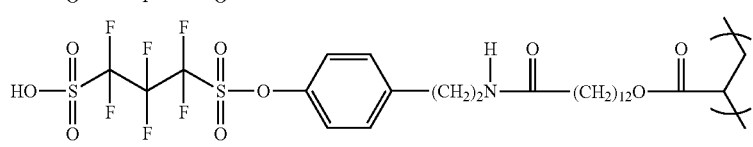
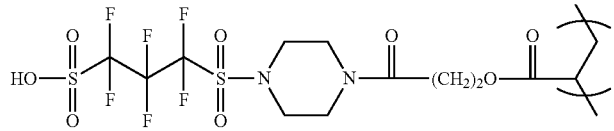
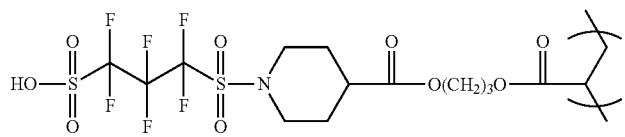

-continued
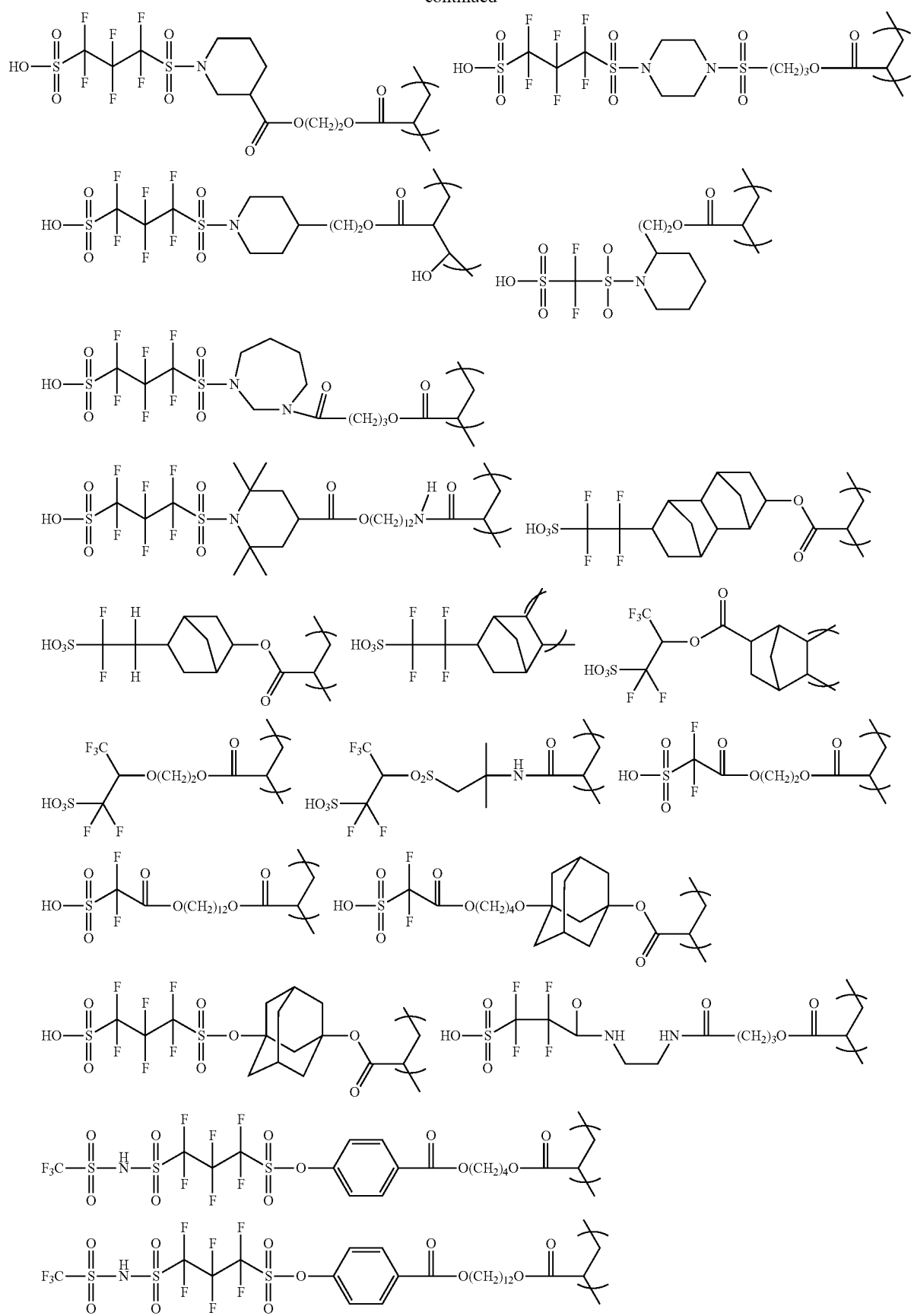

-continued
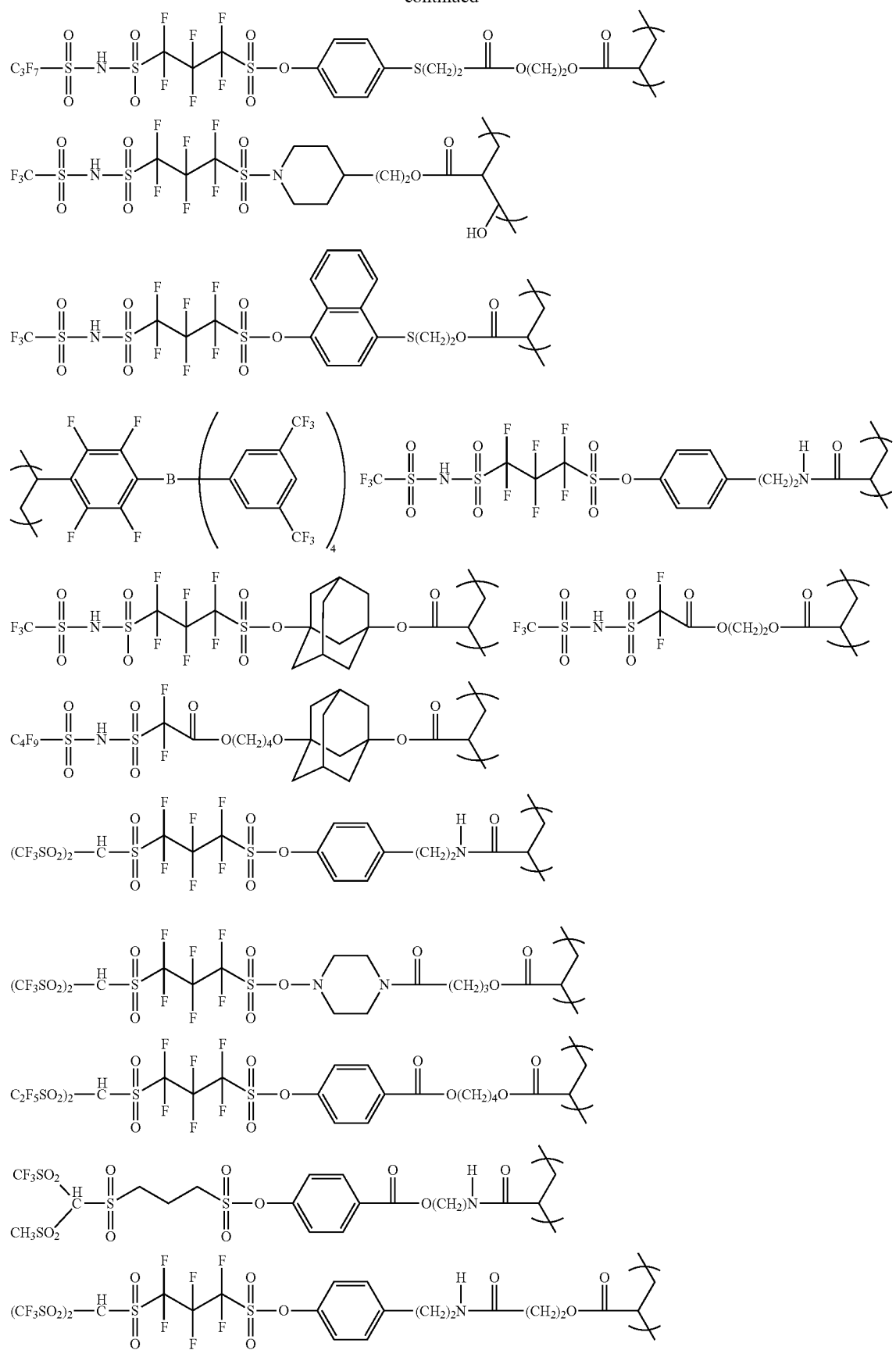

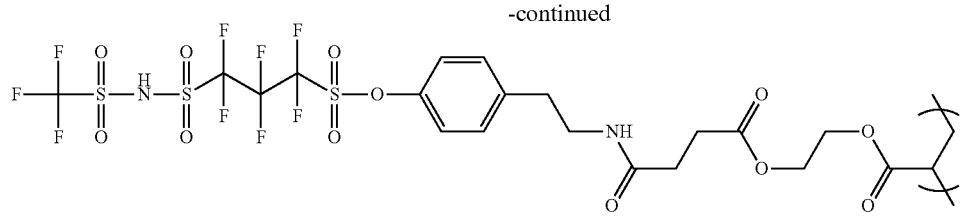
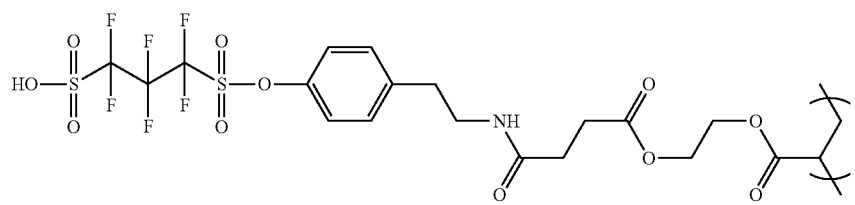
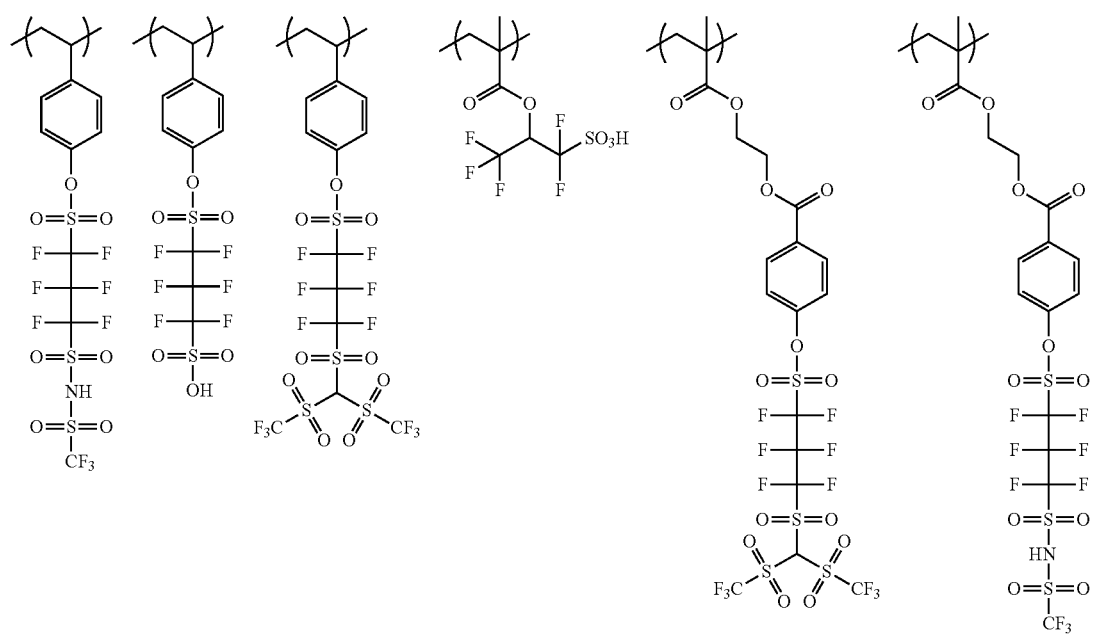
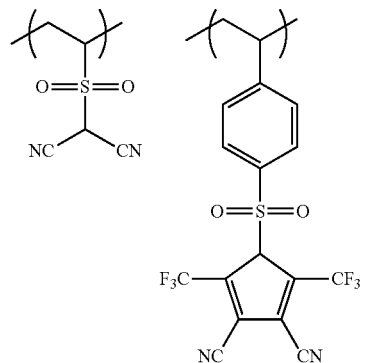
Examples of other repeating units that are preferably used in the colorant multimer of the present invention are shown below. It is certain that the present invention is not limited to these repeating units.
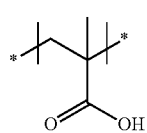
(B-1)

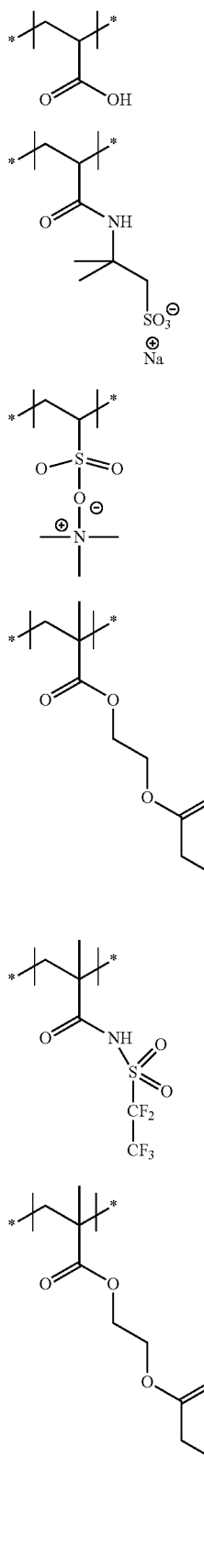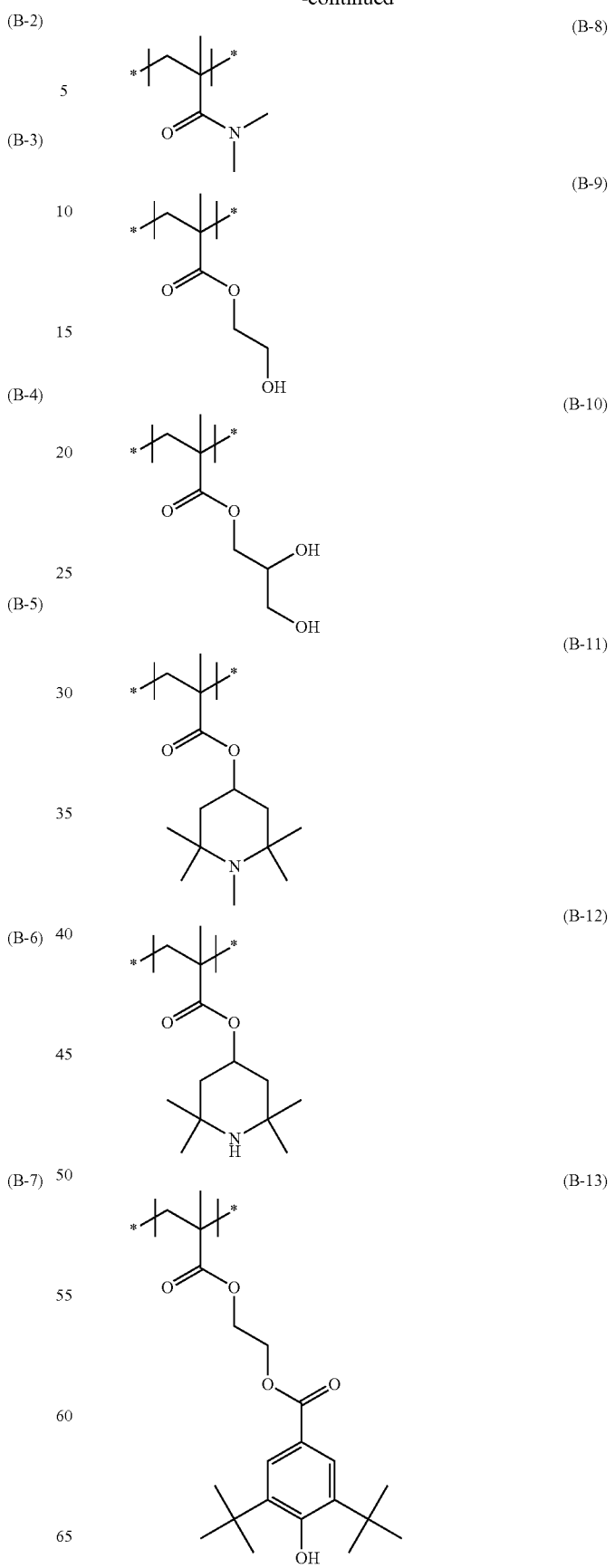

(B-14)
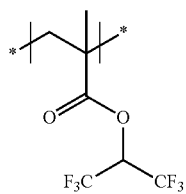
(B-15)
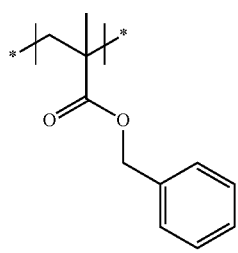
(B-16)
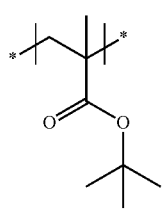
(B-17)
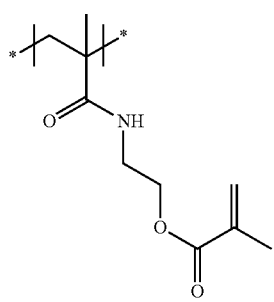
(B-18)
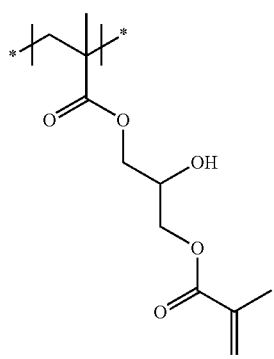
(B-19)
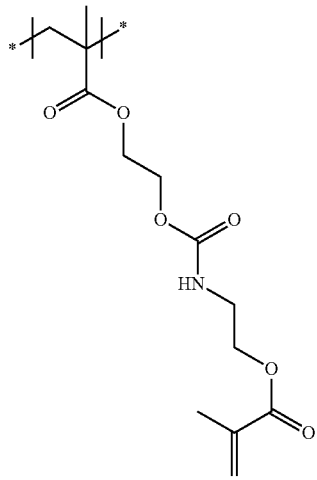
(B-20)
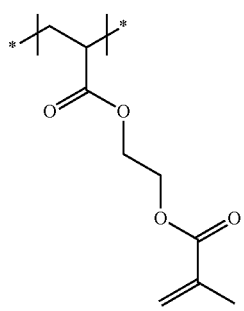
(B-21)
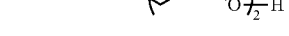
(B-22)
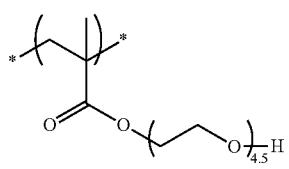
(B-23)
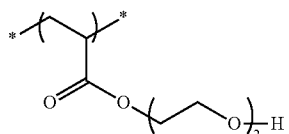
(B-24)
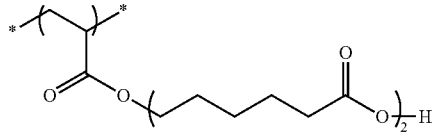
(B-25)
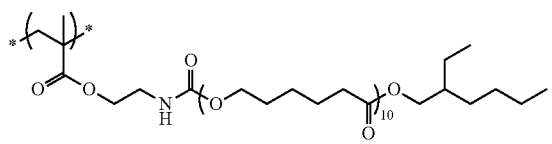

(B-26) 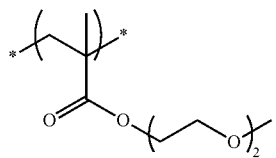
(B-27) 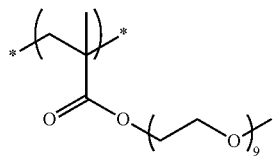
(B-28) 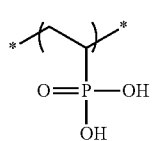
(B-29) 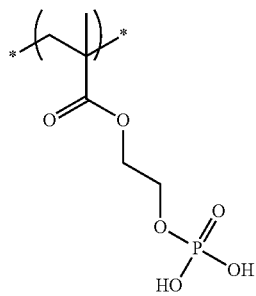
(B-30) 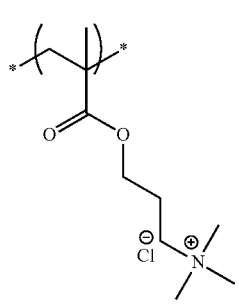
(B-31) 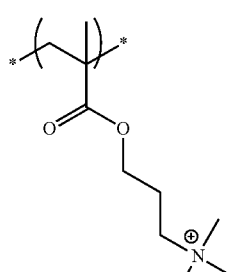
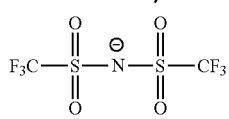
(B-32) 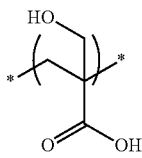
(B-33) 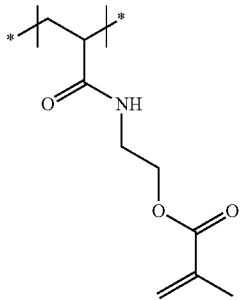
(B-34) 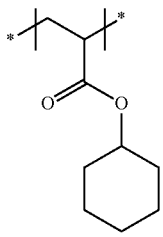
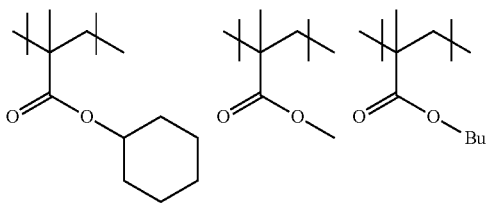
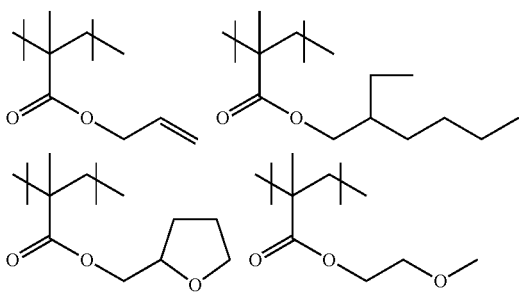
Examples of the compound represented by Formula (1), Formula (2), or Formula (3), of a high-molecular type, which can be used in the present invention are shown below, but are not limited thereto. In the following structures, the numbers on the right side in the parenthesis indicate the amounts (% by mole) of the respective structural units.

107 108
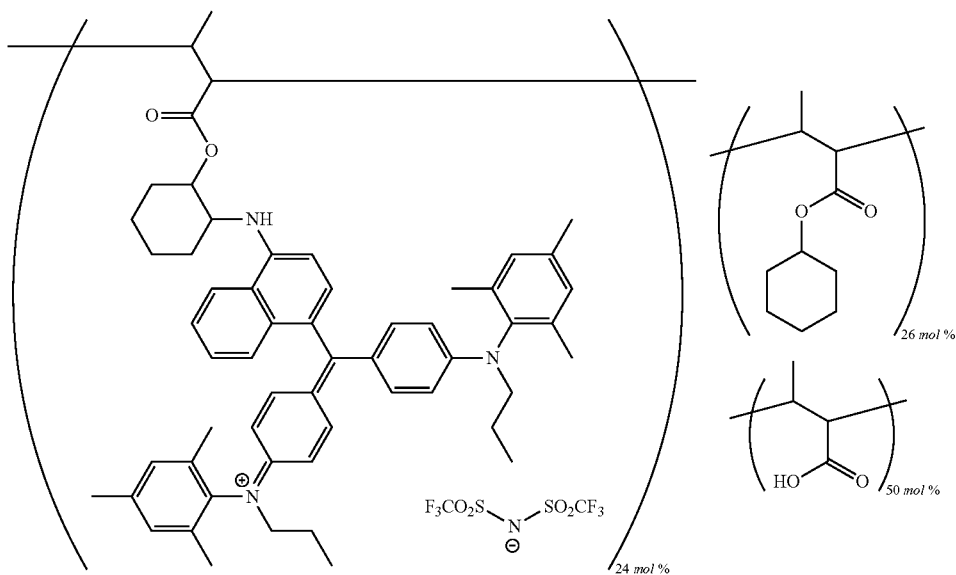
TAM201
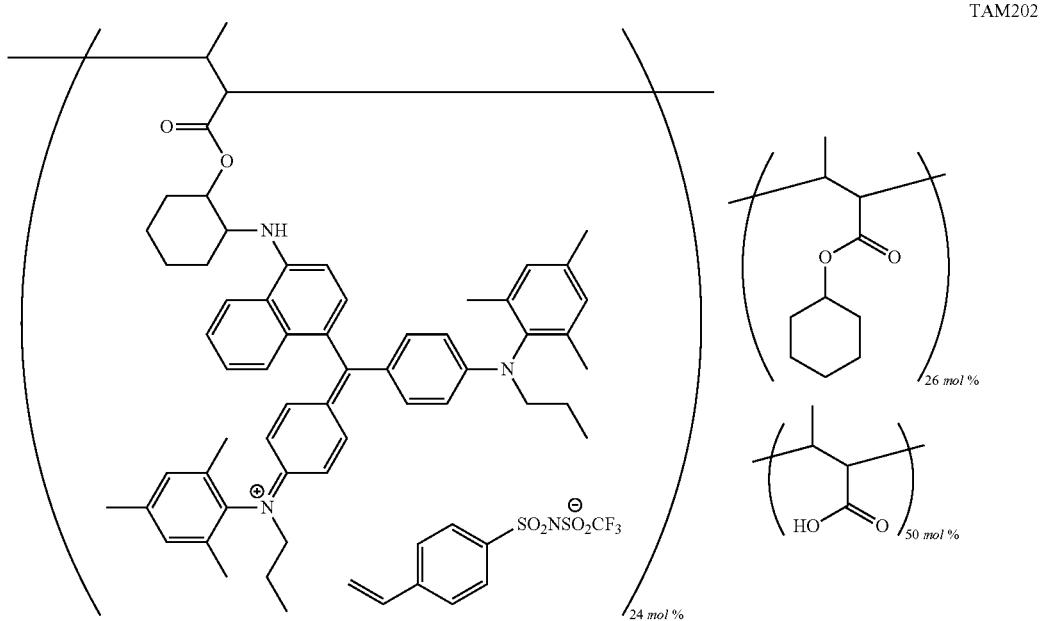
TAM202

-continued
TAM203
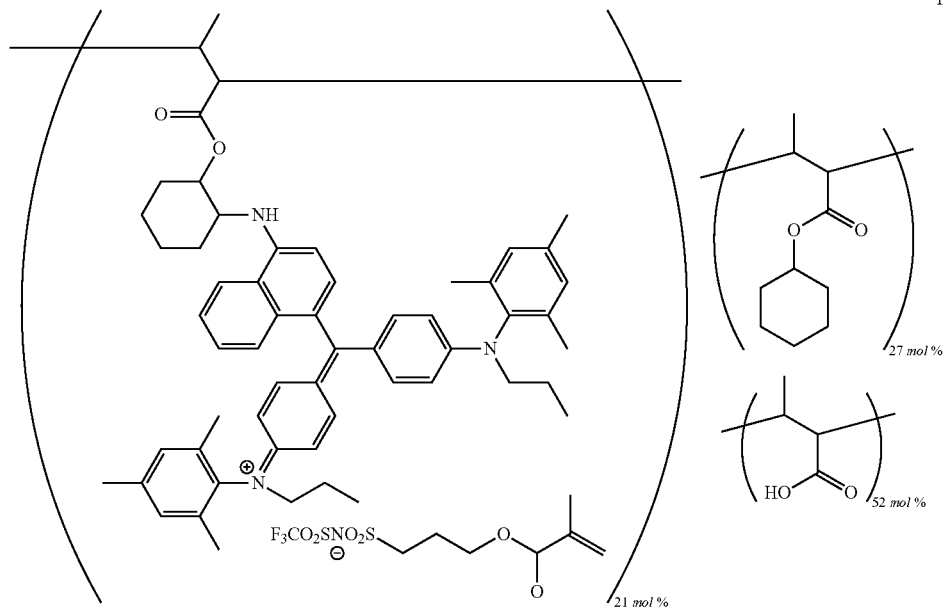
TAM204
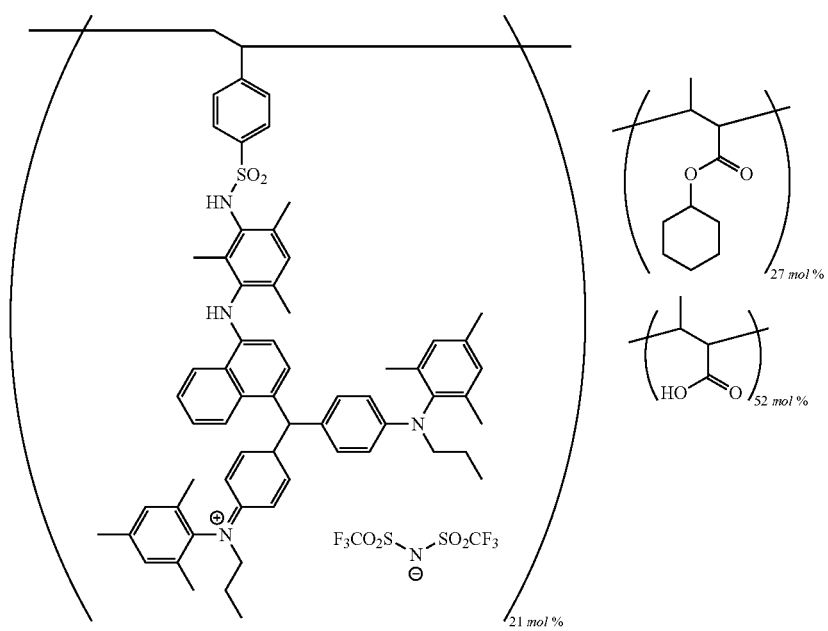

-continued
TAM205
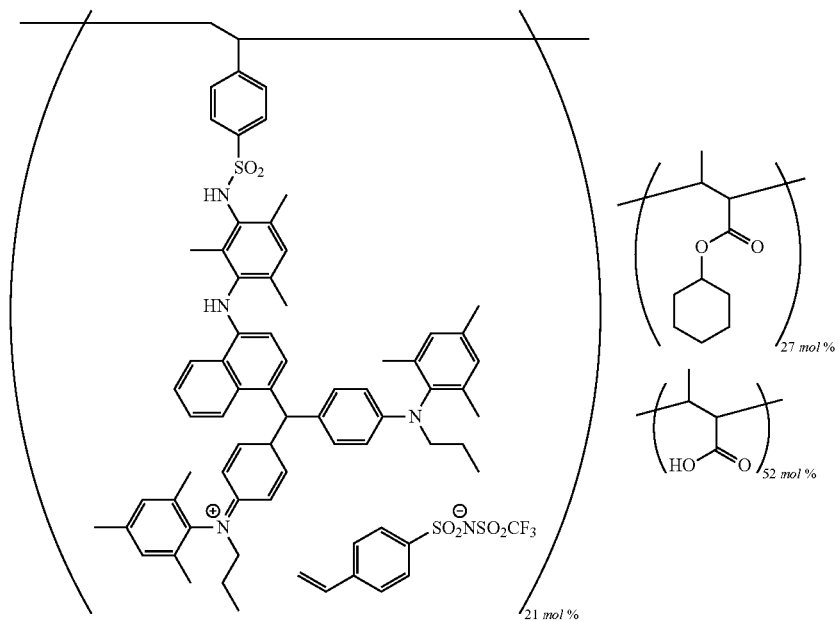
TAM206
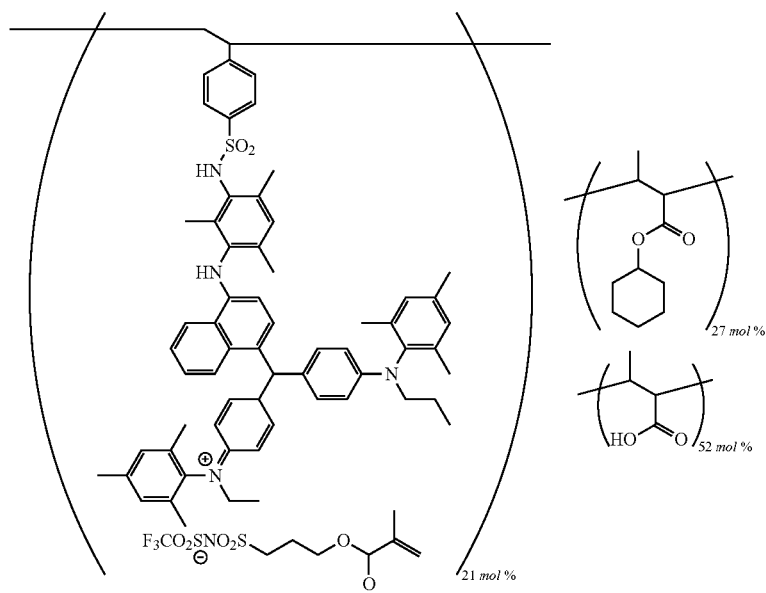

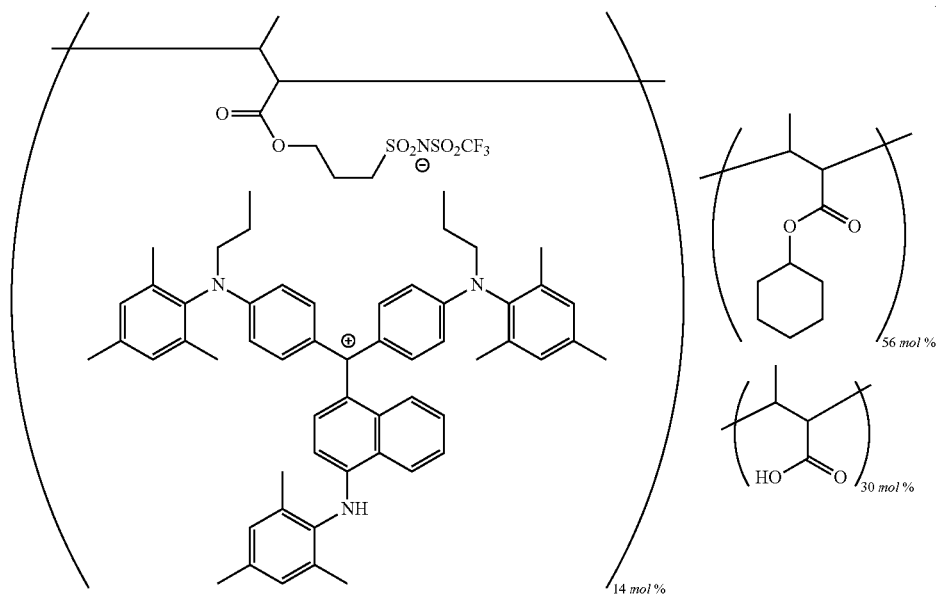
TAM251
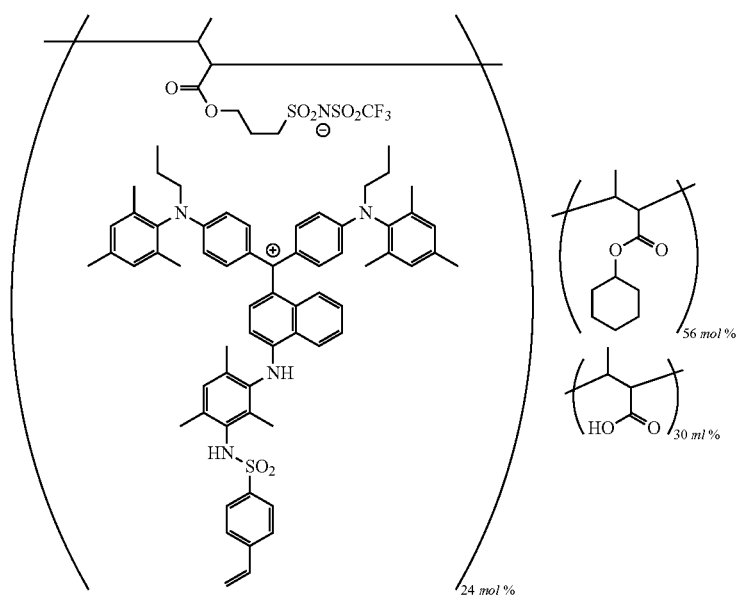
TAM252

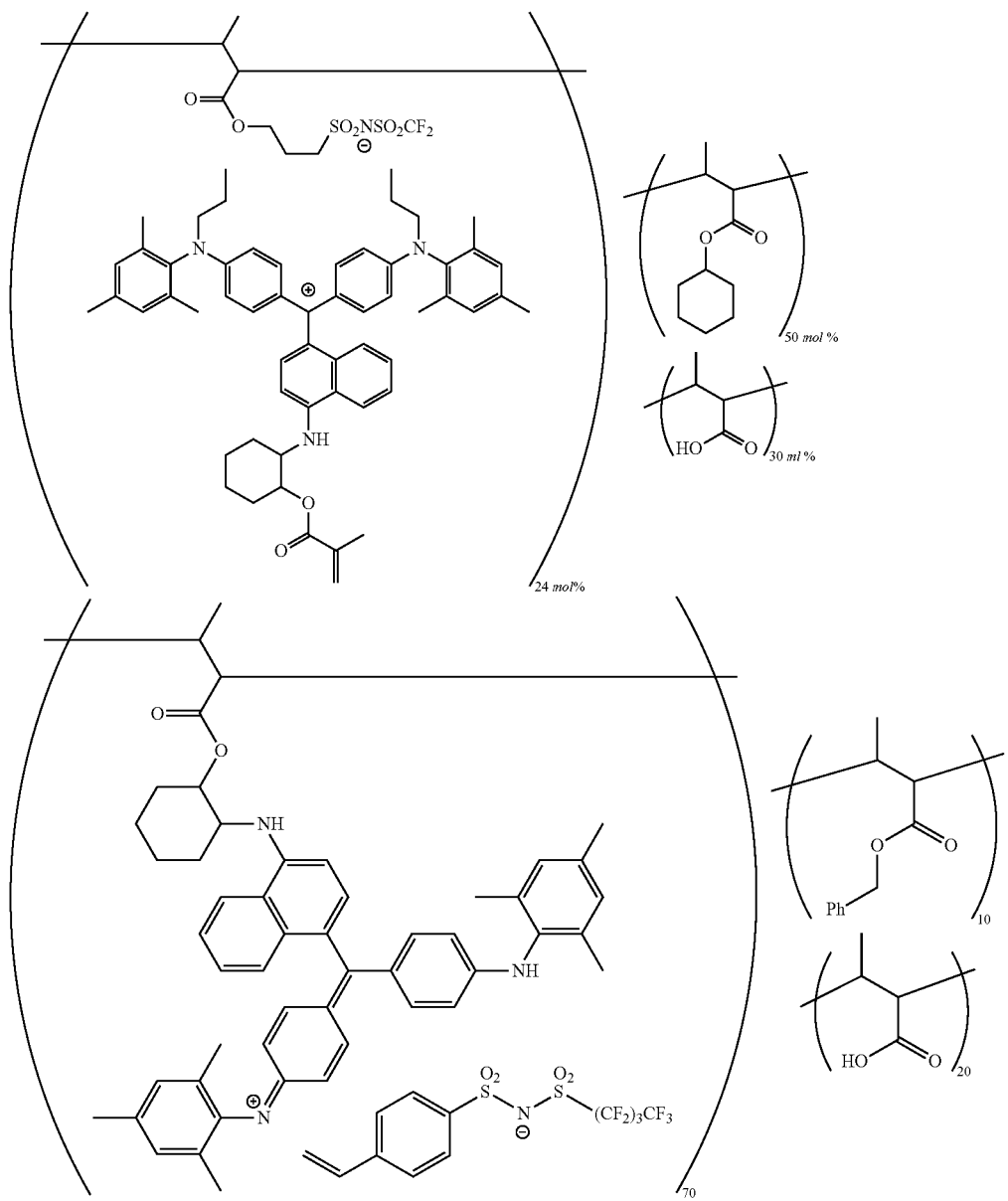

TAM253

<Xanthene Colorant>

The coloring curable resin composition of the present invention may contain a xanthene colorant. The xanthene colorant is a dye including a compound having a xanthene skeleton in the molecule. Examples of the xanthene colorant include C. I. Acid Red 51 (the descriptions of C. I. Acid Red are hereinafter omitted while only the numbers thereof are described, with the others shall be the same), 52, 87, 92, 94, 289, and 388, C. I. Acid Violet 9, 30, and 102, C. I. Basic Red 1 (Rhodamine 6G), 2, 3, 4, and 8, C. I. Basic Red 10 (Rhodamine B), 11, C. I. Basic Violet 10, 11, and 25, C. I. Solvent Red 218, C. I. Mordant Red 27, C. I. Reactive Red 36 (Rose Bengal B), Sulforhodamine G, the xanthene colorants described in JP2010-32999A, and the xanthene colorants described in JP4492760B. The xanthene colorant is preferably one which is dissolved in an organic solvent.

As the xanthene colorant, a dye including a compound represented by Formula (1a) (hereinafter referred to as a "compound (1a)" in some cases) is preferable. The compound (1a) may be a tautomer. In the case of using the compound (1a), the content of the compound (1a) in the xanthene colorant is preferably 50% by mass or more, more preferably 70% by mass or more, and still more preferably 90% by mass or more. Particularly, it is preferable that as the xanthene colorant, only the compound (1a) is used.

Formula (1a)

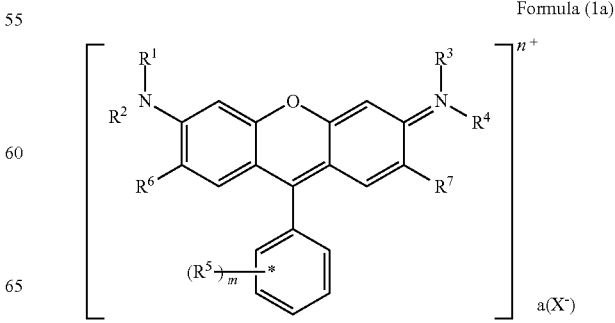

(In Formula (1a), $R^1$ to $R^4$ each independently represent a hydrogen atom, a monovalent saturated hydrocarbon group having 1 to 20 carbon atoms, which may have a substituent, or a monovalent aromatic hydrocarbon group having 6 to 10 carbon atoms, which may have a substituent, in which —$CH_2$— contained in the saturated hydrocarbon group may be substituted with —O—, —CO—, or —$NR^{11}$—.

$R^1$ and $R^2$ may be bonded to each other to form a ring including a nitrogen atom. $R^3$ and $R^4$ may be bonded to each other to form a ring including a nitrogen atom.

$R^5$ represents —OH, —$SO_3^-$, —$SO_3H$, —$SO_3^-Z^+$, —$CO_2H$, —$CO_2^-Z^+$, —$CO_2R^8$, —$SO_3R^8$, or —$SO_2NR^9R^{10}$.

$R^6$ and $R^7$ each independently represent a hydrogen atom or an alkyl group having 1 to 6 carbon atoms.

m represents an integer of 0 to 5. When m is 2 or more, a plurality of $R^5$'s may be the same as or different from each other.

a represents 0 or 1.

X represents a halogen atom.

n represents the total number of anions in the compound (1a).

$Z^+$ represents $N^+(R^{11})_4$, $Na^+$, or $K^+$, and four $R^{11}$'s may be the same as or different from each other.

$R^8$ represents a monovalent saturated hydrocarbon group having 1 to 20 carbon atoms, and the hydrogen atom contained in the saturated hydrocarbon group may be substituted with a halogen atom.

$R^9$ and $R^{10}$ each independently represent a hydrogen atom or a monovalent saturated hydrocarbon group having 1 to 20 carbon atoms, which may have a substituent, in which —$CH_2$— contained in the saturated aliphatic hydrocarbon group may be substituted with —O—, —CO—, —NH—, or —$NR^8$—, and $R^9$ and $R^{10}$ may be bonded to each other to form a 3- to 10-membered heterocycle including a nitrogen atom.

$R^{11}$ represents a hydrogen atom, a monovalent saturated hydrocarbon group having 1 to 20 carbon atoms, or an aralkyl group having 7 to 10 carbon atoms.)

Examples of the monovalent aromatic hydrocarbon group having 6 to 10 carbon atoms in $R^1$ to $R^4$ include a phenyl group, a tolyl group, a xylyl group, a mesityl group, a propylphenyl group, and a butylphenyl group. Among these, a tolyl group, xylyl group, mesityl group, and a propylphenyl group are preferable, and a toluyl group and a xylyl group, especially a 2,6-di-substituted xylyl group are particularly preferable.

Examples of the substituent which h may be contained in the aromatic hydrocarbon group include a halogen atom, —$R^8$, —OH, —$OR^8$, —$SO_3^-$, —$SO_3H$, —$SO_3^-Z^+$, —$CO_2H$, —$CO_2R^8$, —$SR^8$, —$SO_2R^8$, —$SO_3R^8$, and —$SO_2NR^9R^{10}$. Among these, as the substituent, —$SO_3^-$, —$SO_3H$, —$SO_3^-Z^+$ and —$SO_2NR^9R^{10}$ are preferable, and —$SO_3^-Z^+$ and —$SO_2NR^9R^{10}$ are more preferable. As —$SO_3^-Z^+$ in this case, —$SO_3^-N^+(R^{11})_4$ is preferable. When $R^1$ to $R^4$ are these groups, it is possible to form a color filter having reduced generation of foreign materials and excellent heat resistance, with the coloring curable resin composition of the present invention, including the compound (1a).

Examples of the ring formed by the mutual bonding of $R^1$ and $R^2$ and the ring formed by the mutual bonding of $R^3$ and $R^4$ include the following ones.

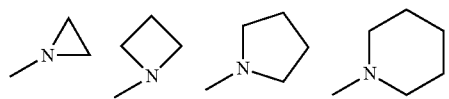

-continued

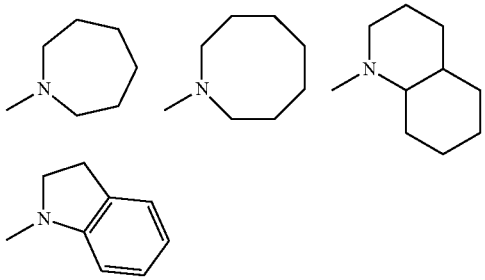

Among these, from the viewpoint of stability of the compound, the structures shown below are preferable.

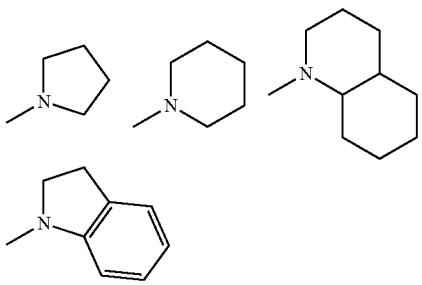

Examples of the monovalent saturated hydrocarbon group having 1 to 20 carbon atoms in $R^8$ to $R^{11}$ include a linear alkyl group such as a methyl group, an ethyl group, a propyl group, a butyl group, a pentyl group, a hexyl group, a heptyl group, an octyl group, a nonyl group, a decyl group, a dodecyl group, a hexadecyl group, and an eicosyl group; a branched alkyl group such as an isopropyl group, an isobutyl group, an isopentyl group, a neopentyl group, and a 2-ethylhexyl group; and an alicyclic saturated hydrocarbon group having 3 to 20 carbon atoms, such as a cyclopropyl group, a cyclopentyl group, a cyclohexyl group, a cycloheptyl group, a cyclooctyl group, and a tricyclodecyl group.

Among these, a methyl group, an ethyl group, a propyl group, an isopropyl group, a butyl group, a pentyl group, a hexyl group, a heptyl group, an octyl group, and a 2-ethylhexyl group are preferable, and a propyl group, an isopropyl group, a butyl group, a hexyl group, and a 2-ethylhexyl group are particularly preferable.

The hydrogen atom included in the monovalent saturated hydrocarbon group having 1 to 20 carbon atoms may be substituted with, for example, an aromatic hydrocarbon group having 6 to 10 carbon atoms, or a halogen atom.

Examples of —$OR^8$ include a methoxy group, an ethoxy group, a propoxy group, a butoxy group, a pentyloxy group, a hexyloxy group, a heptyloxy group, an octyloxy group, a 2-ethylhexyloxy group, and an eicosyloxy group. Among these, a methoxy group, an ethoxy group, a propoxy group, and a butoxy group are preferable.

Examples of —$CO_2R^8$ include a methoxycarbonyl group, ethoxycarbonyl, a propoxycarbonyl group, a tert-butoxycarbonyl group, a hexyloxycarbonyl group, and an eicosyloxycarbonyl group. Among these, a methoxycarbonyl group, an ethoxycarbonyl, and a propoxycarbonyl group are preferable.

Examples of —$SR^8$ include a methylsulfanyl group, an ethylsulfanyl group, a butylsulfanyl group, a hexylsulfanyl group, a decylsulfanyl group, and an eicosylsulfanyl group.

Examples of —SO$_2$R$^8$ include a methylsulfonyl group, an ethylsulfonyl group, a butylsulfonyl group, a hexylsulfonyl group, a decylsulfonyl group, and an eicosylsulfonyl group.

Examples of —SO$_3$R$^8$ include a methoxysulfonyl group, an ethoxy sulfonyl group, a propoxysulfonyl group, a tert-butoxysulfonyl group, a hexyloxysulfonyl group, and eicosyloxysulfonyl group.

Examples of —SO$_2$NR$^9$R$^{10}$ include a sulfamoyl group;

an N-monosubstituted sulfamoyl group such as an N-methylsulfamoyl group, an N-ethylsulfamoyl group, an N-propylsulfamoyl group, an N-isopropylsulfamoyl group, an N-butylsulfamoyl group, an N-isobutylsulfamoyl group, an N-sec-butylsulfamoyl group, an N-tert-butylsulfamoyl group, an N-pentylsulfamoyl group, an N-(1-ethylpropyl)sulfamoyl group, an N-(1,1-dimethylpropyl)sulfamoyl group, an N-(1,2-dimethylpropyl)sulfamoyl group, an N-(2-ethylhexyl)sulfamoyl group, an N-(2,2-dimethylpropyl)sulfamoyl group, an N-(1-methylbutyl)sulfamoyl group, an N-(2-methylbutyl)sulfamoyl group, an N-(3-methylbutyl)sulfamoyl group, an N-cyclopentylsulfamoyl group, an N-hexylsulfamoyl group, an N-(1,3-dimethylbutyl)sulfamoyl group, an N-(3,3-dimethylbutyl)sulfamoyl group, an N-heptylsulfamoyl group, an N-(1-methylhexyl)sulfamoyl group, an N-(1,4-dimethylpentyl)sulfamoyl group, an N-octylsulfamoyl group, an N-(2-ethylhexyl)sulfamoyl group, an N-(1,5-dimethyl)hexylsulfamoyl group, and an N-(1,1,2,2-tetramethylbutyl)sulfamoyl group; and an N,N-disubstituted sulfamoyl group such as an N,N-dimethylsulfamoyl group, an N,N-ethylmethylsulfamoyl group, an N,N-diethylsulfamoyl group, an N,N-propylmethylsulfamoyl group, an N,N-isopropylmethylsulfamoyl group, an N,N-tert-butylmethylsulfamoyl group, an N,N-butylethylsulfamoyl group, an N,N-bis(1-methylpropyl)sulfamoyl group, and an N,N-heptylmethylsulfamoyl group.

Among these, an N-methylsulfamoyl group, an N-ethylsulfamoyl group, an N-propylsulfamoyl group, an N-isopropylsulfamoyl group, an N-butylsulfamoyl group, an N-pentylsulfamoyl group, and an N-(2-ethylhexyl)sulfamoyl group are preferable, and an N-methylsulfamoyl group, an N-ethylsulfamoyl group, an N-propylsulfamoyl group, an N-butylsulfamoyl group, and an N-(2-ethylhexyl)sulfamoyl group are more preferable.

The monovalent saturated hydrocarbon group having 1 to 20 carbon atoms in R$^9$ or R$^{10}$ may have a substituent and examples of the substituent include a hydroxy group and a halogen atom.

R$^5$ represents —OH, —SO$_3^-$, —SO$_3$H, —SO$_3^-$Z$^+$, —CO$_2$H, —CO$_2^-$Z$^+$, —CO$_2$R$^8$, —SO$_3$R$^8$, or —SO$_2$NR$^9$R$^{10}$.

R$^5$ is preferably —CO$_2$H, —CO$_2^-$Z$^+$, —CO$_2$R$^8$, —CO$_2$NHR$^9$, —SO$_3^-$, —SO$_3^-$Z$^+$, —SO$_3$H, —SO$_2$R$^8$, or —SO$_2$NHR$^9$, and more preferably —SO$_3^-$, —SO$_3^-$Z$^+$, —SO$_3$H, or —SO$_2$NHR$^9$.

m is preferably an integer of 1 to 4, and more preferably 1 or 2.

Examples of the alkyl group having 1 to 6 carbon atoms in R$^6$ and R$^7$ include alkyl groups having 1 to 6 carbon atoms among the alkyl groups exemplified for the monovalent saturated hydrocarbon having 1 to 20 carbon atoms as described above.

Examples of the aralkyl group having 7 to 10 carbon atoms in R$^{11}$ include a benzyl group, a phenylethyl group, and a phenylbutyl group.

Z$^+$ is N$^+$(R$^{11}$)$_4$, Na$^+$, or K$^+$, and preferably N$^+$(R$^{11}$)$_4$.

N$^+$(R$^{11}$)$_4$ is preferably a monovalent saturated hydrocarbon group in which at least two of four R$^{11}$'s have 5 to 20 carbon atoms. Further, the total number of carbon atoms of four R$^{11}$'s is preferably 20 to 80, and more preferably 20 to 60. In the case where N$^+$(R$^{11}$)$_4$ is present in the compound (1a), a color filter having less foreign materials can be formed from the coloring curable resin composition of the present invention, including the compound (1a), in which R$^{11}$ is one of these groups.

As the compound (1a), a compound represented by Formula (3a) (hereinafter referred to as a "compound (3a)" in some cases) is also preferable. The compound (3a) may be a tautomer thereof.

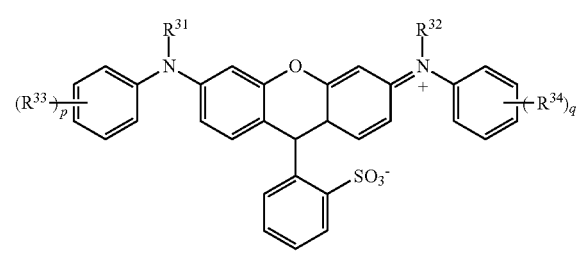

(3a)

(In Formula (3a), R$^{31}$ and R$^{32}$ each independently represent a monovalent saturated hydrocarbon group having 1 to 10 carbon atoms. The hydrogen atom contained in the monovalent saturated hydrocarbon group having 1 to 10 carbon atoms may be substituted with an aromatic hydrocarbon group having 6 to 10 carbon atoms, or a halogen atom. The hydrogen atom contained in the aromatic hydrocarbon group having 6 to 10 carbon atoms may be substituted with an alkoxy group having 1 to 3 carbon atoms, and —CH$_2$— contained in the monovalent saturated hydrocarbon group having 1 to 10 carbon atoms may be substituted with —O—, —CO—, or —NR$^{11}$—.

R$^{33}$ and R$^{34}$ each independently represent an alkyl group having 1 to 4 carbon atoms, an alkylsulfanyl group having 1 to 4 carbon atoms, or an alkylsulfonyl group having 1 to 4 carbon atoms.

R$^{31}$ and R$^{33}$ may be bonded to each other to form a ring containing a nitrogen atom, and R$^{32}$ and R$^{34}$ may be bonded to each other to form a ring containing a nitrogen atom.

p and q each independently represent an integer of 0 to 5. When p is 2 or more, a plurality of R$^{33}$'s may be the same as or different from each other. When q is 2 or more, a plurality of R$^{34}$'s may be the same as or different from each other.

R$^{11}$ has the same definition as R$^{11}$ in Formula (1a)).

Examples of the monovalent saturated hydrocarbon group having 1 to 10 carbon atoms in R$^{31}$ and R$^{32}$ include the monovalent saturated hydrocarbon group having 1 to 10 carbon atoms among the monovalent saturated hydrocarbon groups having 1 to 10 carbon atoms, explained for R$^8$ in Formula (1a). Among these, a methyl group, an ethyl group, a propyl group, a butyl group, a hexyl group, and a 2-ethylhexyl group are preferable. Examples of the aromatic hydrocarbon group having 6 to 10 carbon atoms, which may be included as the substituent, include the monovalent aromatic hydrocarbon group having 6 to 10 carbon atoms, explained for R$^1$ in Formula (1a).

Examples of the alkoxy group having 1 to 3 carbon atoms, which a hydrogen atom contained in the aromatic hydrocarbon group having 6 to 10 carbon atoms may be substituted include a methoxy group, an ethoxy group, and a propoxy group.

$R^{31}$ and $R^{32}$ each independently represent a monovalent saturated hydrocarbon group having 1 to 3 carbon atoms.

Examples of the alkyl group having 1 to 4 carbon atoms in $R^{33}$ and $R^{34}$ include a methyl group, an ethyl group, a propyl group, a butyl group, an isopropyl group, an isobutyl group, a sec-butyl group, and a tert-butyl group. Among these, a methyl group, an ethyl group, and a propyl group are preferable.

Examples of the alkylsulfanyl group having 1 to 4 carbon atoms in $R^{33}$ and $R^{34}$ include a methylsulfanyl group, an ethylsulfanyl group, a propylsulfanyl group, a butylsulfanyl group, and an isopropylsulfanyl group.

Examples of the alkylsulfonyl group having 1 to 4 carbon atoms in $R^{33}$ and $R^{34}$ include a methylsulfonyl group, an ethylsulfonyl group, a propylsulfonyl group, a butylsulfonyl group, and an isopropylsulfonyl group.

p and q are preferably an integer of 0 to 2, and more preferably 0 or 1.

Examples of the compound (1a) include compounds represented by Formulae (1-1) to (1-43). Further, in the formulae, R represents a monovalent saturated hydrocarbon group having 1 to 20 carbon atoms, and is preferably a branched alkyl group having 6 to 12 carbon atoms, and more preferably a 2-ethylhexyl group.

1-1

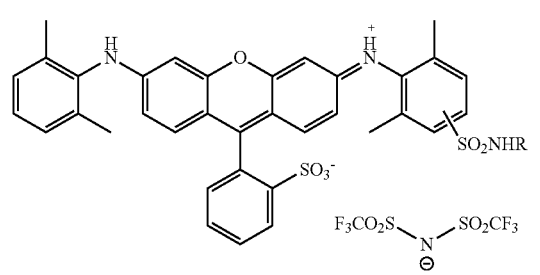

1-2

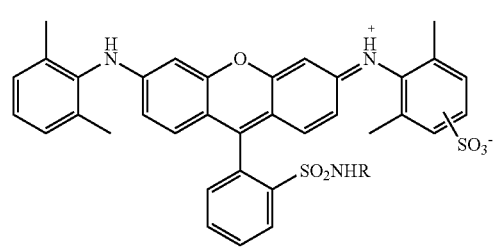

1-3

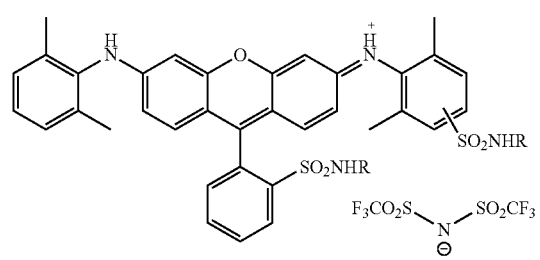

1-4

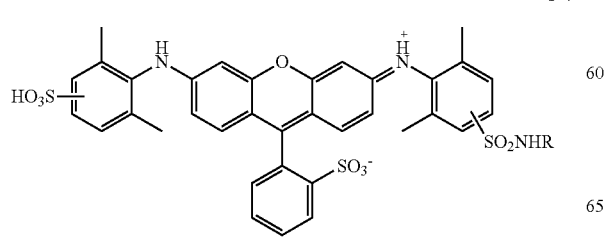

1-5

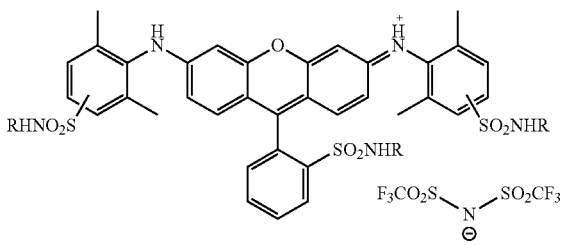

1-6

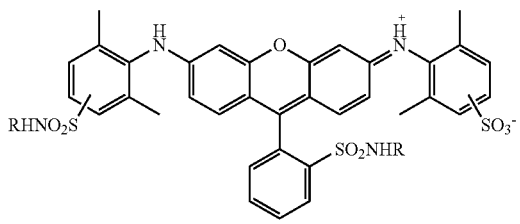

1-7

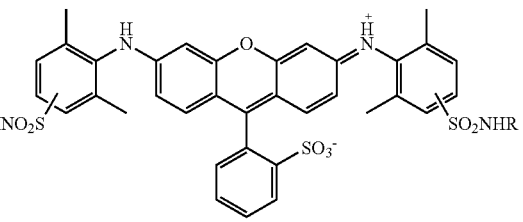

1-8

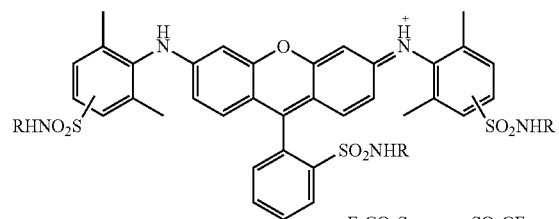

1-9

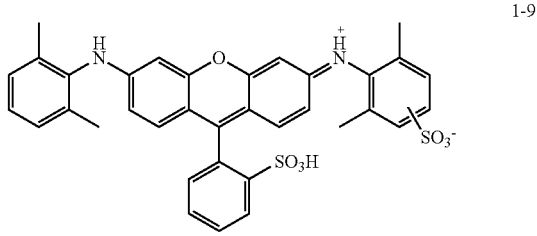

1-10

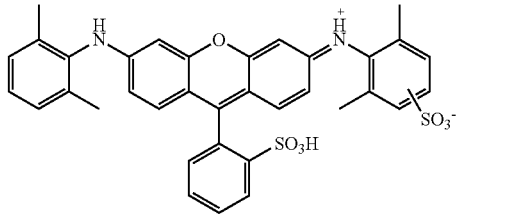

1-11
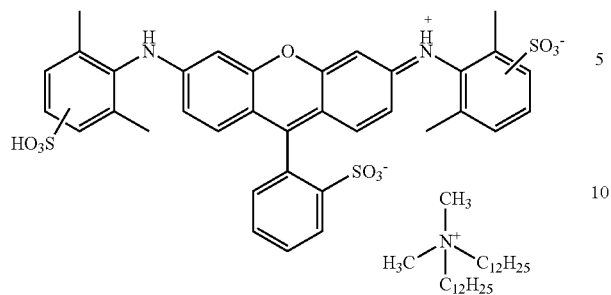
1-12
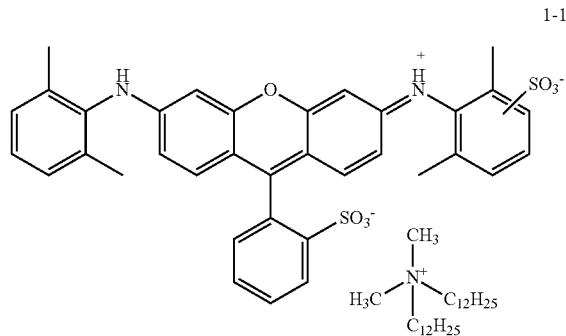
1-13
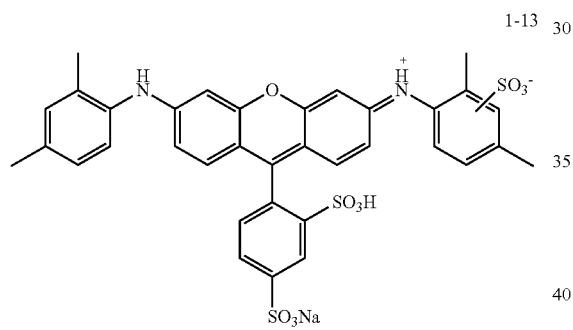
1-14
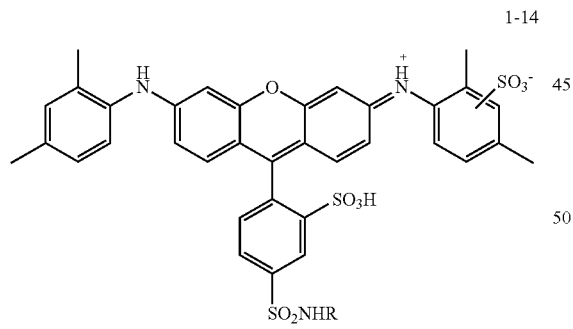
1-15
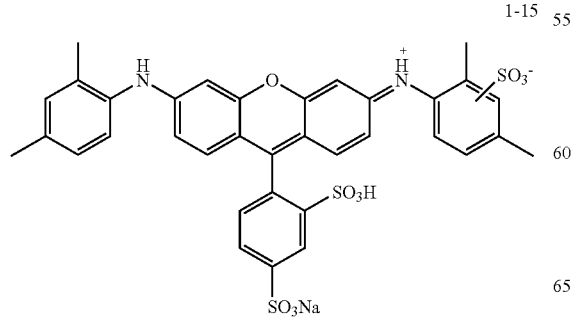
1-16
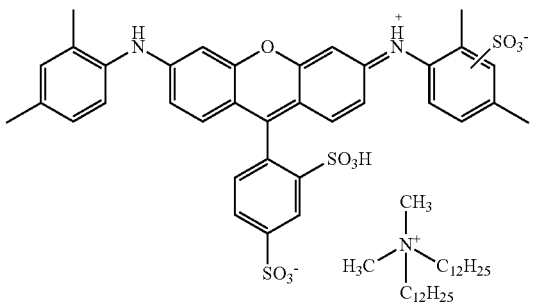
1-17
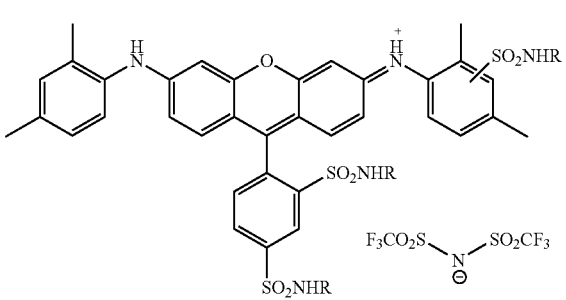
1-18
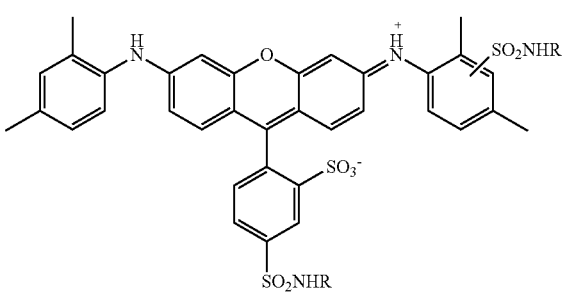
1-19
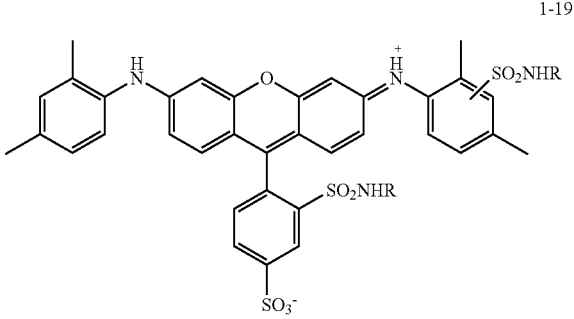
1-20
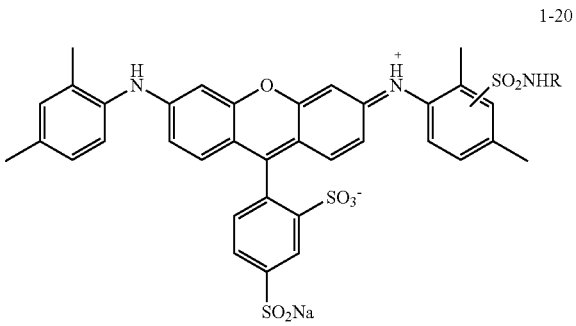

-continued
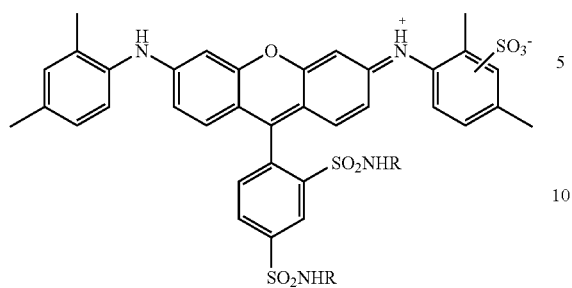
1-21
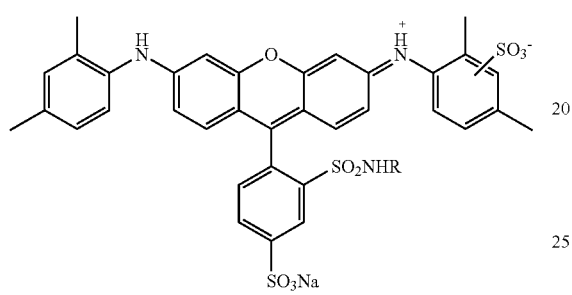
1-22
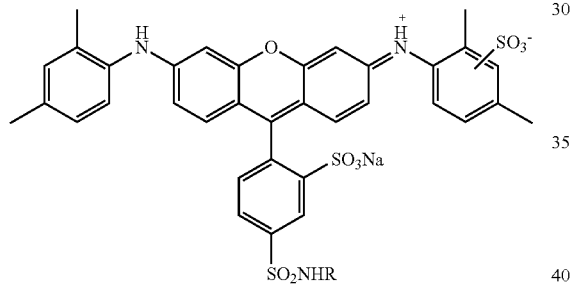
1-23
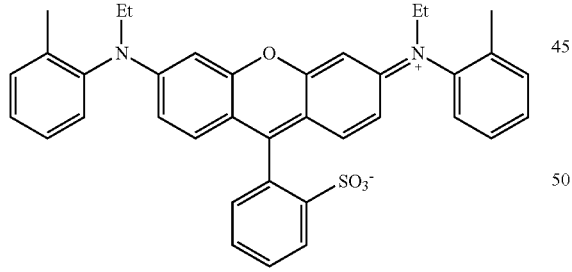
1-24
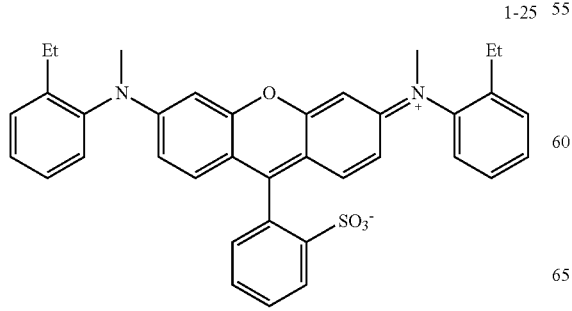
1-25
-continued
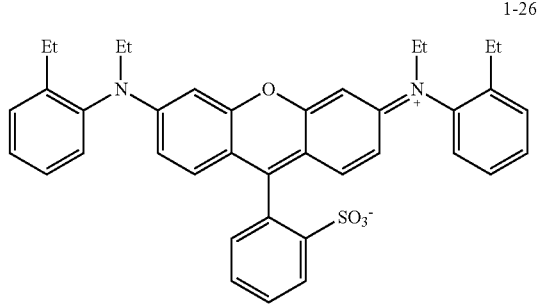
1-26
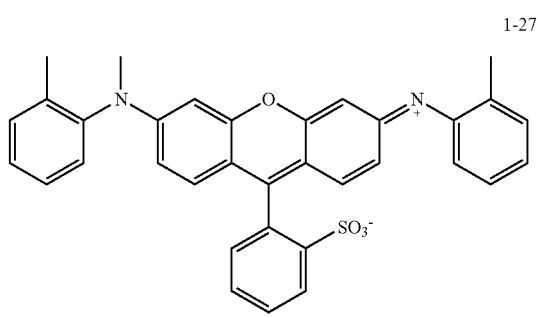
1-27
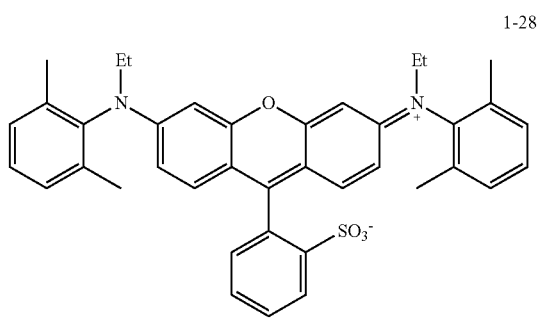
1-28
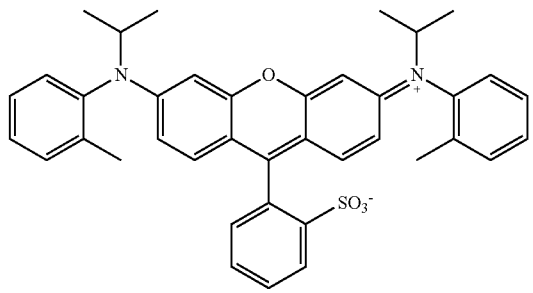
1-29
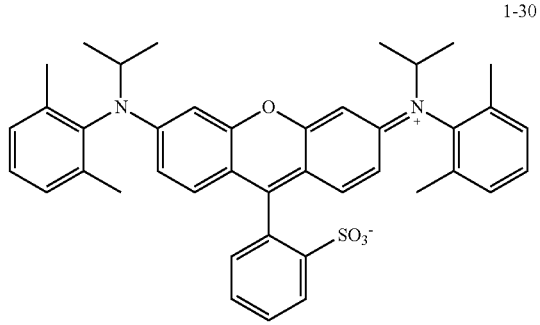
1-30

1-31
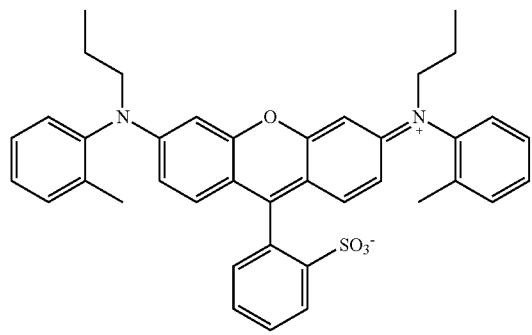
1-32
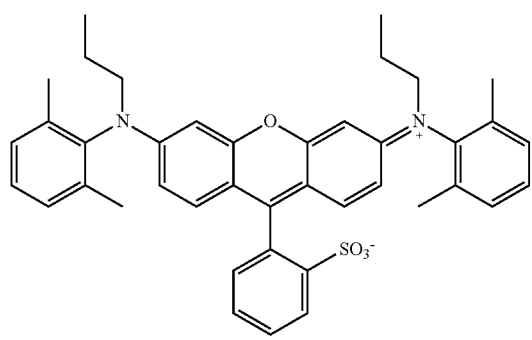
1-33
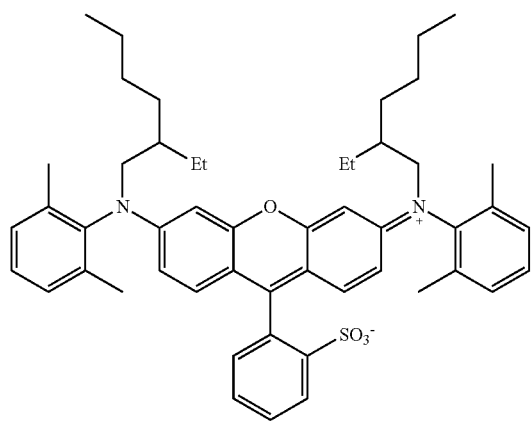
1-34
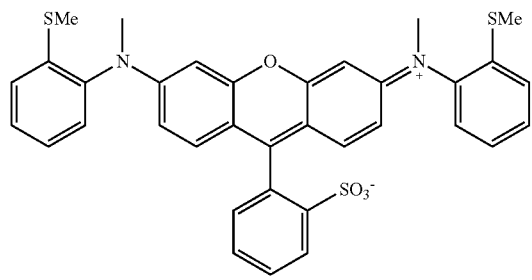
1-35
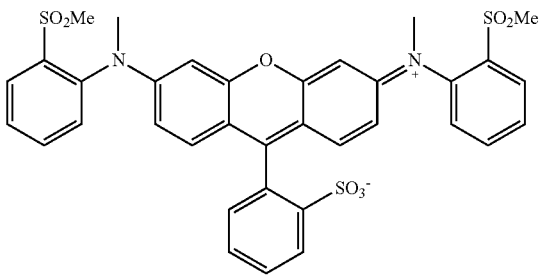
1-36
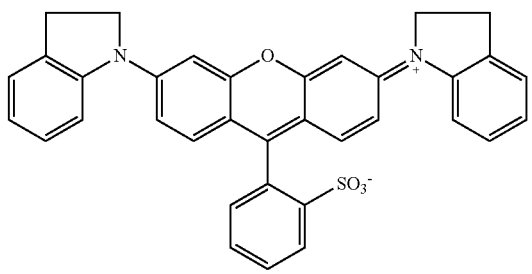
1-37
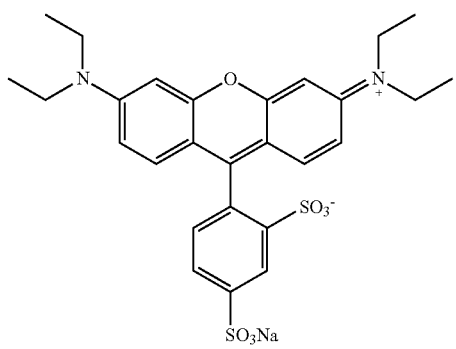
1-38
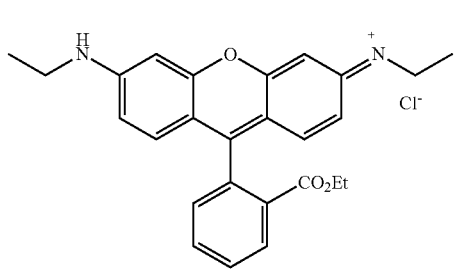
1-39
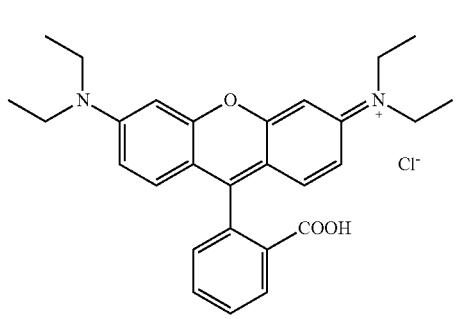

-continued

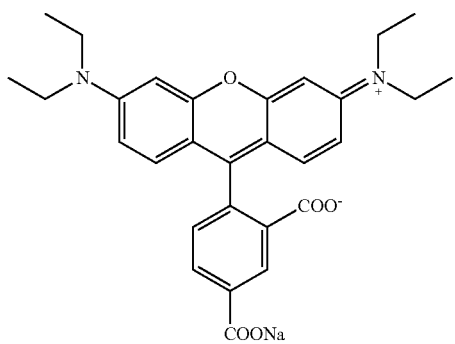

1-40

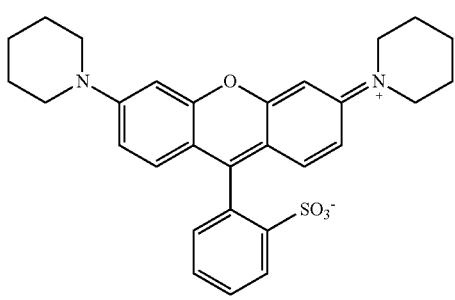

1-41

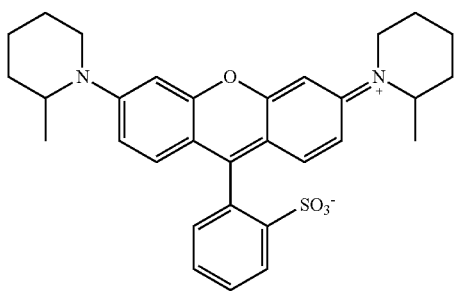

1-42

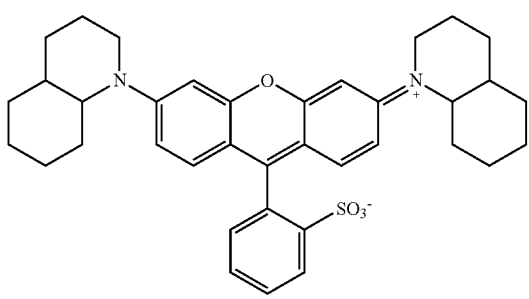

1-43

Among the exemplary compounds, sulfonamides of C. I. Acid Red 289, quaternary ammonium salts of C. I. Acid Red 289, sulfonamides of C. I. Acid Violet 102, or quaternary ammonium salts of C. I. Acid Violet 102 are preferable. Examples of such the compound include compounds represented by Formula (1-1) to (1-8), (1-11), or (1-12).

Furthermore, from the viewpoint that the solubility in an organic solvent is excellent, a compound represented by any one of Formulae (1-24) to (1-33) is also preferable.

As the xanthene colorant, a commercially available xanthene colorant (for example, "Chugai Aminol Fast Pink R-H/C" manufactured by Chugai Kasei K. K, "Rhodamin 6G" manufactured by Taoka Chemical Co., Ltd.) can be used. Further, it also can be synthesized using a commercially available xanthene colorant as a starting raw material with reference to JP2010-32999A, the disclosure of which is incorporated herein by reference.

<Dipyrromethene-Based Metal Complex Compound>

The coloring curable resin composition of the present invention may contain a dipyrromethene-based metal complex compound.

A dipyrromethene-based metal complex compound in which a compound represented by General Formula (I) is coordinated with a metal atom or metal compound will be described in detail.

General Formula (I)

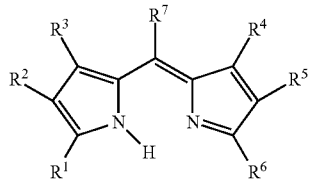

In General Formula (I), $R^1$ to $R^6$ each independently represent a hydrogen atom or a monovalent substituent which can be exemplified as the substituent group A as described above, and $R^7$ represents a hydrogen atom, a halogen atom, an alkyl group, an aryl group, or a heterocyclic group.

In the case where the monovalent group as described above can further be substituted, it may be substituted with any one of the respective groups as described above. Further, in the case where the monovalent group has two or more substituents, the substituents may be the same as or different from each other.

In General Formula (I), $R^1$ and $R^2$, $R^2$ and $R^3$, $R^4$ and $R^5$, and $R^5$ and $R^6$ may be independently bonded to each other to form a 5-, 6-, or 7-membered ring. Examples of the ring thus formed include a saturated ring and an unsaturated ring. Examples of the 5-, 6-, or 7-membered saturated ring or unsaturated ring include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring, and a pyridazine ring, and preferably a benzene ring and a pyridine ring.

Furthermore, in the case where the 5-, 6-, or 7-membered ring thus formed is a group which can further be substituted, it may be substituted with any one of the substituent group A, and in the case where the 5-, 6-, or 7-membered ring thus formed is substituted with 2 or more substituents, the substituents may be the same as or different from each other.

Moreover, the preferred range of $R^7$ in General Formula (I) has the same definition as the case where $R^1$ to $R^6$ are each a halogen atom, an alkyl group, an aryl group, or a heterocyclic group as described above, and preferred ranges thereof are also the same.

In General Formula (I), $R^1$ and $R^6$ are preferably an alkylamino group, an arylamino group, a carbonamido group, a ureido group, an imide group, an alkoxycarbonylamino group, or a sulfonamide group, more preferably a carbonamido group, a ureido group, an alkoxycarbonylamino group, or a sulfonamide group, still more preferably a carbonamido group, a ureido group, an alkoxycarbonylamino group, or a sulfonamide group, and particularly preferably a carbonamido group or a ureido group.

In General Formula (I), $R^2$ and $R^5$ are preferably an alkoxycarbonyl group, an aryloxycarbonyl group, a carbamoyl group, an alkylsulfonyl group, an arylsulfonyl group, a nitrile group, an imide group, or a carbamoylsulfonyl group, more preferably an alkoxycarbonyl group, an aryloxycarbonyl group, a carbamoyl group, an alkylsulfonyl group, a nitrile group, an imide group, or a carbamoylsulfonyl group, still more preferably an alkoxycarbonyl group, an aryloxycarbonyl group, a carbamoyl group, a nitrile group, an imide group, or a carbamoylsulfonyl group, and particularly preferably an alkoxycarbonyl group, an aryloxycarbonyl group, or a carbamoyl group.

In General Formula (I), $R^3$ and $R^4$ are preferably an alkyl group, an aryl group, or a heterocyclic group, and more preferably an alkyl group or an aryl group.

In General Formula (I), in the case where $R^3$ and $R^4$ represent an alkyl group, the alkyl group is preferably a linear, branched, or cyclic alkyl group having 1 to 12 carbon atoms, and examples thereof include a methyl group, an ethyl group, an n-propyl group, an isopropyl group, a cyclopropyl group, an n-butyl group, an i-butyl group, a tert-butyl group, a cyclobutyl group, a cyclopentyl group, a cyclohexyl group, and a benzyl group. Further, a branched or cyclic alkyl group having 1 to 12 carbon atoms is more preferable, and examples thereof include an isopropyl group, a cyclopropyl group, an i-butyl group, a tert-butyl group, a cyclobutyl group, a cyclopentyl group, and a cyclohexyl group. In addition, a secondary or tertiary alkyl group having 1 to 12 carbon atoms is preferable, and examples thereof include an isopropyl group, a cyclopropyl group, an i-butyl group, a tert-butyl group, a cyclobutyl group, and a cyclohexyl group.

In General Formula (I), in the case where $R^3$ and $R^4$ represent an aryl group, as the aryl group, a phenyl group and a naphthyl group are preferable, and a phenyl group is more preferable.

In the case where $R^3$ and $R^4$ represent a heterocyclic group, as the heterocyclic group, a 2-thienyl group, a 4-pyridyl group, a 3-pyridyl group, a 2-pyridyl group, a 2-furyl group, a 2-pyrimidinyl group, a 2-benzothiazolyl group, a 1-imidazolyl group, a 1-pyrazolyl group, or a benzotriazol-1-yl is preferable, and a 2-thienyl group, a 4-pyridyl group, a 2-furyl group, a 2-pyrimidinyl group, or a 1-pyridyl group is more preferable.

Next, the metal atom or metal compound which forms a dipyrromethene-based metal complex compound will be described.

Herein, the metal or the metal compound may be in any type of metal or metal compound as long as they can form a complex, and examples thereof include a divalent metal atom, a divalent metal oxide, a divalent metal hydroxide, and a divalent metal chloride. Examples of the metal or the metal compound include Zn, Mg, Si, Sn, Rh, Pt, Pd, Mo, Mn, Pb, Cu, Ni, Co, Fe, and B, metal chlorides such as AlCl, InCl, FeCl, $TiCl_2$, $SnCl_2$, $SiCl_2$, and $GeCl_2$, metal oxides such as TiO and VO, and metal hydroxides such as $Si(OH)_2$.

Among these, in view of the stability, spectral characteristics, heat resistance, light fastness, and production suitability of the complex, Fe, Zn, Mg, Si, Pt, Pd, Mo, Mn, Cu, Ni, Co, TiO, B, or VO is preferable, Fe, Zn, Mg, Si, Pt, Pd, Cu, Ni, Co, B, or VO is more preferable, and Fe, Zn, Cu, Co, B, or VO (V=O) is particularly preferable. Among these, in particular, Zn is preferable.

In the dipyrromethene-based metal complex compound in which the compound represented by General Formula (I) is coordinated with a metal atom or metal compound, preferred embodiments are shown below. That is, an embodiment in which in General Formula (I), $R^1$ and $R^6$ each independently represent a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamido group, a ureido group, an imide group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group, or a phosphinoylamino group, $R^2$ and $R^5$ each independently represent a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imide group, an alkoxycarbonylamino group, a sulfonamido group, an azo group, an alkylthio group, an arylthio group, a heterocyclic thio group, an alkylsulfonyl group, an arylsulfonyl group, or a sulfamoyl group, $R^3$ and $R^4$ each independently represent a hydrogen atom, a halogen atom, an alkyl group, an alkenyl group, an aryl group, a heterocyclic group, silyl group, a hydroxyl group, a cyano group, an alkoxy group, an aryloxy group, a heterocyclic oxy group, an acyl group, an alkoxycarbonyl group, a carbamoyl group, an anilino group, a carbonamido group, ureido group, an imide group, an alkoxycarbonylamino group, a sulfonamido group, an azo group, an alkylthio group, an arylthio group, a heterocyclic thio group, an alkylsulfonyl group, an arylsulfonyl group, a sulfamoyl group, or a phosphinoylamino group, $R^7$ represents a hydrogen atom, a halogen atom, an alkyl group, an aryl group, or a heterocyclic group, and the metal atom or metal compound represents Zn, Mg, Si, Pt, Pd, Mo, Mn, Cu, Ni, Co, TiO, B, or VO can be mentioned.

A more preferred embodiment than that for the dipyrromethene-based metal complex compound is shown below. That is, an embodiment in which in General Formula (I), $R^1$ and $R^6$ each independently represent a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamido group, ureido group, an imide group, an alkoxycarbonylamino group, an aryloxycarbonylamino group, a sulfonamido group, an azo group, an alkylsulfonyl group, an arylsulfonyl group, or a phosphinoylamino group, $R^2$ and $R^5$ each independently represent alkyl group, an alkenyl group, an aryl group, a heterocyclic group, a cyano group, a nitro group, an acyl group, an alkoxycarbonyl group, an aryloxycarbonyl group, a carbamoyl group, an imide group, an alkylsulfonyl group, an arylsulfonyl group, or a sulfamoyl group, $R^3$ and $R^4$ each independently represent a hydrogen atom, an alkyl group, an alkenyl group, an aryl group, a heterocyclic group, a cyano group, an acyl group, an alkoxycarbonyl group, a carbamoyl group, a carbonamido group, ureido group, an imide group, an alkoxycarbonylamino group, a sulfonamido group, an alkylthio group, an arylthio group, a heterocyclic thio group, an alkylsulfonyl group, an arylsulfonyl group, or a sulfamoyl group, $R^7$ represents a hydrogen atom, a halogen atom, an alkyl group, an aryl group, or a heterocyclic group, and the metal atom or metal compound represents Zn, Mg, Si, Pt, Pd, Cu, Ni, Co, B, or VO can be mentioned.

For a preferred embodiment of the dipyrromethene-based metal complex compound in which the compound represented by General Formula (I) is coordinated with a metal atom or metal compound, a complex compound represented by General Formula (I-1), (I-2), or (I-3) described in paragraphs 0153 to 0176 of JP2012-237985A, the disclosure of which is incorporated herein by reference.

Among the complex compound represented by General Formula (I-1), (I-2), or (I-3) which is the preferred embodiment of the dipyrromethene-based metal complex compound in which the compound represented by General Formula (I) is coordinated with a metal atom or metal compound, the complex compound represented by General Formula (I-3) is particularly preferable.

For the specific examples of the dipyrromethene-based metal complex compound in which the compound represented by General Formula (I) used in the present invention is coordinated with a metal atom or metal compound, reference can be made to the descriptions in paragraphs 0179 to 0186 of JP2012-237985A, the disclosure of which is incorporated herein by reference.

In addition, specific examples of the dipyrromethene-based metal complex compound also include the following compounds.

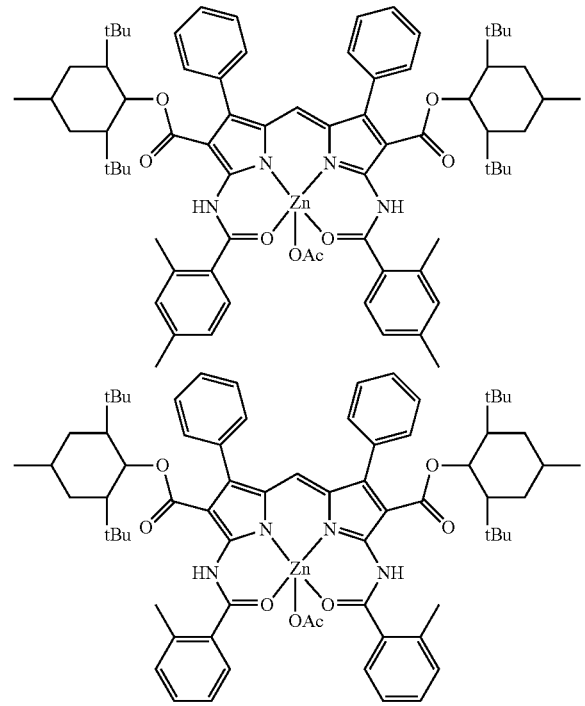

<Other Colorants>

The composition of the present invention may include a dye compound, a pigment compound, and a dispersion thereof, each of which has a different structure. The dye compound may have any structure which does not affect the hue of a colored image, and examples of the dye compound include azo-based dye compounds (for example, Solvent Yellow 162), anthraquinone-based dye compounds (for example, the anthraquinone compounds described in JP2001-10881A), phthalocyanine-based dye compounds (for example, the phthalocyanine compounds described in US2008/0076044A1), methine dyes, and tetraazaporphyrin dyes (for example, the tetraazaporphyrin compounds described in JP2007-99744A).

Examples of the pigment compound include perylene, perynone, quinacridone, quinacridonequinone, anthraquinone, anthathrone, benzimidazolone, condensed disazo, disazo, azo, indanthrone, phthalocyanine, triarylcarbonium, dioxazine, aminoanthraquinone, diketopyrrolopyrrole, indigo, thioindigo, isoindoline, isoindolinone, pyranthrone, and isoviolanthrone. More specific examples of the pigment compound include perylene-compound pigments such as Pigment•Red 190, Pigment•Red 224, Pigment•Violet 29; perynone-compound pigments such as Pigment•Orange 43 and Pigment•Red 194; quinacridone-compound pigments such as Pigment•Violet 19, Pigment•Violet 42, Pigment•Red 122, Pigment•Red 192, Pigment•Red 202, Pigment•Red 207, and Pigment•Red 209; quinacridonequinone-compound pigments such as Pigment•Red 206, Pigment•Orange 48, and Pigment•Orange 49; anthraquinone-compound pigments such as Pigment•Yellow 147; anthathrone-compound pigments such as Pigment•Red 168; benzimidazolone-compound pigments such as Pigment Brown 25, Pigment•Violet 32, Pigment•Orange 36, Pigment•Yellow 120, Pigment•Yellow 180, Pigment•Yellow 181, Pigment•Orange 62, and Pigment•Red 185; condensed disazo-compound pigments such as Pigment•Yellow 93, Pigment•Yellow 94, Pigment•Yellow 95, Pigment•Yellow 128, Pigment•Yellow 166, Pigment•Orange 34, Pigment•Orange 13, Pigment•Orange 31, Pigment•Red 144, Pigment•Red 166, Pigment•Red 220, Pigment•Red 221, Pigment•Red 242, Pigment•Red 248, Pigment•Red 262, and Pigment Brown 23; disazo-compound pigments such as Pigment•Yellow 13, Pigment•Yellow 83, and Pigment•Yellow 188; azo-compound pigments such as Pigment•Red 187, Pigment•Red 170, Pigment•Yellow 74, Pigment•Yellow 150, Pigment•Red 48, Pigment•Red 53, Pigment•Orange 64, and Pigment•Red 247; indanthrone-compound pigments such as Pigment•Blue 60; indanthrene-compound pigments such as Pigment•Green 7, Pigment•Green 36, Pigment•Green 37, Pigment•Green 58, Pigment•Blue 16, Pigment•Blue 75, and Pigment•Blue 15; triaryl carbonium-compound pigments such as Pigment•Blue 56 and Pigment•Blue 61; dioxazine-compound pigments such as Pigment•Violet 23 and Pigment•Violet 37; aminoanthraquinone-compound pigments such as Pigment•Red 177; diketopyrrolopyrrole-compound pigments such as Pigment•Red 254, Pigment•Red 255, Pigment•Red 264, Pigment•Red 272, Pigment•Orange 71, and Pigment•Orange 73; thioindigo-compound pigments such as Pigment•Red 88; isoindoline-compound pigments such as Pigment•Yellow 139 and Pigment•Orange 66; isoindolinone-compound pigments such as Pigment•Yellow 109 and Pigment•Orange 61; pyranthrone-compound pigments such as Pigment•Orange 40 and Pigment•Red 216; and isoviolanthrone-compound pigments such as Pigment•Violet 31.

As the pigment, blue pigments such as Pigment•Blue 15, 15:3, 15:4, 15:6, and 60; and violet pigments such as Pigment•Violet 1, 19, 23, 29, 32, 36, and 38 are preferable, Pigment•Blue 15:3, 15:6, and Pigment•Violet 23 are more preferable, and Pigment•Blue 15:6 is still more preferable.

In the case where the dye or the pigment is blended as a dispersion, preparation can be carried out in accordance with the descriptions of JP1997-197118A (JP-H09-197118A) and JP2000-239544A.

The content of the dye or the pigment can be used within a range not interfering with the effects of the present invention, and is preferably 0.5% by mass to 70% by mass with respect to the total solid content of the coloring curable composition of the present invention. Further, the dye or pigment is preferably added to the coloring curable composition such that the absorption strength ratio (absorption at 450 nm/absorption at 650 nm) is in the range of 0.95 to 1.05.

<Content of Colorant>

The total amount of the colorant represented by Formula (1), Formula (2), or Formula (3) included in the composition of the present invention is preferably 1.0% by mass to 50% by mass, more preferably 5.0% by mass to 30% by mass, and particularly preferably 8% by mass to 25% by mass, with respect to the total solid content in the composition of the present invention.

Furthermore, the total amount of the colorant represented by Formula (1), Formula (2), or Formula (3) in all the colorants included in the composition of the present invention can be set to 50% by mass or more, to 60% by mass or more, or to 70% by mass or more. Further, the upper limit of the total amount of the colorant represented by Formula (1), Formula (2), or Formula (3) in all the colorants included in the composition of the present invention is 100% by mass or less.

Furthermore, the mass ratio of the total amount of the colorant represented by Formula (1), Formula (2), or Formula (3) in all the colorants included in the composition of the present invention to the total amount of xanthene colorant and at least one kind of dipyrromethene-based metal complex compound is preferably 1.0:0.05 to 1.0:1.0, and more preferably 1.0:0.1 to 1.0:0.6.

One kind or two or more kinds of the colorant used in a combination with others the present invention may be used.

«Polymerizable Compound»

The coloring curable composition of the present invention contains a polymerizable compound. Examples of the polymerizable compound include an addition-polymerizable compound having at least one ethylenically unsaturated double bond.

Specifically, the polymerizable compound is selected from the compounds having at least one ethylenically unsaturated bond, preferably two or more ethylenically unsaturated bonds at terminals. Such compound groups are widely known in the industrial field of the relevant art and can be used in the present invention without particular limitation. These may be in any type of chemical forms such as a monomer, a prepolymer, that is, a dimer, a trimer, an oligomer, a mixture thereof, and a (co)polymer thereof.

Examples of the monomer and a (co)polymer thereof include unsaturated carboxylic acid (for example, acrylic acid methacrylic acid, itaconic acid, crotonic acid, isocrotonic acid, and maleic acid), esters and amides thereof, and (co)polymers thereof, and preferably esters of an unsaturated carboxylic acid with an aliphatic polyhydric alcohol compound, amides of an unsaturated carboxylic acid with an aliphatic polyhydric amine compound, and (co)polymers thereof. Further, addition reaction products of an unsaturated carboxylic acid ester or amide having a nucleophilic substituent such as a hydroxyl group, an amino group or a mercapto group with a monofunctional or polyfunctional isocyanate or epoxy, and dehydration condensation reactants with a monofunctional or polyfunctional carboxylic acids are suitably used. Furthermore, addition reaction products of an unsaturated carboxylic acid ester or amide having an electrophilic substituent such as an isocyanate group and an epoxy group with a monofunctional or polyfunctional alcohol, amine or thiol, and substitution reaction products of an unsaturated carboxylic acid ester or amide having a splitting-off substituent such as a halogen group and a tosyloxy group with a monofunctional or polyfunctional alcohol, amine, or thiol are also suitably used. In addition, as other examples, the compound group in which the above-described unsaturated carboxylic acid is replaced by unsaturated phosphonic acid, styrene, vinyl ether, or the like may also be used.

As specific examples of the ester monomers of an aliphatic polyhydric alcohol compound with an unsaturated carboxylic acid, examples of the acrylic acid ester include ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl) ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate, a polyester acrylate oligomer, an isocyanuric acid-EO modified triacrylate.

Furthermore, examples of the methacrylic acid ester include tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, and bis-[p-(methacryloxyethoxy)phenyl] dimethylmethane.

Further, examples of the itaconic acid ester include ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate; examples of the crotonic acid ester include ethylene glycol dicrotonate, tetramethylene glycol dicrotonate, pentaerythritol dicrotonate, and sorbitol tetradicrotonate; examples of the isocrotonic acid ester include ethylene glycol diisocrotonate, pentaerythritol diisocrotonate, and sorbitol tetraisocrotonate; and examples of the maleic acid ester include ethylene glycol dimaleate, triethylene glycol dimaleate, pentaerythritol dimaleate, and sorbitol tetramaleate.

As examples of other esters, the aliphatic alcohol esters described in JP1976-47334B (JP-S51-47334B) and JP1982-196231A (JP-S57-196231A), those including an aromatic backbone described in JP1982-5240A (JP-S59-5240A), JP1982-5241A (JP-S59-5241A), and JP1990-226149A (JP-H02-226149A), and those containing an amino group described in JP1989-165613A (JP-H01-165613A). Further, the above-described ester monomers can also be used as a mixture.

Moreover, a urethane-based addition-polymerizable compounds which is produced by the addition-polymerization of isocyanate and a hydroxyl group is also suitable, and specific examples thereof include a vinylurethane compound having at least two polymerizable vinyl groups in one molecule, which is obtained by adding vinyl monomers having a hydroxyl group represented by the following General Formula (A) to a polyisocyanate compound having at least two isocyanate groups in one molecule as described in JP1973-41708B (JP-S48-41708B).

$$CH_2=C(R)COOCH_2CH(R')OH \qquad (A)$$

[in General Formula (A), R and R' each independently represent H or $CH_3$]

Incidentally, as the polymerizable compound, dipentaerythritol triacrylate (KAYARAD D-330 as a commercially available product; manufactured by Nippon Kayaku Co., Ltd.), dipentaerythritol tetraacrylate (KAYARAD D-320 as a commercially available product; manufactured by Nippon Kayaku Co., Ltd.), dipentaerythritol penta(meth)acrylate (KAYARAD D-310 as a commercially available product; manufactured by Nippon Kayaku Co., Ltd.), dipentaerythritol hexa(meth)acrylate (KAYARAD DPHA as a commercially available product; manufactured by Nippon Kayaku Co., Ltd.), and a structure in which ethylene glycol or a propylene glycol residue is interposed between these (meth)acryloyl groups are also preferable. Oligomer types thereof can also be used.

The details in a use method, such as structures, sole use or combination use, and addition amounts of the polymerizable compound can be arbitrarily set in accordance with the final performance design of the coloring curable composition. For example, from the viewpoint of sensitivity, structures having a large content of unsaturated groups per molecule are preferable, and in many cases, bifunctional or higher functional compounds are preferable. Further, from the viewpoint of increasing the strength of the colored cured film, trifunctional or higher functional compounds are preferable and a method of using the compound in combination with a different polymerizable group different in the function number (for example, an acrylic acid ester, a methacrylic acid ester, a styrene-base compound, and a vinyl ether-base compound) to control both the sensitivity and the strength is also effective. In addition, the selection and use method of the polymerizable compound is an important factor for the compatibility and the dispersibility with other components (for example, a photopolymerization initiator, a colorant (pigment), and a binder polymer) contained in the coloring curable composition. For example, by using a low-purity compound or using two or more compounds in combination, the compatibility can be improved in some cases, and further, for the purpose of improving the adhesiveness to a hard surface of a substrate or the like, a specific structure may be selected in some cases.

The content of the polymerizable compound in the total solid content of the coloring curable composition is preferably 10% by mass to 80% by mass, more preferably 15% by mass to 75% by mass, and particularly preferably 20% by mass to 60% by mass, from the viewpoint of more effectively obtaining the effects of the present invention.

The composition of the present invention may include one kind or two or more kinds of polymerizable compound. In the case where the composition includes two or more kinds of polymerizable compound, the total sum is preferably within the above range.

«Polymerization Initiator»

It is preferable that the coloring curable composition of the present invention contains a polymerization initiator, and contains at least one kind of photopolymerization initiator. The photopolymerization initiator is not particularly limited as long as it may polymerize a colorant containing a polymerizable group or a polymerizable compound, and is preferably selected from the viewpoints of properties, initiation efficiency, absorption wavelength, availability, cost, and the like.

Examples of the photopolymerization initiator include at least one active halogen compound selected from halomethyloxadiazole compounds and halomethyl-s-triazine compounds, 3-aryl-substituted coumarin compounds, lophine dimers, benzophenone compounds, acetophenone compounds, and derivatives thereof, cyclopentadiene-benzene- iron complexes and salts thereof, and oxime compounds. Specific examples of the photopolymerization initiator include those described in the paragraphs [0070] to [0077] of JP2004-295116A. Among these, oxime compounds or biimidazole-based compounds are preferable in view of a rapid polymerization reaction and the like.

The oxime-based compound (hereinafter also referred to as an "oxime-based photopolymerization initiator") is not particularly limited and examples thereof include the oxime-based compounds described in JP2000-80068A, WO02/100903A1, JP2001-233842A, and the like.

For the specific examples of the oxime-based compound, reference can be made to the descriptions in paragraph 0053 of JP2013-182215A, the disclosure of which is incorporated herein by reference.

Moreover, in the present invention, the oxime-based compound is more preferably a compound represented by the following Formula (1) or General Formula (2) from the viewpoints of sensitivity, stability over time, and coloration during post-heating.

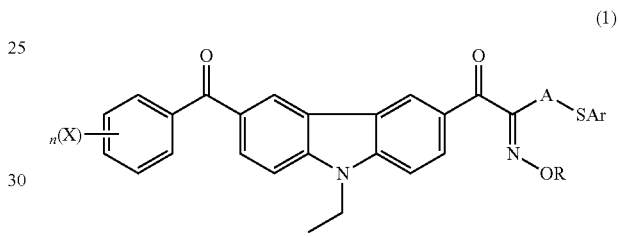

(1)

(in Formula (1), R and X each represent a monovalent substituent, A represents a divalent organic group, Ar represents an aryl group, and n represents an integer of 1 to 5)

As R, an acyl group is preferable, and specifically, an acetyl group, a propionyl group, a benzoyl group, and a toluyl group are preferable, from the viewpoint of obtaining high sensitivity.

From the viewpoint of increasing sensitivity and suppressing coloration due to heating over time, A is preferably an unsubstituted alkylene group, an alkylene group substituted by an alkyl group (for example, a methyl group, an ethyl group, a tert-butyl group, and a dodecyl group), an alkylene group substituted by an alkenyl group (for example, a vinyl group and an allyl group), or an alkylene group substituted by an aryl group (for example, a phenyl group, a p-tolyl group, a xylyl group, a cumenyl group, a naphthyl group, an anthryl group, a phenanthryl group, and a styryl group).

From the viewpoint of increasing sensitivity and suppressing coloration due to heating over time, Ar is preferably a substituted or unsubstituted phenyl group. In the case where the phenyl group is substituted, the substituent is preferably a halogen group such as a fluorine atom, a chlorine atom, a bromine atom, and an iodine atom.

From the viewpoint of improving solubility in a solvent and absorption efficiency at a longer wavelength range, X is preferably an alkyl group which may have a substituent, an aryl group which may have a substituent, an alkenyl group which may have a substituent, an alkynyl group which may have a substituent, an alkoxy group which may have a substituent, an aryloxy group which may have a substituent, an alkylthioxy group which may have a substituent, an arylthioxy group which may have a substituent, or an amino group which may have a substituent. Further, n in Formula (1) is preferably an integer of 1 or 2.

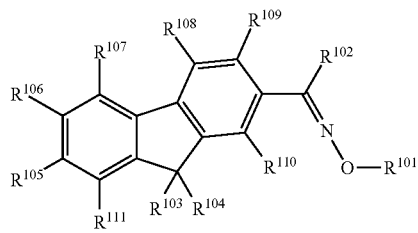

(2)

In General Formula (2), $R^{101}$ represents an alkyl group, an alkanoyl group, an alkenoyl group, an aryloyl group, an alkoxycarbonyl group, an aryloxycarbonyl group, a heterocyclic oxycarbonyl group, a heteroaryloxycarbonyl group, an alkylthiocarbonyl group, an arylthiocarbonyl group, a heterocyclic thiocarbonyl group, a heteroarylthiocarbonyl group, or —CO—CO—Rf. Rf represents a carbocyclic aromatic ring or a heterocyclic aromatic ring.

$R^{102}$ represents an alkyl group, an aryl group, or a heterocyclic group, and these may be substituted.

$R^{103}$ and $R^{104}$ each independently represent an alkyl group, an aryl group, or a heterocyclic group, and these may further be substituted with a halogen atom, an alkyl group, an aryl group, an alkoxy group, an alkylcarbonyl group, or the like.

$R^{105}$ to $R^{111}$ each independently represent a hydrogen atom, a halogen atom, an alkyl group, an aryl group, a heterocyclic group, an alkoxy group, an aryloyl group, a heteroaryloyl group, an alkylthio group, an aryloylthio group, a heteroaryloyl group, an alkylcarbonyl group, an arylcarbonyl group, an alkoxycarbonyl group, an aryloxycarbonyl group, a heterocyclic oxycarbonyl group, a nitro group, an amino group, a sulfonic acid group, a hydroxy group, a carboxylic acid group, an amide group, a carbamoyl group, or a cyano group.

It is preferable that one or two members of $R^{105}$ to $R^{111}$ are an electron-withdrawing substituent, that is, a nitro group, a cyano group, a halogen atom, an alkylcarbonyl group, or an arylcarbonyl group since a coloring curable composition having higher curability is obtained.

Specific examples of the compound having a fluorene structure represented by General Formula (2) are shown below, but are not limited to these compounds.

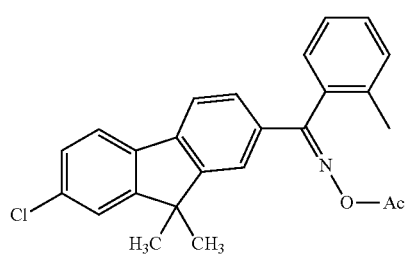

-continued

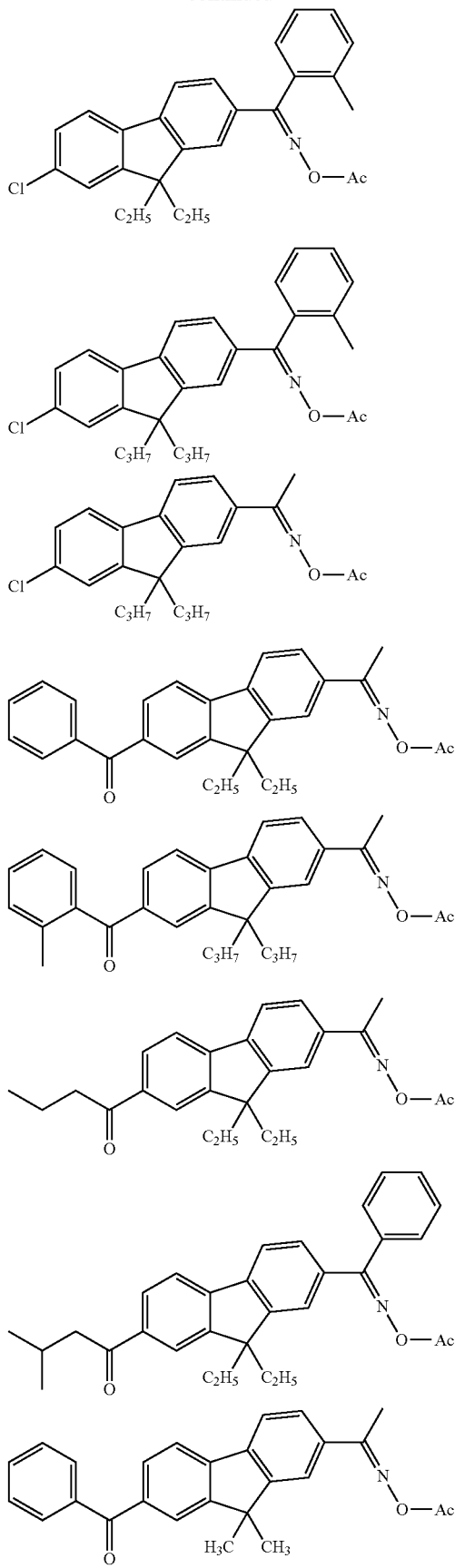

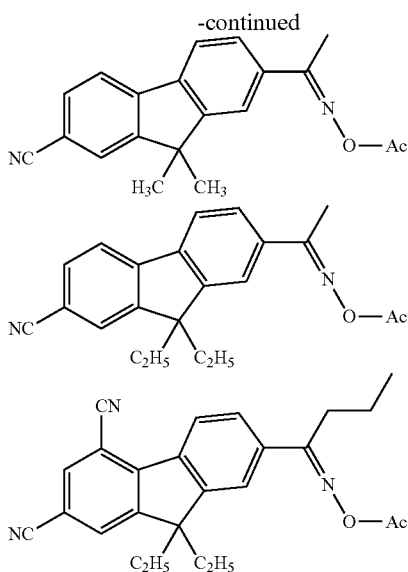

The compound having the fluorene structure represented by General Formula (2) can be synthesized in accordance with, for example, the synthesis method described in WO2014/050738A.

With regard to specific examples of the biimidazole-based compound, reference can be made to the descriptions in paragraphs 0061 to 0070 of JP2013-182213A, the disclosure of which is incorporated herein by reference.

Furthermore, for the coloring curable composition of the present invention, other known photopolymerization initiators described in paragraph No. 0079 of JP2004-295116A may be used, in addition to the photopolymerization initiator.

The content of the photopolymerization initiator is preferably 3% by mass to 20% by mass, more preferably 4% by mass to 19% by mass, and particularly preferably 5% by mass to 18% by mass, with respect to the total solid content of the coloring curable composition, from the viewpoint of more effectively obtaining the effects of the present invention.

The composition of the present invention may include one kind or two or more kinds of the photopolymerization initiator. In the case where the composition includes two or more kinds of the photopolymerization initiator, the total sum thereof is preferably within the above range.

«Organic Solvent»

It is preferable that the coloring curable composition of the present invention contains at least one kind of organic solvent.

Basically, the organic solvent is not particularly limited as long as the solubility of the respective components or the coatability when forming into a coloring curable composition, and in particular, it is preferably selected in consideration of the solubility, the coatability, and the safety of a binder.

As the organic solvent, esters, ethers, ketones, or aromatic hydrocarbons are used, and specific examples thereof include those described in paragraph Nos. 0161 and 0162 of JP2012-032754A.

From the solubility of the respective components; in the case of including the alkali-soluble polymer, the solubility of the alkali-soluble polymer; and the improvement of the coated surface conditions, the organic solvents may be used as a mixture of two or more kinds thereof. In this case, a mixed solution composed of two or more kinds selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol monomethyl ether acetate is particularly preferable.

The content of the organic solvent in the coloring curable composition is an amount such that the total solid concentration in the composition more preferably becomes 10% by mass to 80% by mass, and still more preferably becomes 15% by mass to 60% by mass.

The composition of the present invention may include one kind or two or more kinds of the organic solvent. In the case where the composition includes two or more kinds of the organic solvent, the total sum thereof is preferably within the above range.

«Resin»

It is preferable that the coloring curable composition of the present invention includes a resin and includes an alkali-soluble resin as the resin. The alkali-soluble resin is not particularly limited as long as it is alkali-soluble, and it can be preferably selected from the viewpoints of heat resistance, developability, availability, and the like.

The alkali-soluble resin is preferably a high-molecular-weight organic linear polymer, which is soluble in an organic solvent and developable with a weakly alkaline aqueous solution. Examples of such a high-molecular-weight organic linear polymer include polymers having a carboxylic acid in the side chain, such as methacrylic acid copolymers, acrylic acid copolymers, itaconic acid copolymers, crotonic acid copolymers, maleic acid copolymers, partially esterified maleic acid copolymers, and the like, as respectively described in JP1984-44615A (JP-S59-44615A), JP1979-34327B (JP-S54-34327B), JP1983-12577B (JP-S58-12577B), JP1979-25957B (JP-S54-25957B), JP1984-53836A (JP-S59-53836A), and JP1984-71048A (JP-S59-71048A), as well as acidic cellulose derivatives having a carboxylic acid in the side chain.

Besides the above-mentioned resins, adducts of polymers having hydroxy groups with acid anhydrides, polyhydroxystyrene resins, polysiloxane resins, poly(2-hydroxyethyl (meth)acrylate), polyvinyl pyrrolidone, polyethylene oxides, polyvinyl alcohols, and the like are also useful as the alkali-soluble resin in the present invention. The linear organic high molecular polymer may be a copolymer with a hydrophilic monomer. Examples thereof include alkoxyalkyl (meth)acrylates, hydroxyalkyl (meth)acrylates, glycerol (meth)acrylates, (meth)acrylamides, N-methylolacrylamides, secondary or tertiary alkylacrylamides, dialkylaminoalkyl (meth)acrylates, morpholine (meth)acrylates, N-vinylpyrrolidone, N-vinylcaprolactam, vinylimidazole, vinyltriazole, methyl (meth)acrylates, ethyl (meth)acrylates, branched or linear propyl (meth)acrylates, branched or linear butyl (meth)acrylates, and phenoxyhydroxy propyl (meth)acrylates. Other examples of useful hydrophilic monomer include monomers including a tetrahydrofurfuryl group, a phosphoric acid group, a phosphoric acid ester group, a quaternary ammonium salt group, an ethyleneoxy chain, a propyleneoxy chain, a sulfonic acid group, and a group derived from a salt thereof or a morpholinoethyl group.

As the alkali-soluble resin, a copolymer of benzyl methacrylate and methacrylic acid is also preferable.

Moreover, a copolymer of maleimide and ethylene oxide, as represented by the following Formulae (b1) and (b2) can also be preferably used as the alkali-soluble resin.

Formula (b1)

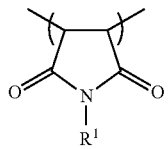

(b1)

(In Formula (b1), $R^1$ represents a hydrogen atom, an aryl group, or an alkyl group)

In the case where $R^1$ represents an alkyl group, examples of the alkyl group include a linear alkyl group having 1 to 10 carbon atoms, a branched alkyl group having 3 to 10 carbon atoms, and a cyclic alkyl group having carbon atoms 5 to 20, and more specifically a methyl group, an ethyl group, a t-butyl group, and a cyclohexyl group.

The alkyl group may further include a substituent, and examples of the substituent which may be introduced into the alkyl group include a phenyl group, a carbonyl group, an alkoxy group, a hydroxy group, and an amino group.

In the case where $R^1$ represents an aryl group, examples of the aryl group include an aryl group having a monocyclic structure, an aryl group having a polycyclic structure, an aryl group having a condensed structure, and heteroaryl group having a hetero atom. More specific examples thereof include a phenyl group, a naphthyl group, a biphenyl group, a benzimidazolyl group, a pyridyl group, and a furyl group.

The aryl group may further include a substituent, and examples of the substituent which may be introduced into the aryl group include alkyl groups such as a methyl group, an ethyl group, a t-butyl group, and a cyclohexyl group, alkoxy groups such as a methoxy group, a carboxy group, a hydroxy group, an amino group, a nitro group, a chloro group, and a bromo group.

Formula (b2)

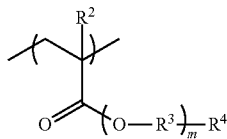

(b2)

(in Formula (b2), $R^2$ represents a hydrogen atom or a methyl group. $R^3$ represents an alkylene group having 2 or 3 carbon atoms, $R^4$ represents a hydrogen atom, an aryl group, or an alkyl group, and m represents an integer of 1 to 15)

In the case where $R^4$ represents an alkyl group, examples of the alkyl group include a linear alkyl group having 1 to 20 carbon atoms, a branched alkyl group having 1 to 20 carbon atoms, and a cyclic alkyl group having carbon atoms 5 to 20, and more specifically a methyl group, an ethyl group, a t-butyl group, a cyclohexyl group, and a 2-ethylhexyl group.

The alkyl group may further include a substituent, and examples of the substituent which may be introduced into the alkyl group include a phenyl group, a carbonyl group, and an alkoxy group.

In the case where $R^4$ represents an aryl group, examples of the aryl group include an aryl group having a monocyclic structure, an aryl group having a polycyclic structure, an aryl group having a condensed structure, and heteroaryl group having a hetero atom. More specific examples thereof include a phenyl group, a naphthyl group, an anthranyl group, a biphenyl group, a benzimidazolyl group, an indolyl group, an imidazolyl group, an oxazolyl group, a carbazolyl group, a pyridyl group, and a furyl group.

The aryl group may further include a substituent, and examples of the substituent which may be introduced into the aryl group include a nonyl group, alkyl groups such as a methyl group, an ethyl group, a t-butyl group, and a cyclohexyl group, alkoxy groups such as a methoxy group, a carboxy group, a hydroxy group, an amino group, a nitro group, a chloro group, and a bromo group.

Furthermore, in order to improve the crosslinking efficiency, the alkali-soluble resin may have a polymerizable group in the side chain, and polymers containing, for example, an allyl group, a (meth)acryl group, an allyloxyalkyl group, or the like in the side chain are also useful. Examples of the polymer containing a polymerizable group include KS RESIST-106 (manufactured by Osaka Organic Chemical Industry Ltd.) and CYCLOMER P series (manufactured by Daicel Company Ltd.), which are commercially available products. In addition, in order to enhance the strength of a cured film, alcohol-soluble nylon, polyether formed of 2,2-bis-(4-hydroxyphenyl)-propane and epichlorohydrin, and the like are also useful.

Among various alkali-soluble resins above, from the viewpoint of heat resistance, a polyhydroxystyrene-based resin, a polysiloxane-based resin, an acryl-based resin, an acrylamide-based resin, and an acryl/acrylamide copolymer resin are preferable, and from the viewpoint of controlling developability, an acryl-based resin, an acrylamide-based resin, and an acryl/acrylamide copolymer resin are preferred.

In particular, a copolymer having a repeating unit as represented by the following General Formula (2) and an acidic group is preferable, and more preferred examples of the copolymer include a copolymer having a structural unit represented by General Formula (3), in addition to General Formula (2) and the acidic group.

General Formula (2)

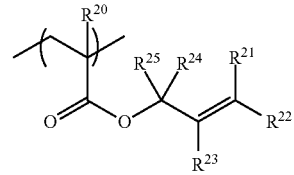

(in General Formula (2), $R^{20}$ represents a hydrogen atom or a methyl group, and $R^{21}$ to $R^{25}$ each independently represent a hydrogen atom, a halogen atom, a cyano group, an alkyl group, or an aryl group)

General Formula (3)

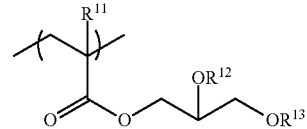

(in General Formula (3), $R^{11}$ represents a hydrogen atom or a methyl group. $R^{12}$ and $R^{13}$ each independently represent a hydrogen atom or a carbonyl group having 3 to 20 carbon atoms, including an unsaturated double bond as a partial structure, and both of $R^{12}$ and $R^{13}$ is a hydrogen atom in no case. In the case where at least one of $R^{12}$ or $R^{13}$ represents a carbonyl group having 3 to 20 carbon atoms, including an unsaturated double bond as a partial structure, it may further include a carboxy group as a partial structure.)

As the acryl-based resin, a copolymer formed from benzyl (meth)acrylate, (meth)acrylic acid, hydroxyethyl (meth)acrylate, (meth)acrylamide, and the like, and KS RESIST-106 (manufactured by Osaka Organic Chemical Industry Ltd.), CYCLOMER P series (manufactured by Daicel Company Ltd.), and the like, which are commercially available products, are preferable.

Furthermore, the alkali-soluble resin may include a structural unit derived from an ethylenically unsaturated monomer represented by the following Formula (X).

General Formula (X)

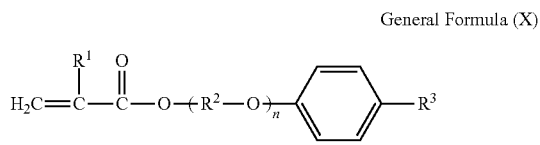

(in Formula (X), $R^1$ represents a hydrogen atom or a methyl group, $R^2$ represents an alkylene group having 2 to 10 carbon atoms, $R^3$ represents a hydrogen atom or an alkyl group having 1 to 20 carbon atoms, which may include a benzene ring, and n represents an integer of 1 to 15)

In Formula (X), the alkylene group of $R^2$ preferably has 2 to 3 carbon atoms. Further, the alkyl group of $R^3$ has 1 to 20 carbon atoms, and more preferably has 1 to 10 carbon atoms, and the alkyl group of $R^3$ may include a benzene ring. Examples of the alkyl group including a benzene ring, represented by $R^3$, include a benzyl group and a 2-phenyl (iso)propyl group.

The alkali-soluble resin is preferably a polymer having a weight-average molecular weight (a value in terms of polystyrene as measured by a GPC method) of 1,000 to 200,000, more preferably 2,000 to 100,000, and particularly preferably 5,000 to 50,000 from the viewpoints of developability, liquid viscosity, and the like.

The blending amount of the alkali-soluble resin is preferably 10% by mass to 80% by mass, and more preferably 20% by mass to 60% by mass, with respect to the total solid content of the coloring curable composition.

Furthermore, the acid value of the alkali-soluble resin is preferably 10 mg/KOH to 1,000 mg/KOH, more preferably 50 mg/KOH to 300 mg/KOH, still more preferably 50 mg/KOH to 200 mg/KOH, and particularly preferably 90 mg/KOH to 200 mg/KOH.

The composition of the present invention may include one kind or two or more kinds of the alkali-soluble resin. In the case where the composition includes two or more kinds of the alkali-soluble resin, the total sum thereof is preferably within the above range.

«Crosslinking Agent»

The coloring curable composition of the present invention may further include a crosslinking agent.

The crosslinking agent is not particularly limited as long as it can cure a film by a crosslinking reaction, and examples thereof include (a) an epoxy resin, (b) a melamine compound, a guanamine compound, a glycoluril compound, or a urea compound substituted with at least one substituent selected from a methylol group, an alkoxymethyl group, and an acyloxymethyl group, and (c) a phenol compound, a naphthol compound, or a hydroxyanthracene compound, which is substituted with at least one substituent selected from a methylol group, an alkoxymethyl group, and an acyloxymethyl group. Among these, a polyfunctional epoxy resin is preferable.

With regard to details such as specific examples and the like of the crosslinking agent, reference can be made to the descriptions in paragraphs 0134 to 0147 of JP2004-295116A, the disclosure of which is incorporated herein by reference.

«Surfactant»

The coloring curable composition of the present invention may include a surfactant. The surfactant may be any one of a non-ionic surfactant, a cationic surfactant, and an anionic surfactant, but a surfactant having an ethylene oxide structure and a fluorine-based surfactant are preferable. In particular, a surfactant having an ethylene oxide structure, which has an HLB value in the range of 9.2 to 15.5, or the fluorine-based surfactant described in JP1990-54202A (JP-H02-54202A) is preferable.

In the case where the coloring curable composition of the present invention contains a surfactant, the addition amount of the surfactant is preferably 0.0001% by mass to 2.0% by mass, and more preferably 0.005% by mass to 1.0% by mass, with respect to the total solid content of the coloring curable composition.

The composition of the present invention may include one kind or two or more kinds of the surfactant. In the case where the composition includes two or more kinds of the composition of the present invention, the total sum thereof is preferably within the above range.

The coloring curable composition of the present invention may further include various additives such as a thermal acid generator, a filler, an antioxidant, an ultraviolet absorber, an aggregation inhibitor, a photosensitizer, and a light stabilizer, as desired.

«Dye Stabilizer»

It is preferable to further add a dye stabilizer to the composition of the present invention, in addition to the dye cation. As the stabilizer, for example, a cationic stabilizer, an anionic stabilizer, a nonionic stabilizer, an amphoteric stabilizer, a silicone-based stabilizer, a fluorine-based surfactant, or the like can be used. Among the surfactants, a high-molecular-weight surfactant (a high-molecular-weight dispersant) is preferable since it can provide uniform and fine dispersion.

Examples of the high-molecular-weight dispersant include (co)polymers of unsaturated carboxylic acid esters such as polyacrylic acid esters; (partial) amine salts, (partial) ammonium salts, or (partial) alkylamine salts of (co)polymers of unsaturated carboxylic acids such as polyacrylic acids; (co)polymers of hydroxyl group-containing unsaturated carboxylic acid esters such as hydroxyl group-containing polyacrylic acid esters, or combinations thereof; and polymerization products of sulfonic acid or phosphoric acid having a crosslinking group.

As the crosslinking group, crosslinkable groups which can be crosslinked by radicals, acids, or heat can be used. Specific examples thereof include a (meth)acryl group, a styrene group, a vinyl group, a cyclic ether group, and a methylol group, but a (meth)acryl group, a styrene group, and a vinyl group are preferable, and a (meth)acryl group and a styrene group are more preferable.

In addition, in addition to these surfactants, it is also effective to add bistrifluoromethanesulfonimide sodium salts or salts (sodium salts, potassium salts, or the like) of the following anions.

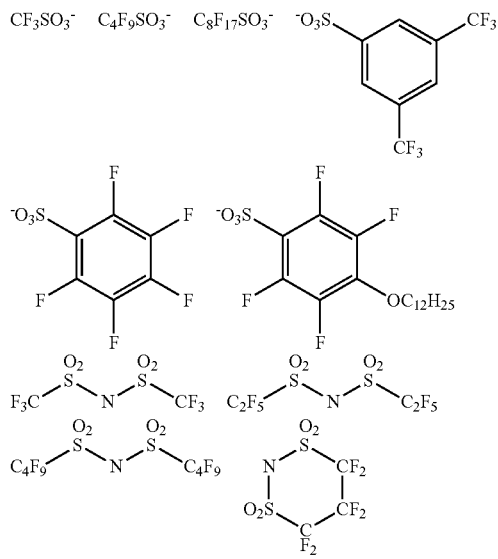

<Antioxidant>

The composition of the present invention may include an antioxidant. Examples of the antioxidant include a radical scavenger, a peroxide decomposer, an ultraviolet absorber, and a singlet oxygen quencher.

Examples of the radical scavenger include a phenol-based antioxidant and a hindered amine-based antioxidant. Examples of the phenol-based antioxidant include a hydroxyphenylpropionate-based compound, a hydroxybenzyl-based compound, a thiobisphenol-based compound, a thiomethylphenol-based compound, and an alkanediyl phenol-based compound. Among these, from the viewpoint of the stability of the color characteristics, a hydroxyphenyl propionate-based compound is preferable.

For example, the compounds described in paragraphs 0013 to 0034 of JP2012-155243A, and paragraphs 0030 to 0042 of JP2013-14748A can be preferably used.

The peroxide decomposer is a compound which decomposes peroxides generated by exposure to light or the like into harmless materials while not causing new radicals to be generated, and examples thereof include a phosphorus-based antioxidant and a sulfur-based antioxidant. Among these, a sulfur-based antioxidant is preferable from the viewpoint of the stability of color characteristics.

Examples of the ultraviolet absorber include a salicylic acid ester-based antioxidant and a benzophenone-based antioxidant.

The singlet oxygen quencher is a compound which can deactivate singlet oxygen by energy transfer from oxygen in a singlet state, and examples thereof include ethylenic compounds such as tetramethylethylene and cyclopentene, amines such as diethylamine, triethylamine, 1,4-diazabicyclooctane (DABCO), and N-ethylimidazole, condensed polycyclic aromatic compounds such as naphthalene which may be substituted, dimethylnaphthalene, dimethoxyanthracene, anthracene, and diphenylanthracene; and in addition to aromatic compounds such as 1,3-diphenylisobenzofuran, 1,2,3,4-tetraphenyl-1,3-cyclopentadiene, and pentaphenyl-cyclopentadiene, the compounds described as a singlet oxygen quencher in Harry H. wasserman, "Singlet Oxygen", Chapter 5, Academic Press (1979), Nicholas J. Turro, "Modern Molecular Photochemistry", Chapter 14, The Benjamin Cummings Publishing Co., Inc. (1978), and "High Functional Chemicals for Color Photographic Photosensitive Materials", Chapter 7 (2002), published by CMC.

Other examples thereof include metal complexes having a compound containing a sulfur atom as a ligand. Examples of such a compound include transition metal chelate compounds of a nickel complex, a cobalt complex, a copper complex, a manganese complex, and a platinum complex, each of which has bisdithio-α-diketone, bisphenyldithiol, or thiobisphenol as a ligand.

Examples of the sulfur-based antioxidant include a thiopropionate-based compound and a mercaptobenzimidazole-based compound. Among these, the thiopropionate-based compound is preferable from the viewpoint of the stability of color characteristics.

In the present invention, the antioxidant may be used singly or as a mixture of two or more kinds thereof. The content of the antioxidant is preferably 0.01 parts by mass to 20 parts by mass, and particularly preferably 0.1 parts by mass to 10 parts by mass, with respect to 100 parts by mass of the colorant.

<Curing Agent>

The coloring curable composition of the present invention may contain a compound which functions as a curing agent.

As the curing agent, for example, at least one compound selected from the group consisting of an aromatic amine compound, a tertiary amine compound, an amine salt, a phosphonium salt, an amidine salt, an amide compound, a thiol compound, a block isocyanate compound, and an imidazole ring-containing compound can be used.

The coloring curable composition can effectively realize low-temperature curing of a colored pattern by incorporating a curing agent selected from the specific compound group. Further, the preservation stability of the coloring curable composition can also be further improved.

<Reduction Inhibitor>

A compound which is more likely to be reduced than the dye can also be added as a reduction inhibitor for a dye to the coloring curable composition of the present invention. As a result, it is possible to further inhibit dye reduction discoloration at a time of ITO sputtering after pixel formation. Specifically, a quinone compound is preferable, and a quinone compound having the following structure having a molecular weight of approximately 100 to 800 is preferable.

The coloring curable composition of the present invention may further include a filler, an ultraviolet absorber, an aggregation inhibitor, a photosensitizer, a light stabilizer, or the like, as desired.

<Acid Generator>

The acid generator may be either a photoacid generator or a thermal acid generator, with the thermal acid generator being preferable. If the thermal acid generator is used, the heat resistance of the cured film tends to be further improved. This is one of the causes for reduction in heat resistance, which is based on reduction in the acidity due to penetration of an alkali developer into a cured film. That is, the acidity of the cured film is reduced by the post-curing baking treatment step, and thus, the heat resistance deteriorates, but acids are generated during the baking by blending a thermal acid generator, and thus, it is possible to inhibit the reduction in the acidity by the penetration of the alkali developer into the cured film.

The thermal acid generator refers to an acid generator which generates acids when heated to 100° C. to 250° C. at 1013.25 hPa. As the generated acids, acids having pKa 5 or less are preferable. Specific examples of the generated acids include sulfonic acid, carboxylic acid, and phosphoric acid, with sulfonic acid being more preferable.

For the photoacid generator, reference may be made to the description in paragraphs 0103 to 0113 of JP2006-259002A, the disclosure of which is incorporated herein by reference.

Examples of the thermal acid generator include an ionic compound (onium salt) and a non-ionic compound.

It is preferable that the ionic compound (onium salt) does not contain a heavy metal or a halogen ion, with the onium salt of the sulfonic acid being more preferable.

Examples of the ionic thermal acid generator include triphenylsulfonium, 1-dimethylthionaphthalene, 1-dimethylthio-4-hydroxynaphthalene, 1-dimethylthio-4,7-dihydroxynaphthalene, 4-hydroxyphenyldimethylsulfonium, benzyl-4-hydroxyphenylmethylsulfonium, 2-methylbenzyl-4-hydroxyphenylmethylsulfonium, 2-methylbenzyl-4-acetylphenylmethylsulfonium, 2-methylbenzyl-4-benzoyloxyphenylmethylsulfonium, and methanesulfonates thereof, trifluoromethanesulfonates, camphorsulfonates, p-toluenesulfonates, and hexafluorophosphonates thereof.

<Photosensitizer>

The composition of the present invention may contain a photosensitizer. Examples of the photosensitizer include those disclosed in [J. V. Crivello, Adv. in Polymer Sci, 62, 1 (1984)], and specifically include pyrene, perylene, acridine, thioxanthone, 2-chlorothioxanthone, benzoflavin, N-vinylcarbazole, 9,10-dibutoxyanthracene, anthraquinone, benzophenone, coumarin, ketocoumarin, phenanthrene, camphorquinone, and phenothiazine derivatives. The photosensitizer is preferably in the amount of 50% by mass to 200% by mass with respect to that of the photopolymerization initiator.

<Chain Transfer Agent>

The composition of the present invention may contain a chain transfer agent. Examples of the chain transfer agent include alkyl N,N-dialkylaminobenzoate esters such as ethyl N,N-dimethylaminobenzoate ester, mercapto compounds having heterocycles, such as 2-mercaptobenzothiazole, 2-mercaptobenzoxazole, 2-mercaptobenzoimidazole, N-phenylmercaptobenzoimidazole, 1,3,5-tris(3-mercaptobutyloxyethyl)-1,3,5-triazine-2,4,6(1H,3H,5H)-trione, and aliphatic polyfunctional mercapto compounds such as pentaerythritol tetrakis(3-mercaptobutyrate) and 1,4-bis(3-mercaptobutyryloxy)butane.

The chain transfer agents may be used singly or in combination of two or more kinds thereof.

From the viewpoint of reducing variations in sensitivity, the content of the chain transfer agent is preferably 0.01% by mass to 15% by mass, more preferably 0.1% by mass to 10% by mass, and particularly preferably 0.5% by mass to 5% by mass, with respect to the total solid content of the composition of the present invention.

<Polymerization Initiator>

The composition according to the present invention may contain a polymerization inhibitor. The polymerization inhibitor is a substance that performs hydrogen donation (or hydrogen transfer), energy donation (or energy transfer), electron donation (or electron transfer), or the like to a polymerization initiating species, such as a radical, generated in the composition by light or heat, thereby deactivating the polymerization initiating species and suppressing unintended initiation of polymerization. The polymerization inhibitors disclosed in paragraphs 0154 to 0173 of JP2007-334322A, and the like can be used as the polymerization inhibitor. Among these, p-methoxyphenol is preferable as a polymerization inhibitor.

The content of the polymerization inhibitor in the composition of the present invention is preferably 0.0001% by mass to 5% by mass, more preferably 0.001% by mass to 5% by mass, and particularly preferably 0.001% by mass to 1% by mass, with respect to the total mass of the polymerizable compound.

<Adhesion Improving Agent>

The composition of the present invention may contain an adhesion improving agent. The adhesion improving agent is a compound which improves the adhesion between a cured film of the colored photosensitive composition layer and an inorganic material serving as a support, for example, a silicon compound such as glass, silicon, silicon oxide, and silicon nitride, gold, copper, and aluminum. Specific examples thereof include a silane coupling agent and a thiol-based compound. The silane coupling agent serving as an adhesion improving agent is used with a view to modifying the properties of the interface, and known silane coupling agents can be used without particularly restrictions.

As the silane coupling agent, the silane coupling agents described in paragraph 0048 of JP2009-98616A are preferable, and among these, γ-glycidoxypropyl trialkoxysilane and γ-methacryloxypropyl trialkoxysilane are more preferable. These may be used singly or in combination of two or more kinds thereof.

The content of the adhesion improving agent in the composition of the present invention is preferably 0.1% by mass to 20% by mass, and more preferably 0.2% by mass to 5% by mass, with respect to the total solid content of the composition.

<Development Accelerator>

A development accelerator may be added in the case of promoting the alkali solubility of unexposed regions to improve the developability of the coloring curable resin composition. The development accelerator is preferably a low-molecular-weight organic carboxylic acid compound having a molecular weight of 1,000 or less, or a low-molecular-weight phenolic compound having a molecular weight of 1,000 or less.

Specific examples of the development accelerator include aliphatic monocarboxylic acids such as formic acid, acetic acid, propionic acid, butyric acid, valeric acid, pivalic acid, caproic acid, diethylacetic acid, enanthoic acid, and caprylic acid; aliphatic dicarboxylic acids such as oxalic acid, malonic acid, succinic acid, glutaric acid, adipic acid, pimelic acid, suberic acid, azelaic acid, sebacic acid, brasylic acid, methylmalonic acid, ethylmalonic acid, dimethylmalonic acid, methylsuccinic acid, tetramethylsuccinic acid, and citraconic acid; aliphatic tricarboxylic acids such as tricarballylic acid, aconitic acid, and camphoronic acid; aromatic monocarboxylic acids such as benzoic acid, toluic acid, cuminic acid, hemellitic acid, and mesitylenic acid; aromatic polycarboxylic acids such as phthalic acid, isophthalic acid, terephthalic acid, trimellitic acid, trimesic acid, mellophanic acid, and pyromellitic acid; phenyl acetate, hydratropic acid, hydrocinnamic acid, mandelic acid, phenylsuccinic acid, atropic acid, cinnamic acid, methyl cinnamate, benzyl cinnamate, cinnamylidene acetic acid, coumaric acid, and umbellic acid.

(Other Additives)

The coloring curable resin composition of the present invention may further include various additives such as a filler, polymer compounds other than those described above, an ultraviolet absorber, and an aggregation inhibitor.

Examples of these additives include those described in paragraphs [0155] to [0156] of JP2004-295116A.

The coloring curable resin composition of the present invention may contain photostabilizers described in paragraph [0078] of JP2004-295116A and thermal polymerization inhibitors described in paragraph [0081] of JP2004-295116A.

[Method for Preparing Coloring Curable Composition]

The coloring curable composition of the present invention is prepared by mixing the respective components with optional components, as desired.

Furthermore, in the preparation of the coloring curable composition, the respective components constituting the coloring curable composition may be blended at once or the respective components may be dissolved/dispersed in solvents and then sequentially blended. Further, the order of introduction and operating conditions during the blending are not particularly limited. For example, all the components may be dissolved/dispersed in a solvent simultaneously to prepare a composition, or as desired, two or more solutions/dispersions may be appropriately prepared from the respective components and mixed during the use (during the coating) to prepare a composition.

The coloring curable compositions prepared as described above can be provided for use after they are filtered off and separated through a filter preferably having a pore size of approximately 0.01 μm to 3.0 μm, more preferably 0.05 μm to 0.5 μm, or the like.

The coloring curable composition of the present invention can form a colored cured film having excellent hue and contrast so that they can be conveniently used for forming colored pixels in a color filter and the like for use in liquid crystal display devices (LCDs) and solid-state imaging devices (for example, a CCD and a CMOS), or for manufacturing an ink for printing, an ink for ink jet printing, a paint, and the like. In particular, the coloring curable composition is suitable for forming colored pixels for liquid crystal display devices.

<Compound>

The present invention also relates to a compound represented by Formula (11), a compound represented by Formula (12), or a compound represented by Formula (13).

Formula (11)

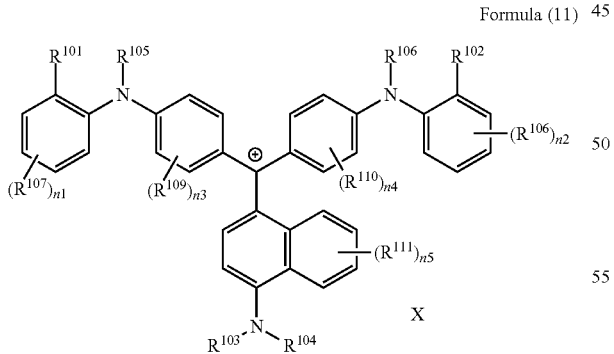

(in Formula (11), $R^{101}$ and $R^{102}$ each independently represent a hydrogen atom, a cyano group, $-SO_2N(C_2H_4OCH_3)_2$, or an alkyl group having 1 to 3 carbon atoms, $R^{103}$ to $R^{106}$ each independently represent a hydrogen atom, an alkyl group having 1 to 8 carbon atoms or aryl group, $R^{107}$ to $R^{111}$ each independently represent a hydrogen atom, a fluorine atom, a chlorine atom, a cyano group, a nitro group, $-NHCOCH_3$, $-SO_2NHC_2H_4OCH_3$, $-NHSO_2CH_3$ or an alkyl group having 1 to 3 carbon atoms, n1 to n4 each independently represent an integer of 1 to 4, n5 represents an integer of 0 to 6, X represents an anion or is not present, and at least one of $R^{101}$, . . . , or $R^{111}$ includes an anion, provided that in the case where $R^{101}$ and $R^{102}$ represent hydrogen atoms, $R^{103}$ represents an aryl group having a methyl group or an ester group as a substituent at at least the ortho-position), Formula (12)

(in Formula (12), $R^{201}$ and $R^{202}$ each independently represent a hydrogen atom or a methyl group, at least one of $R^{201}$ or $R^{202}$ represents a methyl group, $R^{203}$ to $R^{209}$ each independently represent a hydrogen atom, a fluorine atom, $-SO_2N(C_2H_4OCH_3)_2$, or an alkyl group having 1 to 3 carbon atoms, $R^{210}$ and $R^{211}$ each independently represent a methyl group or a phenyl group, n6 to n10 each independently represent an integer of 1 to 4, X represents an anion or is not present, and at least one of $R^{201}$, . . . , or $R^{211}$ includes an anion), and Formula (13)

(in Formula (13), $R^{301}$ and $R^{302}$ each independently represent a methyl group or an ethyl group, $R^{303}$ to $R^{305}$ each independently represent a hydrogen atom or a methyl group, $R^{306}$ represents an ester group, $R^{307}$ to $R^{310}$ represents a hydrogen atom, n11 to n13 each independently represent an integer of 1 to 4, n14 represents an integer of 1 to 6, X represents an anion or is not present, and at least one of $R^{301}$, . . . , or $R^{310}$ includes an anion).

It is preferable that the compound represented by Formula (11) is represented by Formula (14).

Formula (14)

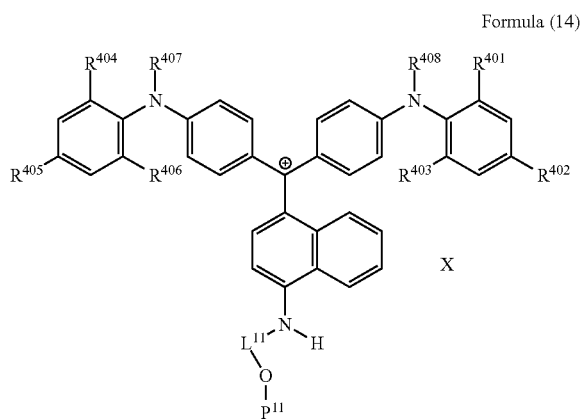

(in Formula (14), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, $P^{11}$ represents an acryloyl group, a methacryloyl group, or a —$CH_2C_6H_4CH=CH_2$ group; and X represents a bistrifluoromethanesulfonylimide anion, a tristrifluoromethanesulfonylmethide anion, or a perfluoromethanesulfonic acid anion. In Formula (14), it is preferable that $L^{11}$ represents an alkylene group having 2 to 10 carbon atoms, and $P^{11}$ represents an acryloyl group or a methacryloyl group).

It is preferable that the compound represented by Formula (11) is a compound represented by Formula (15).

Formula (15)

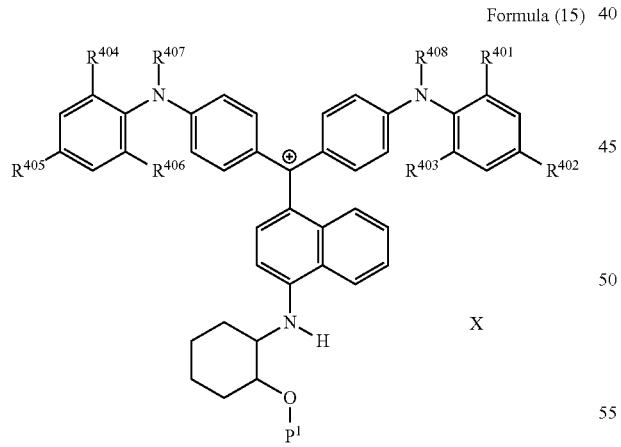

(in Formula (15), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $P^1$ represents a polymerizable group, and X represents a bistrifluoromethanesulfonylimide anion, a tristrifluoromethanesulfonylmethide anion, or a perfluoromethanesulfonic acid anion)

It is preferable that the compound represented by Formula (11) is represented by Formula (16).

Formula (16)

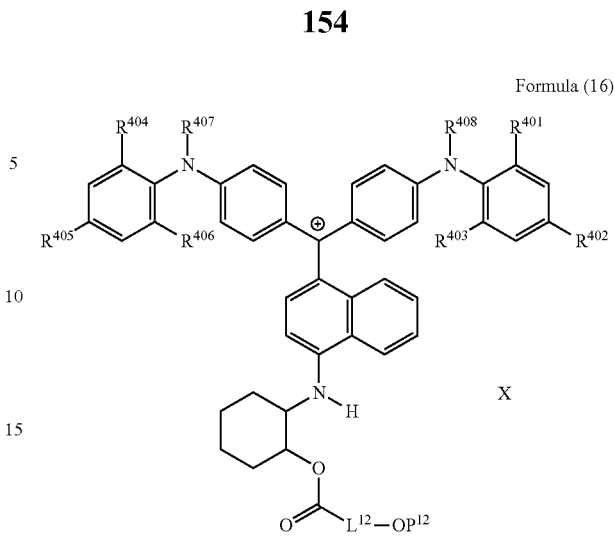

(in Formula (16), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents an alkylene group having 2 to 12 carbon atoms, a cycloalkylene group, a phenylene group, or a group formed by combination of these groups, $P^{12}$ represents an acryloyl group or a methacryloyl group; and X represents a bistrifluoromethanesulfonylimide anion, a tristrifluoromethanesulfonylmethide anion, or a perfluoromethanesulfonic acid anion)

It is preferable that the compound represented by Formula (11) is represented by Formula (17).

Formula (17)

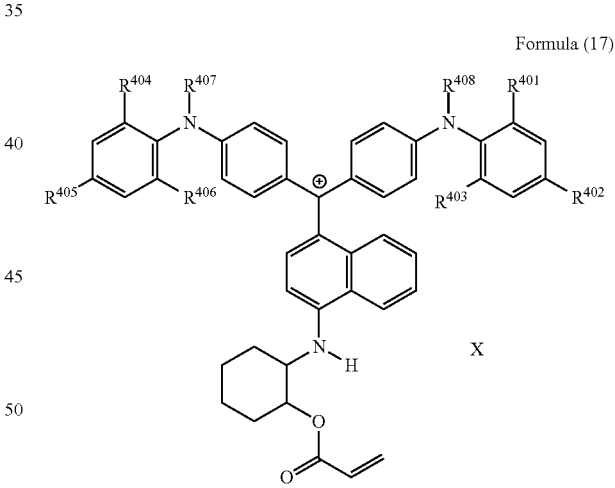

(in Formula (17), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and X represents a bistrifluoromethanesulfonylimide anion, a tristrifluoromethanesulfonylmethide anion, or a perfluoromethanesulfonic acid anion)

Further, the preferred ranges of $R^{101}$ to $R^{111}$, $R^{201}$ to $R^{211}$, $R^{301}$ to $R^{310}$ of the compounds represented by Formulae (11) to (13) are the same as the preferred examples of $R^{101}$ to $R^{111}$, $R^{201}$ to $R^{211}$, $R^{301}$ to $R^{310}$ of the compounds represented by Formulae (1) to (3), respectively. Further, the preferred ranges of $R^{401}$ to $R^{408}$ of the compounds represented by Formulae (14) to (17) are the same as the preferred examples of $R^{401}$ to $R^{408}$ of the compounds represented by Formulae (1B) and (1C), respectively.

The present invention also relates to a cation represented by Formula (4).

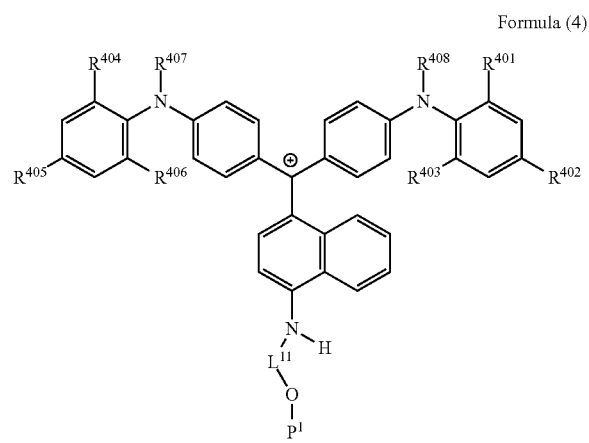

Formula (4)

(in Formula (4), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, and $P^1$ represents a polymerizable group. In Formula (4), $P^1$ preferably represents an acryloyl group, a methacryloyl group, or a —$CH_2C_6H_4CH=CH_2$ group).

The cation of the present invention may be a cation represented by any one of Formulae (5) to (7).

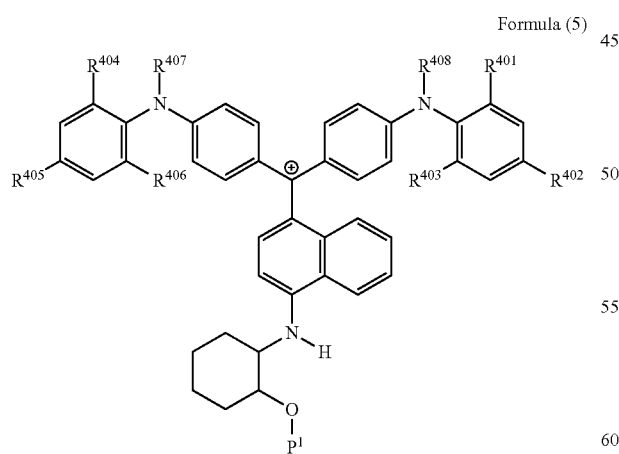

Formula (5)

(in Formula (5), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and $P^1$ represents a polymerizable group)

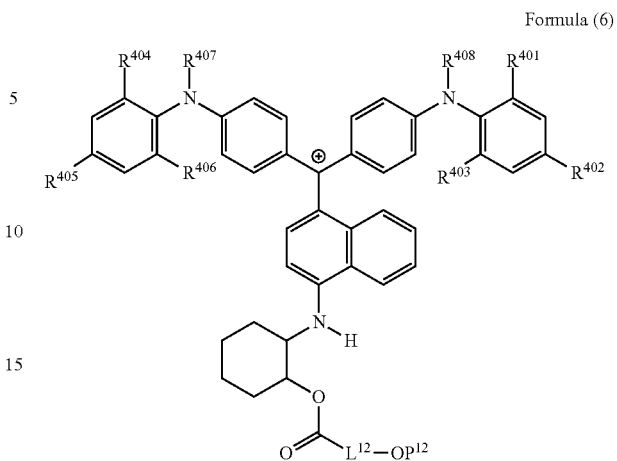

Formula (6)

(in Formula (6), $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents a combination of an alkylene group having 2 to 12 carbon atoms, a cycloalkylene group, a phenylene group, or a group formed by combination of these groups, and $P^{12}$ represents an acryloyl group or a methacryloyl group)

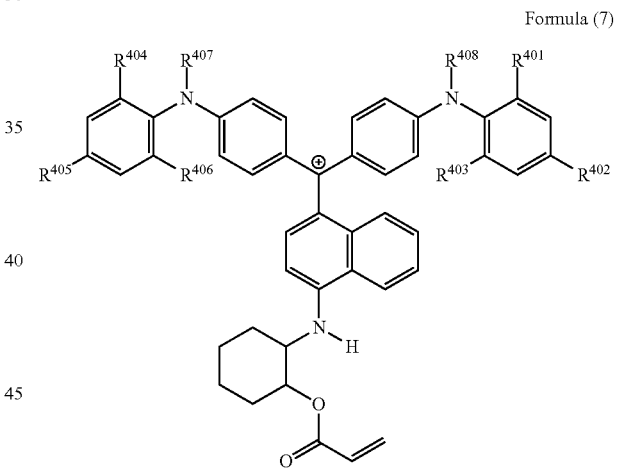

Formula (7)

(in Formula (7), $R^{401}$ to $R^{406}$ each independently represent a hydrogen atom or an alkyl group having 1 to 3 carbon atoms, and $R^{407}$ and $R^{408}$ each independently represent an alkyl group having 1 to 6 carbon atoms)

Furthermore, the preferred ranges of $R^{401}$ to $R^{408}$ of the cation represented by Formulae (4) to (7) are the same as the preferred examples of $R^{401}$ to $R^{408}$ of the compounds represented by Formulae (1B) and (1C), respectively.

[Color Filter and Method for Manufacturing Same]

The color filter of the present invention is composed of a substrate and a colored region including the coloring curable resin composition of the present invention on the substrate. The colored region on the substrate consists of colored films of, for example, red (R), green (G), blue (B) and the like, which form pixels in the color filter.

The method for manufacturing a color filter of the present invention includes a step (A) of coating the coloring composition of the present invention onto a support to form a colored layer (also referred to as a coloring curable resin composition layer), and a step (B) of patternwise exposing and developing the coloring curable resin composition layer formed in the step (A) to form a colored region (colored pattern). Further, in a preferred aspect, the method for manufacturing a color filter of the present invention particularly further includes a step (C) of irradiating the colored pattern formed in the step (B) with ultraviolet rays and a step (D) of subjecting the colored pattern irradiated with ultraviolet rays in the step (C) to a heating treatment.

Moreover, it is also preferable that the method for manufacturing a color filter of the present invention further includes a step of applying a coloring composition of the present invention as described above onto a support to form a colored curable composition layer, a step of patternwise exposing the coloring curable resin composition layer, and a step of removing the unexposed area by development to form a colored pattern.

Hereinafter, the method for manufacturing a color filter of the present invention will be described in more detail.

—Step (A)—

In the method for manufacturing a color filter of the present invention, the coloring curable resin composition of the present invention as mentioned above is first coated onto a support by a coating method such as spin coating, slit coating, cast coating, roll coating, bar coating, and ink jet to form a coloring curable resin composition layer, and then the coloring curable resin composition layer was dried by heating (prebaking), vacuum drying, or the like.

Examples of the support include sodium glass, non-alkali glass, borosilicate glass, quartz glass, a silicon substrate, and a resin substrate. Further, an undercoat layer may be provided on this support, as desired, to improve adhesion to the overlying layer, to prevent diffusion of substance, or to smoothen the surface.

Examples of the prebaking conditions include heating with a hot plate or an oven at 70° C. to 130° C. for about 0.5 minutes to 15 minutes.

Moreover, the thickness of the coloring curable resin composition layer formed with the coloring curable resin composition is appropriately selected according to the purposes. In the color filter for a liquid crystal display device, the thickness of the coloring curable resin composition layer is preferably in the range of 0.2 µm to 5.0 µm, and more preferably in the range of 1.0 µm to 4.0 µm. Further, in the color filter for a solid-state imaging device, the thickness is preferably in the range of 0.2 µm to 5.0 µm, and more preferably in the range of 0.3 µm to 2.5 µm. Incidentally, the thickness of the coloring curable resin composition layer is a film thickness after prebaking.

—Step (B)—

Next, in the method for manufacturing a color filter of the present invention, the coloring curable resin composition layer formed on the substrate is subjected to patternwise exposure. As the light or radiation that can be applied for the exposure, a g-ray, an h-ray, an i-ray, and various types of laser light are preferable, and an i-ray is particularly preferable. In the case where the i-ray is used as an irradiation light, it is preferably irradiated at an exposure dose of 5 mJ/cm$^2$ to 500 mJ/cm$^2$.

In addition, as other exposure light sources, various laser light sources such as ultra-high-pressure, high-pressure, medium-pressure, and low-pressure mercury lamps, chemical lamps, carbon arc lamps, xenon lamps, and metal halide lamps can also be used.

~Exposing Step Using Laser Light Source~

As irradiation light in an exposure system using a laser light source, an ultraviolet laser having a wavelength in the range of 300 nm to 410 nm is preferable, and an ultraviolet laser having a wavelength in the range of 300 nm to 360 nm is more preferable. Specifically, the third harmonic generation (355 nm) of Nd:YAG lasers which are solid-state lasers as relatively inexpensive lasers with especially high output, or excimer lasers XeCl (308 nm) and XeF (353 nm) can be suitably used. The exposure dose of the pattern is in the range of 1 mJ/cm$^2$ to 100 mJ/cm$^2$, and more preferably in the range of 1 mJ/cm$^2$ to 50 mJ/cm$^2$ from the viewpoint of productivity.

The exposure apparatus is not particularly limited, and commercial products such as CALLISTO (manufactured by V-Technology Co., Ltd.), EGIS (manufactured by V-Technology Co., Ltd.), DF2200G (manufactured by DAINIPPON SCREEN MFG. CO., LTD.), or the like can be used. Further, other apparatuses than those described above may also be suitably used.

Subsequently, the coloring curable resin composition layer after the exposure is subjected to development with a developer. Thus, a colored pattern can be formed. With regard to a developer, a combination of various organic solvents or an aqueous alkaline solution can be used so long as it dissolves the uncured areas of the coloring curable resin composition while it does not dissolve cured areas. In the case where the developer is an aqueous alkaline solution, the alkaline concentration is preferably adjusted such that the pH preferably becomes 10 to 13. Examples of the aqueous alkaline solution include an aqueous alkaline solution include aqueous alkaline solutions of sodium hydroxide, potassium hydroxide, sodium carbonate, sodium hydrogen carbonate, sodium silicate, sodium metasilicate, aqueous ammonia, ethylamine, diethylamine, dimethylethanolamine, tetramethylammonium hydroxide, tetraethylammonium hydroxide, corrin, pyrrole, piperidine, 1,8-diazabicyclo-[5,4,0]-7-undecene, and the like.

The developing time is preferably 30 seconds to 300 seconds, and more preferably 30 seconds to 120 seconds. The developing temperature is preferably 20° C. to 40° C., and more preferably 23° C.

The development can be carried out in a paddle type, a shower type, a spray type, or the like.

In addition, after carrying out development using an aqueous alkaline solution, it is preferable to perform washing with water.

—Step (C)—

In particular, in the method for manufacturing a color filter of the present invention, the colored pattern (pixel) formed by using a coloring curable resin composition of the present invention can also be postexposed by irradiation with ultraviolet rays.

—Step (D)—

The colored pattern postexposed by irradiation with ultraviolet rays as described above is preferably further subjected to a heat treatment. The heat treatment (so-called a postbaking treatment) of the formed colored pattern allows the colored pattern to be further cured. This heat treatment can be carried out using, for example, a hot plate, various heaters, an oven, or the like.

The temperature during the heat treatment is preferably 100° C. to 300° C., and more preferably 150° C. to 250° C. Further, the heating time is preferably approximately 10 minutes to 120 minutes.

The colored pattern thus obtained constitutes a pixel in a color filter. When a color filter having multiple hue pixels is manufactured, the step (A), the step (B), and optionally the step (C) or the step (D) may be repeated to suit a desired number of colors.

Alternatively, the step (C) and/or the step (D) may be carried out each time when the formation, exposure and development of a monochromatic coloring curable resin composition layer is completed (for each color), or the step (C) and/or the step (D) may be carried out once after the formation, exposure and development of all coloring curable resin composition layers of a desired number of colors have been completed.

The color filter obtained by the method for manufacturing the color filter of the present invention (the color filter of the present invention) is excellent in hue and contrast in view of a fact that the coloring curable resin composition of the present invention is used. In the case where the color filter is used in a liquid crystal display device, display of an image with excellent spectral characteristics and contrast can be realized while achieving a good hue.

Moreover, the film thickness of the colored pattern (colored pixel) of the color filter of the present invention is preferably 3.0 μm or less, and more preferably 2.5 μm or less.

[Image Display Device]

The color filter of the present invention can be used for an image display device such as a liquid crystal display device and an organic EL display device, and is particularly suitable for the use of a liquid crystal display device. A liquid crystal display device including the color filter of the present invention can display a high-quality image having good tint of a display image and excellent display characteristics.

The image display device of the present invention has a color filter in at least three colors of red, green, and blue, and the color filter in blue preferably uses the coloring curable resin composition.

The definition of display devices or details of the respective display devices are described in, for example, "Electronic Display Device (Akio Sasaki, Kogyo Chosakai Publishing Co., Ltd., published in 1990)", "Display Device (Sumiaki Ibuki, Sangyo Tosho Co., Ltd., published in 1989), and the like. In addition, the liquid crystal display device is described in, for example, "Liquid Crystal Display Technology for Next Generation (edited by Tatsuo Uchida, Kogyo Chosakai Publishing Co., Ltd., published in 1994)". The liquid crystal display device to which the present invention can be applied is not particularly limited, and for example, the present invention can be applied to liquid crystal display devices employing various systems described in the "Liquid Crystal Display Technology for Next Generation".

The color filter of the present invention may be used for a liquid crystal display device using a color TFT system. The liquid crystal display device using a color TFT system is described in, for example, "Color TFT Liquid Crystal Display (KYORITSU SHUPPAN Co., Ltd., published in 1996)". Further, the present invention can be applied to a liquid crystal display device having an enlarged view angle, which uses an in-plane switching driving system such as IPS and a pixel division system such as MVA, or to STN, TN, VA, OCS, FFS, R-OCB, and the like.

In addition, the color filter in the present invention can be provided to a color-filter on array (COA) system which is bright and has a high definition.

If the color filter of the present invention is used in a liquid crystal display device, high contrast can be realized when the color filter is combined with a three-wavelength tube of a cold cathode tube known in the related art. Further, if a light source of LED in red, green, and blue (RGB-LED) is used as a backlight, a liquid crystal display device having high luminance, high color purity, and good color reproducibility can be provided.

[Solid-state Imaging Device]

The coloring curable composition of the present invention can be preferably used in the applications of a solid-state imaging device. The configuration of the solid-state imaging device is not particularly limited as long as it includes a color filter manufactured using the coloring curable composition of the present invention and functions as a solid-state imaging device, but may include, for example, the configurations as follows.

The solid-state imaging device is configured as follows: a plurality of photodiodes constituting a light receiving area of a solid-state imaging device (for example, a CCD image sensor and a CMOS image sensor) and a transmission electrode composed of, for example, polysilicon are provided on a support; a light shielding film which is composed of, for example, tungsten and has openings corresponding to only light receiving areas of the photodiodes is provided on the photodiodes and the transmission electrode; a device protecting film which is composed of, for example, silicon nitride is formed on the light shielding film so as to cover the entire surface of the light shielding film and the light receiving areas of the photodiodes; and the color filter for a solid-state imaging device of the present invention is provided on the device protecting film.

In addition, the solid-state imaging device may also be configured such that it has a light collecting unit (for example, a microlens. This shall apply hereinafter) on a device protective film and under a color filter (on the side closer to a supporter) or has a light collecting unit on a color filter.

EXAMPLES

Hereinafter, the present invention will be described in more detail with reference to Examples. The materials, use amounts, ratios, the treatment specifications, the treatment orders, and the like shown in Examples below can be appropriately modified as long as the gist of the present invention is not impaired. Thus, the scope of the present invention is not limited to the specific examples shown below. Further, "%" and "part (s)" are based on mass unless otherwise specified.

Synthesis Examples of Colorants

<Low-Molecular Type>

«Synthesis of TAM001»

12.5 g of 4,4'-dichlorobenzophenone (manufactured by Tokyo Chemical Industry Co., Ltd.), 15.0 g of 2,4,6-trimethylaniline (manufactured by Tokyo Chemical Industry Co., Ltd.), 14.4 g of tert-butoxysodium, and 150 mL of toluene were put into a flask, followed by stirring at room temperature in a nitrogen atmosphere. 56 mg of palladium acetate (manufactured by Wako Pure Chemical Industry Ltd.) and 266 mg of tri-tert-butylphosphonium tetrafluoroborate (manufactured by Wako Pure Chemical Industry Ltd.) were added thereto, followed by stirring for 4 hours under the heating and refluxing conditions. After cooling, 200 mL of ethyl acetate and 200 mL of water were added thereto and the precipitated crystals were collected by filtration. The crystals were washed with 100 mL of ethyl acetate under heating, and then 8.0 g of crystals of the obtained TAM001-A were collected by filtration.

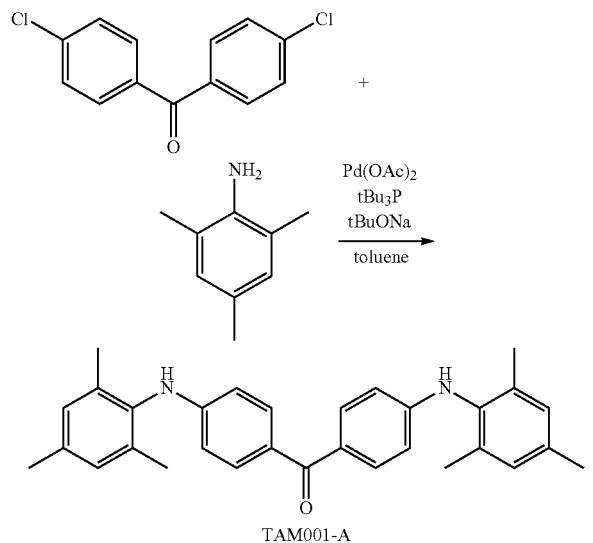

29 g of 1-bromonaphthalene (manufactured by Tokyo Chemical Industry Co., Ltd.), 21 g of 2,4,6-trimethylaniline (manufactured by Tokyo Chemical Industry Co., Ltd.), 7.2 g of tert-butoxysodium, and 300 mL of toluene were put into a flask, followed by stirring at room temperature in a nitrogen atmosphere. 56 mg of palladium acetate (manufactured by Wako Pure Chemical Industry Ltd.) and 266 mg of tri-tert-butylphosphonium tetrafluoroborate (manufactured by Wako Pure Chemical Industry Ltd.) were added thereto, followed by stirring for 1 hour under the heating and refluxing conditions. After cooling, the mixture was extracted by addition of 200 mL of ethyl acetate and 200 mL of water, and the obtained organic phase was dehydrated over sodium sulfate. The residue was concentrated and then purified by silica gel column chromatography to obtain 37 g of crystals of TAM001-B.

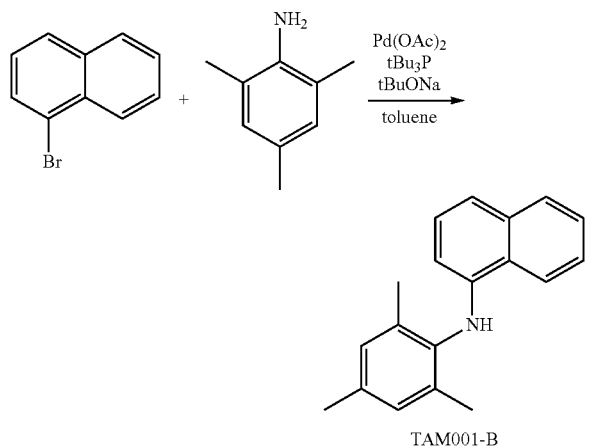

4.5 g of TAM001-A, 2.6 g of TAM001-B, 2.3 g of phosphoryl chloride, and 30 mL of toluene were put into a flask, followed by heating to 90° C. and stirring for 5 hours. After the flask was cooled to room temperature, 30 mL of saturated brine and 50 mL of ethyl acetate were added thereto, followed by stirring for 30 minutes. The precipitated crystals were collected by filtration, and washed with 50 mL of water and then with 30 mL of ethyl acetate to obtain 5.1 g of crystals of TAM001-Cl.

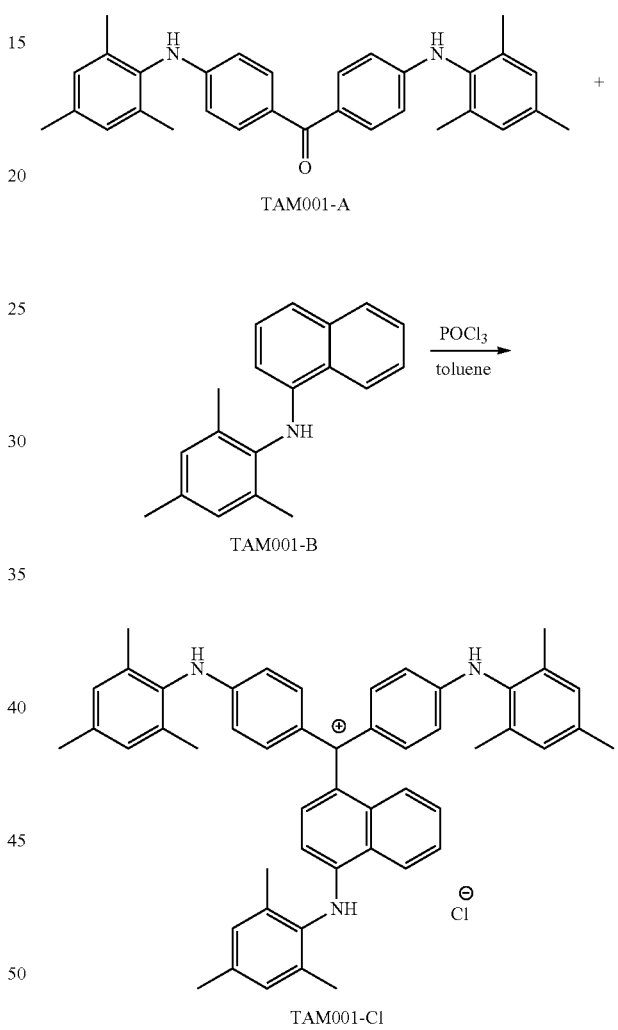

3.6 g of TAM001-Cl, 5.8 g of bis(trifluoromethanesulfonyl)imide lithium (manufactured by Tokyo Chemical Industry Co., Ltd.), and 30 mL of methanol were put into a flask, followed by stirring and dissolving at room temperature. 100 mL of water was added dropwise thereto to carry out precipitation. The obtained crystals were purified by silica gel column chromatography to obtain 3.0 g of crystals of TAM001. It was found to be as follows: MALDI-MASS (posi): 695.4, and MALDI-MASS (nega): 279.9. The λmax (ethyl acetate solution) of the absorption spectrum was 571 nm.

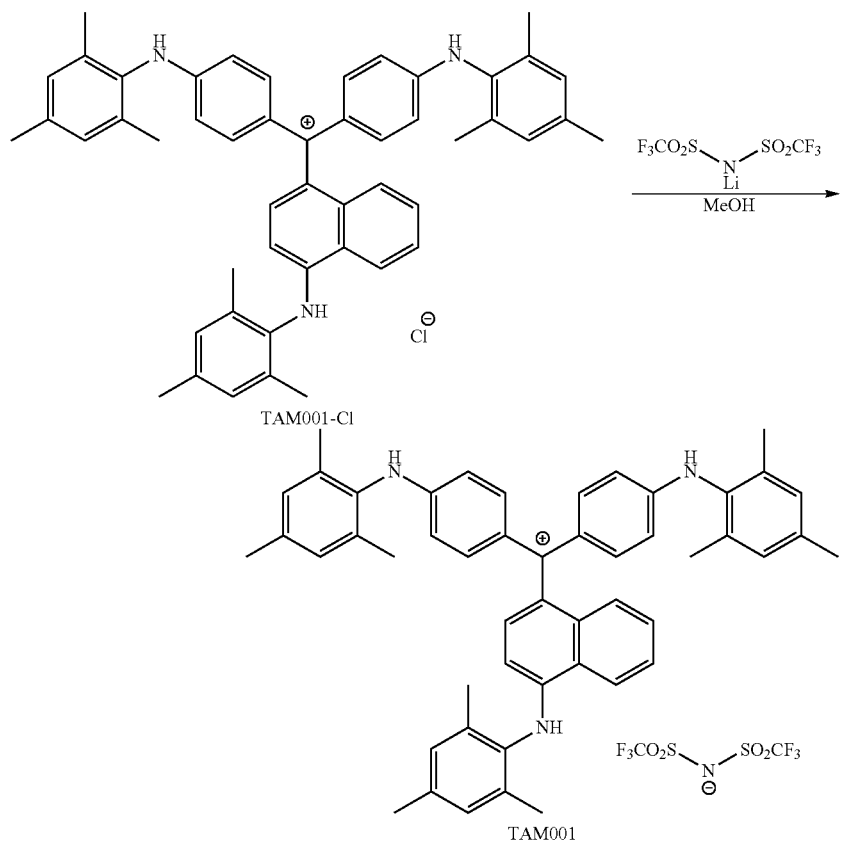

«Synthesis of TAM002»

By the same method as in the synthesis of TAM001-A except that 2,6-diisopropylaniline (manufactured by Tokyo Chemical Industry Co., Ltd.) was used instead of 2,4,6-trimethylaniline, TAM002-A was obtained.

By the same method as in the synthesis of TAM001-B except that 2,6-diisopropylaniline (manufactured by Tokyo Chemical Industry Co., Ltd.) was used instead of 2,4,6-trimethylaniline, TAM002-B was obtained.

By the same method as in the synthesis of TAM001-Cl, TAM002-A was used instead of TAM001-A and TAM002-B was used instead of TAM001-B, TAM002-Cl was obtained.

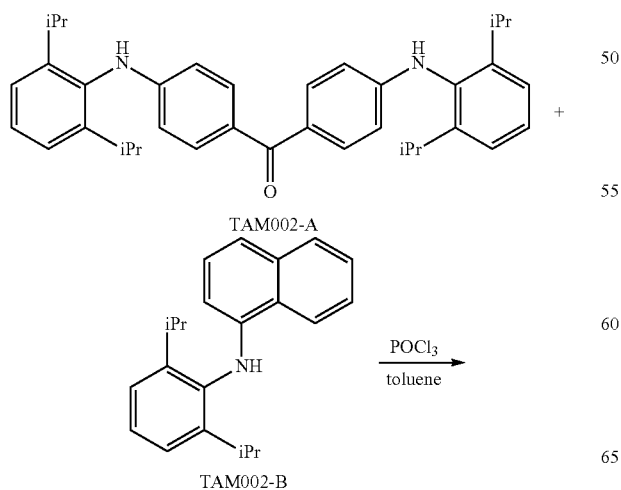

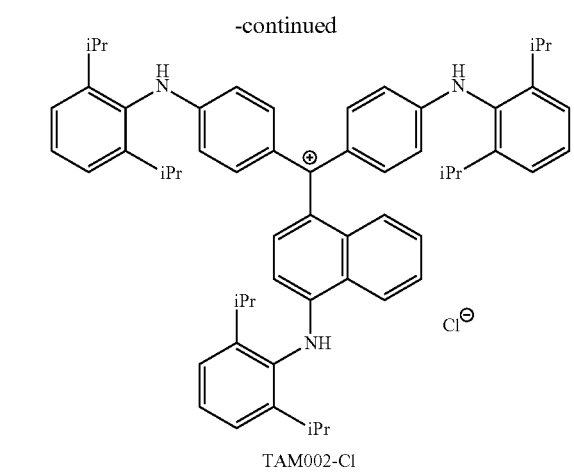

By the same method as in the synthesis of TAM001 except that TAM002-Cl was used instead of TAM001-Cl and a lithiumtetrakis(pentafluorophenyl)borate/ethyl ether complex (manufactured by Tokyo Chemical Industry Co., Ltd.) was used instead of bis(trifluoromethanesulfonyl)imide lithium, TAM002 was obtained. It was found to be as follows: MALDI-MASS (posi): 818.5, and MALDI-MASS (nega): 679.0. The λmax (ethyl acetate solution) of the absorption spectrum was 579 nm.

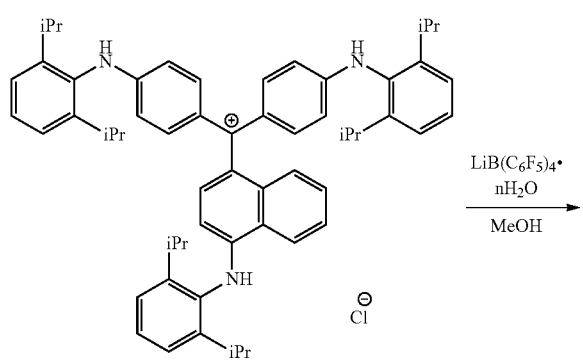

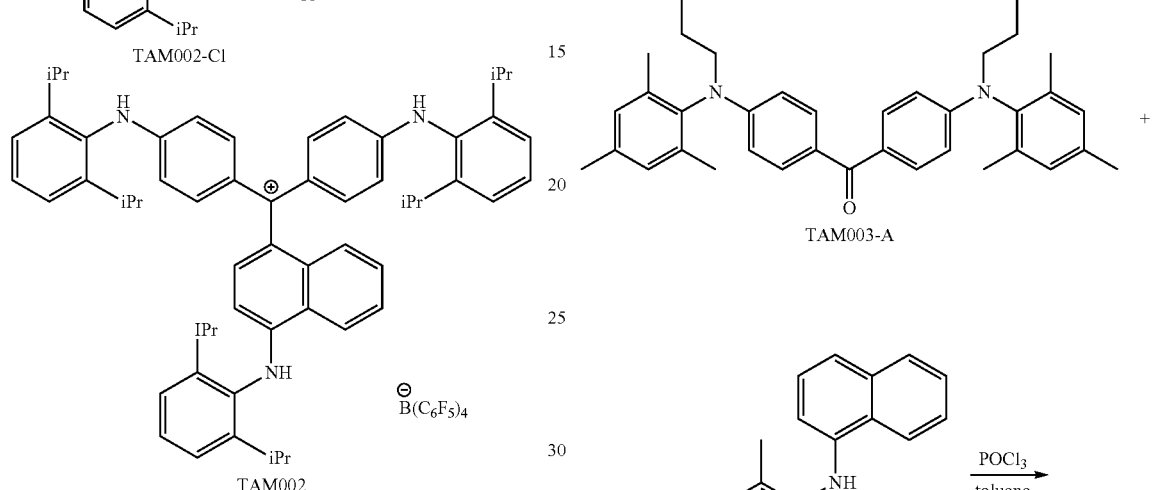

«Synthesis of TAM003»

To a mixed solution of TAM001-A (2.6 g), sodium hydride (an oil mixture, a content of 60% by mass, manufactured by Tokyo Chemical Industry Co., Ltd.), and 25 mL of N-methylpyrrolidone was added dropwise 14 g of propane 1-iodide (manufactured by Kanto Chemical Co., Inc.) at room temperature. The solution after dropwise addition was stirred at 75° C. for 2 hours. After the reaction solution was cooled to room temperature, 100 mL of water was added thereto. After adjusting the pH to 6 to 7 with a solution of hydrochloric acid, the crude precipitated crystals were filtered. The crude crystals were suspended and washed with n-hexane to obtain 2.0 g of crystals of TAM003-A.

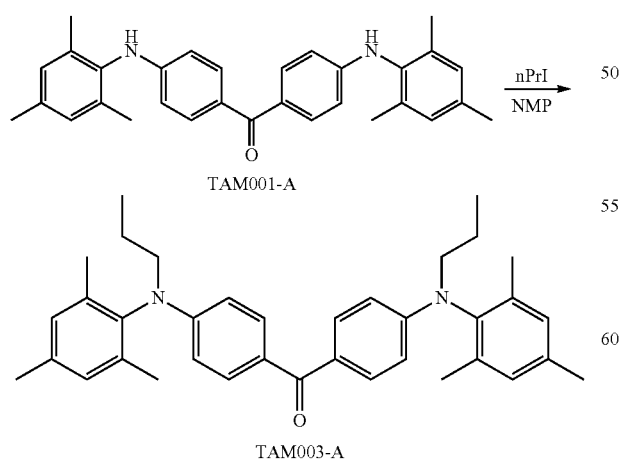

1.0 g of TAM003-A, 0.59 g of TAM001-B, 1.0 g of phosphoryl chloride, and 10 mL of toluene were put into a flask, followed by heating to 100° C. and stirring for 2 hours. After the flask was cooled to room temperature, 30 mL of saturated brine was added thereto, followed by stirring for 30 minutes. 30 mL of n-hexane was added thereto and the solution fraction was decanted. The residual gummy materials were washed twice with 20 mL of water, and washed with 20 mL of hexane-ethyl acetate(3/1) to obtain 0.9 g of TAM003-Cl as a gummy material.

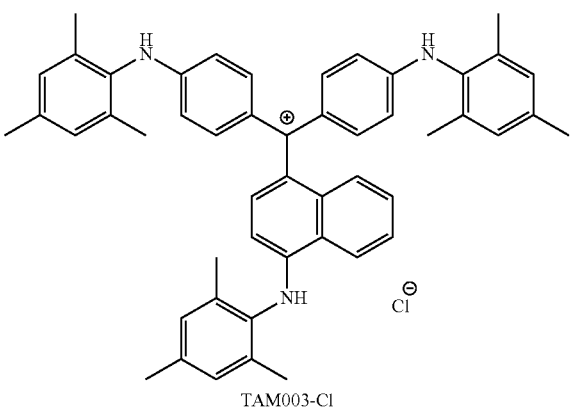

TAM003-Cl (0.9 g) and 3.0 g of bis(trifluoromethanesulfonyl)imide lithium were dissolved in 50 mL of ethyl acetate, and 50 mL of hexane was added thereto. This solution was directly charged into a silica gel column and purified with ethyl acetate/n-hexane (1/1→1/0) as a developing solvent. After purification, 600 mg of crystals of TAM003 were obtained. It was found to be as follows: MALDI-MASS (posi): 776.5, and MALDI-MASS (nega): 279.9. The λmax (ethyl acetate solution) of the absorption spectrum was 600 nm.

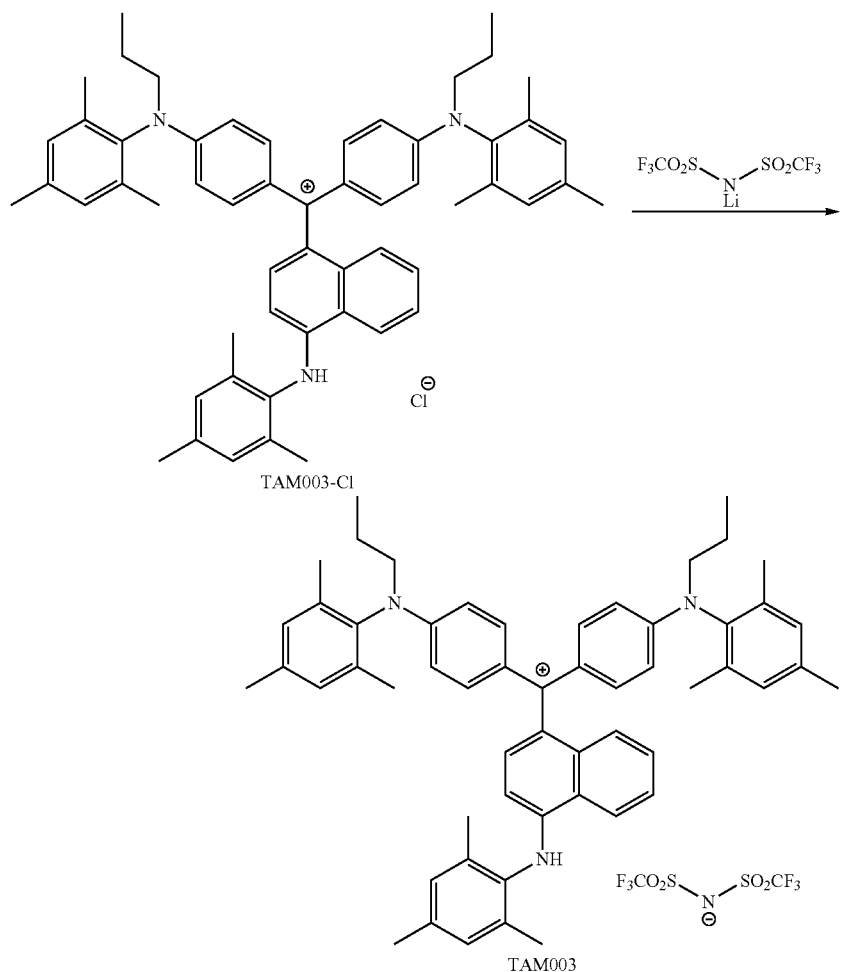

«Synthesis of TAM004»

20 g of 2-bromobenzoic acid, 15 g of 1-aminonaphthalene, 0.6 g of copper powder, 0.6 g of copper (II) oxide, 14 g of potassium carbonate, and 34 mL of ethoxyethanol were put into a flask, followed by stirring at 130° C. for 24 hours. After cooling, 200 mL of water was added thereto, concentrated hydrochloric acid was further added dropwise thereto until the pH became 3, and the crude precipitated crystals were collected by filtration. The obtained crude crystals were suspended and washed with methanol to obtain 20 g of TAM004-B.

TAM004-B (2.6 g), 2.2 g of ethyl p-toluenesulfonate, 1.6 g of potassium carbonate, and 25 mL of N-methylpyrrolidone were put into a flask, followed by heating and stirring at 90° C. for 24 hours. After cooling, 200 mL of water was added thereto, followed by extraction with ethyl acetate, and the combined organic phase was dried over sodium sulfate. This was purified by silica gel column chromatography to obtain 2.2 g of TAM004-A.

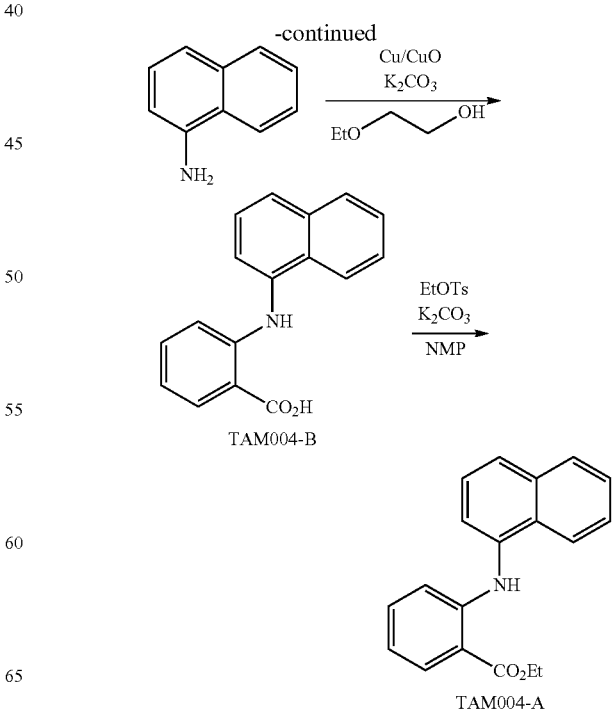

By the same method as in the synthesis of TAM001-Cl except that TAM004-A was used instead of TAM001-B, TAM004-Cl was obtained.

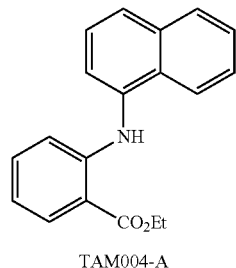

TAM004-A

+

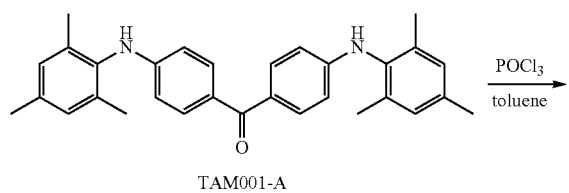

TAM001-A

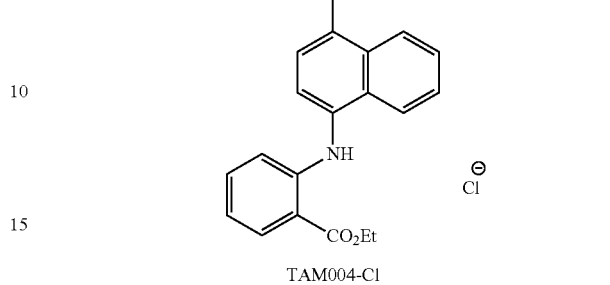

TAM004-Cl

By the same method as in the synthesis of TAM001-Cl except that TAM004-Cl was used instead of TAM001-Cl, TAM004 was obtained. It was found to be as follows: MALDI-MASS (posi): 722.4, and MALDI-MASS (nega): 279.9. The λmax (ethyl acetate solution) of the absorption spectrum was 604 nm.

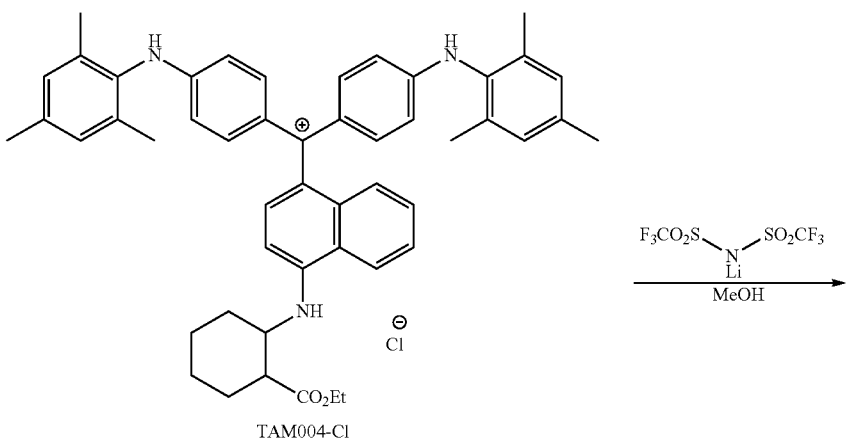

TAM004-Cl

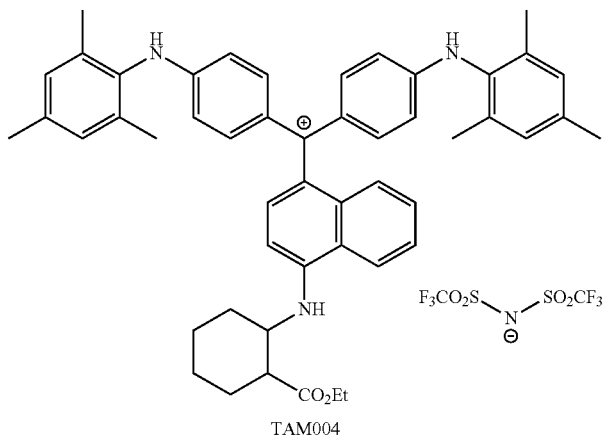

TAM004

«Synthesis of TAM005»

50 g of 1-aminonaphthalene, 38 g of 1,2-epoxycyclohexane, and 150 mL of 1,3-hexafluoro-2-propanol were added to a flask, followed by stirring for 5 hours under heating and refluxing. After the mixture was cooled to room temperature, the solvent was concentrated and the residue was suspended and washed with 200 mL of hexane, and the obtained crystals were filtered and additionally washed with isopropyl alcohol to obtain TAM005-A (56 g).

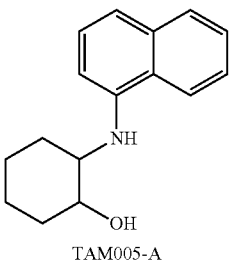

TAM005-A

TAM005-A (1.2 g), TAM001-A (2.2 g), 1.84 g of phosphoryl chloride, and 20 mL of toluene were added to a flask, followed by heating and stirring at 90° C. for 4 hours. After the mixture was cooled to room temperature, 20 mL of hexane was added thereto, and the hexane phase was removed by decantation. The same operation was carried out twice to obtain TAM005-Cl as a viscous oil. 20 mL of methanol was added thereto, and 3.0 g of bis(trifluoromethanesulfonyl)imide lithium was further added thereto and dissolved therein. While stirring, 60 mL of water was added dropwise to the mixture. The separated aqueous phase was removed and the obtained viscous oil was purified by silica gel column chromatography to obtain 2.2 g of TAM005. It was found to be as follows: MALDI-MASS (posi): 690.4, and MALDI-MASS (nega): 279.9. The λmax (ethyl acetate solution) of the absorption spectrum was 563 nm.

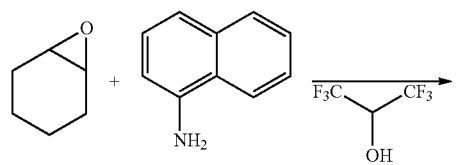

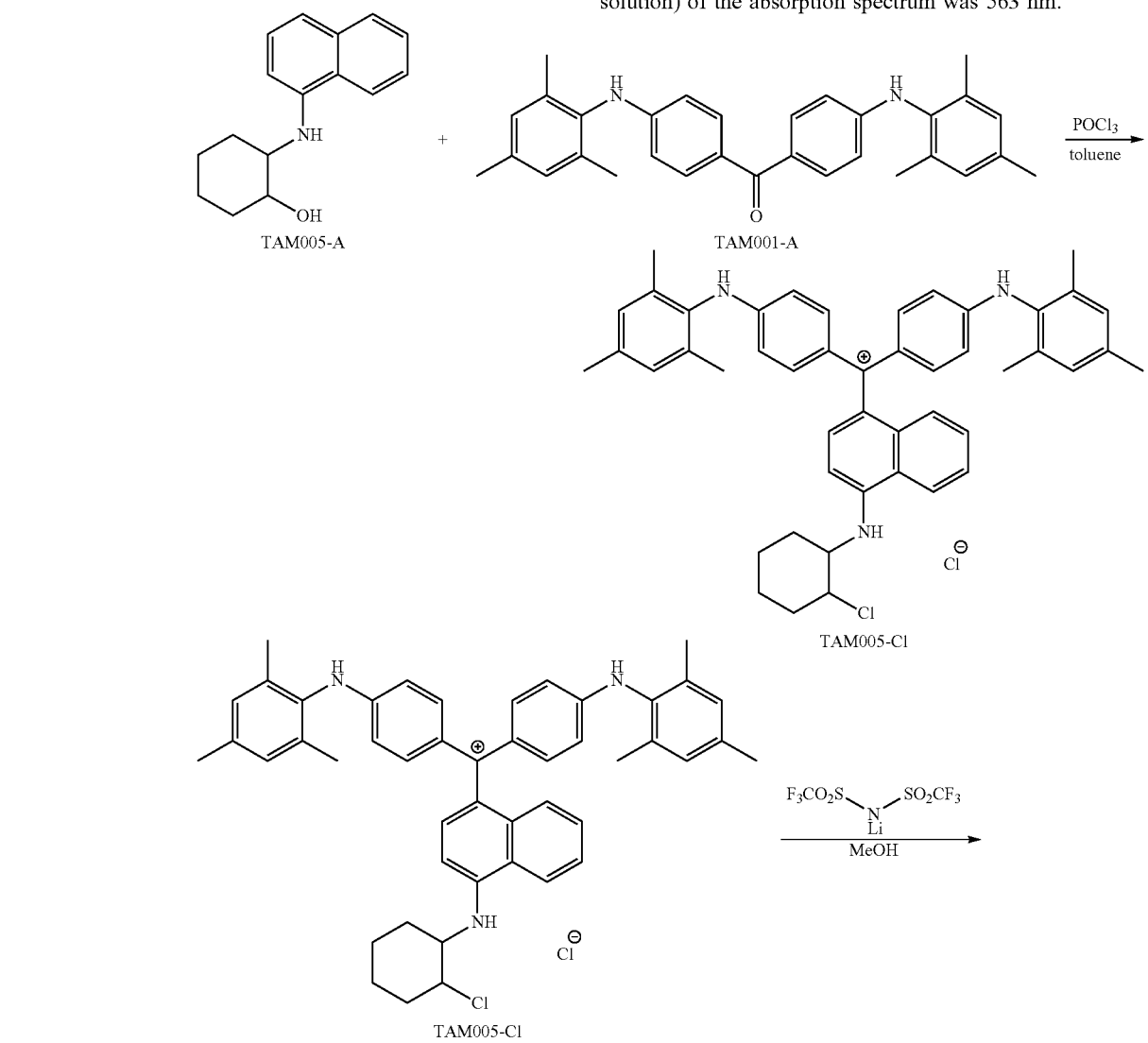

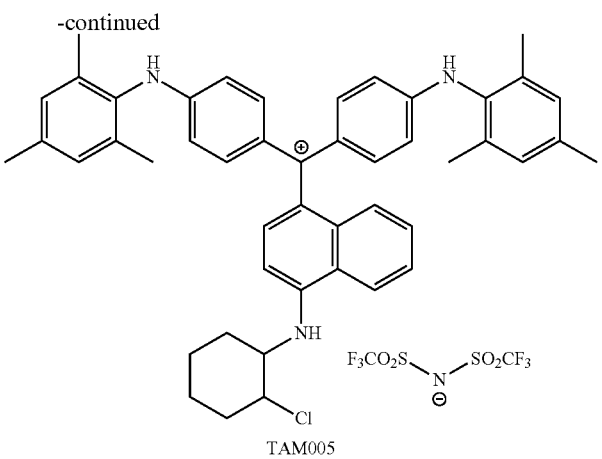
TAM005
《Synthesis of TAM006》
By the same method as in the synthesis of TAM005-Cl except that TAM002-A was used instead of TAM001-A, TAM006-C was obtained. Further, by the same method as in the synthesis of TAM006, TAM006-Cl was used instead of TAM005-Cl, TAM006 was obtained. It was found to be as follows: MALDI-MASS (posi): 774.5, and MALDI-MASS (nega): 279.9. The λmax (ethyl acetate solution) of the absorption spectrum was 619 nm.
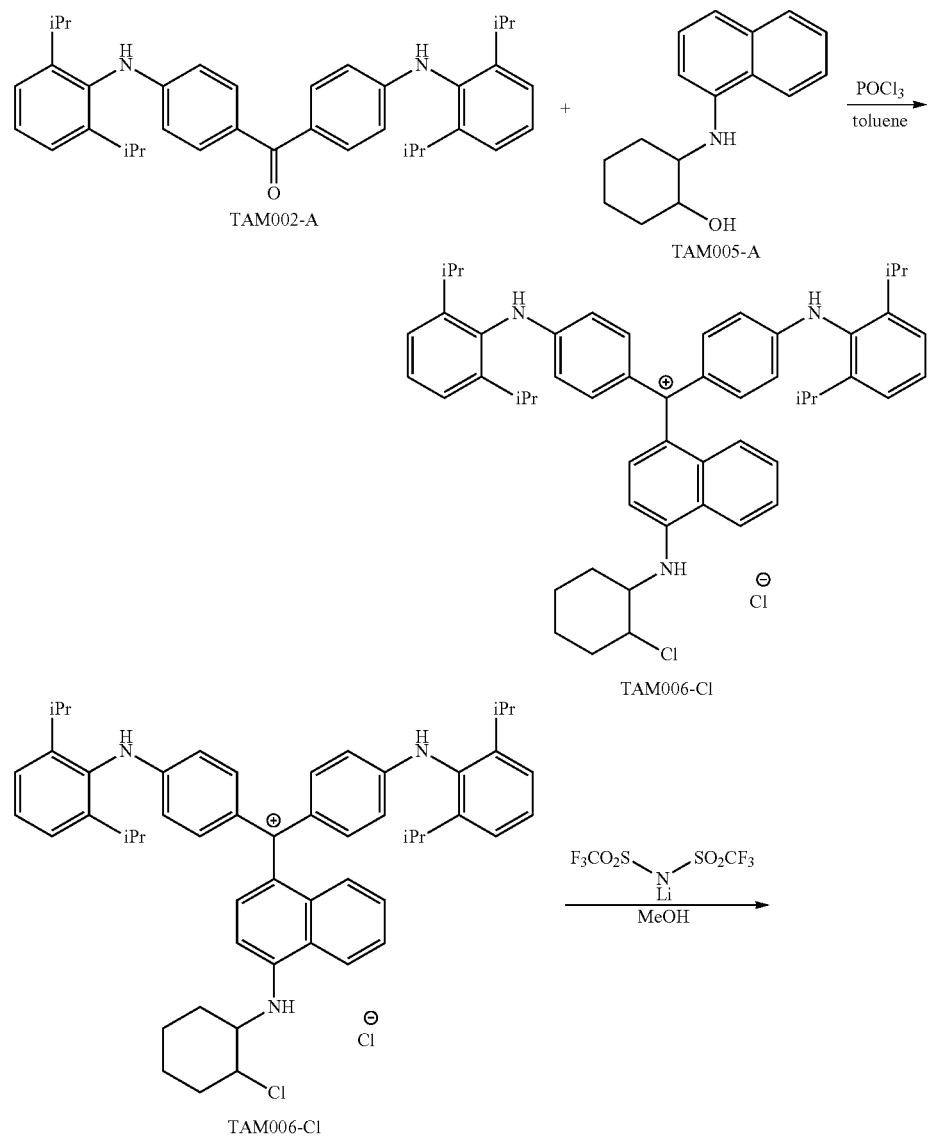

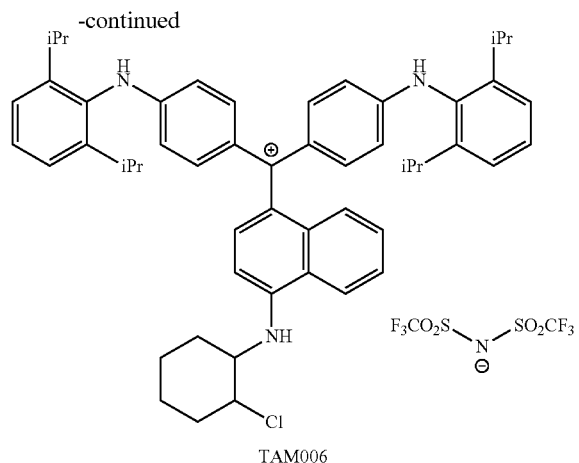

TAM006

«Synthesis of TAM007»

By the same method as in the synthesis of TAM005 except that potassium tris(trifluoromethanesulfonyl)methide (manufactured by Central Glass Co., Ltd.) was used instead of bis(trifluoromethanesulfonyl)imide lithium, TAM007 was obtained. It was found to be as follows: MALDI-MASS (posi): 690.4, and MALDI-MASS (nega): 410.9. The λmax ethyl acetate solution) of the absorption spectrum was 564 nm.

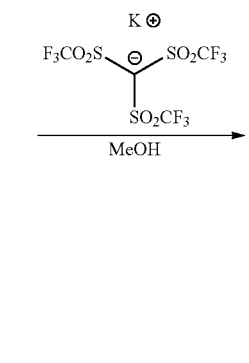

TAM005-Cl

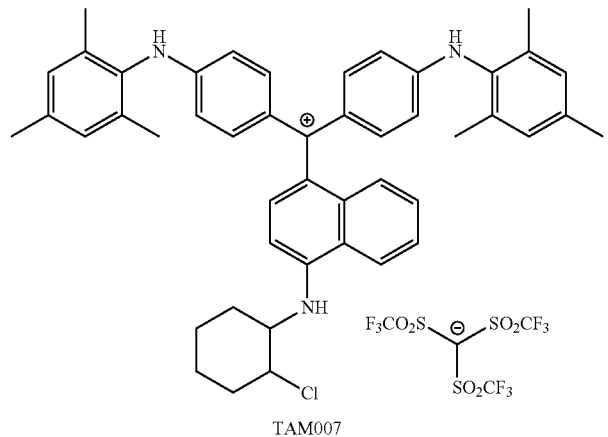

TAM007

«Synthesis of TAM008»

By the same method as in the synthesis of TAM005 except that 1,1,2,2,3,3-hexafluoropropane-1,3-disulfoneimidepotassium (manufactured by Tokyo Chemical Industry Co., Ltd.) was used instead of bis(trifluoromethanesulfonyl) imide lithium, TAM008 was obtained. It was found to be as follows: MALDI-MASS (posi): 690.4, and MALDI-MASS (nega): 291.9. The λmax (ethyl acetate solution) of the absorption spectrum was 563 nm.

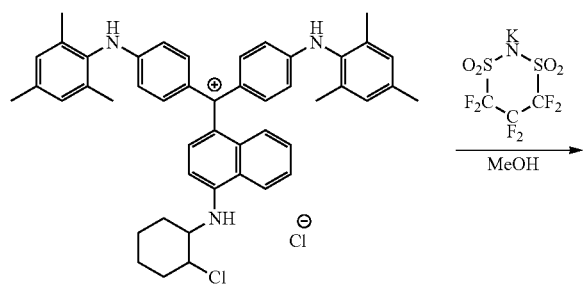

TAM005-Cl

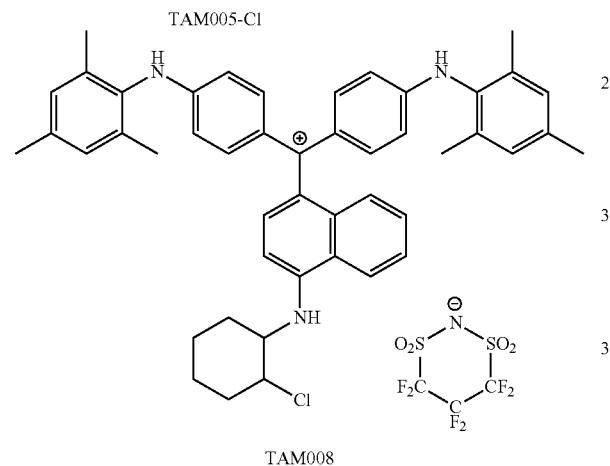

TAM008

«Synthesis of TAM009»

By the same method as in the synthesis of TAM001-A except that 2,6-diethylaniline (manufactured by Tokyo Chemical Industry Co., Ltd.) was used instead of 2,4,6-trimethylaniline, TAM009-A was obtained.

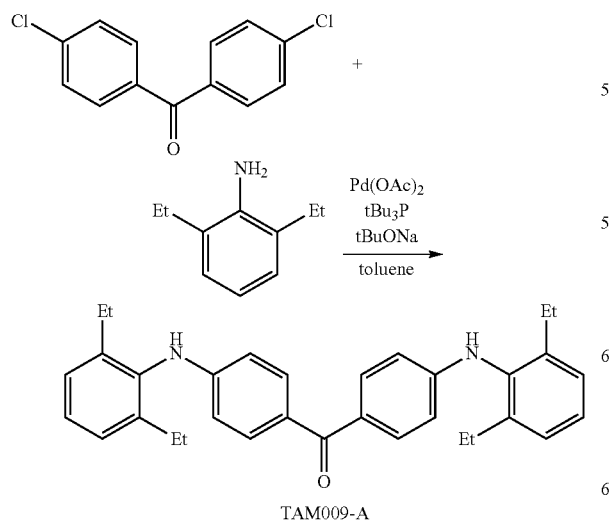

TAM009-A

By the same method as in the synthesis of TAM005-Cl except that TAM009-A was used instead of TAM001-A, TAM009-C was obtained. Further, by the same method as in the synthesis of TAM005, TAM009-Cl was used instead of TAM005-Cl, TAM009 was obtained. It was found to be as follows: MALDI-MASS (posi): 718.4, and MALDI-MASS (nega): 279.9. The λmax (ethyl acetate solution) of the absorption spectrum was 617 nm.

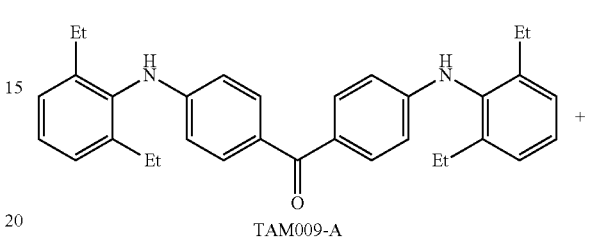

TAM009-A

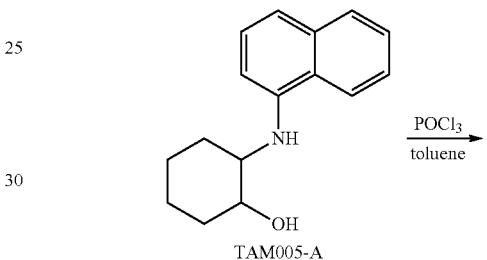

TAM005-A

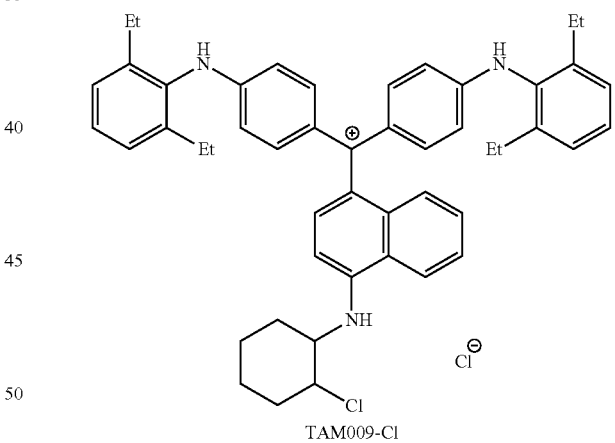

TAM009-Cl

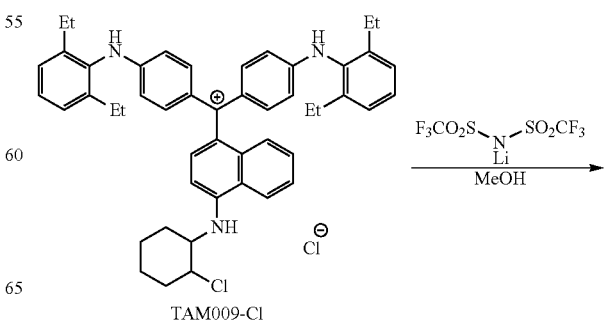

TAM009-Cl

-continued

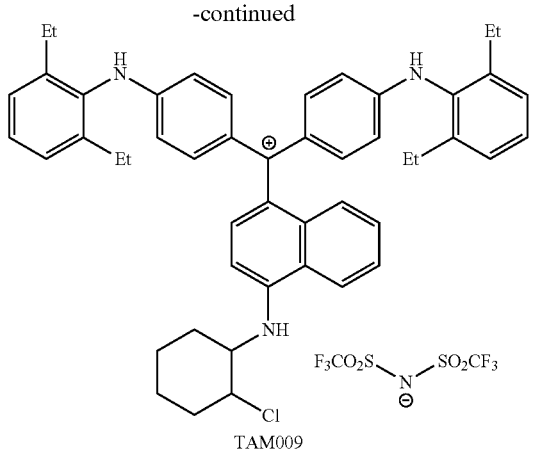

TAM009

«Synthesis of TAM010»

By the same method as in the synthesis of TAM002 except that TAM005-Cl was used instead of TAM002-Cl, TAM010 was obtained. It was found to be as follows: MALDI-MASS (posi): 690.4, and MALDI-MASS (nega): 679.0. The λmax (ethyl acetate solution) of the absorption spectrum was 563 nm.

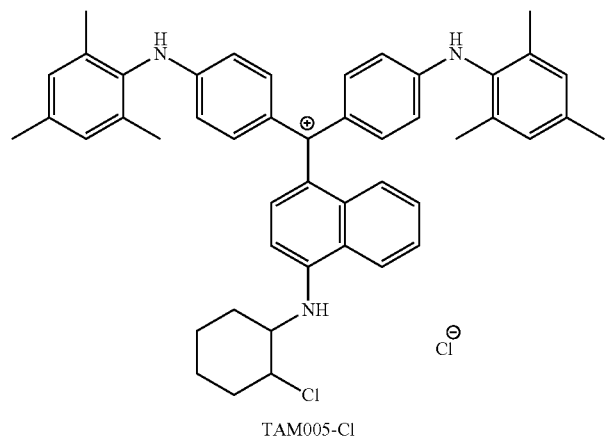

TAM005-Cl

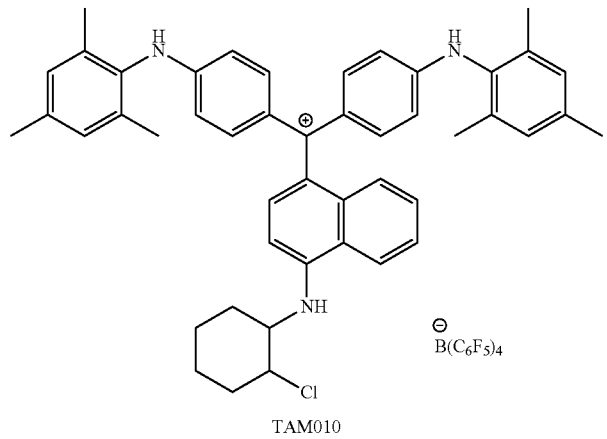

TAM010

«Synthesis of TAM011»

4.6 g of sodium 1-naphthalenesulfonate (manufactured by Tokyo Chemical Industry Co., Ltd.) was dissolved in 100 mL of water. To 100 mL of the obtained aqueous sodium 1-naphthalenesulfonate solution was added dropwise a methanol solution formed by dissolving TAM005-Cl (0.73 g) in 10 mL of methanol. The precipitated crystals were collected by filtration, these crystals were dissolved in 10 mL of methanol, and the solution was added dropwise to 100 mL of the aqueous sodium 1-naphthalenesulfonate solution. The precipitated crystals were collected by filtration to obtain 0.68 g of TAM011. It was found to be as follows: MALDI-MASS (posi): 690.4, and MALDI-MASS (nega): 207.0. The λmax (ethyl acetate solution) of the absorption spectrum was 563 nm.

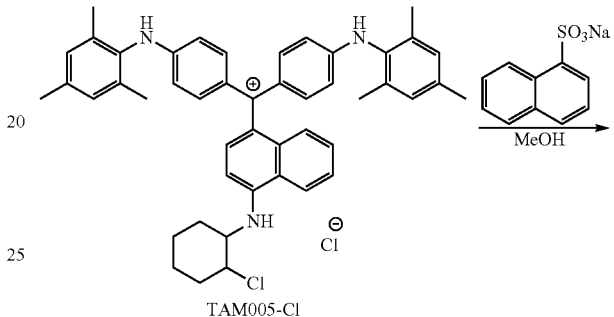

TAM005-Cl

-continued

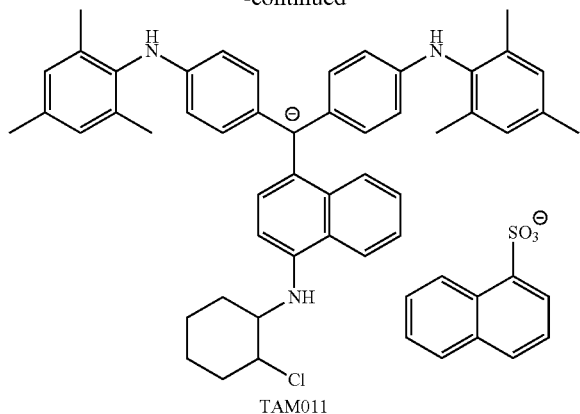

TAM011

«Synthesis of TAM012»

19.1 g of p-toluenesulfonyl chloride, 14.9 g of trifluoromethanesulfonamide, 27.6 g of potassium carbonate, and 300 mL of acetonitrile were put into a flask, followed by stirring for 3 hours under heating and refluxing. The mixture was concentrated and acetonitrile was removed. To the residue was added 500 mL of acetone, followed by stirring. The insoluble materials were removed by filtration and the acetone solution was concentrated to obtain crude crystals. The crude crystals were washed with 200 mL of n-hexane with heating to obtain 30.1 g of ANION001.

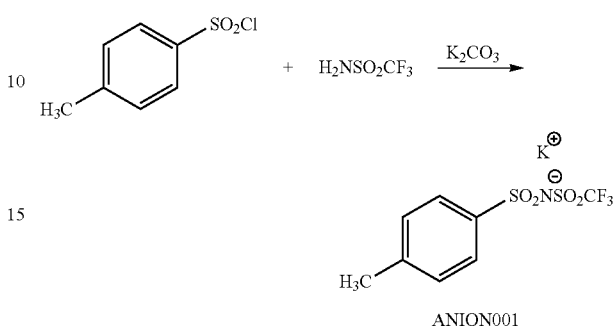

ANION001

By the same method as in the synthesis of TAM011 except that ANION001 was used instead of sodium 1-naphthalenesulfonate, TAM012 was obtained. It was found to be as follows: MALDI-MASS (posi): 690.4, and MALDI-MASS (nega): 302.0. The λmax (ethyl acetate solution) of the absorption spectrum was 564 nm.

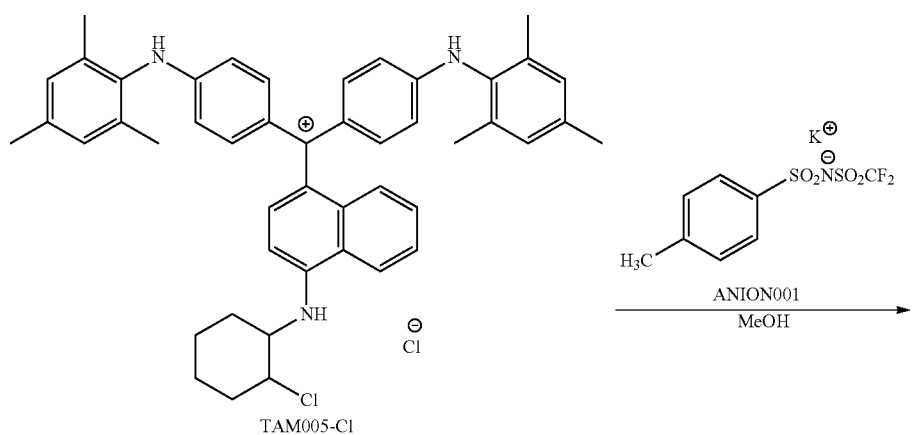

TAM005-Cl

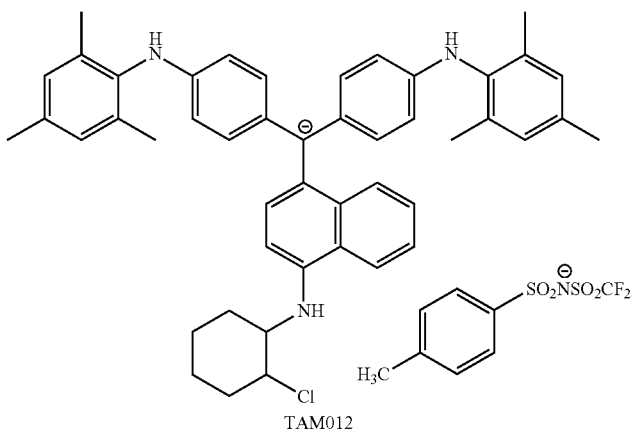

TAM012

«Synthesis of TAM013»

By the same method as in the synthesis of TAM011 except that sodium methanesulfonate was used instead of sodium 1-naphthalenesulfonate, TAM013 was obtained. It was found to be as follows: MALDI-MASS (posi): 690.4, and MALDI-MASS (nega): 95.0. The λmax (ethyl acetate solution) of the absorption spectrum was 563 nm.

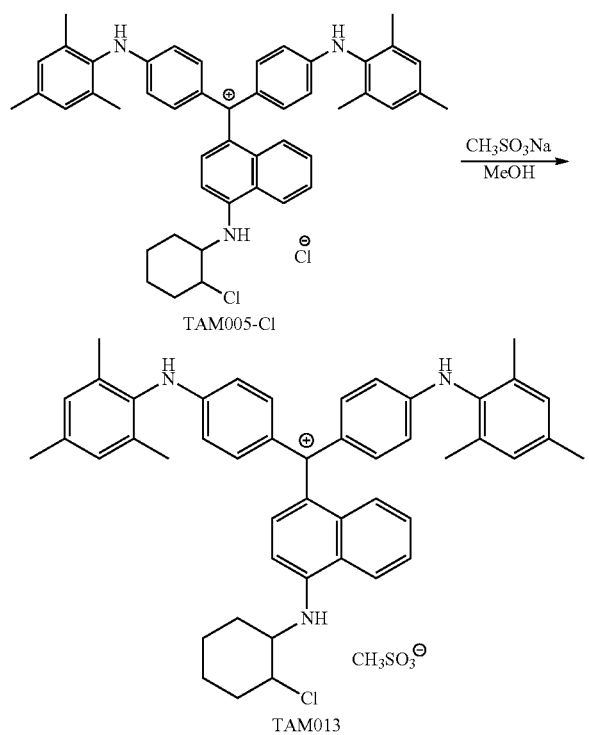

«Synthesis of TAM014»

By the same method as in the synthesis of TAM001-A except that o-toluidine was used instead of 2,4,6-trimethylaniline, TAM014-A was obtained.

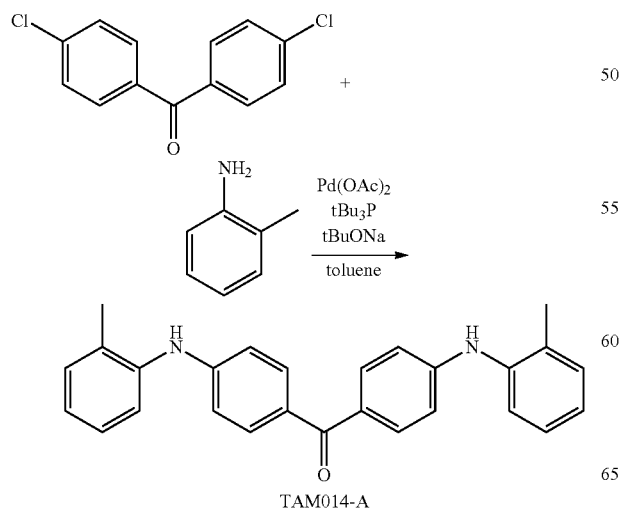

By the same method as in the synthesis of TAM001-Cl except that TAM014-A was used instead of TAM001-A, TAM014-Cl was obtained.

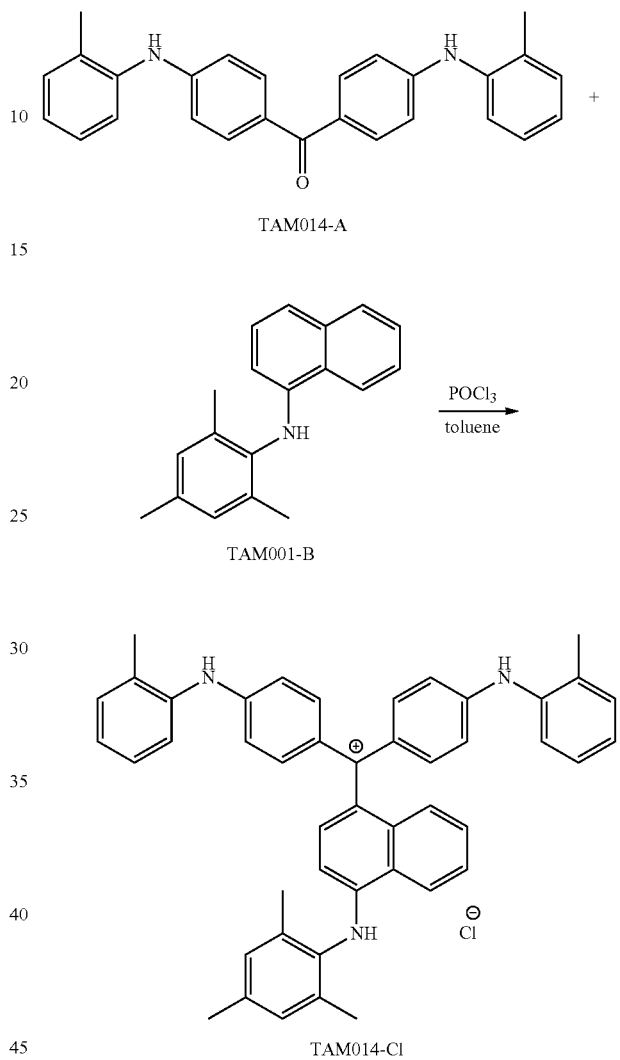

By the same method as in the synthesis of TAM001 except that TAM014-Cl was used instead of TAM001-Cl, TAM014 was obtained. It was found to be as follows: MALDI-MASS (posi): 636.3, and MALDI-MASS (nega): 279.9. The λmax (ethyl acetate solution) of the absorption spectrum was 623 nm.

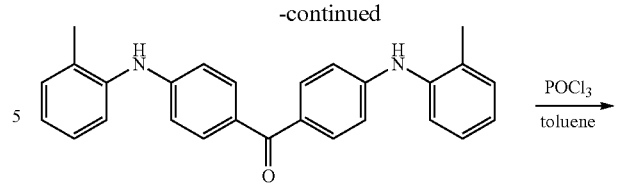

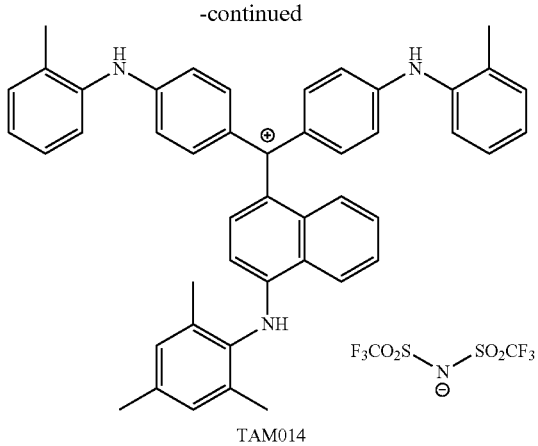

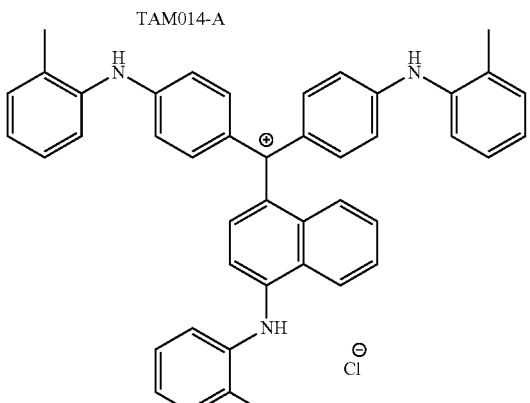

«Synthesis of TAM015»

By the same method as in the synthesis of TAM004-Cl except that TAM014-A was used instead of TAM001-A, TAM015-Cl was obtained.

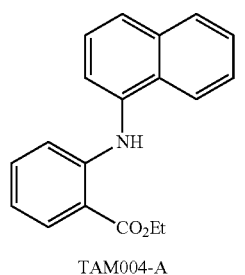

TAM004-A

By the same method as in the synthesis of TAM004 except that TAM015-Cl was used instead of TAM004-Cl, TAM015 was obtained. It was found to be as follows: MALDI-MASS (posi): 666.3, and MALDI-MASS (nega): 279.9. The λmax (ethyl acetate solution) of the absorption spectrum was 611 nm.

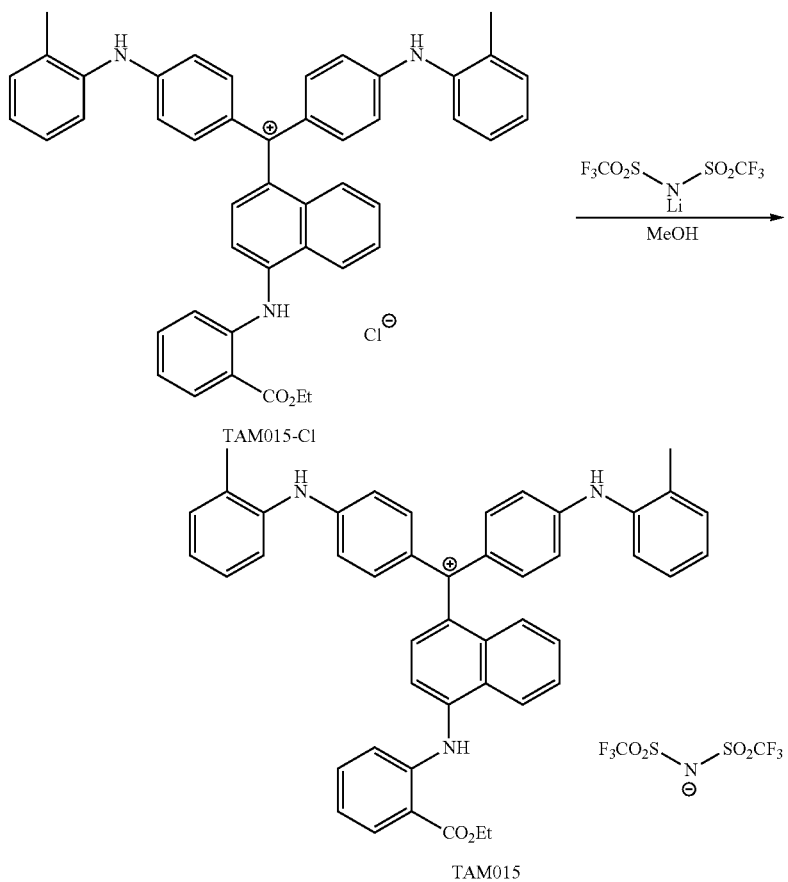

«Synthesis of TAM016»
By the same method as in the synthesis of TAM001-A except that aniline was used instead of 2,4,6-trimethylaniline, TAM0016-A was obtained.

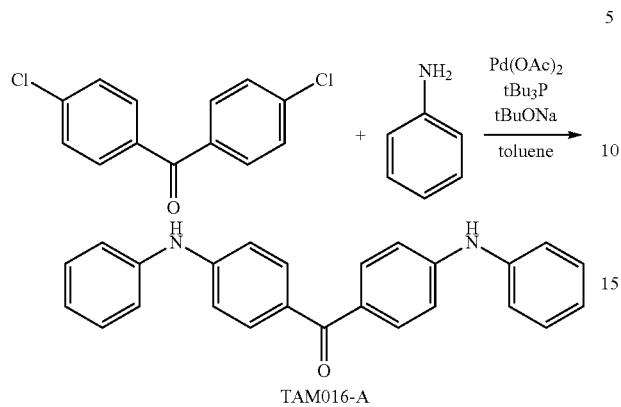

By the same method as in the synthesis of TAM001-Cl except that TAM016-A was used instead of TAM001-A, TAM016-Cl was obtained.

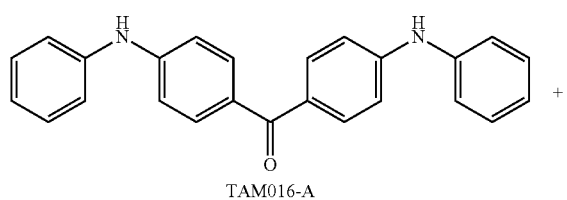

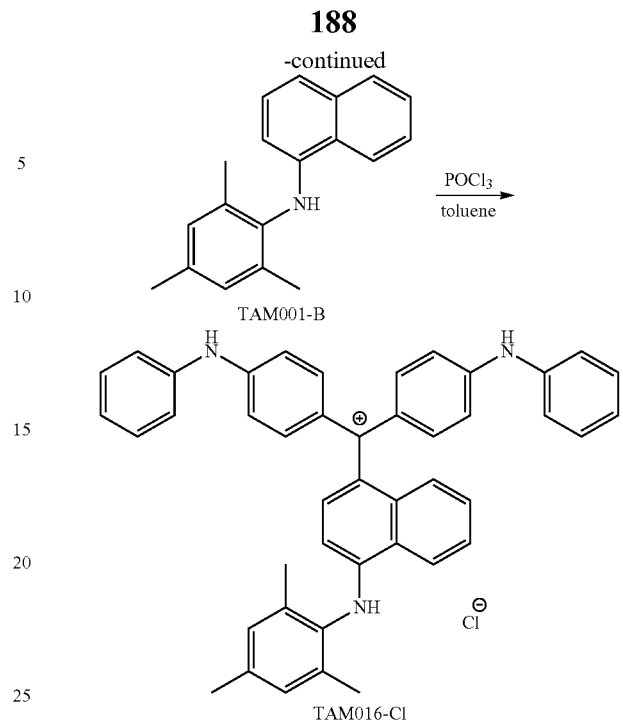

By the same method as in the synthesis of TAM001 except that TAM016-Cl was used instead of TAM001-Cl, TAM016 was obtained. It was found to be as follows: MALDI-MASS (posi): 608.3, and MALDI-MASS (nega): 279.9. The λmax (ethyl acetate solution) of the absorption spectrum was 634 nm.

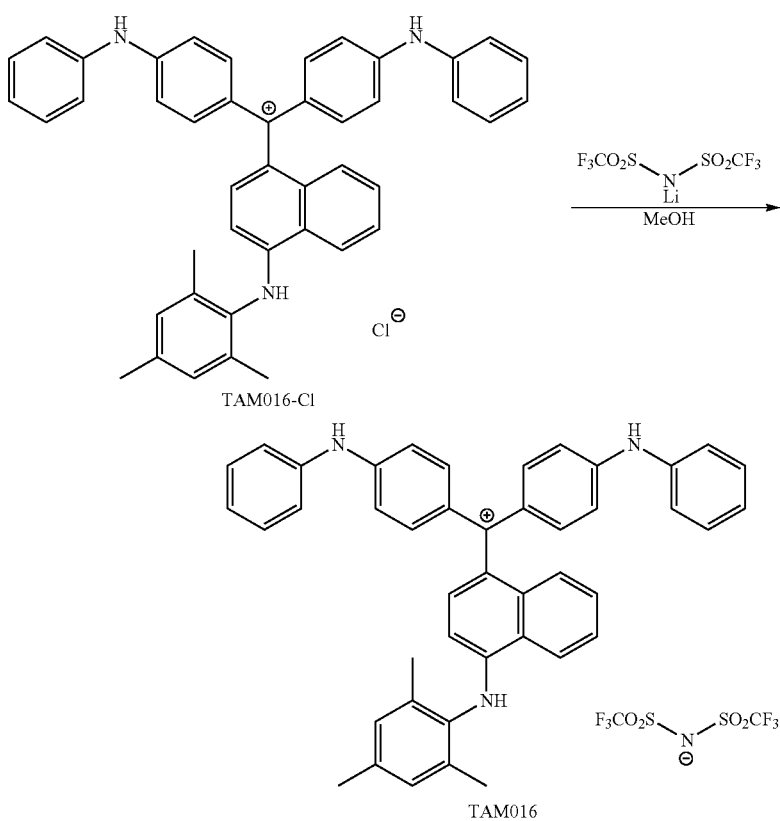

«Synthesis of TAM017»

By the same method as in the synthesis of TAM004-Cl except that TAM016-A was used instead of TAM001-A, TAM017-Cl was obtained.

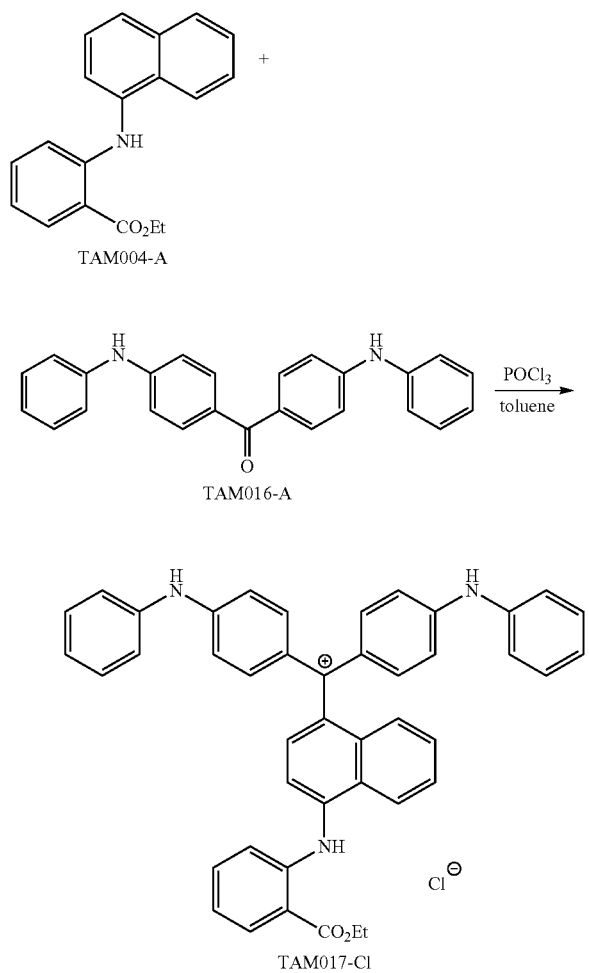

By the same method as in the synthesis of TAM001 except that TAM017-Cl was used instead of TAM001-Cl, TAM017 was obtained. It was found to be as follows: MALDI-MASS (posi): 638.3, and MALDI-MASS (nega): 279.9. The λmax (ethyl acetate solution) of the absorption spectrum was 621 nm.

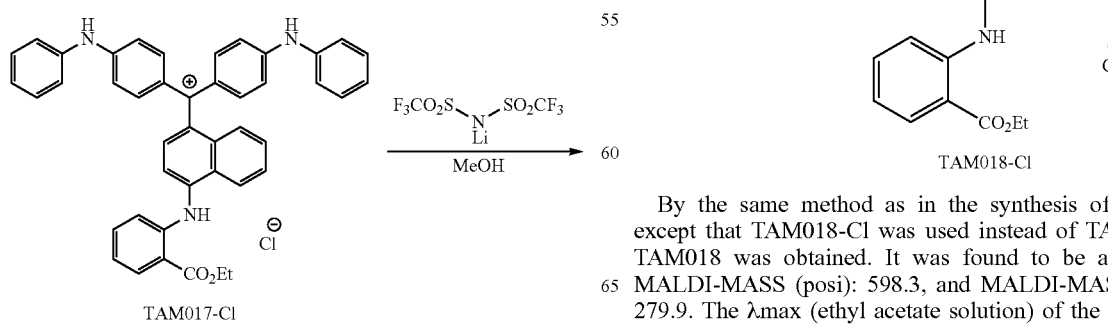

«Synthesis of TAM018»

By the same method as in the synthesis of TAM001-Cl except that TAM004-A was used instead of TAM001-B and 4,4'-bis(diethylamino)benzophenone (manufactured by Tokyo Chemical Industry Co., Ltd.) was used instead of TAM001-A, TAM018-Cl was obtained.

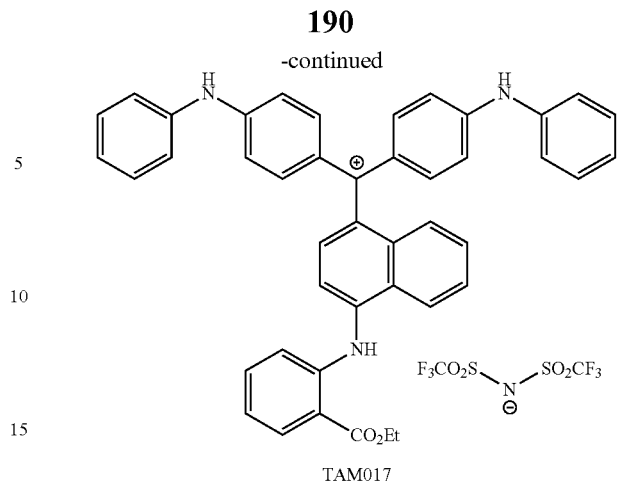

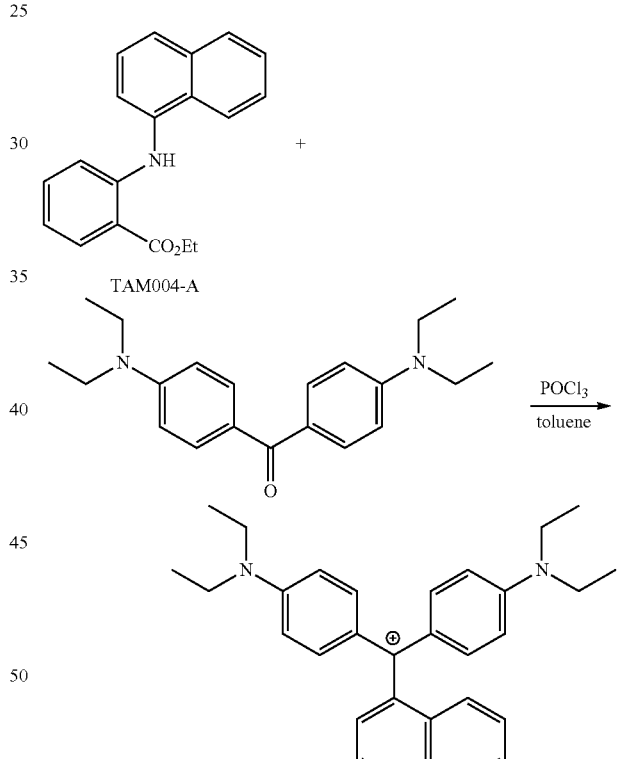

By the same method as in the synthesis of TAM001 except that TAM018-Cl was used instead of TAM001-Cl, TAM018 was obtained. It was found to be as follows: MALDI-MASS (posi): 598.3, and MALDI-MASS (nega): 279.9. The λmax (ethyl acetate solution) of the absorption spectrum was 603 nm.

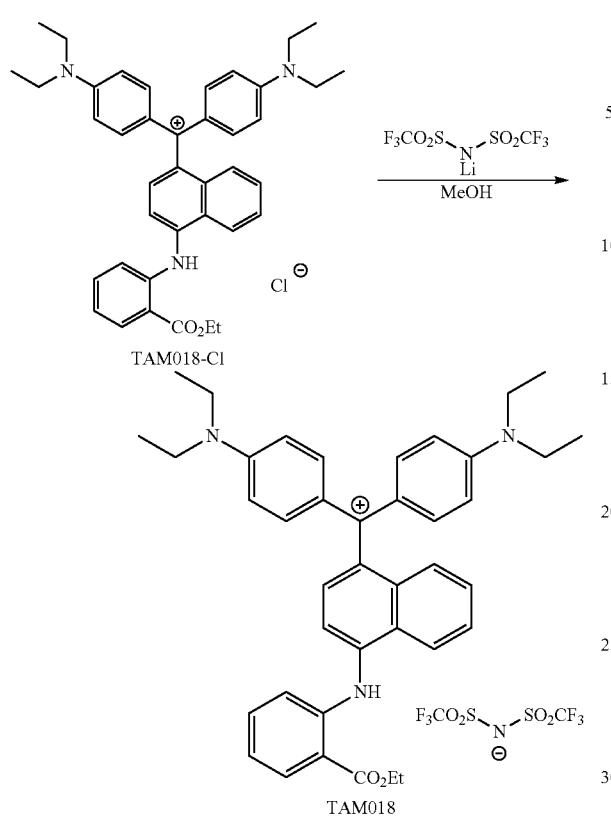

TAM018-Cl

TAM018

«Synthesis of TAM19»

By the same method as in the synthesis of TAM001-Cl except that 1-methyl-2-phenylindole (manufactured by Tokyo Chemical Industry Co., Ltd.) was used instead of TAM001-B, TAM019-Cl was obtained. It was found to be as follows: MALDI-MASS (posi): 638.4, and MALDI-MASS (nega): 279.9. The λmax (methanol solution) of the absorption spectrum was 578 nm.

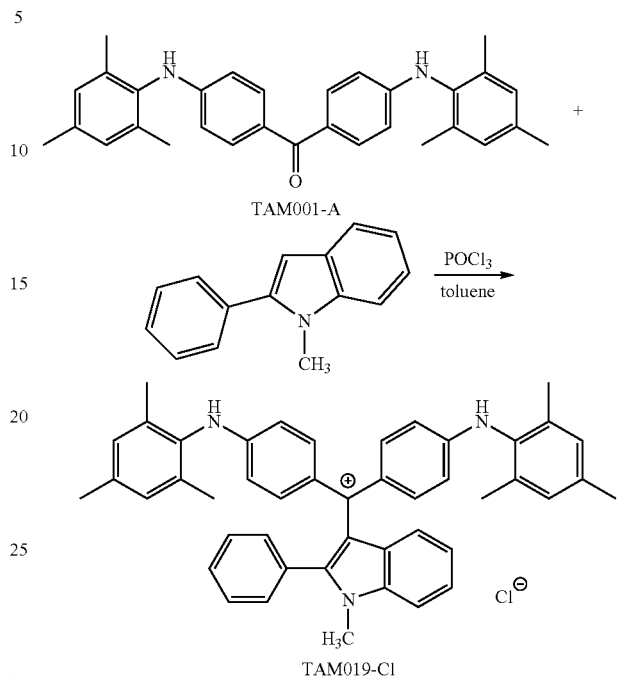

TAM001-A

TAM019-Cl

By the same method as in the synthesis of TAM001 except that TAM019-Cl was used instead of TAM001-Cl, TAM019 was obtained. It was found to be as follows: MALDI-MASS (posi): 638.4, and MALDI-MASS (nega): 279.9. The λmax (methanol solution) of the absorption spectrum was 578 nm.

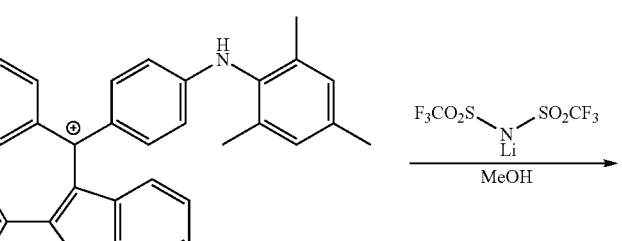

TAM019-Cl

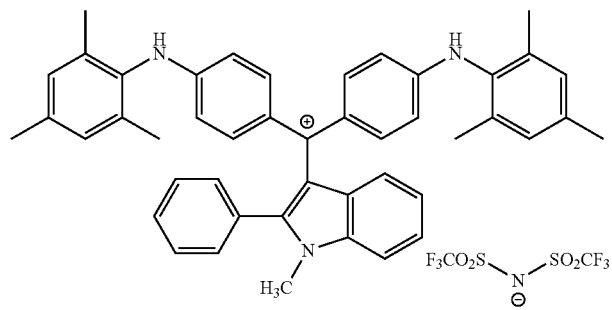

TAM019

«Synthesis of TAM020»

By the same method as in the synthesis of TAM001-Cl except that TAM014-A as used instead of TAM001-A and 1-methyl-2-phenylindole (manufactured by Tokyo Chemical Industry Co., Ltd.) was used instead of TAM001-B, TAM020-Cl was obtained.

«Synthesis of Dye901»

By the same method as in the synthesis of TAM016-Cl except that N-ethyl-1-naphthylamine was used instead of TAM001-B, Dye901-Cl was obtained. By the same method as in the synthesis of TAM001 except that Dye901-Cl was used instead of TAM001-Cl, Dye901 was obtained.

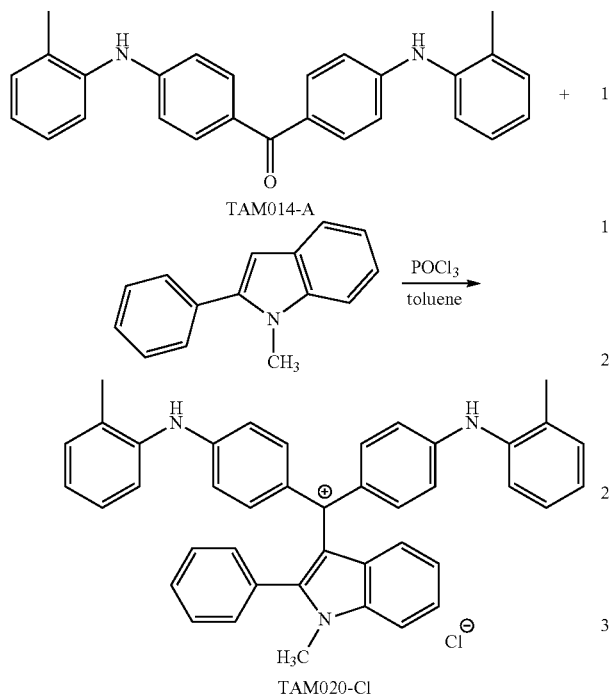

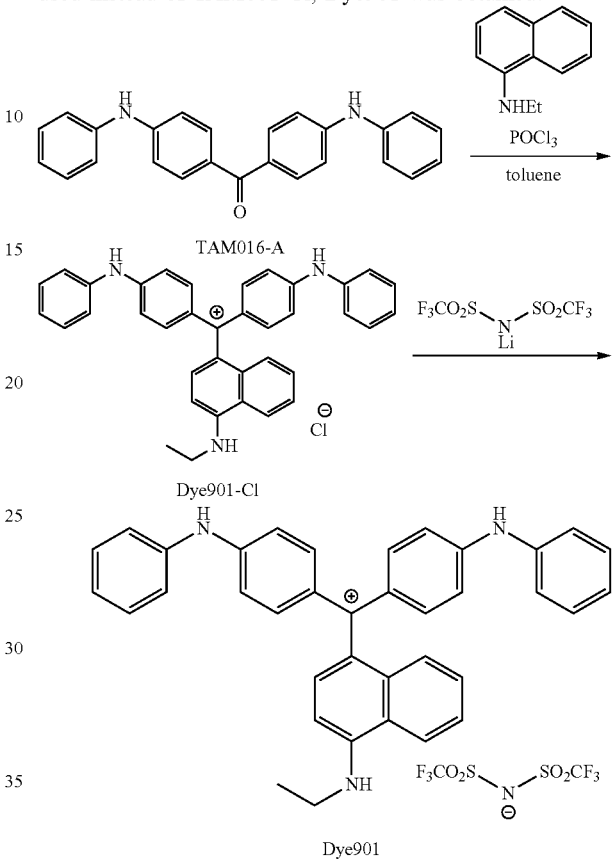

By the same method as in the synthesis of TAM001 except that TAM020-Cl was used instead of TAM001-Cl, TAM020 was obtained. It was found to be as follows: MALDI-MASS (posi): 582.3, and MALDI-MASS (nega): 279.9. The λmax (methanol solution) of the absorption spectrum was 591 nm.

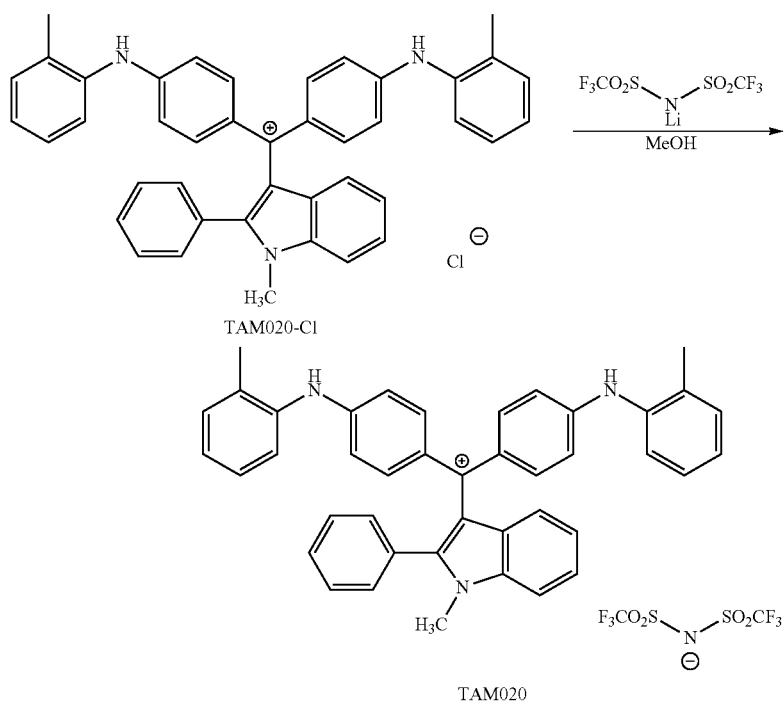

«Synthesis of Dye902»

By the same method as in the synthesis of TAM001 except that C. I. Basic Blue 7 was used instead of TAM001-Cl, Dye902 was obtained.

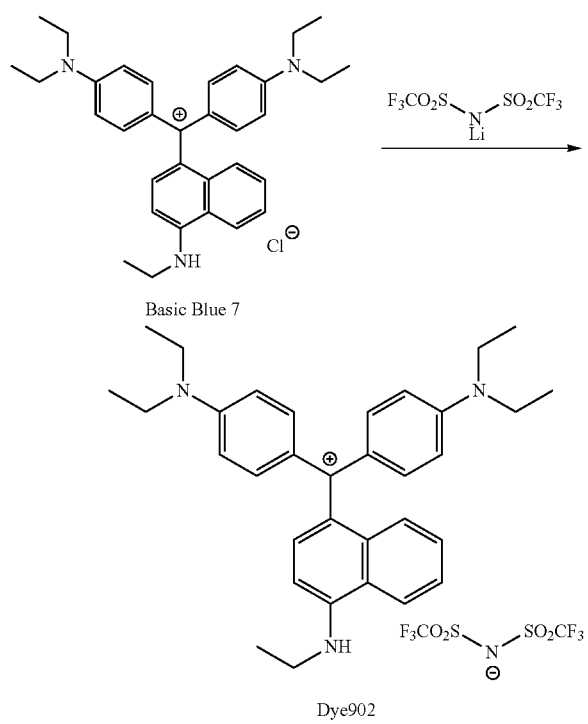

«Synthesis of Dye903»

By the same method as in the synthesis of TAM005-Cl except that TAM005-A was used instead of TAM001-A, Dye903-Cl was obtained. By the same method as in the synthesis of TAM001 except that Dye903-Cl was used instead of TAM001-Cl, Dye903 was obtained.

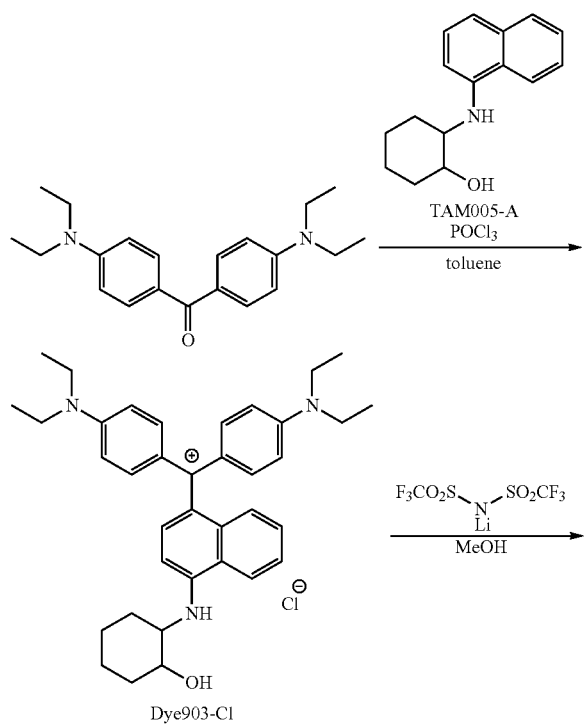

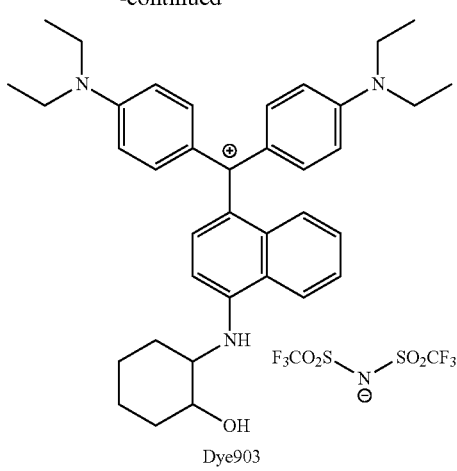

«Synthesis of Dye904»

TAM005-A (60 g), 38 g of triethylamine, 300 mL of acetonitrile, and 50 mL of tetrahydrofuran were put into a flask, and 32 g of acrylic acid chloride was added dropwise thereto under cooling with ice water, while keeping the internal temperature at no higher than 5° C. After stirring under ice-cooling for 2 hours, the solvent was removed by concentration, and the residue was extracted by addition of water and ethyl acetate. The obtained organic layer was concentrated and purified by silica gel column chromatography to obtain 44 g of TAM102-A.

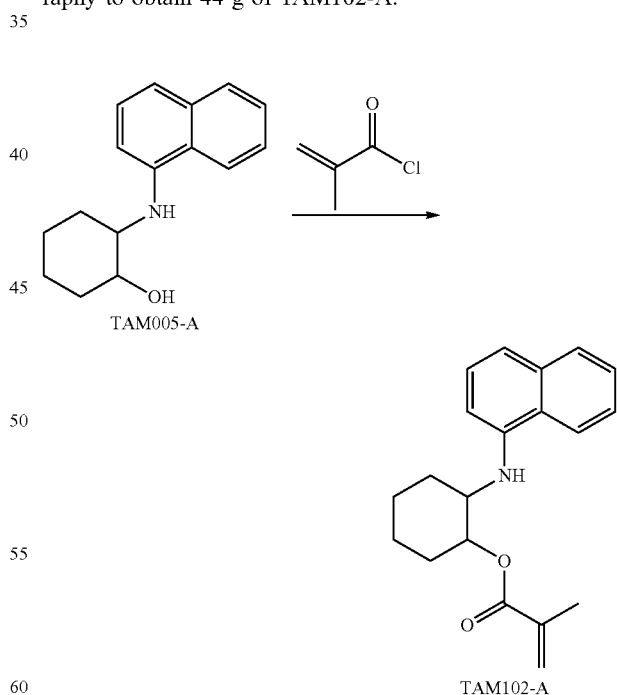

By the same method as in the synthesis of TAM903-Cl except that TAM102-A was used instead of TAM005-A, Dye904-Cl was obtained. By the same method as in the synthesis of TAM001 except that Dye904-Cl was used instead of TAM001-Cl, Dye904 was obtained.

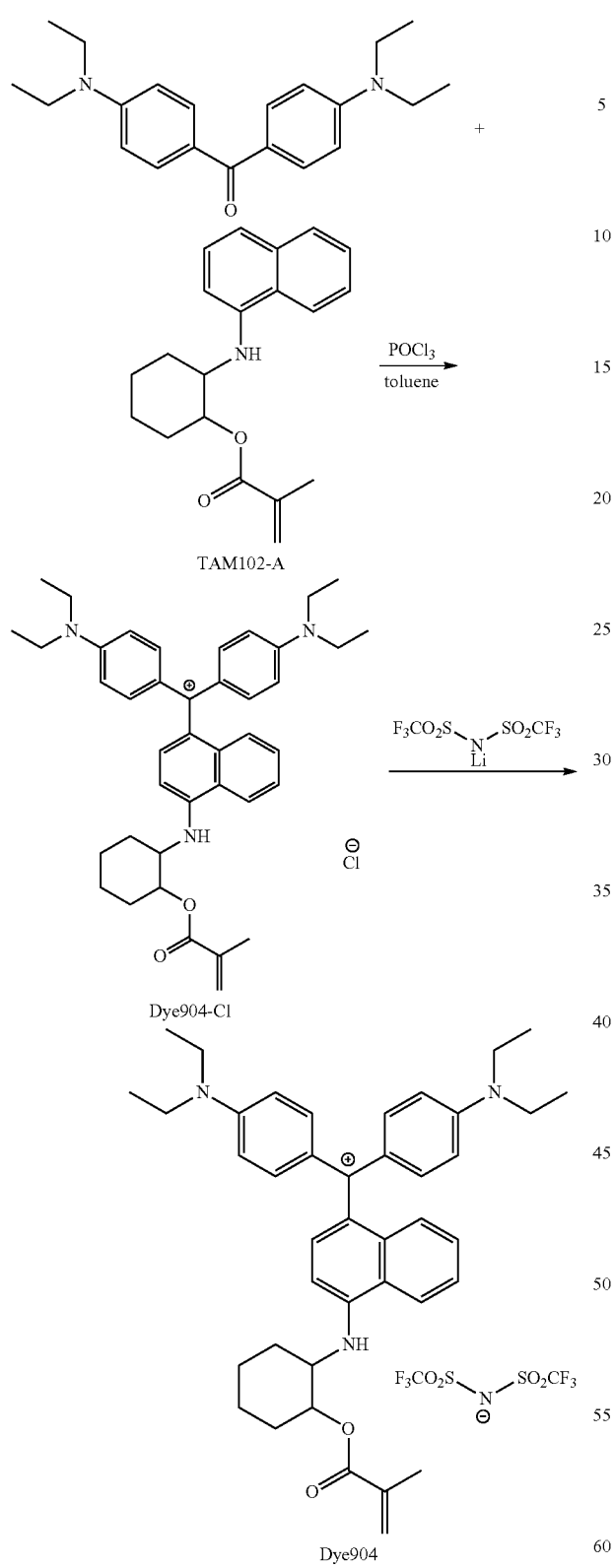

«Synthesis of Dye905»

By the same method as in the synthesis of the compound D described in the specification of WO2012128318A1 except that ethylaniline was used instead of N-ethyl-p-toluidine, Dye905-A was obtained.

By the same method as in the synthesis of Dye904-Cl except that Dye905-A was used instead of 4,4'-bis(diethylamino)benzophenone, Dye905-Cl was obtained. By the same method as in the synthesis of TAM001 except that Dye905-Cl was used instead of TAM001-Cl, Dye905 was obtained.

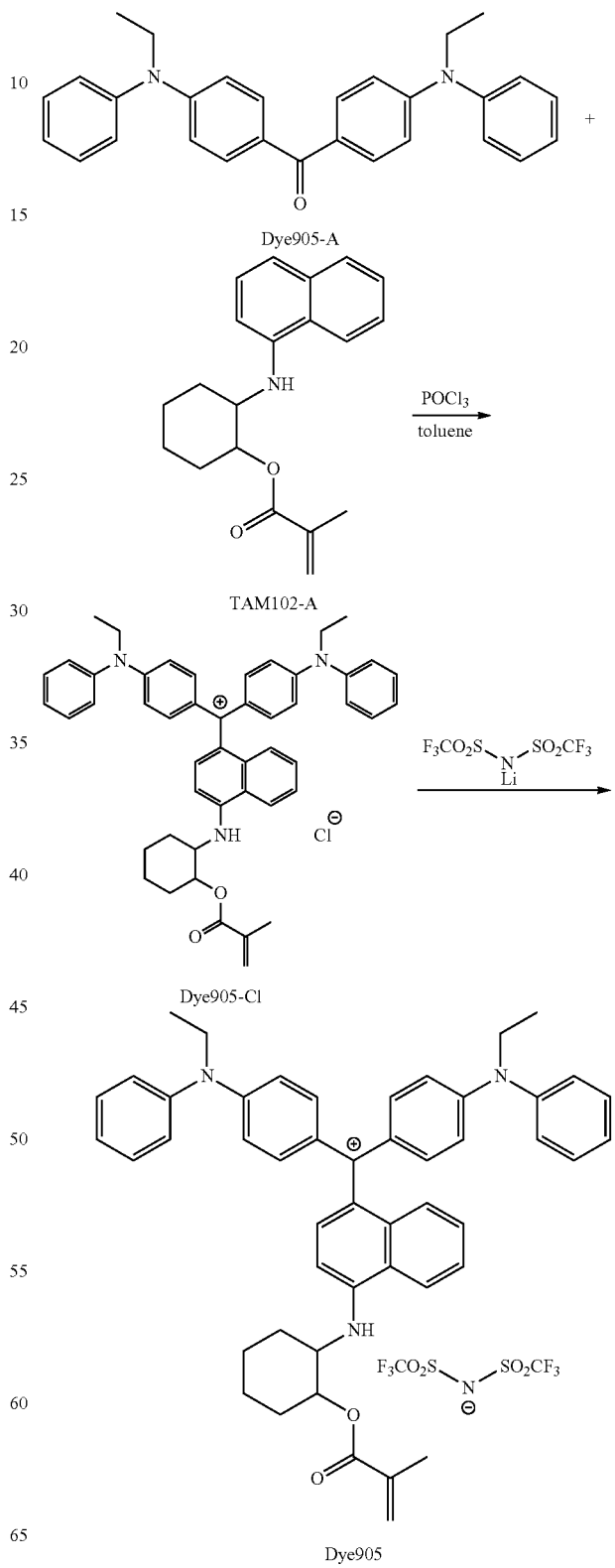

«Synthesis of Dye906»

By using the method described in the specification of WO2012128318A1, the compound D described in the specification of WO2012128318A1 was synthesized.

By the same method as in the synthesis of Dye904-Cl except that the compound D described in the specification of WO2012128318A1 was used instead of 4,4'-bis(diethylamino)benzophenone, Dye906-Cl was obtained. By the same method as in the synthesis of TAM001 except that Dye906-Cl was used instead of TAM001-Cl, Dye906 was obtained.

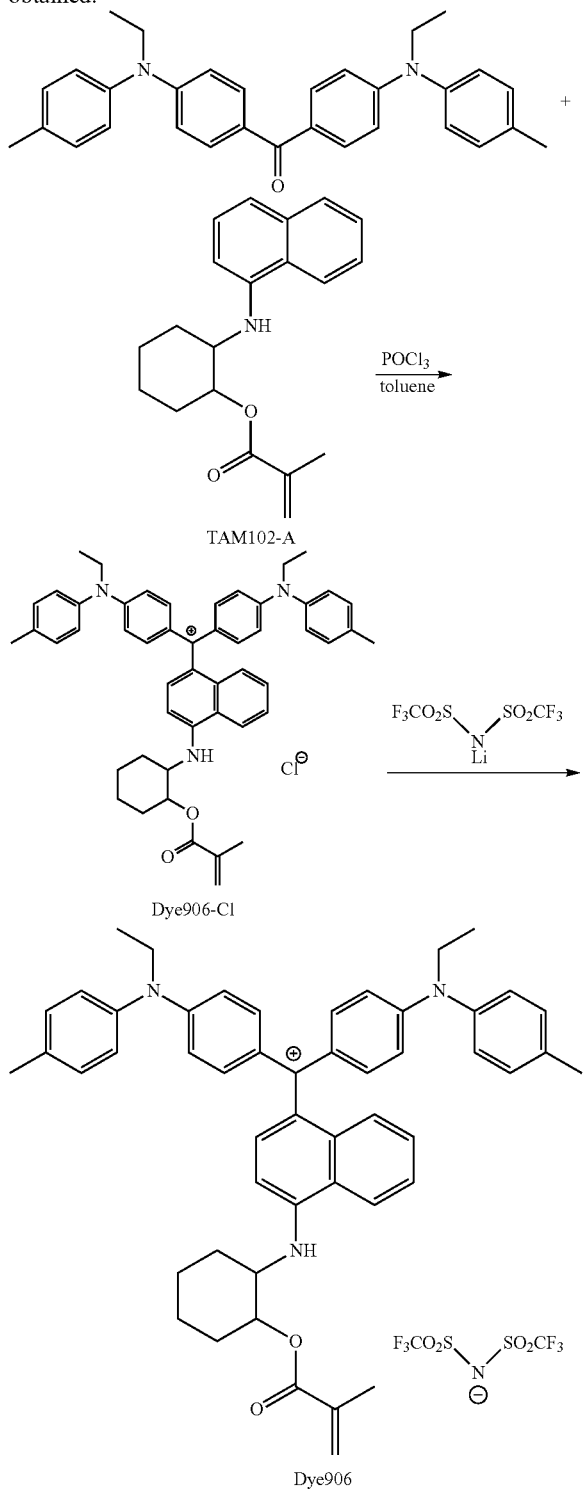

«Synthesis of Dye907»

By the same method as in the synthesis of TAM018-Cl except that N-phenyl-1-naphthylamine (manufactured by Tokyo Chemical Industry Co., Ltd.) was used instead of TAM004-A, Dye907-Cl was obtained. By the same method as in the synthesis of TAM001 except that Dye907-Cl was used instead of TAM001-Cl, Dye907 was obtained.

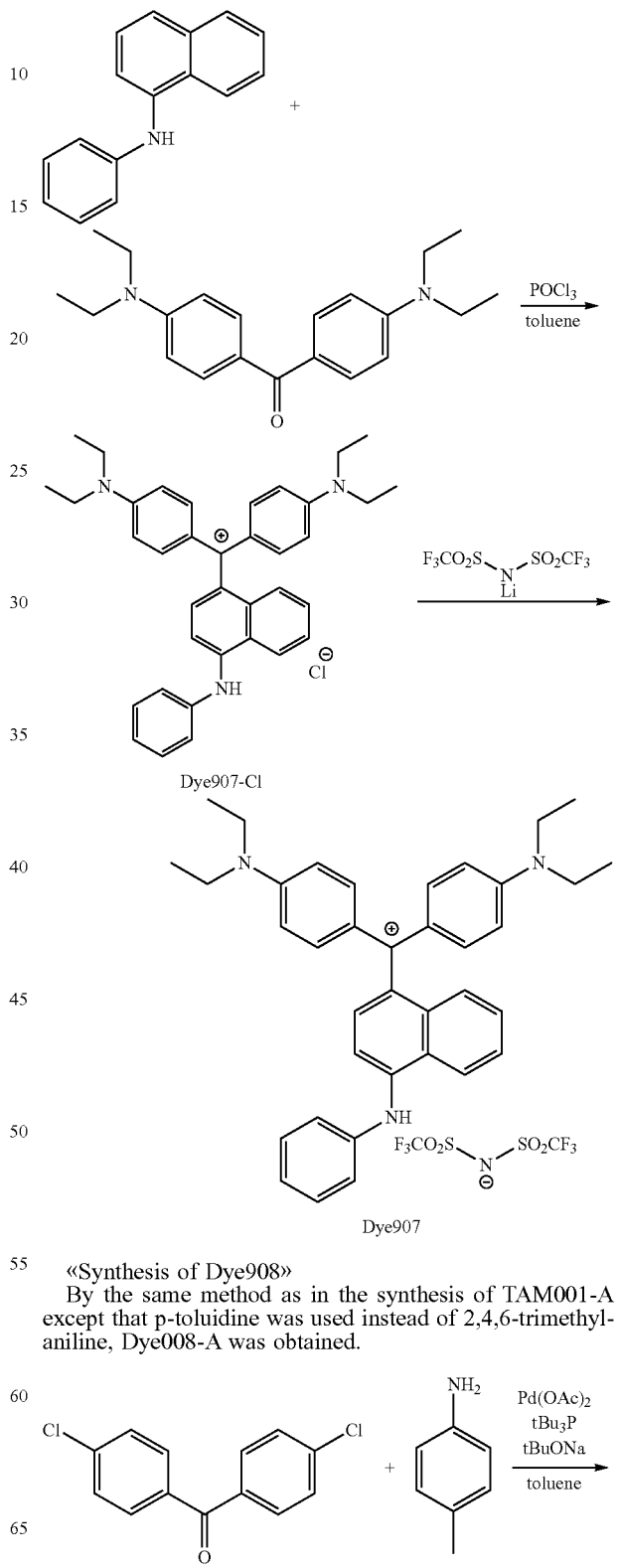

«Synthesis of Dye908»

By the same method as in the synthesis of TAM001-A except that p-toluidine was used instead of 2,4,6-trimethylaniline, Dye008-A was obtained.

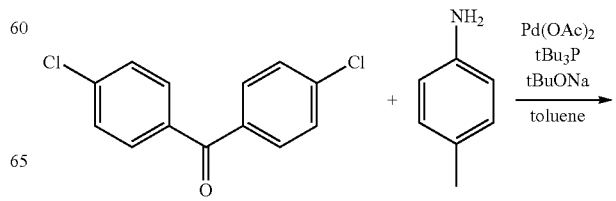

-continued

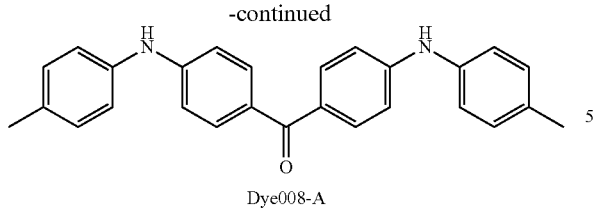

Dye008-A

By the same method as in the synthesis of TAM001-B except that p-toluidine was used instead of 2,4,6-trimethylaniline, Dye008-B was obtained.

-continued

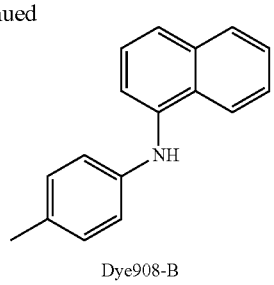

Dye908-B

By the same method as in the synthesis of TAM001-Cl except that Dye908-A was used instead of TAM001-A and Dye908-B was used instead of TAM001-B, Dye908-Cl was obtained. By the same synthesis method using Dye908-Cl instead of TAM001-Cl in the synthesis of TAM001, Dye008 was obtained.

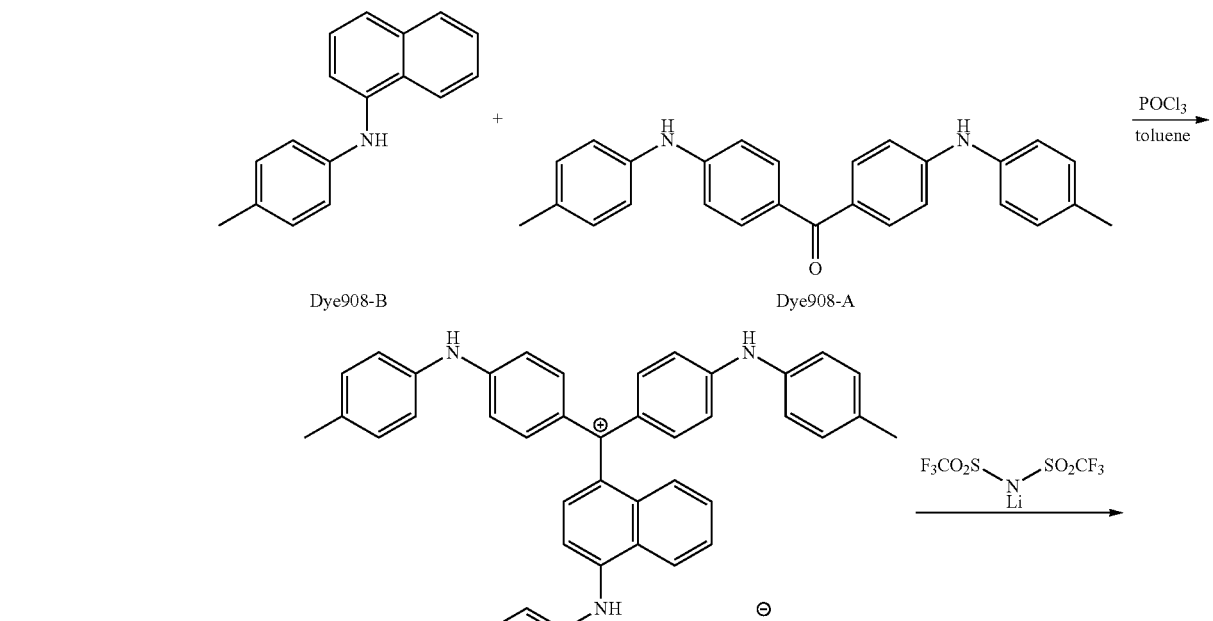

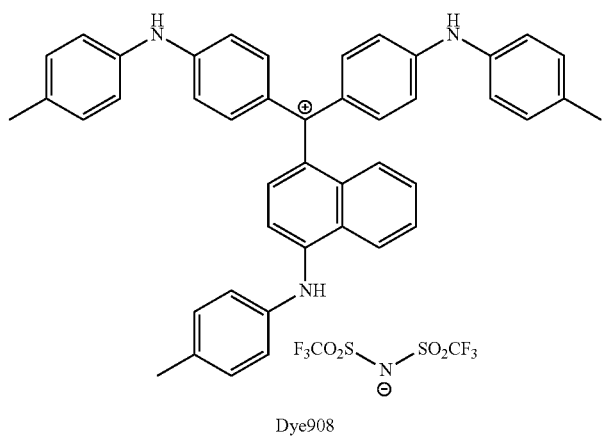

Dye908

«Synthesis of Dye909»

By synthesizing the dye (4) described in the specification of WO2012128318A1 in accordance with the description in the specification of WO2012128318A1, Dye909 was obtained.

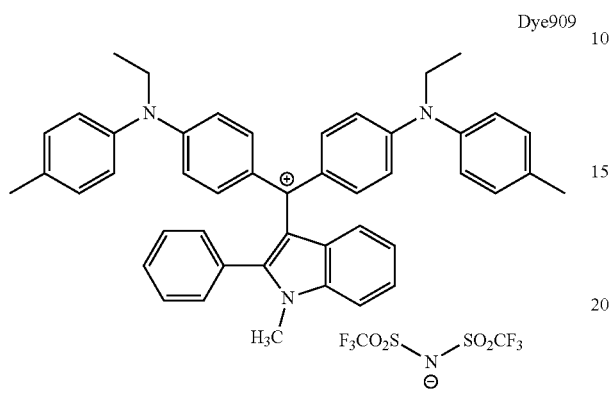

Dye909

«Synthesis of Dye910»

By the same method as in the synthesis of TAM019-Cl except that 4,4'-bis(dimethylamino)benzophenone (manufactured by Tokyo Chemical Industry Co., Ltd.) was used instead of TAM001-A, Dye910-Cl was obtained. By the same method except that Dye910-Cl was used instead of TAM001-Cl in the synthesis of TAM001, Dye910 was obtained.

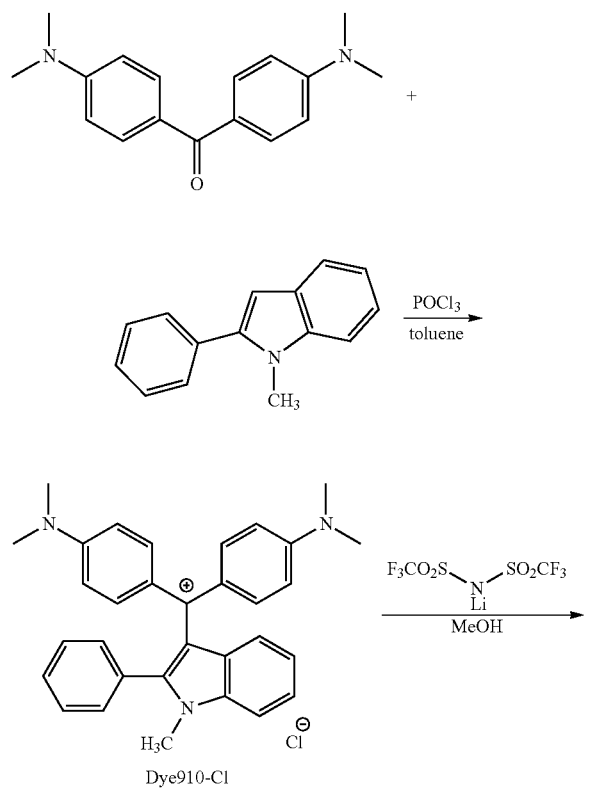

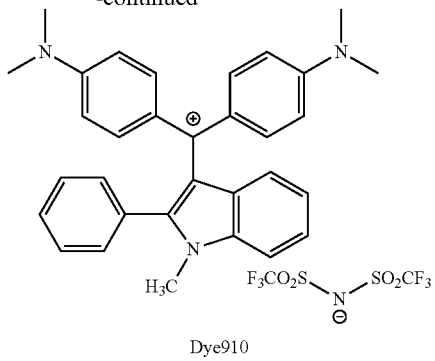

Dye910

«Synthesis of TAM101»

25 g of sodium styrenesulfonate (manufactured by Tokyo Chemical Industry Co., Ltd.) and 50 mL of dimethylformamide were added to a flask, followed by mixing, and 50 mL of thionyl chloride was added dropwise thereto while keeping the internal temperature at no higher than 45° C. After dropwise addition, the mixture was stirred for 4 hours and the reaction liquid was added dropwise to 500 mL of ice water. The mixture was extracted by addition of 200 mL of ethyl acetate, dried over sodium sulfate, and then concentrated to obtain 21 g of styrenesulfonic acid chloride.

20 g of styrenesulfonic acid chloride, 15 g of trifluoromethanesulfonamide, and 200 mL of acetonitrile were put into a flask, and 27 g of potassium carbonate was portionwise added thereto. After addition, the mixture was stirred for 3 hours under heating and refluxing. After cooling, the reaction liquid was concentrated, to the residue was added 500 mL of acetone, followed by stirring, and the insoluble materials were removed by filtration. The filtrate was concentrated and the obtained crude crystals were suspended and washed with 400 mL of hexane to obtain 28 g of ANION002.

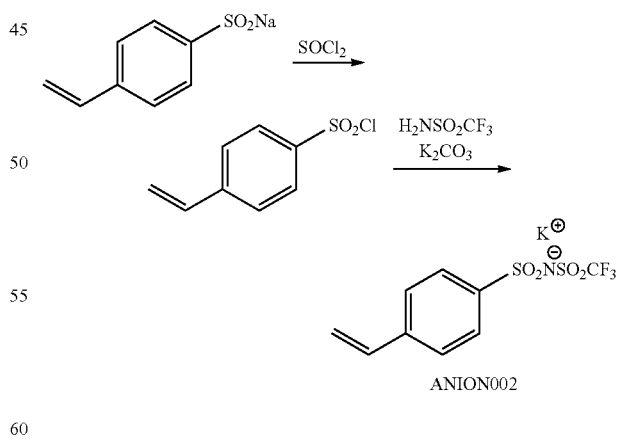

By the same method as in the synthesis of TAM011 except that ANION002 was used instead of sodium 1-naphthalenesulfonate, TAM101 was synthesized. It was found to be as follows: MALDI-MASS (posi): 690.4, and MALDI-MASS (nega): 314.0. The λmax (ethyl acetate solution) of the absorption spectrum was 563 nm.

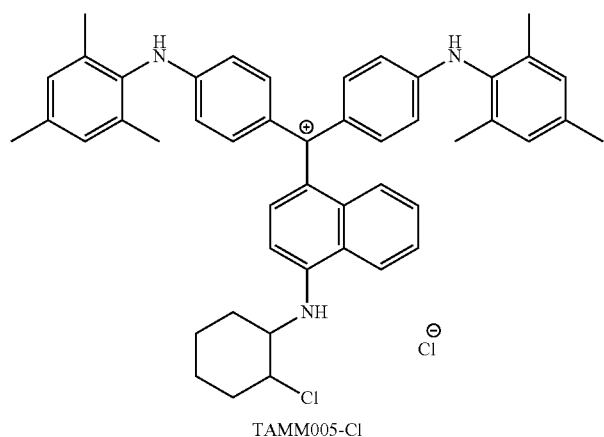

TAMM005-Cl

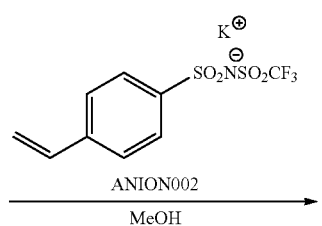

ANION002
———————→
MeOH

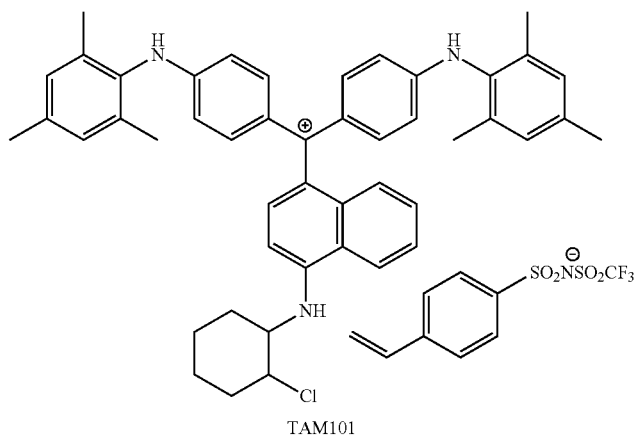

TAM101

«Synthesis of TAM102»

By the same method as in the synthesis of TAM001-Cl except that TAM102-A was used instead of TAM001-B, TAM102-Cl was obtained. By the same method as in the synthesis of TAM001 except that TAM102-Cl was used instead of TAM001-Cl, TAM102 was obtained. It was found to be as follows: MALDI-MASS (posi): 740.4, and MALDI-MASS (nega): 279.9. The λmax (ethyl acetate solution) of the absorption spectrum was 563 nm.

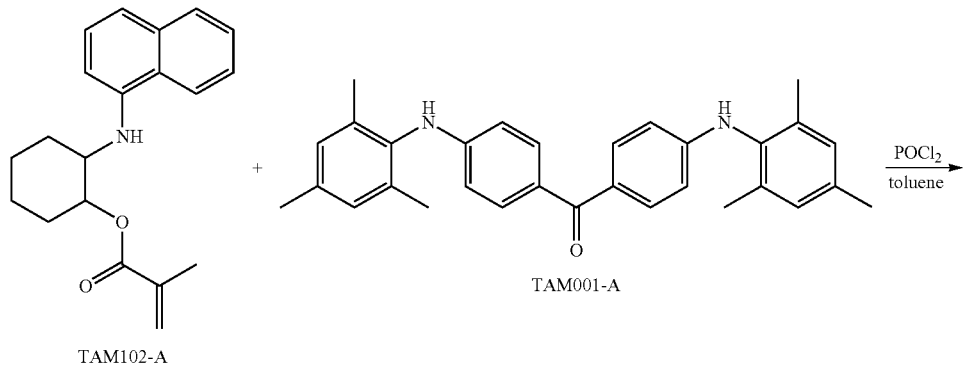

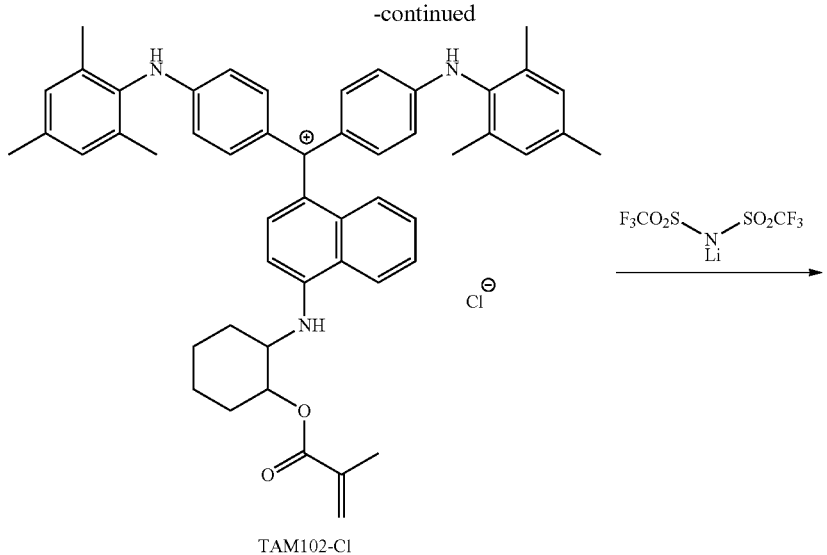
TAM102-Cl
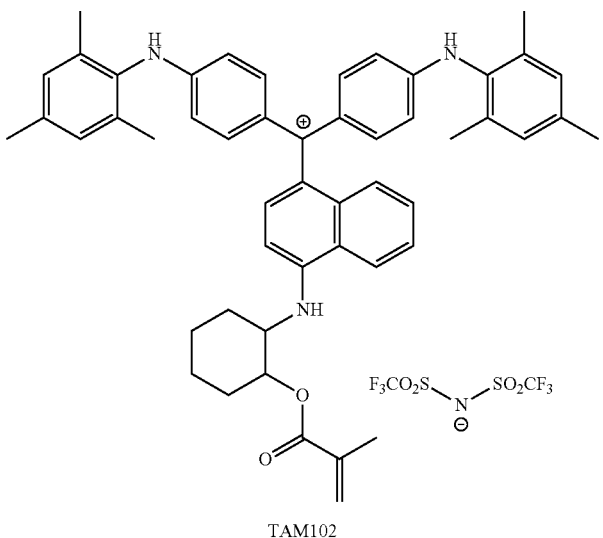
TAM102
«Synthesis of TAM103»
By the same method as in the synthesis of TAM101 except that TAM102-Cl was used instead of TAM005-Cl, TAM103 was obtained. It was found to be as follows: MALDI-MASS (posi): 740.4, and MALDI-MASS (nega): 314.0. The λmax (ethyl acetate solution) of the absorption spectrum was 563 nm.

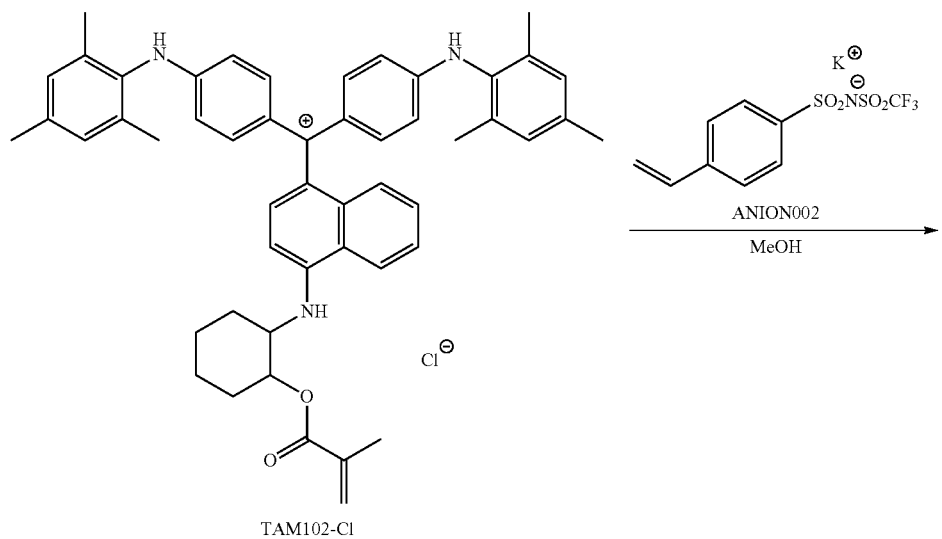

TAM102-Cl

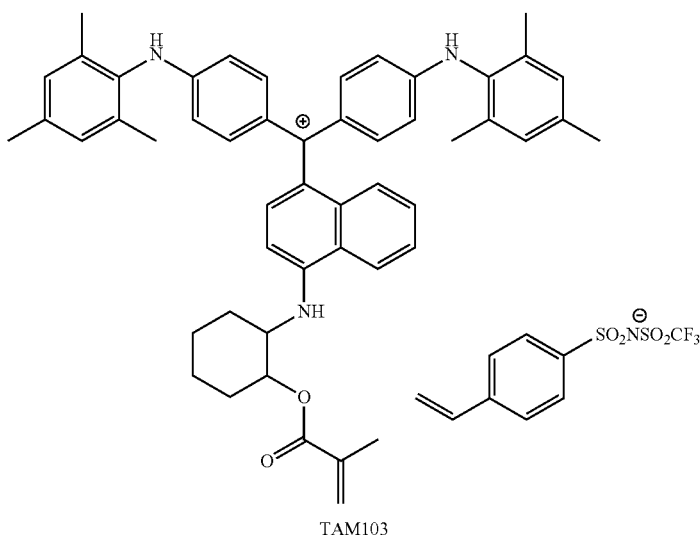

TAM103

«Synthesis of TAM104»

15.0 g of 2,4,6-trimethyl-1,3-phenylenediamine (manufactured by Tokyo Chemical Industry Co., Ltd.), 12.0 g of triethylamine, 150 mL of tetrahydrofuran, and 0.1 g of 4-(dimethylamino)pyridine were put into a flask, followed by cooling with ice water. 20.2 g of styrenesulfonic acid was added dropwise thereto, followed by stirring at room temperature for 4 hours. The reaction liquid was poured into water, followed by extraction with ethyl acetate, and the obtained organic phase was dried over sodium sulfate. After concentration, the residue was purified by column chromatography to obtain 26.6 g of TAM104-B.

By the same method as in the synthesis of TAM001-B except that TAM104-B was used instead of 2,4,6-trimethylaniline, TAM104-A was obtained. By the same method as in the synthesis of TAM003-Cl except that TAM104-A was used instead of TAM001-B, TAM104-Cl was obtained. By the same method as in the synthesis of TAM001 except that TAM104-Cl was used instead of TAM001-Cl, TAM104 was obtained. It was found to be as follows: MALDI-MASS (posi): 957.5, MALDI-MASS (nega): 279.9. The λmax (ethyl acetate solution) of the absorption spectrum was 602 nm.

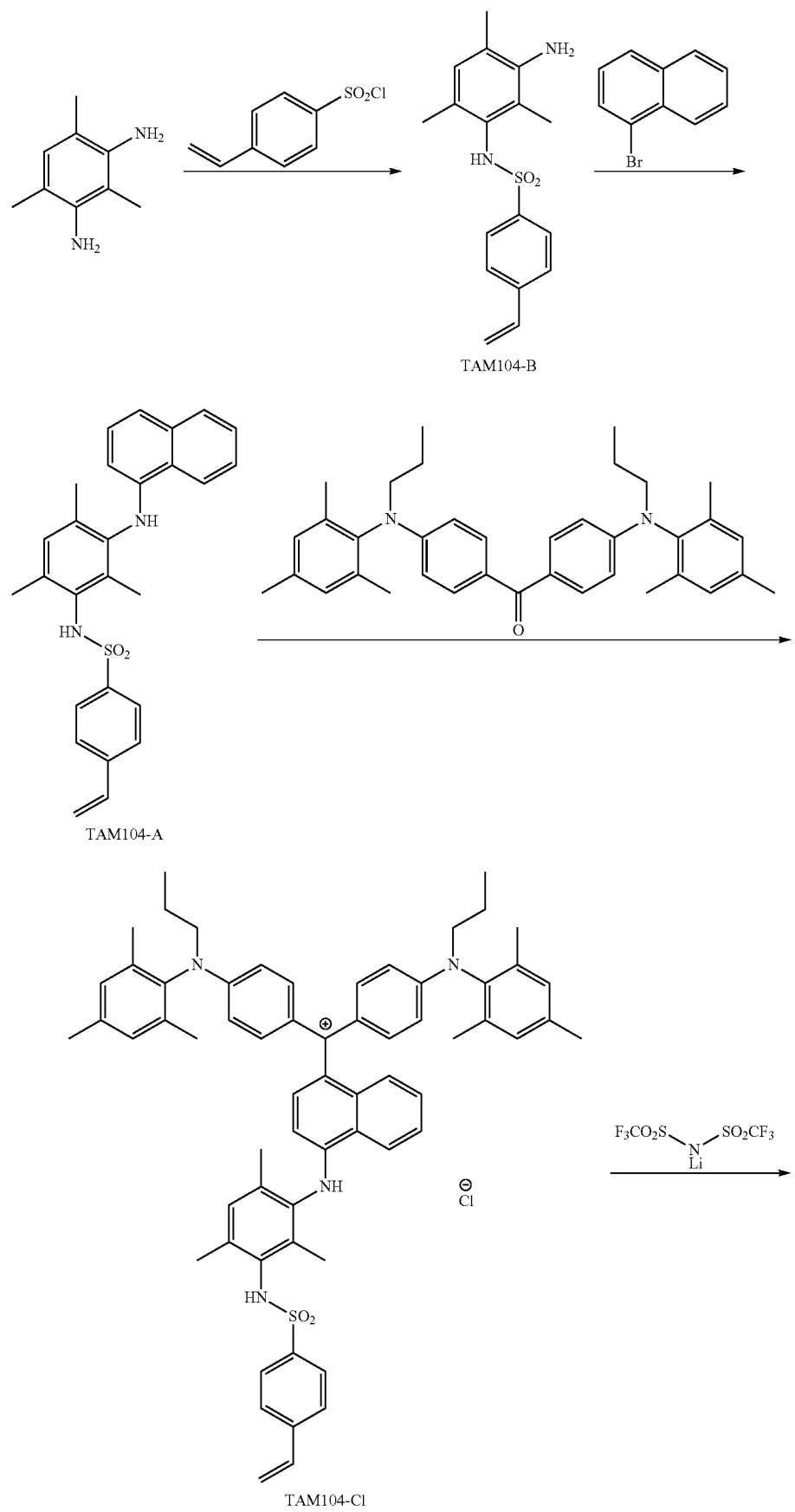

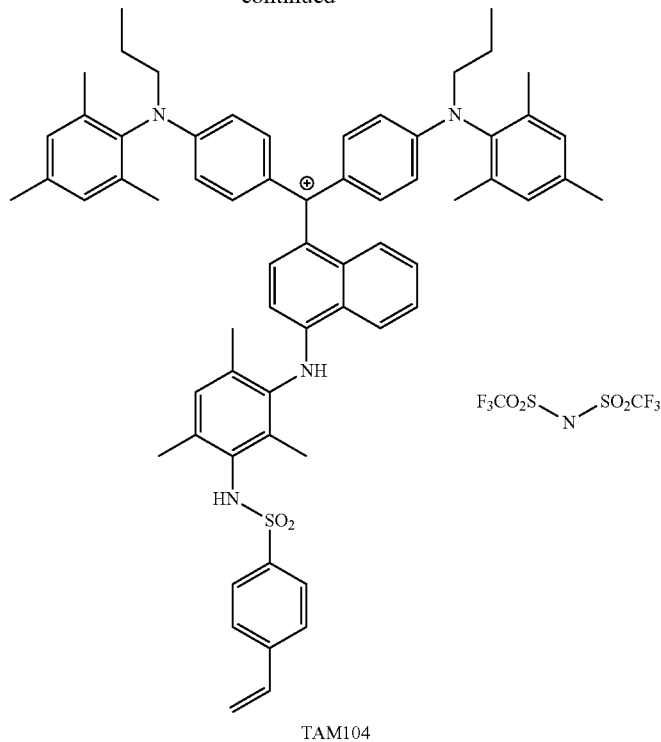

TAM104

«Synthesis of TAM105»

20 g of 3-sulfopropylpotassium methacrylate (manufactured by Tokyo Chemical Industry Co., Ltd.), 20 mL of dimethylacetamide, 0.7 g of 4-(dimethylamino)pyridine, and 14 mL of acetonitrile were put into a flask, followed by stirring. 37.3 g of phosphorous oxychloride was added dropwise thereto. The reaction liquid was heated to 65° C. and stirred for 3 hours. The reaction liquid was cooled and added dropwise to water at room temperature, followed by stirring for 30 minutes. The organic phase was combined, dried over sodium sulfate, and concentrated. 11.2 g of trifluoromethanesulfonamide, 20.7 g of potassium carbonate, and 50 mL of acetonitrile were added thereto, followed by stirring for 4 hours under heating and refluxing. The reaction liquid was concentrated, 100 mL of acetone was added thereto, and the insoluble materials were removed by filtration. The obtained filtrate was concentrated and the obtained crude crystals were suspended and washed with 200 mL of hexane to obtain 17.7 g of ANION003.

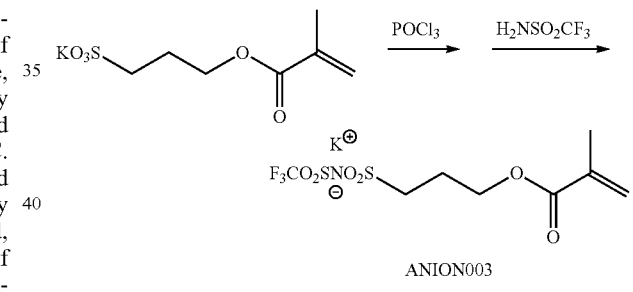

ANION003

By the same method as in the synthesis of TAM102-Cl except that TAM004-A was used instead of TAM001-A, TAM105-Cl was obtained. By the same method as in the synthesis of TAM011 except that TAM105-Cl was used instead of TAM005-Cl and ANION003 was used instead of sodium 1-naphthalenesulfonate, TAM105 was obtained.

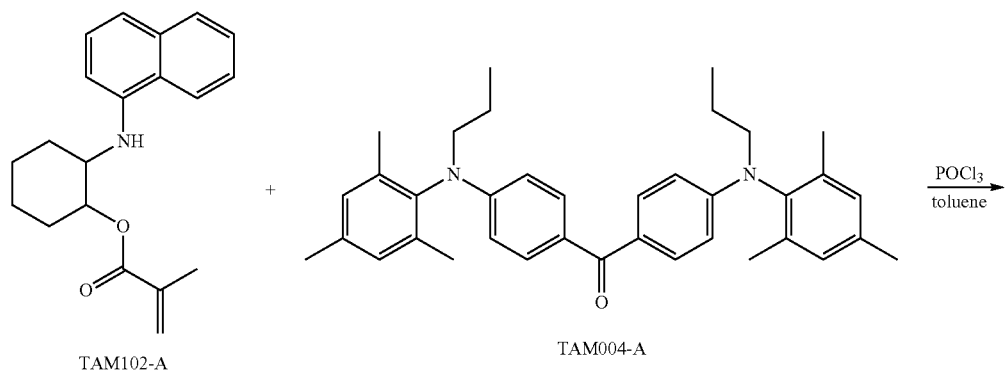

TAM102-A  TAM004-A

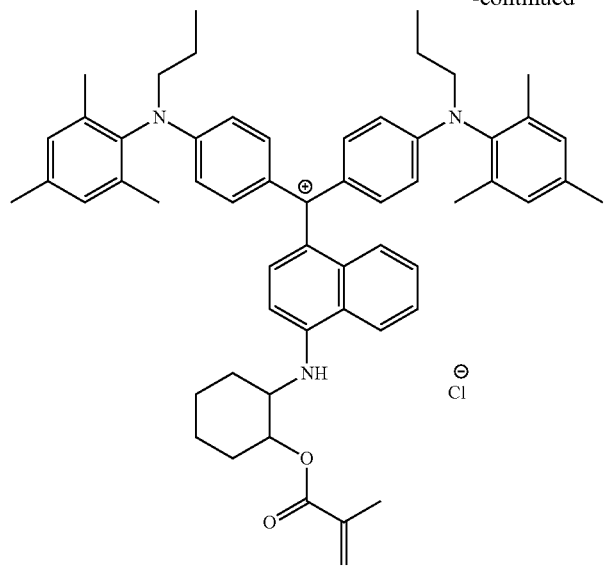

TAM105-Cl

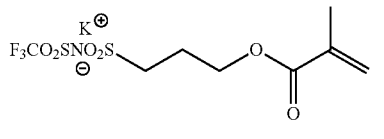

ANION003

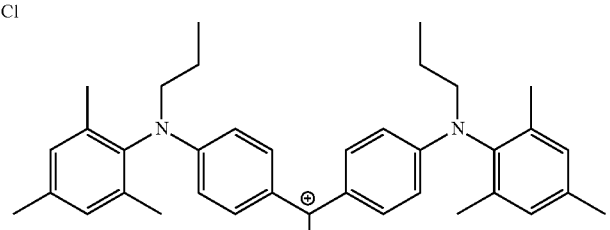

TAM105

«Synthesis of TAM106»

A mixed solution of 0.26 g of nickel (II) acetyl acetate (manufactured by Aldrich), 0.77 g of 95% sodium hydride (manufactured by Aldrich), 0.85 g of 1,3-bis(2,6-diisopropylphenyl)imidazolinium chloride (manufactured by Aldrich), and 12 mL of tetrahydrofuran containing a stabilizer was refluxed. A mixed liquid of 2.7 g of tert-butanol and 6 mL of tetrahydrofuran containing a stabilizer, and then 3.64 g of 2,6-dimethylaniline (manufactured by Tokyo Chemical Industry Co., Ltd.) were added dropwise thereto, followed by stirring for 30 minutes for refluxing. Then, a liquid formed by dissolving 2.51 g of 4,4'-dichlorobenzophenone (manufactured by Tokyo Chemical Industry Co., Ltd.) in 7 mL of tetrahydrofuran containing a stabilizer was added dropwise thereto, followed by stirring for 2 hours under refluxing. The reaction solution was cooled to room temperature, added to 100 mL of water, and subjected to liquid separation by addition of 150 mL of ethyl acetate. The ethyl acetate layer was dried, concentrated, and then purified by silica gel chromatography to obtain 2.0 g of a pale yellow oily material of TAM106-A1.

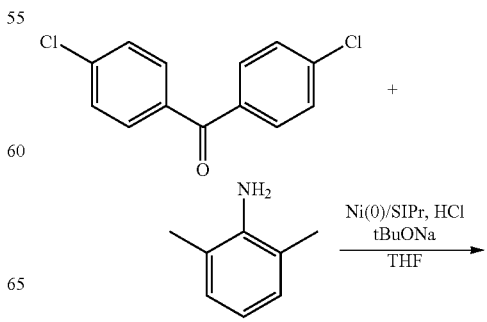

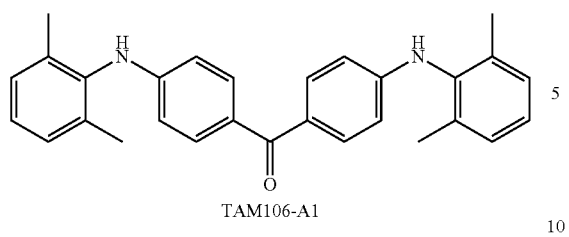

TAM106-A1

To a mixed solution of 10.0 g of TAM106-A1, 4.3 g of sodium hydride (an oil mixture, a content of 60% by mass, manufactured by Tokyo Chemical Industry Co., Ltd.), and 100 mL of N-methylpyrrolidone was added dropwise 12.1 g of propane 1-iodide (manufactured by Kanto Chemical Co., Inc.) at room temperature. The solution after dropwise addition was stirred at 50° C. for 2 hours. After the reaction solution was cooled to room temperature, 500 mL of water was added thereto, and the crude precipitated crystals were filtered. The crude crystals were suspended and washed with acetonitrile to obtain 10.5 g of crystals of TAM106-A2.

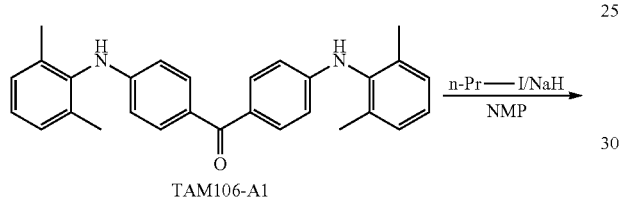

TAM106-A1

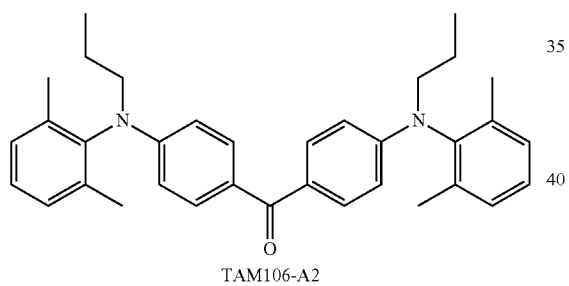

TAM106-A2

By the same method as in the synthesis of TAM005-Cl except that TAM106-A2 was used instead of TAM001-A and TAM102-A was used instead of TAM005-A, TAM106-Cl was obtained. Further, by the same method as in the synthesis of TAM005 except that TAM106-Cl was used instead of TAM005-Cl, TAM106 was obtained. The λmax (ethyl acetate solution) of the absorption spectrum was 582 nm, and the ε (ethyl acetate solution) was 77,000.

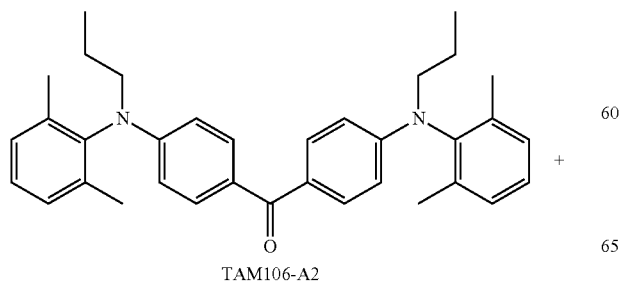

TAM106-A2

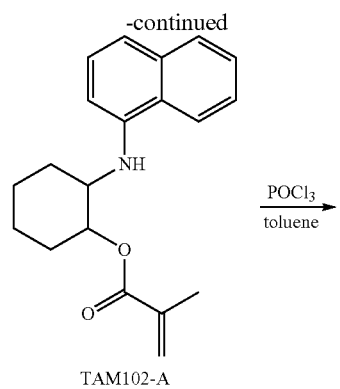

TAM102-A

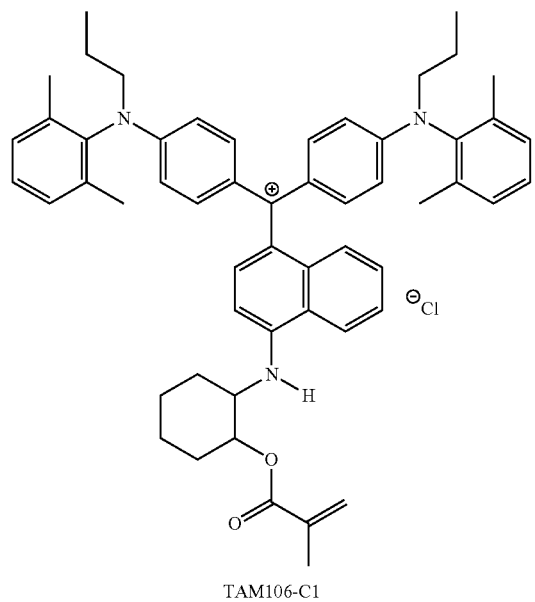

TAM106-C1

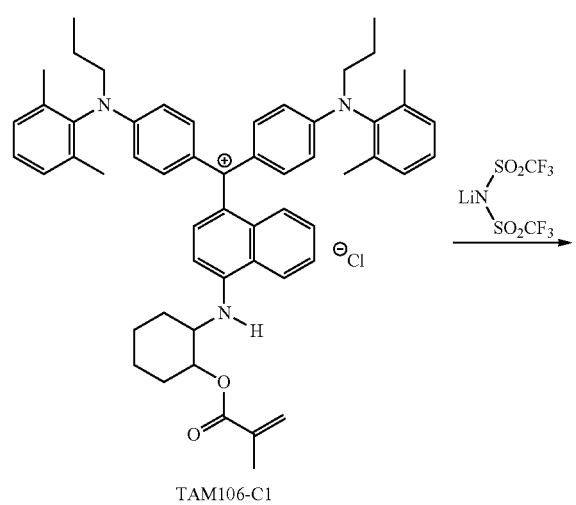

TAM106-C1

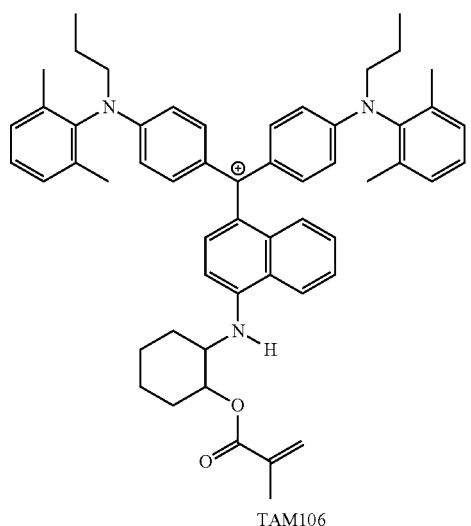

TAM106

«Synthesis of TAM107»

8.6 g of TAM102-Cl, 8.6 g of bis(trifluoromethanesulfonyl)imide lithium (manufactured by Tokyo Chemical Industry Co., Ltd.), and 250 mL of ethyl acetate were put into a flask, followed by stirring and dissolving at room temperature. This solution was directly charged into a silica gel column and purified with ethyl acetate/n-hexane (1/1→1/0) as a developing solvent. After purification, 9.1 g of crystals of TAM007 were obtained. The λmax (ethyl acetate solution) of the absorption spectrum was 587 nm, and the ε (ethyl acetate solution) was 65,000. Further, the salt tolerant amount was measured by 19F.NMR, and as a result, found to be about 140% for TAM. The absorption spectrum is shown in FIG. 1.

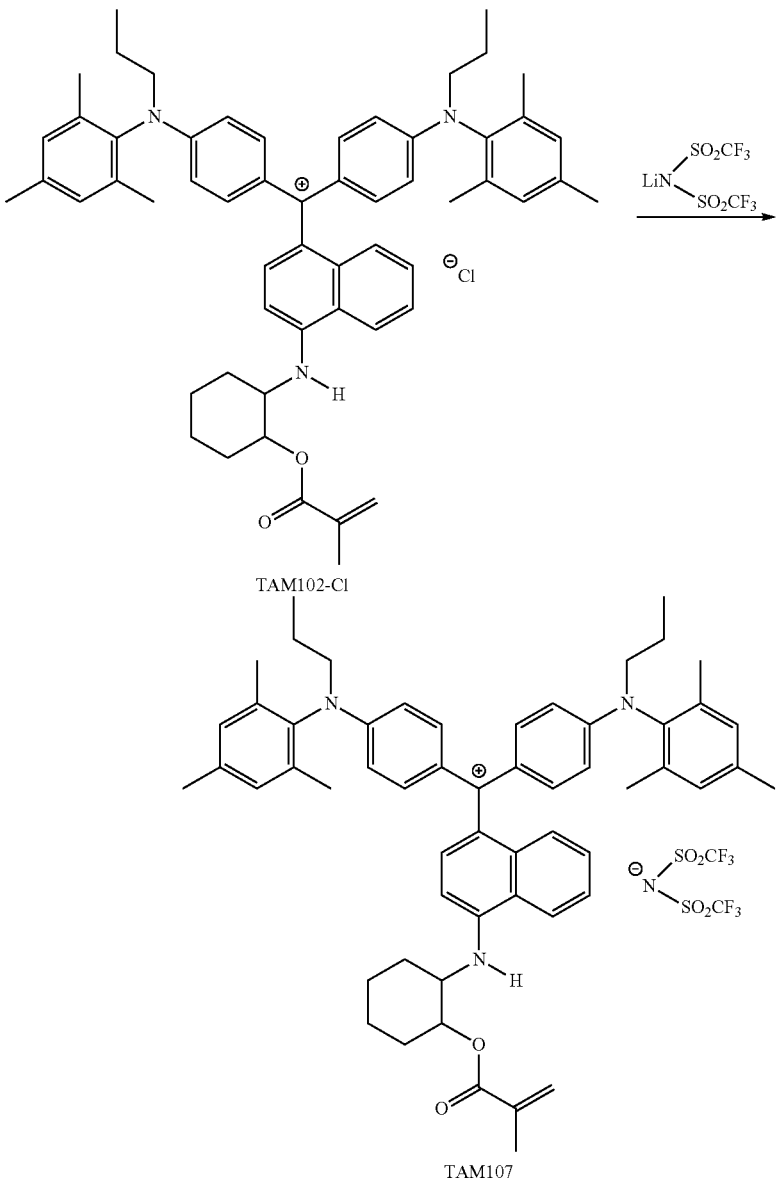

«Synthesis of TAM108»

To a mixed solution of 10.0 g of TAM001-A, 4.0 g of sodium hydride (an oil mixture, a content of 60% by mass, manufactured by Tokyo Chemical Industry Co., Ltd.), and 100 mL of N-methylpyrrolidone was added dropwise 12.5 g of methyl p-toluenesulfonate (manufactured by Wako Pure Chemical Industry Ltd.) at room temperature. The solution after dropwise addition was stirred at 75° C. for 2 hours. After the reaction solution was cooled to room temperature, 500 mL of water was added. After adjusting the pH of the solution to 6 to 7 with a solution of hydrochloric acid, the crude precipitated crystals were filtered. The crude crystals were suspended and washed with acetonitrile to obtain 10.5 g of crystals of TAM108-A.

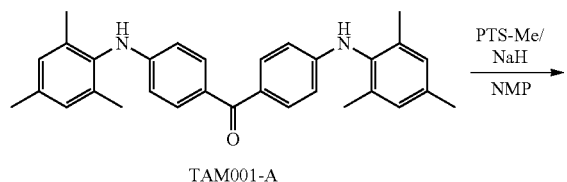

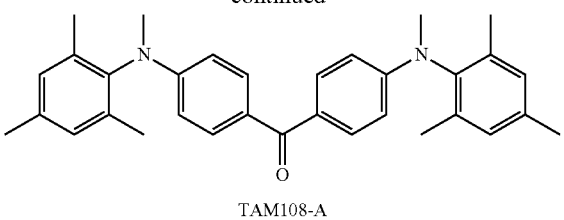

Figure 2:
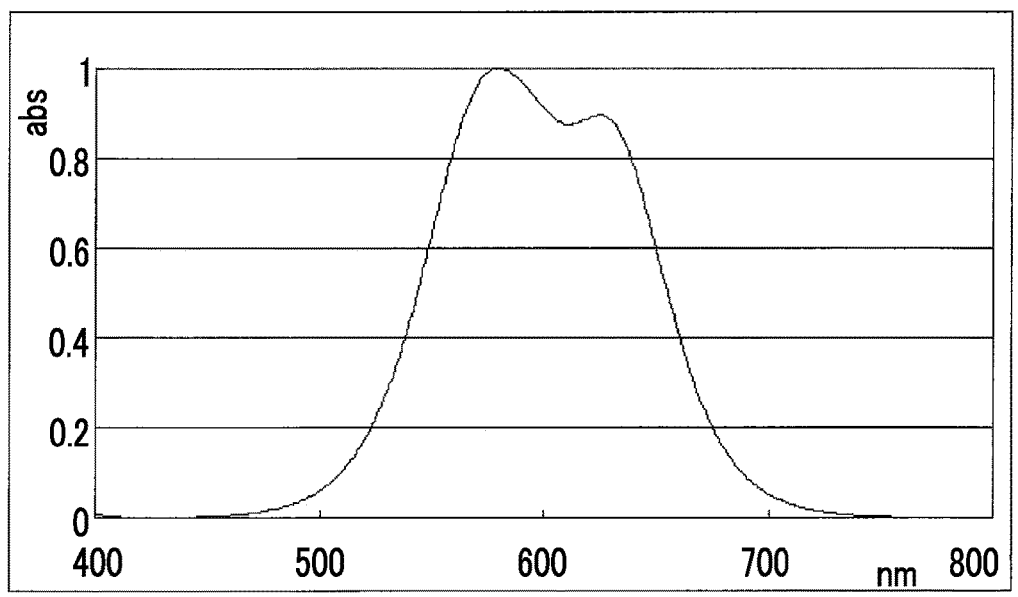
FIG. 2 is a view showing an absorption spectrum of a colorant TAM108.

By the same method as in the synthesis of TAM103-Cl except that TAM108-A was used instead of TAM004-A, TAM108-Cl was obtained. By the same method as in the synthesis of TAM001 except that TAM108-C was used instead of TAM001-Cl, TAM108 was obtained. The λmax (ethyl acetate solution) of the absorption spectrum was 579 nm, and the ε (ethyl acetate solution) was 80,000. The absorption spectrum is shown in FIG. 2.

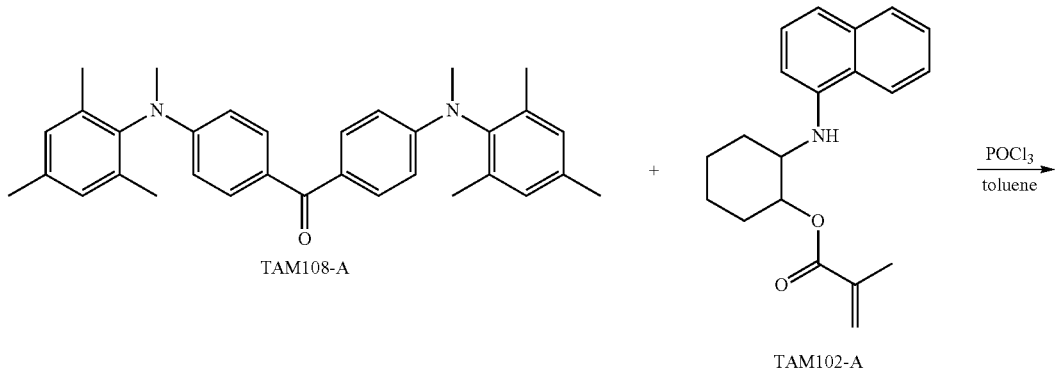

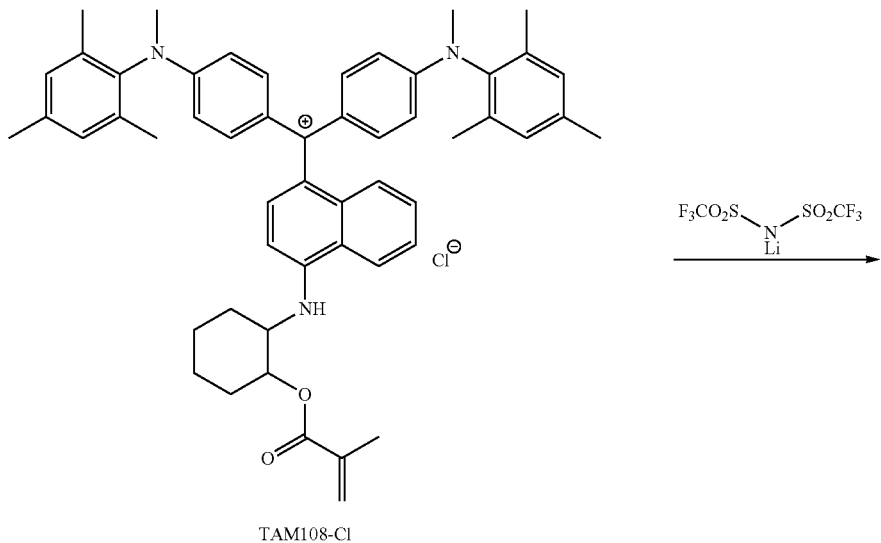

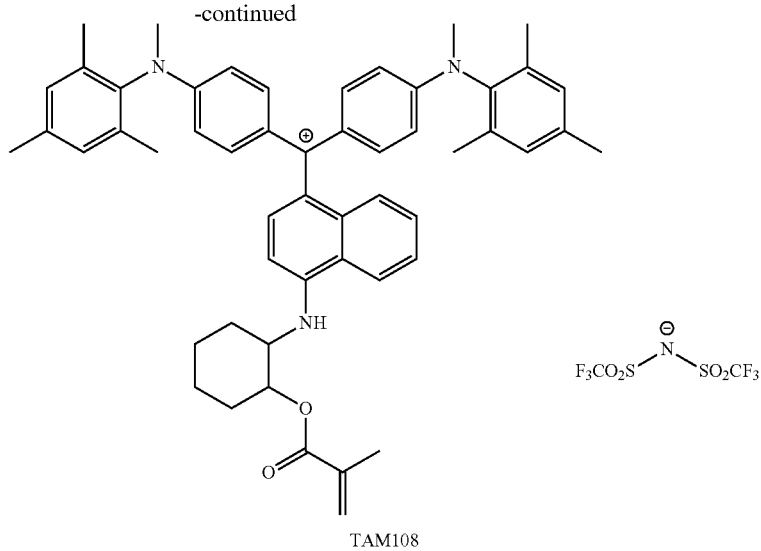

TAM108

«Synthesis of TAM109»

By the same method as in the synthesis of TAM108-A except that 1-brominated butane (manufactured by Wako Pure Chemical Industry Ltd.) was used instead of methyl p-toluenesulfonate, TAM109-A was obtained.

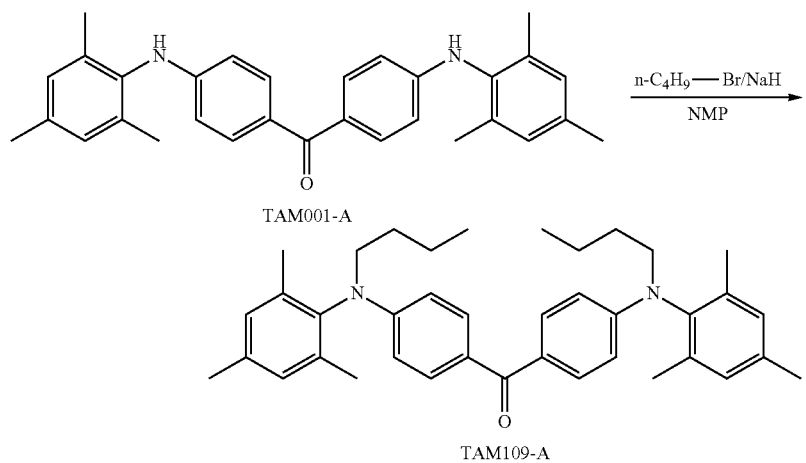

By the same method as in the synthesis of TAM103-Cl except that TAM109-A was used instead of TAM004-A, TAM109-Cl was obtained. By the same method as in the synthesis of TAM001 except that TAM109-Cl was used instead of TAM001-Cl, TAM109 was obtained. The λmax (ethyl acetate solution) of the absorption spectrum was 589 nm, and the ε (ethyl acetate solution) was 90,000.

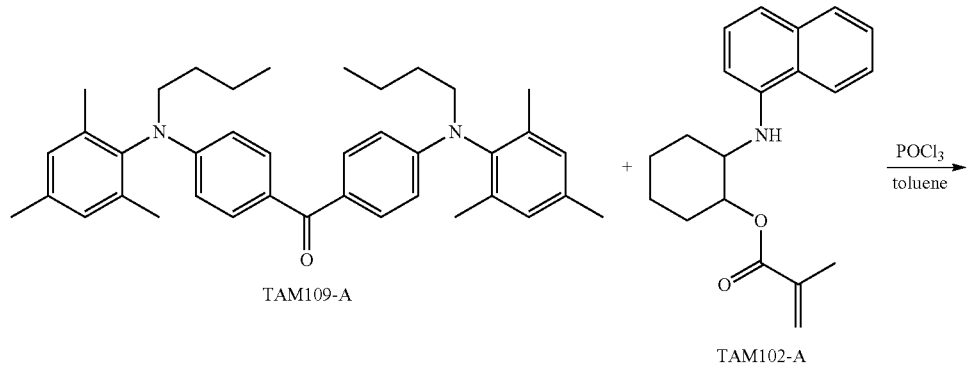

-continued
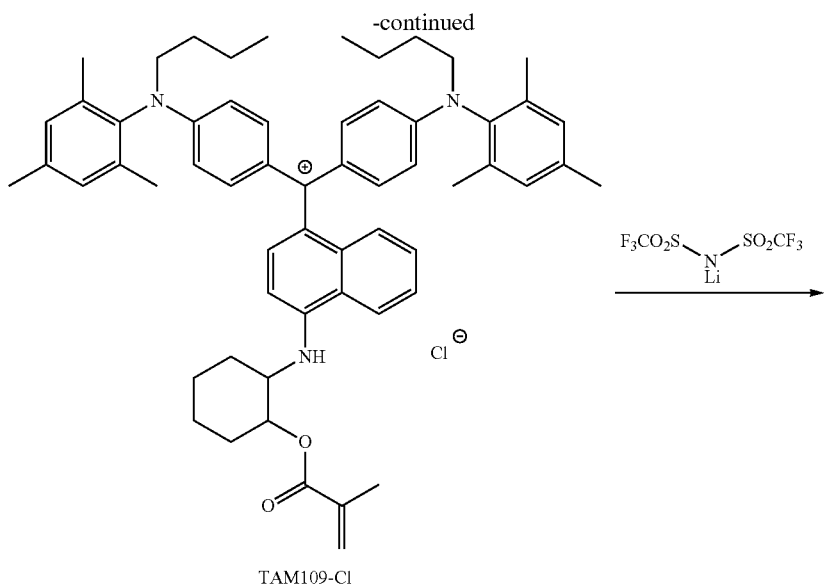
TAM109-Cl
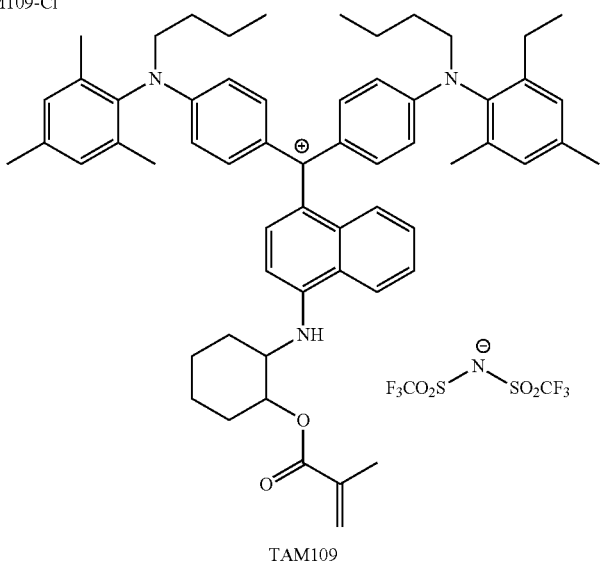
TAM109
«Synthesis of TAM110»
By the same method as in the synthesis of TAM109-A except that 1-brominated hexane (manufactured by Wako Pure Chemical Industry Ltd.) was used instead of 1-brominated butane, TAM110-A was obtained.
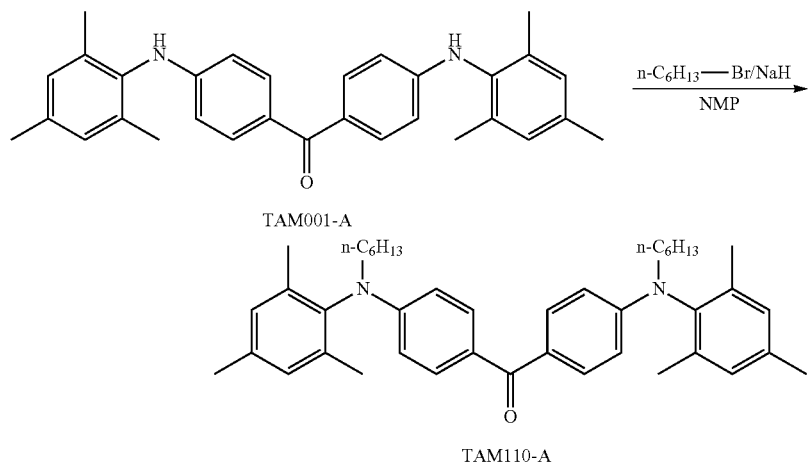

Figure 3:
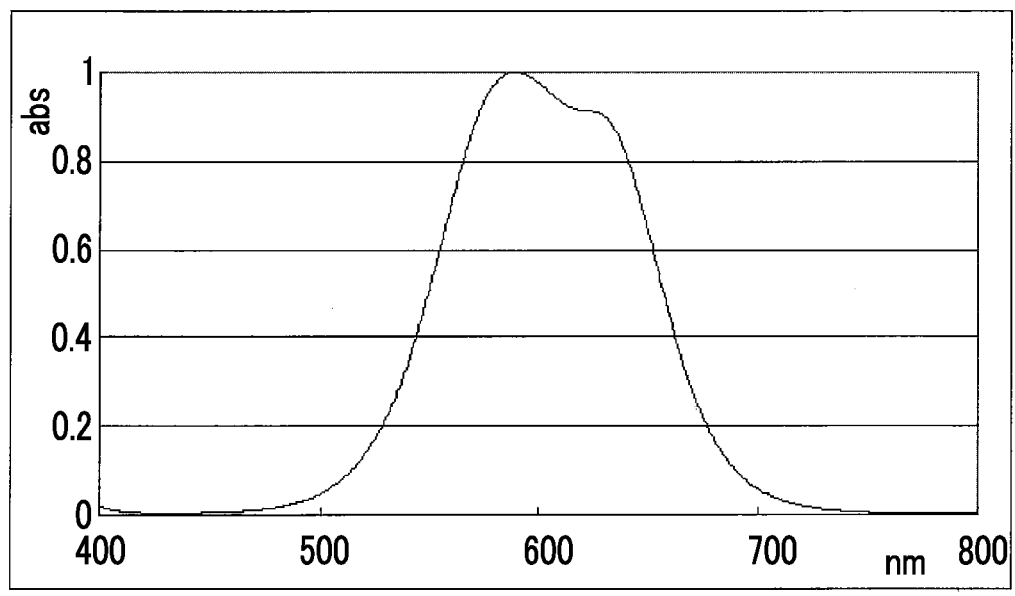
FIG. 3 is a view showing an absorption spectrum of a colorant TAM110.

By the same method as in the synthesis of TAM103-Cl except that TAM110-A was used instead of TAM004-A, TAM110-Cl was obtained. By the same method as in the synthesis of TAM001 except that TAM110-Cl was used instead of TAM001-Cl, TAM110 was obtained. The λmax (ethyl acetate solution) of the absorption spectrum was 589 nm, and the ε (ethyl acetate solution) was 82,000. The absorption spectrum is shown in FIG. 3.

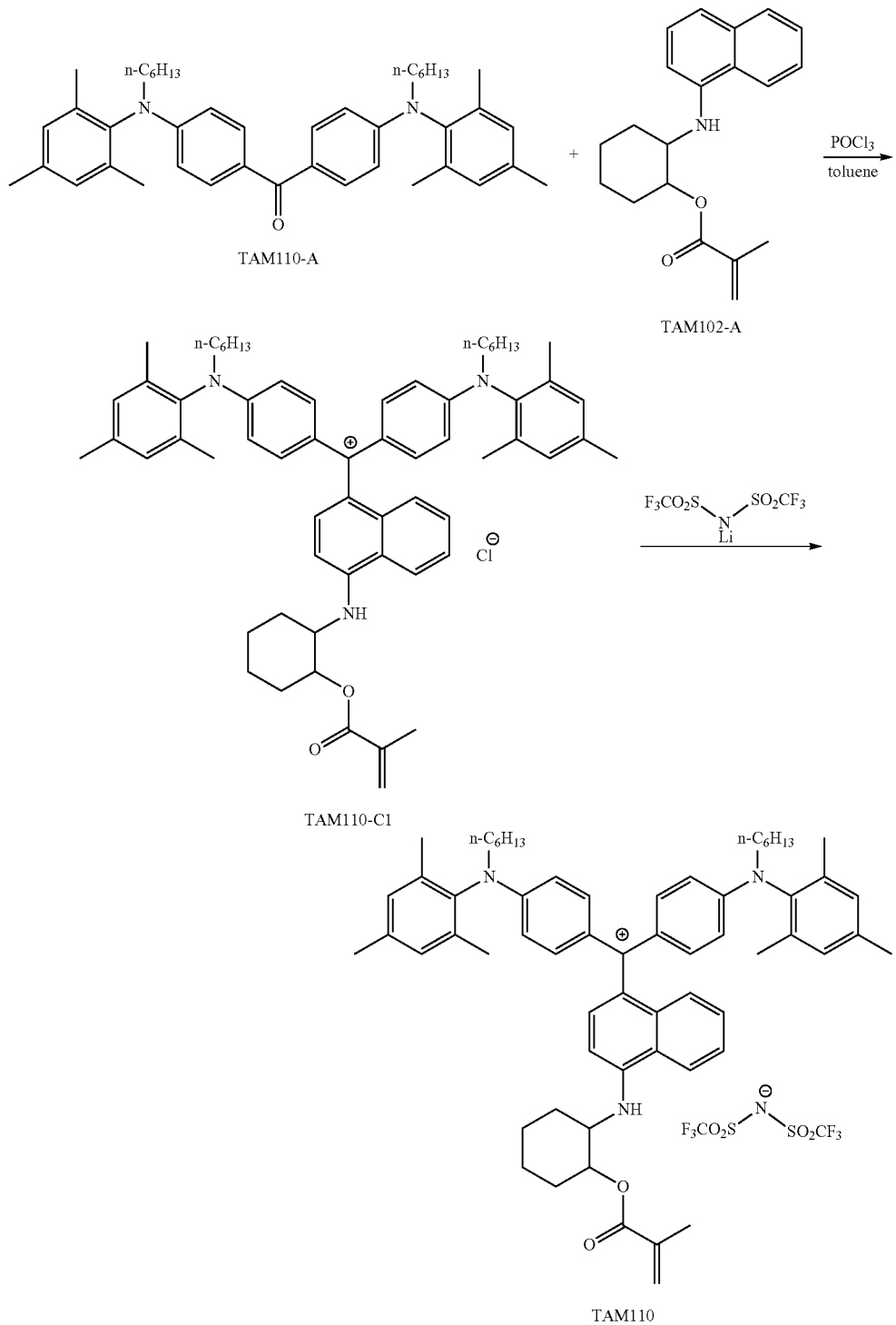

«Synthesis of TAM111»

By the same method as in the synthesis of TAM109-A except that 1-brominated allyl (manufactured by Tokyo Chemical Industry Co., Ltd.) was used instead of 1-brominated hexane, TAM111-A was obtained.

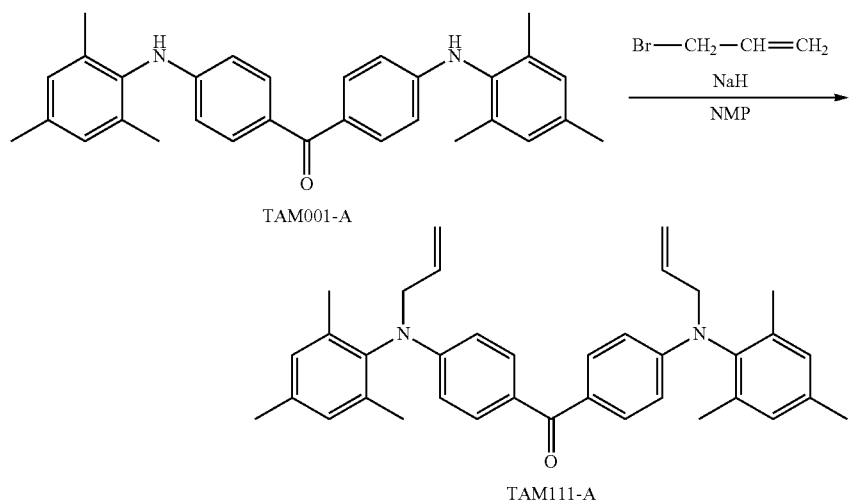
By the same method as in the synthesis of TAM103-Cl except that TAM111-A was used instead of TAM004-A, TAM111-Cl was obtained. By the same method as in the synthesis of TAM001 except that TAM111-Cl was used instead of TAM001-Cl, TAM111 was obtained. The λmax (ethyl acetate solution) of the absorption spectrum was 577 nm, and the ε (ethyl acetate solution) was 82,000.
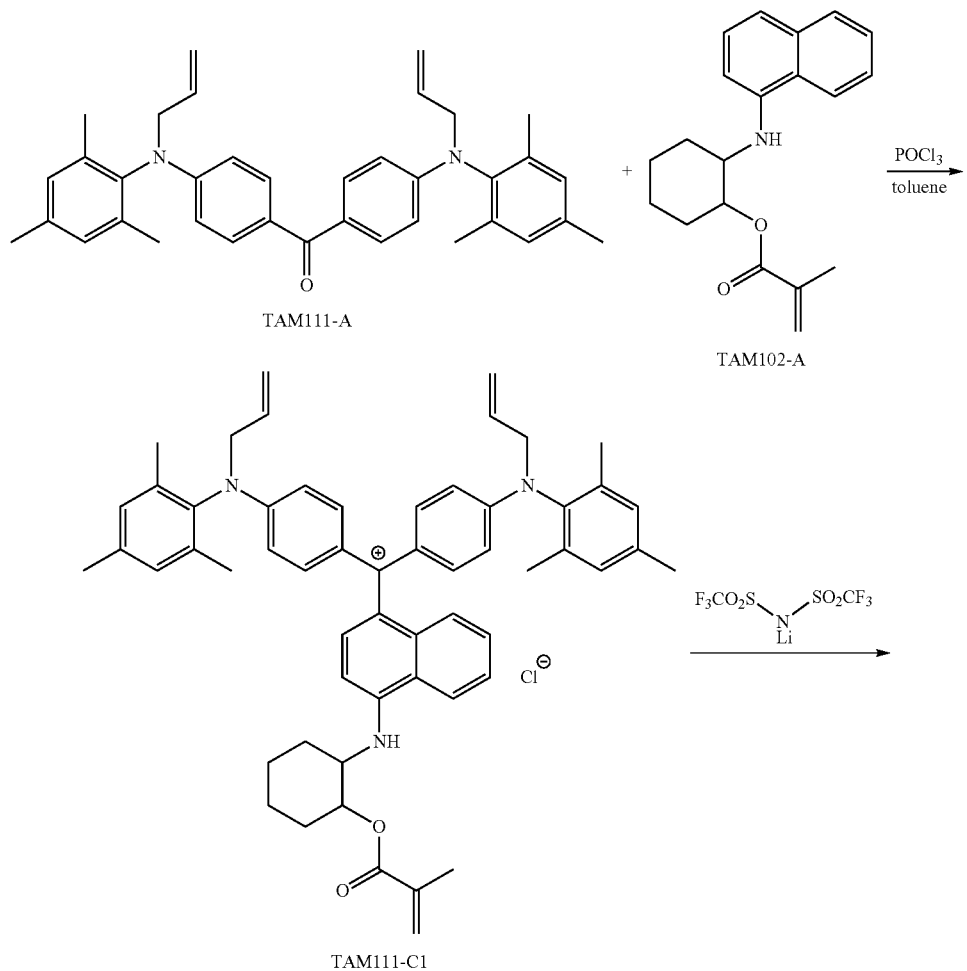

-continued

TAM111

«Synthesis of TAM112»

By the same method as in the synthesis of TAM106-A2 except that TAM002-A was used instead of TAM106-A1, TAM112-A was obtained.

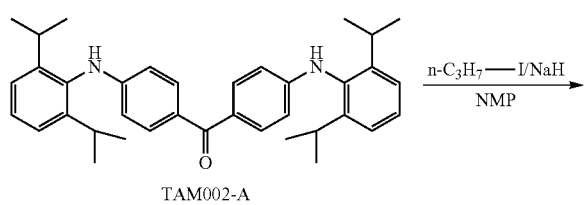

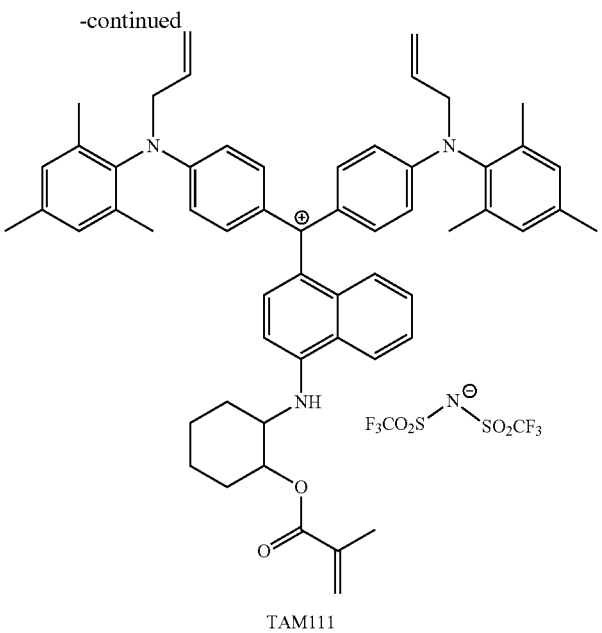

Figure 4:
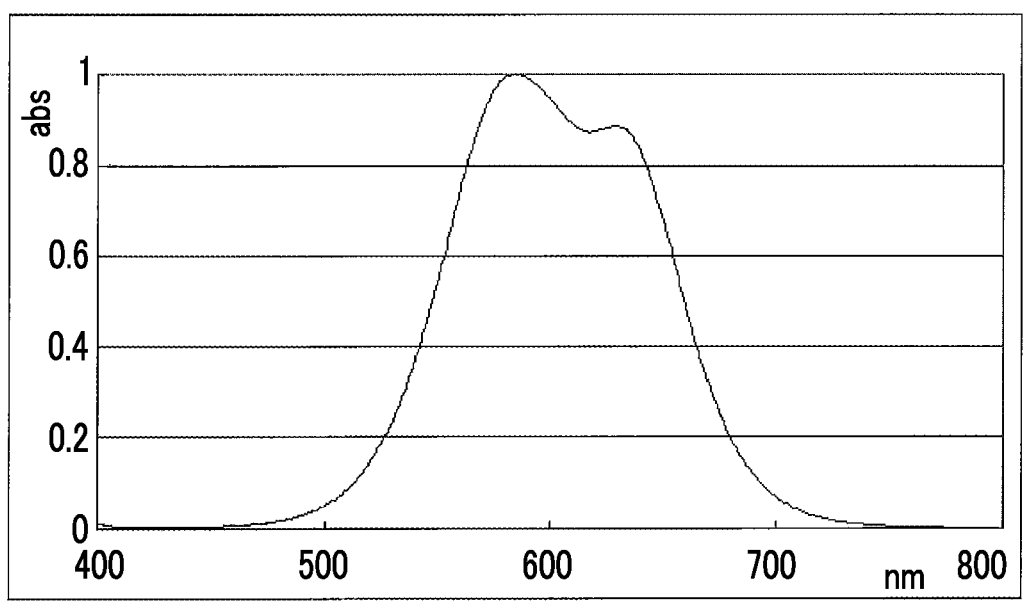
FIG. 4 is a view showing an absorption spectrum of a colorant TAM112.

By the same method as in the synthesis of TAM103-Cl except that TAM112-A was used instead of TAM004-A, TAM112-Cl was obtained. By the same method as in the synthesis of TAM001 except that TAM112-Cl was used instead of TAM001-Cl, TAM112 was obtained. The λmax (ethyl acetate solution) of the absorption spectrum was 584 nm, and the ε (ethyl acetate solution) was 72,000. The absorption spectrum is shown in FIG. 4.

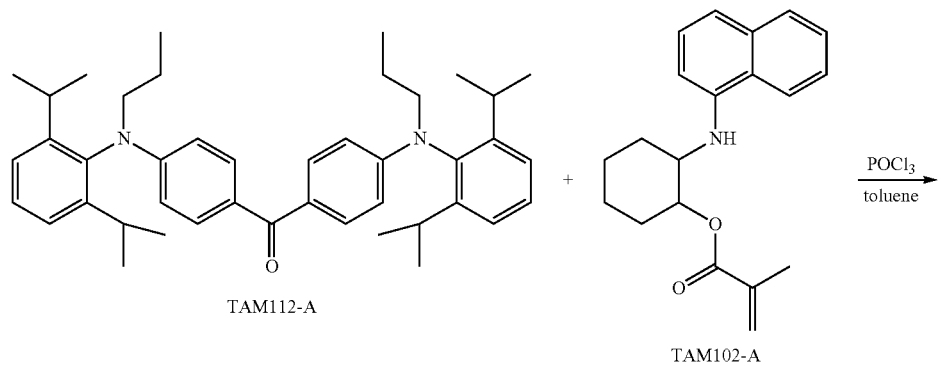

-continued
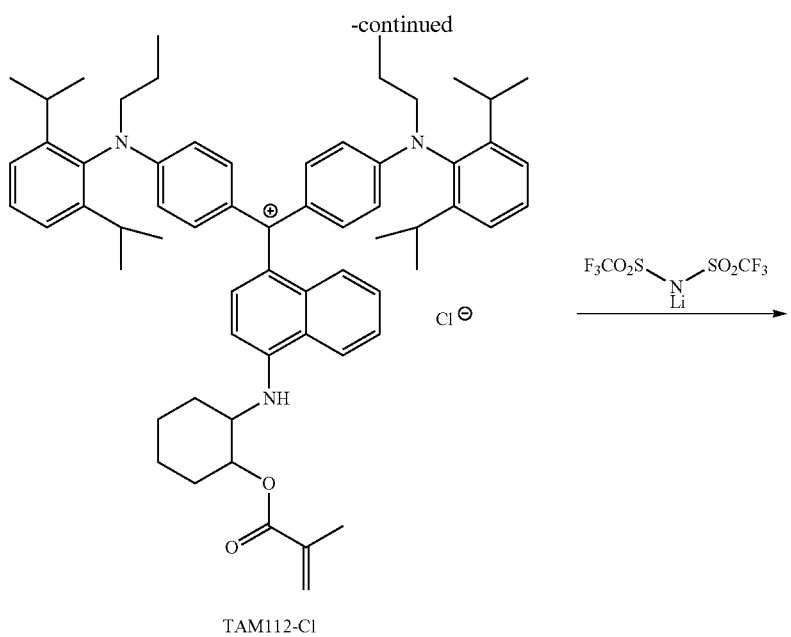
TAM112-Cl
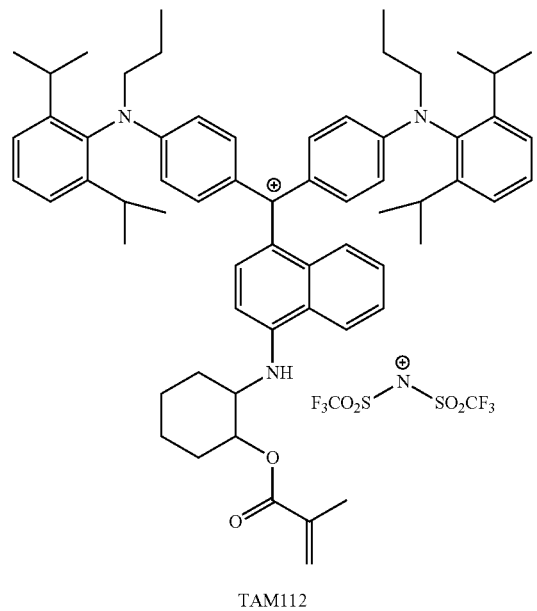
TAM112
«Synthesis of TAM113»
By the same method as in the synthesis of TAM106-A2 except that TAM009-A was used instead of TAM106-A1, TAM113-A was obtained.
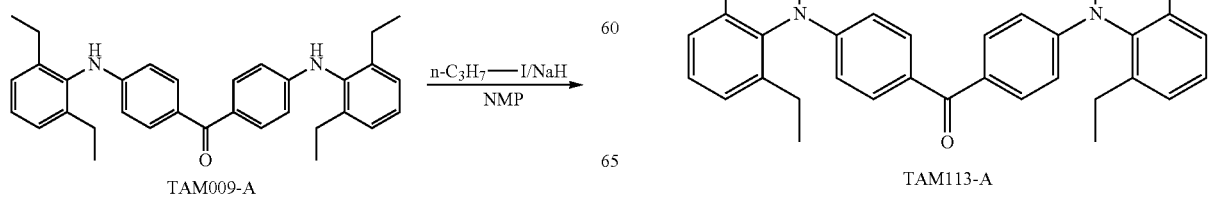

By the same method as in the synthesis of TAM103-Cl except that TAM113-A was used instead of TAM004-A, TAM113-Cl was obtained. By the same method as in the synthesis of TAM001 except that TAM113-Cl was used instead of TAM001-Cl, TAM113 was obtained. The λmax (ethyl acetate solution) of the absorption spectrum was 584 nm, and the ε (ethyl acetate solution) was 73,000.

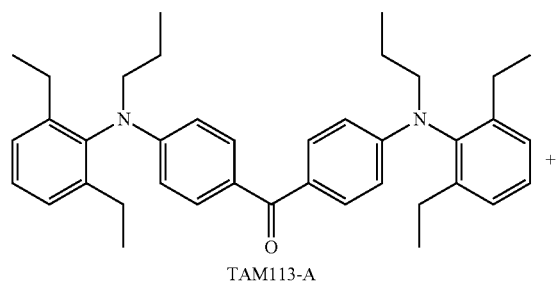

TAM113-A

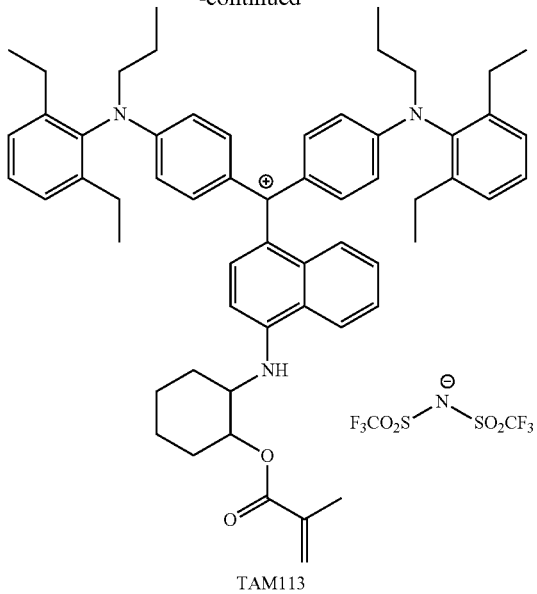

TAM113

«Synthesis of TAM114»

By the same method as in the synthesis of TAM102-A except that chloromethylstyrene was used instead of acrylic acid chloride, TAM005-A2 was obtained.

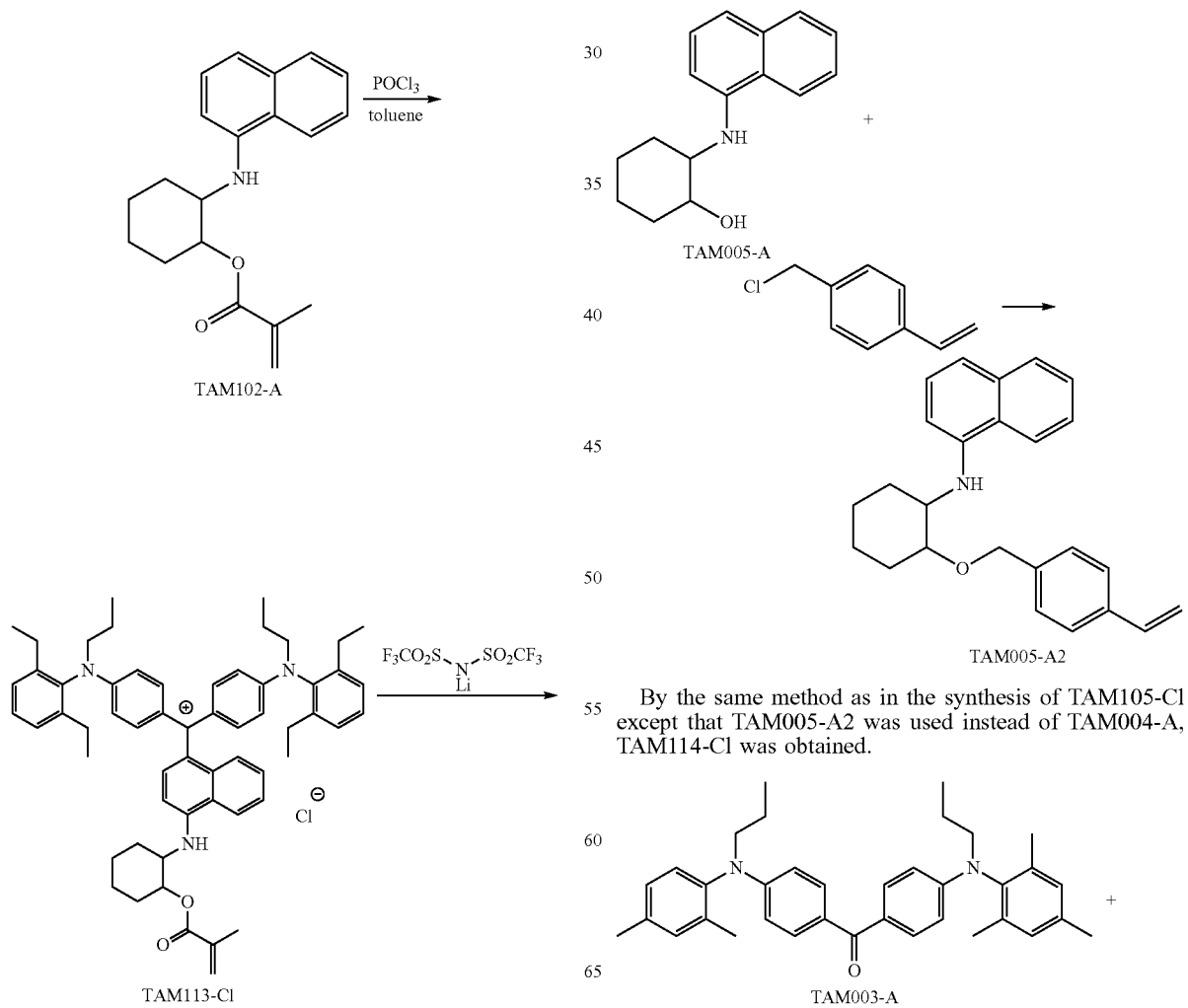

By the same method as in the synthesis of TAM105-Cl except that TAM005-A2 was used instead of TAM004-A, TAM114-Cl was obtained.

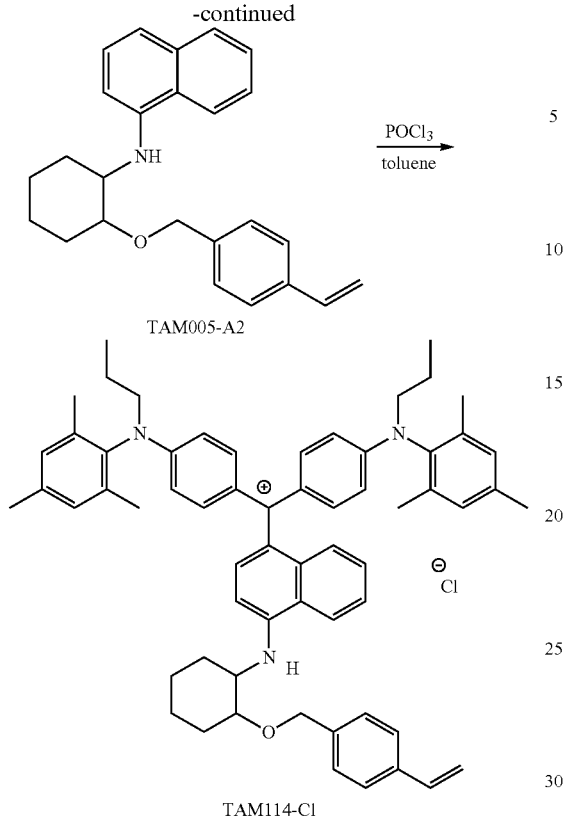

TAM005-A2

TAM114-Cl 10 g of TAM114-Cl, 9.5 g of bis(trifluoromethanesulfonyl)imide lithium (manufactured by Tokyo Chemical Industry Co., Ltd.), and 100 mL of methanol were put into a flask, followed by stirring and dissolving at room temperature. 500 mL of water was added dropwise thereto to carry out precipitation. The obtained crystals were purified by silica gel column chromatography to obtain 8.5 g of crystals of TAM114. The λmax (ethyl acetate solution) of the absorption spectrum was 577 nm, and the ε (ethyl acetate solution) was 76,000.

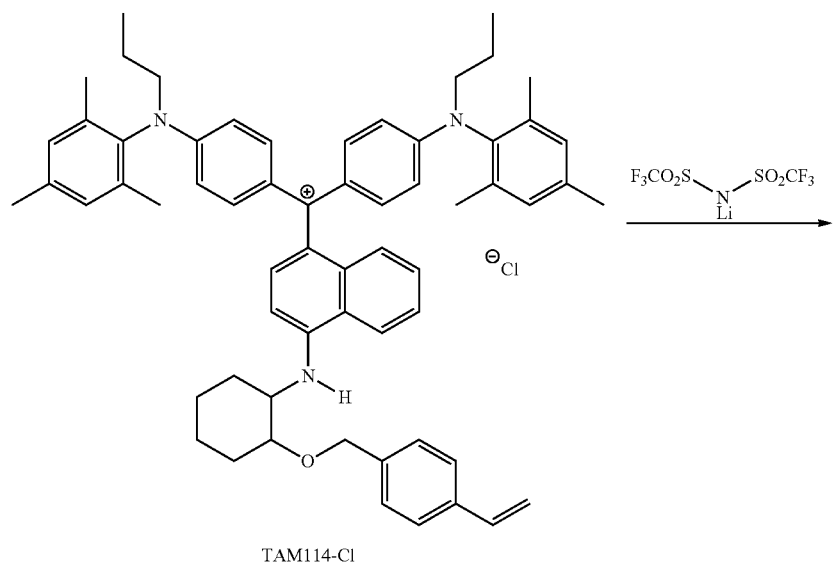

TAM114-Cl

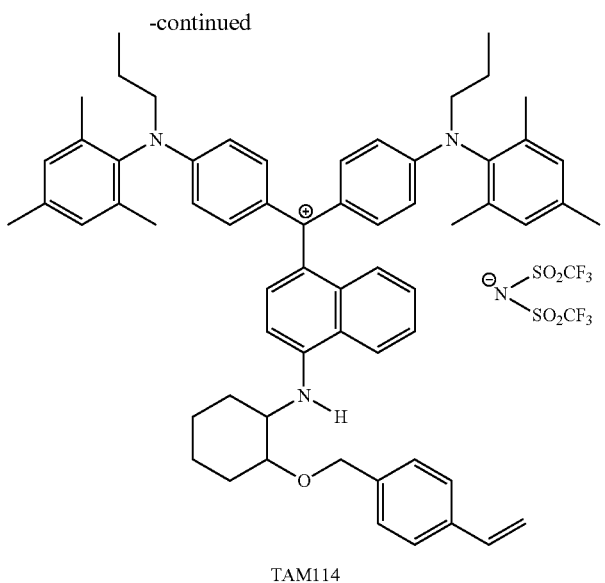

TAM114

«Synthesis of TAM115»

To a mixed solution of 23 g of LIGHT ESTER HO-MS (N) (manufactured by KYOEISHA CHEMICAL CO., LTD.), several droplets of N,N-dimethylacetamide, and 100 mL of methylene chloride was added dropwise 35.4 g of oxalyl chloride for 1 hour. Thereafter, the mixture was stirred at 25° C. for 1 hour and 30 minutes, and then to an oily material obtained by distilling the mixture off under reduced pressure was added 40 mL of trifluoroacetic acid (manufactured by Wako Pure Chemical Industry Ltd.), followed by stirring under ice-cooling. Subsequently, 10 g of TAM005-A was carefully added thereto, followed by stirring at 25° C. for 2 hours and 30 minutes. The reaction liquid was poured into 400 mL of water having 40 g of sodium hydroxide (manufactured by Wako Pure Chemical Industry Ltd.) dissolved therein. Sodium hydrogen carbonate was added thereto so that the pH of water became about 7, and the mixture was extracted with ethyl acetate, then dried over anhydrous magnesium sulfate, and distilled off under reduced pressure. The obtained oily material was purified by silica gel chromatography to obtain 8.0 g of a pale yellow oily material of TAM005-A3.

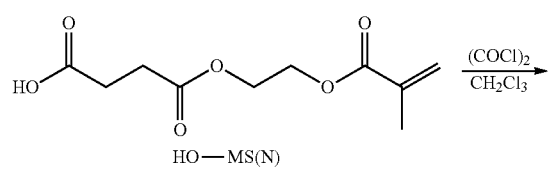

HO—MS(N)

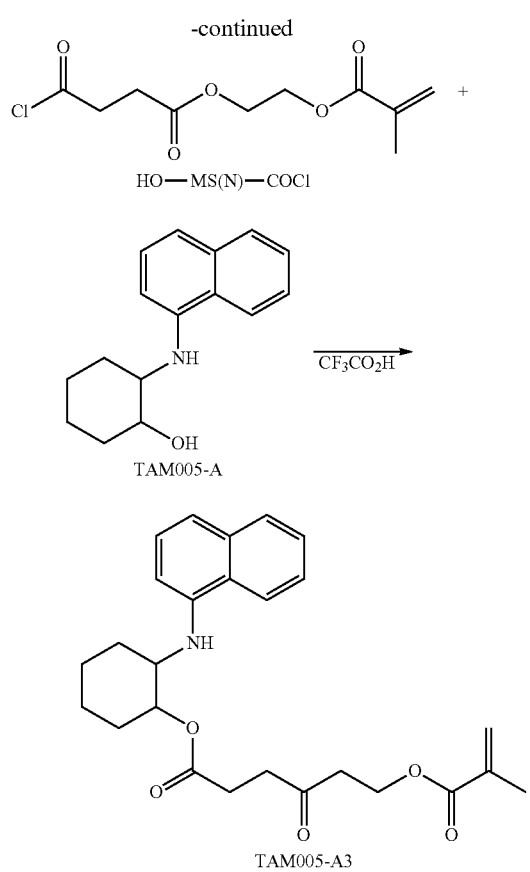

TAM005-A3

By the same method as in the synthesis of TAM105-Cl except that TAM005-A3 was used instead of TAM004-A, TAM115-Cl was obtained. By the same method as in the synthesis of TAM001 except that TAM113-Cl was used instead of TAM001-Cl, TAM113 was obtained. The λmax (ethyl acetate solution) of the absorption spectrum was 586 nm, and the ε (ethyl acetate solution) was 115,000.

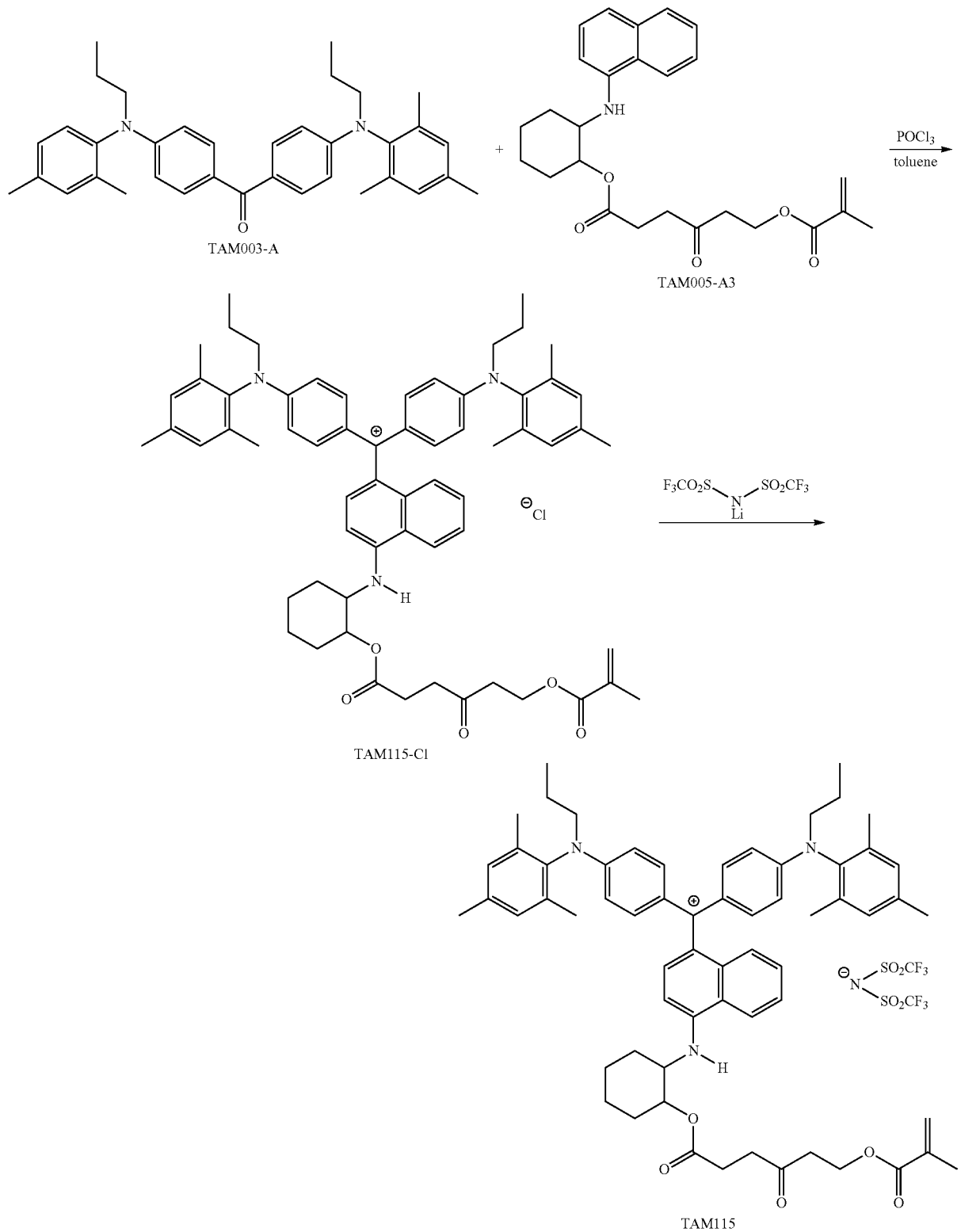

«Synthesis of TAM116»

By the same method as in the synthesis of TAM106 except that TAM116-A was used instead of TAM102-A and triethylamine was added after completion of the synthesis of a colorant with phosphorous oxychloride, TAM116-Cl was obtained. Further, by the same method as in the synthesis of TAM005 except that TAM106-Cl was used instead of TAM005-Cl, TAM116 was obtained. The λmax (ethyl acetate solution) of the absorption spectrum was 583 nm, and the ε (ethyl acetate solution) was 79,000.

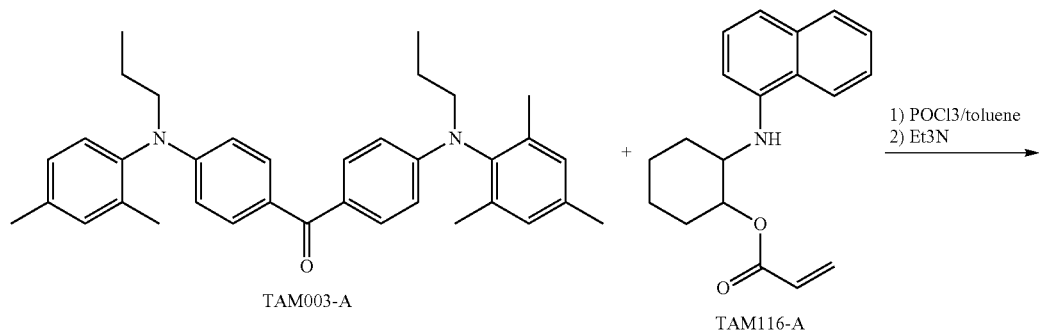
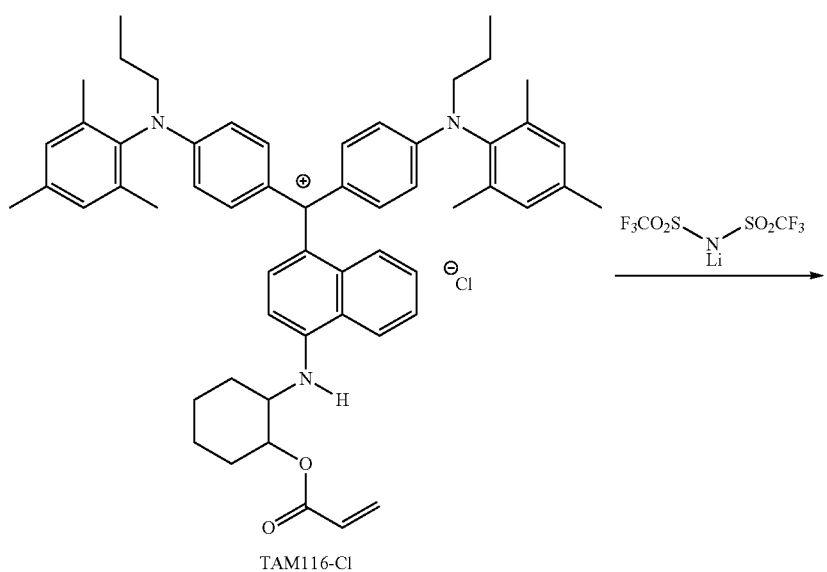
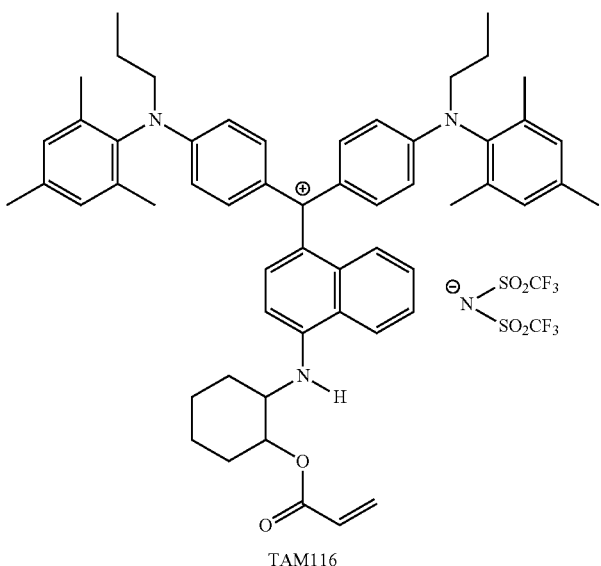
«Synthesis of TAM117»
In accordance with the following route by the same procedure as for TAM107, TAM117 was synthesized. The λmax (ethyl acetate solution) of the absorption spectrum was 580 nm, and the ε (ethyl acetate solution) was 77,000.

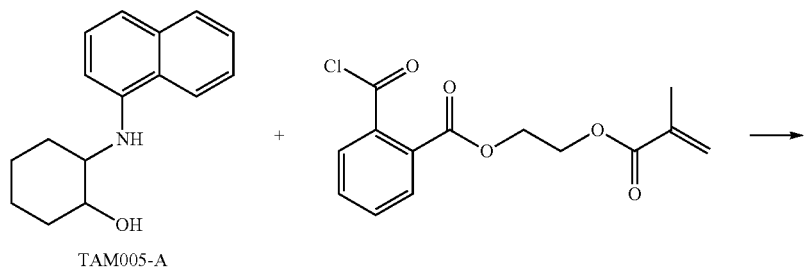
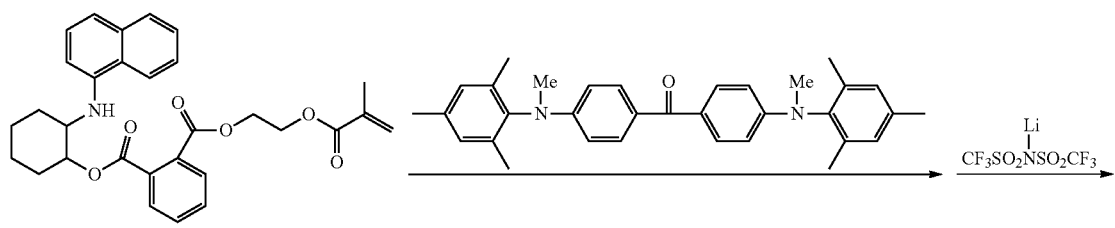
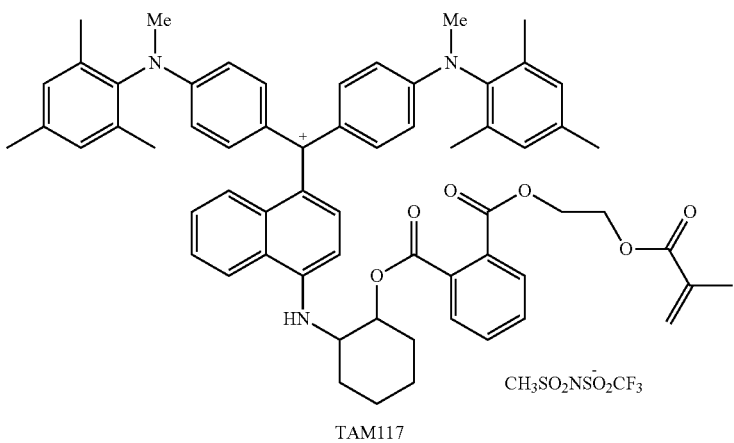
TAM117
«Synthesis of TAM118»
In accordance with the following route by the same procedure as for TAM107, TAM118 was synthesized. The λmax (ethyl acetate solution) of the absorption spectrum was 579 nm, and the ε (ethyl acetate solution) was 78,000.
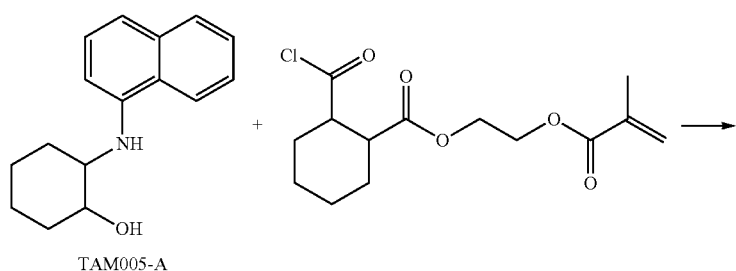

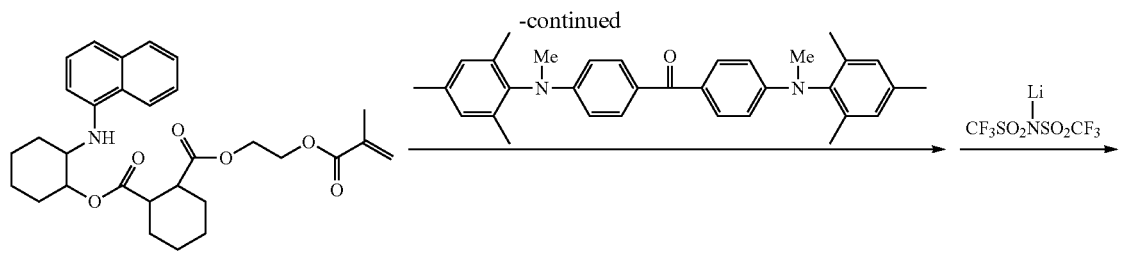
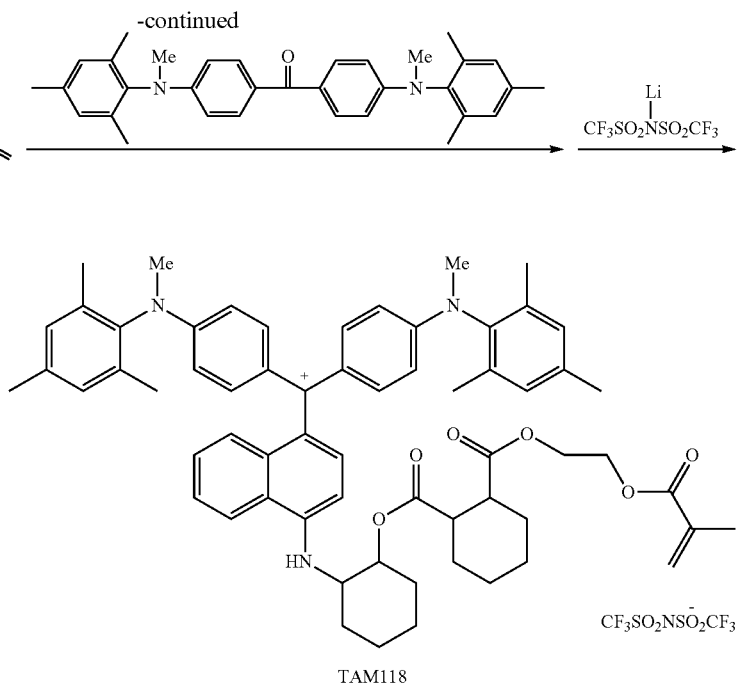
«Synthesis of TAM119»
In accordance with the following route by the same procedure as for TAM107, TAM119 was synthesized. The λmax (ethyl acetate solution) of the absorption spectrum was 580 nm, and the ε (ethyl acetate solution) was 80,000.
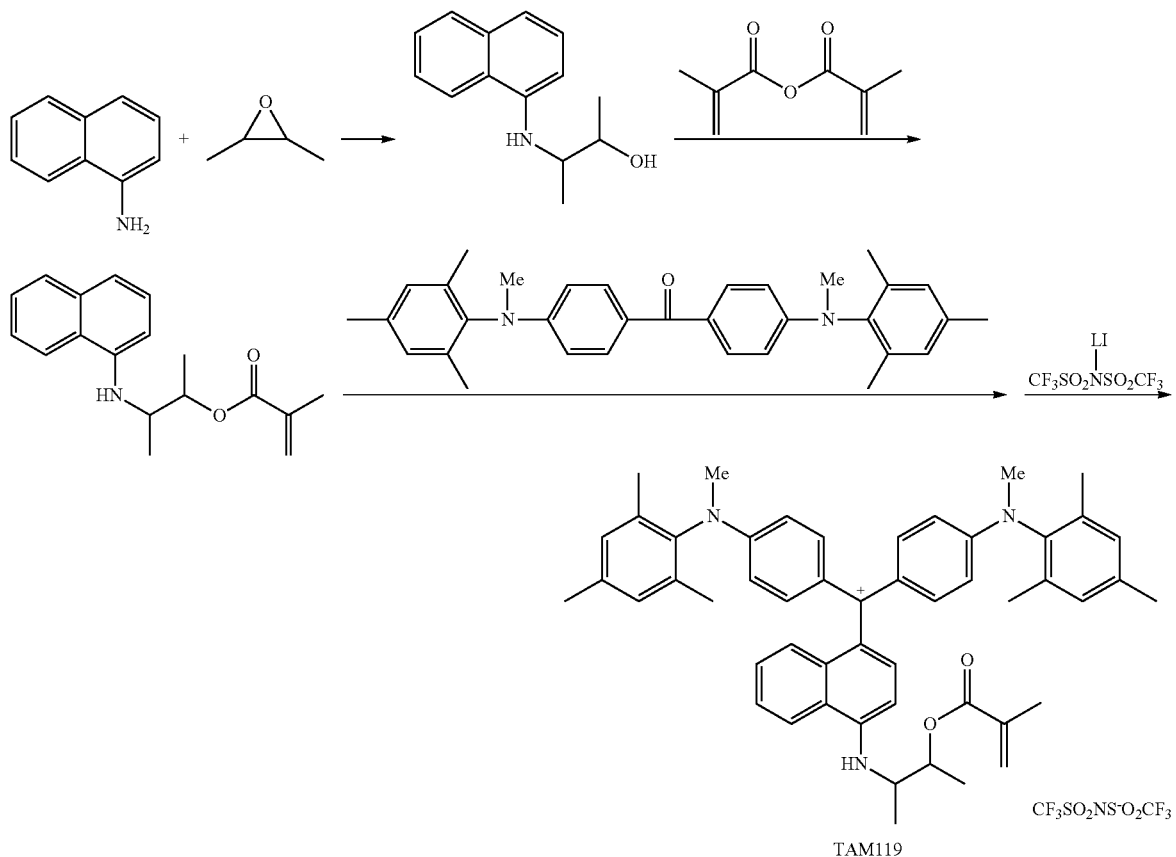

«Synthesis of TAM120»

In accordance with the following route by the same procedure as for TAM107, TAM120 was synthesized. The λmax (ethyl acetate solution) of the absorption spectrum was 579 nm, and the ε (ethyl acetate solution) was 78,000.

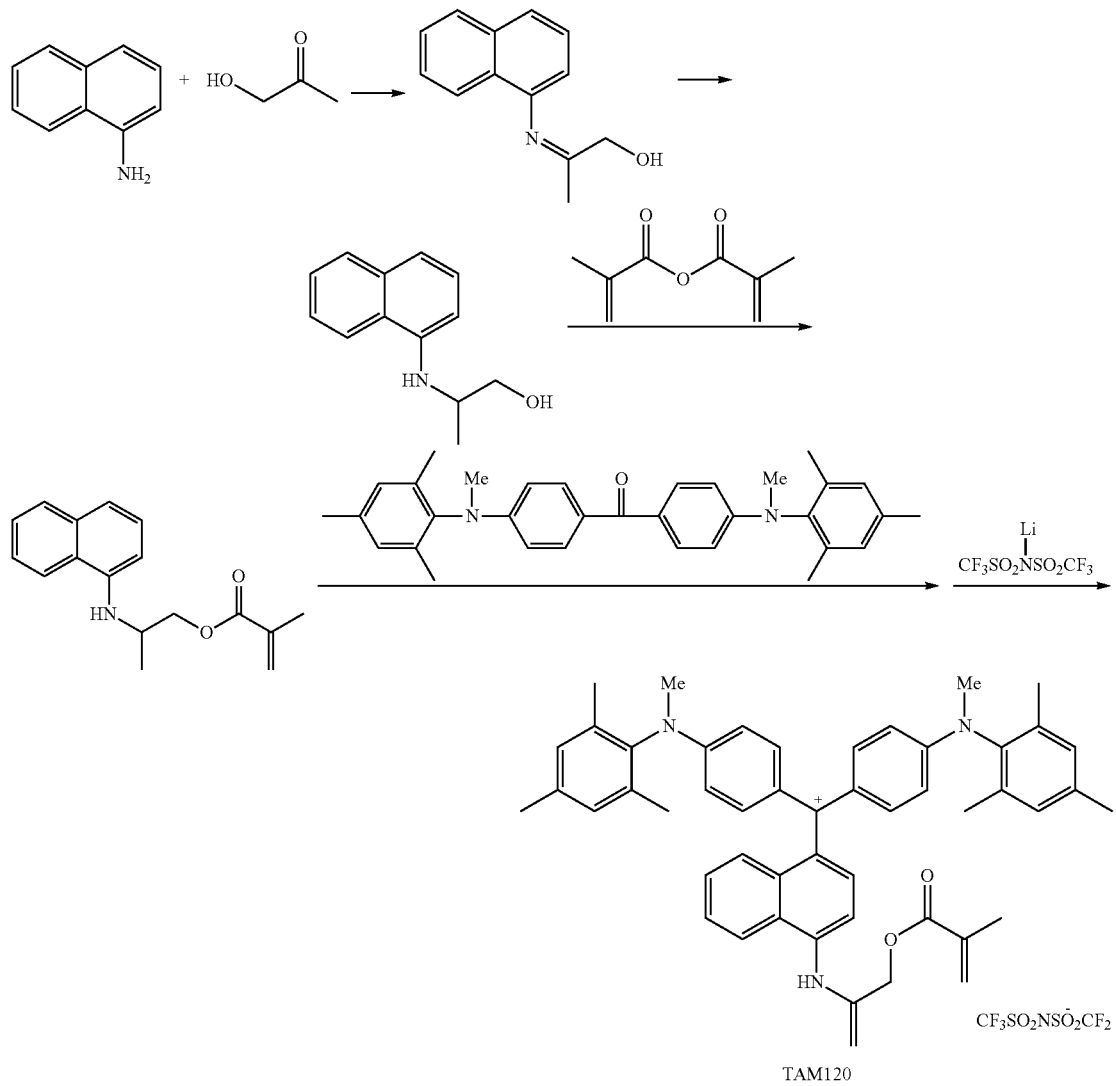

TAM120

«Synthesis of TAM121»

In accordance with the following route by the same procedure as for TAM107, TAM121 was synthesized. The λmax (ethyl acetate solution) of the absorption spectrum was 578 nm, and the ε (ethyl acetate solution) was 79,000.

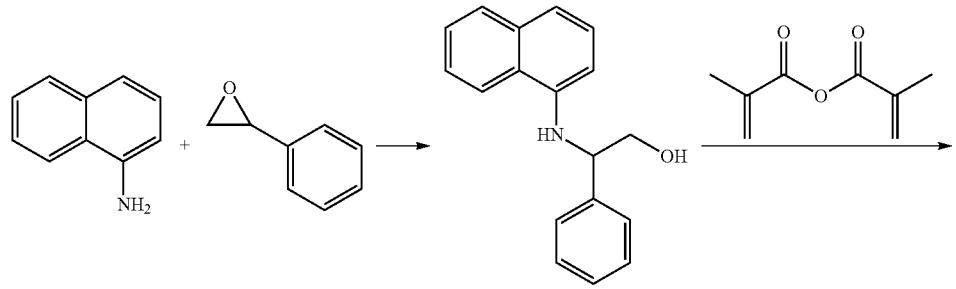

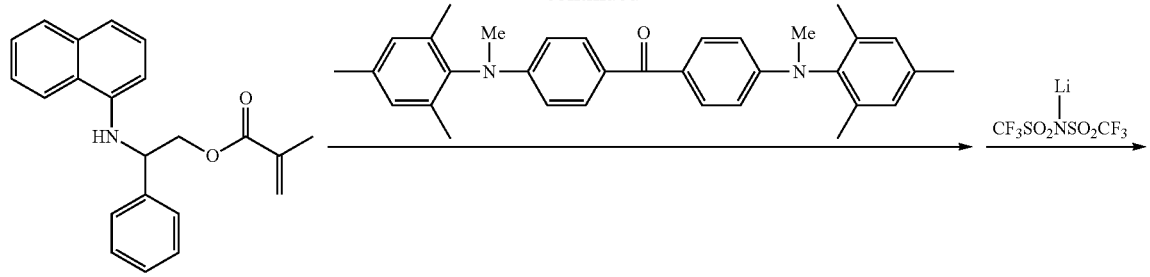
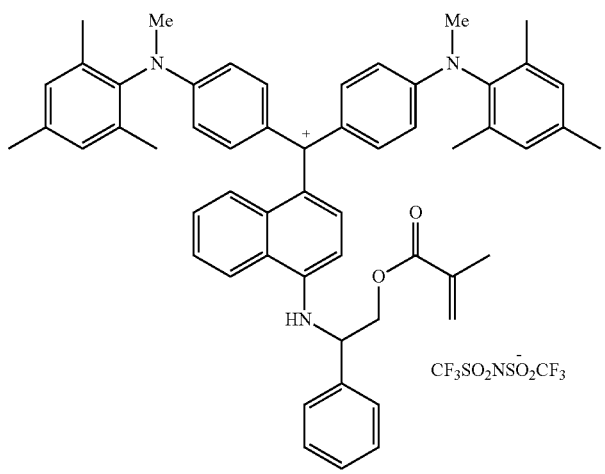
TAM121
«Synthesis of TAM122»
In accordance with the following route by the same procedure as for TAM107, TAM122 was synthesized. The λmax (ethyl acetate solution) of the absorption spectrum was 578 nm, and the ε (ethyl acetate solution) was 77,000.
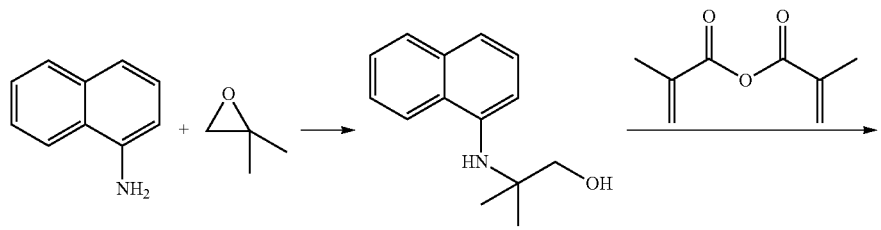
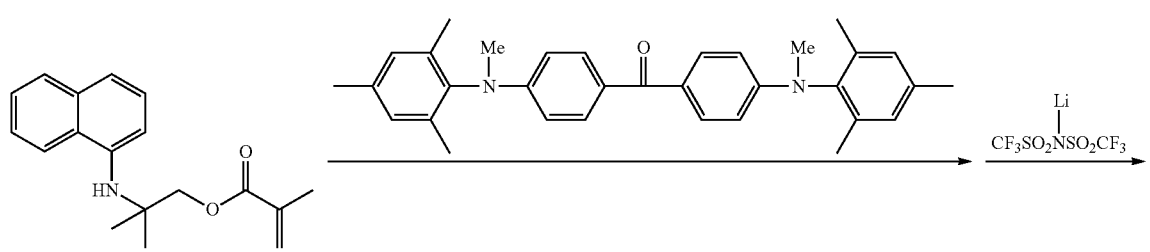

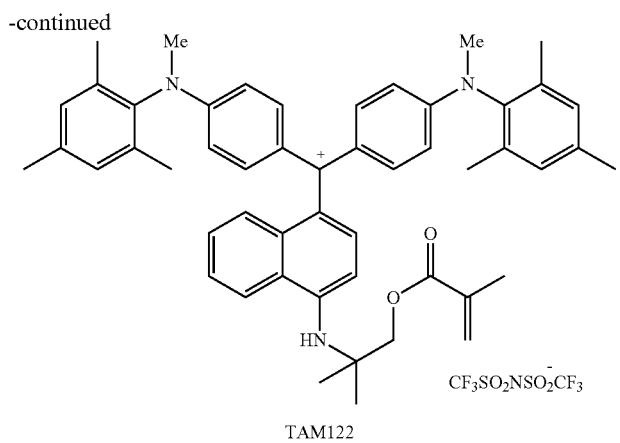

TAM122

«Synthesis of TAM123»

In accordance with the following route by the same procedure as for TAM107, TAM123 was synthesized. The λmax (ethyl acetate solution) of the absorption spectrum was 577 nm, and the ε (ethyl acetate solution) was 80,000.

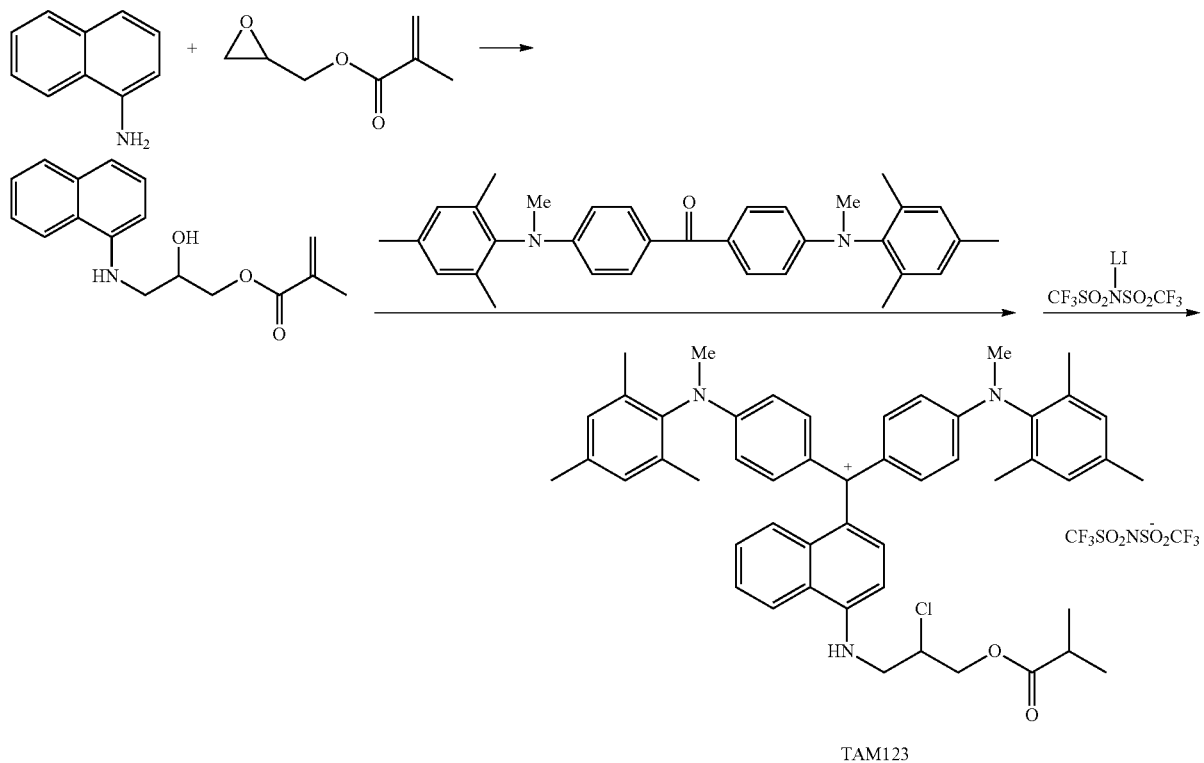

TAM123

«Synthesis of TAM124»

In accordance with the following route by the same procedure as for TAM107, TAM124 was synthesized. The λmax (ethyl acetate solution) of the absorption spectrum was 580 nm, and the ε (ethyl acetate solution) was 79,000.

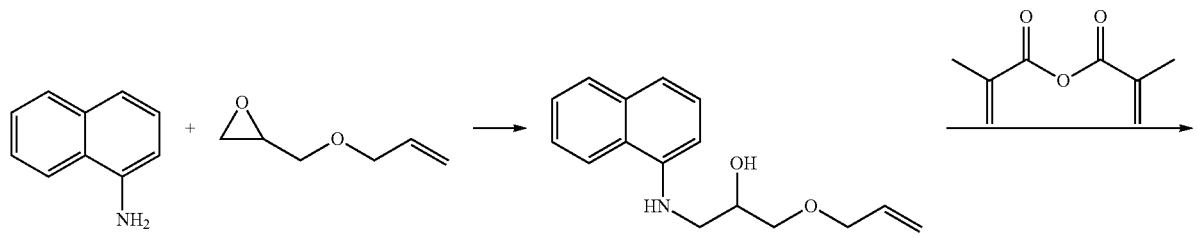

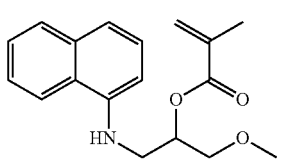
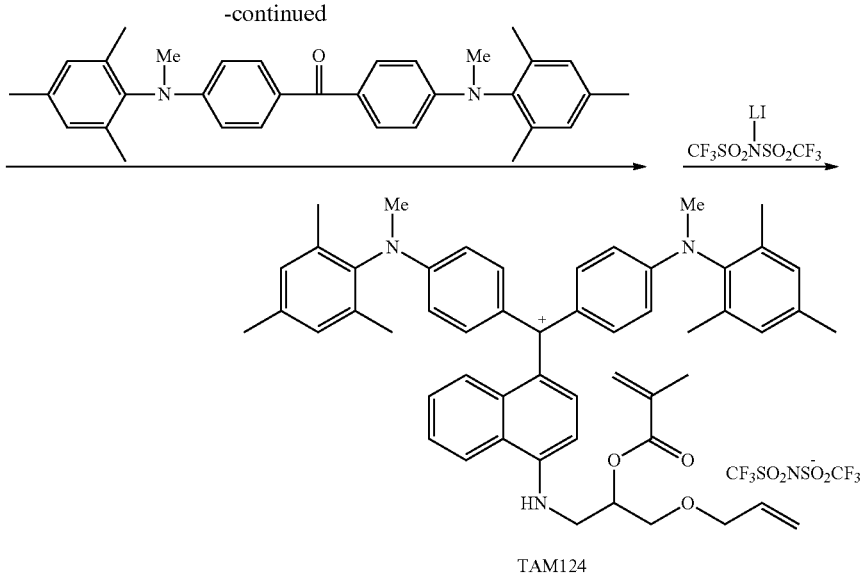

TAM124

<High-Molecular Type>

| Synthesis of Colorant Multimers TAM201 to TAM206 | |
|---|---|
| (Composition of Polymerization Reaction Liquids) | |
| Component 1-1: The component described in the following table | 3.00 g |
| Component 2-1: c-Hexyl methacrylate | 0.64 g |
| Component 3-1: Methacrylic acid | 0.64 g |
| Component 4-1: $C_{12}H_{23}SH$ | 0.16 g |
| Component 5-1: V-601 (manufactured by Wako Pure Chemical Industry Ltd.) | 0.10 g |
| Component 6-1: Propylene glycol monomethyl ether (Salt Tolerant Component) | 10 mL |
| Component 7-1: Anion component described in the following table | |

The component 1-1 to the component 6-1 were put into a flask, followed by stirring at 80° C. for 4 hours in a nitrogen atmosphere. The reaction liquid was cooled and then put into 200 mL of hexane, and the precipitated solid was collected by filtration. In addition, the mixture was suspended and washed with 200 mL of hexane. The weight-average molecular weight (Mw) in terms of polystyrene was measured by GPC. The measurement results are shown in the following table. The solid collected by filtration and the component 7-1 were dissolved in 200 mL of acetone, and the solution was put into 500 mL of water. The precipitated solid was collected by filtration and additionally suspended and washed with 200 mL of water. The obtained powder was air-dried at 50° C. overnight.

Figure 5:
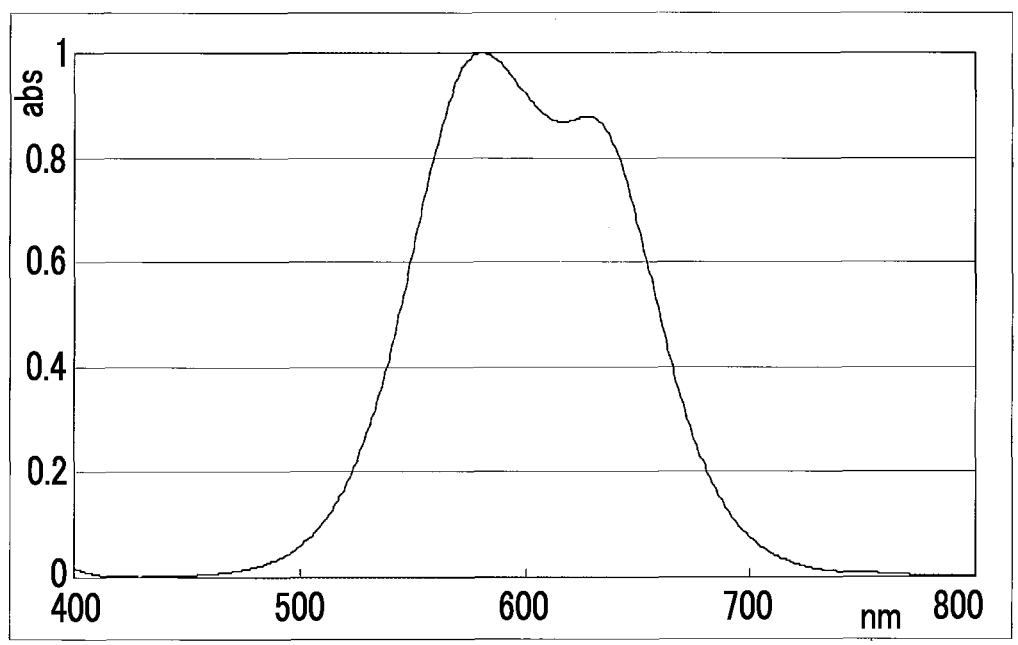
FIG. 5 is a view showing an absorption spectrum of a colorant TAM201.

In the following table, TAM201 to TAM206 represent TAM201 to TAM206 mentioned as examples of the compound represented by Formula (1), Formula (2), or Formula (3) of a high-molecular type. Further, in the following table, TAM104-Cl, TAM105-Cl, ANION002, and ANION003 represent the compounds described in above synthesis examples above. The λmax (ethyl acetate solution) of the absorption spectrum of TAM201 was 580.5 nm. The absorption spectrum is shown in FIG. 5.

TABLE 1

| Colorant multimer | Component 1-1 | | Component 7-1 | | Mw |
|---|---|---|---|---|---|
| TAM201 | TAM105-Cl | 3.00 g | LiN $(SO_2CF_3)_2$ | 1.20 g | 4,800 |
| TAM202 | TAM105-Cl | 3.00 g | ANION002 | 1.58 g | 5,000 |
| TAM203 | TAM105-Cl | 3.00 g | ANION003 | 1.48 g | 5,200 |
| TAM204 | TAM104-Cl | 3.00 g | LiN $(SO_2CF_3)_2$ | 1.39 g | 5,000 |
| TAM205 | TAM104-Cl | 3.00 g | ANION002 | 1.83 g | 5,300 |
| TAM206 | TAM104-Cl | 3.00 g | ANION003 | 1.72 g | 4,700 |

Synthesis of Colorant Multimers TAM251 to TAM253

| (Composition of Polymerization Reaction Liquid) | |
|---|---|
| Component 1-2: Anion monomer | 1.32 g |
| Component 2-2: c-Hexyl methacrylate | 2.32 g |
| Component 3-2: Methacrylic acid | 0.64 g |
| Component 4-2: $C_{12}H_{23}SH$ | 0.26 g |
| Component 5-2: V-601 (manufactured by Wako Pure Chemical Industry Ltd.) | 0.10 g |
| Component 6-2: Propylene glycol monomethyl ether (Salt Tolerant Component) | 20 mL |
| Component 7-2: Triarylmethane component | |

The component 1-2 to the component 6-2 were put into a flask, followed by stirring at 80° C. for 4 hours in a nitrogen atmosphere. The reaction liquid was cooled and then put into 400 mL of hexane, and the precipitated solid was collected by filtration. In addition, the mixture was suspended and washed with 200 mL of hexane. The weight-average molecular weight (Mw) in terms of polystyrene was measured by GPC. The measurement results are shown in the following table. The solid collected by filtration and the component 7-2 were dissolved in 200 mL of acetone, and the solution was put into 100 mL of water. The precipitated solid was collected by filtration and additionally suspended and washed with 200 mL of water. The obtained powder was air-dried at 50° C. overnight.

In the following table, TAM251 to TAM253 represent TAM251 to TAM253 mentioned as examples of the compound represented by Formula (1), Formula (2), or Formula (3) of a high-molecular type. Further, in the following table, TAM003-Cl, TAM104-Cl and TAM105-Cl represent the compounds described in Synthesis Examples above.

TABLE 2

| Colorant Multimer | Component 7-2 | | Mw |
|---|---|---|---|
| TAM251 | TAM003-Cl | 2.85 g | 4,500 |
| TAM252 | TAM104-Cl | 3.50 g | 5,300 |
| TAM253 | TAM105-Cl | 3.02 g | 5,100 |

<Preparation of Blue Colored Film>

«Preparation of Coloring Curable Resin Composition (Coating Liquid)»

The components in the following composition were mixed to prepare a coloring curable resin composition.

| | |
|---|---|
| Colorant | X parts by mass (the amount described in the table which will be described later) |
| (T-1) Photopolymerizable compound | 6.5 parts by mass |
| (U-1) Alkali-soluble resin | 8.5 parts by mass |
| (V-3) Photopolymerization initiator | 1.0 parts by mass |
| (X-1) Solvent | 40.0 parts by mass |
| (X-2) Solvent | 12.0 parts by mass |
| (Z-1) Surfactant | 0.006 parts by mass |

(T-1) Photopolymerizable compound: KAYARAD DPHA (manufacturd by Nippon Kayaku Co., Ltd., a mixture of dipentaerythritol pentaacrylate and dipentaerythritol hexaacrylate)
(U-1) Alkali-soluble resin: benzyl methacrylate/methacrylic acid (85/15 [mass ratio] copolymer (weight-average molecular weight: 12,000) acid value (100 mgKOH/g))
(V-3) Photopolymerization initiator: Oxime-based compound having the following structure.

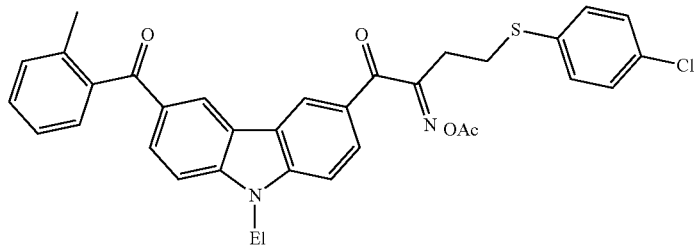

(X-1) Solvent: Propylene glycol monomethyl ether acetate
(X-2) Solvent: Ethyl 3-Ethoxypropionate
(Z-1) Surfactant: MEGAFACE F781-F (manufactured by DIC CORPORATION)
(Colored Layer A)

The coloring curable resin composition prepared above was coated onto a glass (#1737; manufactured by Corning Incorporated) by a spin coating method, and then dried at room temperature for 30 minutes to volatilize volatile components to obtain an colored layer. This colored layer was irradiated with an i-line (with a wavelength of 365 nm) for exposure of entire surfaces not via a photomask to form a latent image. By using an ultra-high-pressure mercury lamp as a light source for the i-line, the light was made into parallel light and irradiated. At this time, the irradiation dose was set to 40 mJ/cm². Then, the colored layer having the latent image formed thereon was exposed at 26° C. for 45 seconds by using an aqueous sodium carbonate/sodium hydrogen carbonate (at a concentration of 2.4% by mass), rinsed with running water for 20 seconds, and then dried with a spray. The dried film was calcined using a clean oven at 230° C. for 20 minutes to obtain a blue colored layer A.

(1) Spectral Properties

The transmission spectrum of the colored layer A obtained above was measured using a photometric system (MCPD-3700, manufactured by Otsuka Electronics Co., Ltd.). From the transmission spectrum, the chromaticity (C light source) in the color-difference formula according to CIE 1931 was determined.

(2) Heat Resistance

The color difference ΔE*ab between the transmission spectrum (a1) of the colored layer A obtained above and the transmission spectrum (b1) when the colored layer A was further calcined at 230° C. for 60 minutes was calculated.

(3) ITO Resistance (Durability in Sputtering Process)

The colored layer A was subjected to DC sputtering by using a sputtering apparatus (SIH-3030 manufactured by ULVAC Inc.) in an atmosphere with an oxygen flow rate of 2 sccm, an Ar flow rate of 84 sccm, and a sputtering temperature of 230° C. such that the film thickness of ITO would be 1,500 angstroms. The color difference ΔE*ab between the transmission spectrum (a2) of the colored layer A equipped with ITO which had been subjected to sputtering and the transmission spectrum (b2) when the colored layer A equipped with ITO was calcined at 230° C. for 60 minutes was calculated.

(4) Light Fastness

The color difference ΔE*ab between the transmission spectrum (a3) of the colored layer A obtained above and the transmission spectrum (b3) of the colored layer A after irradiating the colored layer A using a xenon weather meter (XL-75 manufactured by Suga Testing Machine Co., Ltd.) at an irradiance of 390 W/m² for 48 hours was calculated.

(5) Liquid Crystal Resistivity (Electrical Properties)

The colored layer A obtained above was scraped from the substrate, and 9.0 mg of the scraped layer was added to 2.00 g of a liquid crystal material ZLI-4792 (manufactured by Merck), followed by heating at 120° C. for 5 hours. Thereafter, the mixture was filtered and the resistivity of the liquid crystal material was measured using a liquid crystal resistivity measuring apparatus (Product No. ADVANTEST R8340 ULTRA HIGHT RESISTANCE ME, manufactured by Advantest Corporation).

<Evaluation Criteria>

A: Resistivity≥$1.0\times10^{11}$ MΩ, at which image sticking was not observed when being mounted in a liquid crystal display apparatus to provide a panel.

B: Resistivity≥$1.0\times10^{10}$ MΩ, at which image sticking was substantially not observed when being mounted in a liquid crystal display apparatus to provide a panel, and thus, there is no problem in performance.

C: Resistivity<$1.0\times10^{10}$ MΩ, at which image sticking occurred when being mounted in a liquid crystal display apparatus to provide a panel.

<Solvent Resistance (Chromaticity Difference)>

The colored cured film which had been heated at 230° C. for 20 minutes was immersed in N-methylpyrrolidone (NMP) at 25° C. for 10 minutes, the chromaticity before and after immersion was measured, and the color difference index ΔEab was calculated. Further, in the case where the value of ΔEab is 3 or less, the change in hue is small, and thus, the solvent resistance was considered excellent.

TABLE 3

| | Colorant | Amount of colorant (X parts by mass) | Heat resistance ΔEab | ITO resistance ΔEab |
|---|---|---|---|---|
| Example 1 | TAM001 | 2 parts by mass | 1.7 | 2.8 |
| Example 2 | TAM002 | 2 parts by mass | 1.5 | 2.5 |
| Example 3 | TAM003 | 2 parts by mass | 1.9 | 2.8 |
| Example 4 | TAM004 | 2 parts by mass | 2.2 | 3.3 |
| Example 5 | TAM005 | 2 parts by mass | 2.8 | 3.6 |
| Example 6 | TAM006 | 2 parts by mass | 3.1 | 5.4 |
| Example 7 | TAM007 | 2 parts by mass | 3.0 | 5.2 |
| Example 8 | TAM008 | 2 parts by mass | 3.3 | 5.5 |
| Example 9 | TAM009 | 2 parts by mass | 3.1 | 5.4 |
| Example 10 | TAM010 | 2 parts by mass | 3.1 | 5.4 |
| Example 11 | TAM011 | 2 parts by mass | 3.4 | 5.8 |
| Example 12 | TAM012 | 2 parts by mass | 3.4 | 5.9 |
| Example 13 | TAM013 | 2 parts by mass | 3.5 | 6.0 |
| Example 14 | TAM014 | 2 parts by mass | 2.8 | 4.8 |
| Example 15 | TAM015 | 2 parts by mass | 3.2 | 5.9 |
| Example 16 | TAM016 | 2 parts by mass | 3.3 | 5.8 |
| Example 17 | TAM017 | 2 parts by mass | 4.1 | 7.2 |
| Example 18 | TAM018 | 2 parts by mass | 4.0 | 7.5 |
| Example 19 | TAM019 | 2 parts by mass | 1.9 | 2.9 |
| Example 20 | TAM020 | 2 parts by mass | 3.4 | 5.8 |
| Comparative Example 1 | Dye901 | 2 parts by mass | >10 | >10 |
| Comparative Example 2 | Dye902 | 2 parts by mass | >10 | >10 |
| Comparative Example 3 | Dye903 | 2 parts by mass | >10 | >10 |
| Comparative Example 4 | Dye904 | 2 parts by mass | >10 | >10 |
| Comparative Example 5 | Dye905 | 2 parts by mass | >10 | >10 |
| Comparative Example 6 | Dye906 | 2 parts by mass | >10 | >10 |
| Comparative Example 7 | Dye907 | 2 parts by mass | >10 | >10 |
| Comparative Example 8 | Dye908 | 2 parts by mass | >10 | >10 |
| Comparative Example 9 | Dye909 | 2 parts by mass | >10 | >10 |
| Comparative Example 10 | Dye910 | 2 parts by mass | >10 | >10 |

In the following table, the colorants TAM001 to TAM020 represent TAM001 to TAM020 mentioned as examples of the compound represented by Formula (1), Formula (2), or Formula (3) of the above low-molecular type. Further, Dye901 to Dye910 represent Dye901 to Dye910 described in Synthesis Examples of the colorants above.

From the table, it could be seen that with the coloring curable compositions of Examples, the heat resistance and the ITO resistance (durability in a sputtering process) could be remarkably improved. On the other hand, it could be seen that with the coloring curable compositions of Comparative Examples, it was difficult to satisfy both of the heat resistance and the ITO resistance.

TABLE 4

| Example or Comparative Example | Colorant | Amount of colorant (X parts by mass) | Heat resistance ΔEab | ITO resistance ΔEab | Light fastness ΔEab |
|---|---|---|---|---|---|
| Example 1 | TAM001 | 2 parts by mass | 1.7 | 2.8 | 2.8 |
| Example 101 | TAM001 Dye001 | 2 parts by mass 0.4 parts by mass | 1.6 | 2.5 | 3.5 |
| Example 102 | TAM001 Dye002 | 2 parts by mass 0.4 parts by mass | 1.6 | 2.5 | 3.2 |
| Example 103 | TAM001 SolventBlue70 | 2 parts by mass 0.4 parts by mass | 2.0 | 2.4 | 2.5 |
| Example 104 | TAM001 PB15:6 | 2 parts by mass 0.4 parts by mass | 2.0 | 2.5 | 2.6 |
| Example 105 | TAM001 Dye001 PB15:6 | 2 parts by mass 0.4 parts by mass 0.2 parts by mass | 1.8 | 2.4 | 2.5 |
| Example 106 | TAM001 Dye001 SolventBlue70 | 2 parts by mass 0.4 parts by mass 0.2 parts by mass | 1.9 | 2.6 | 2.4 |
| Example 107 | TAM001 Dye001 Dye004 | 2 parts by mass 0.4 parts by mass 0.2 parts by mass | 1.7 | 2.4 | 2.5 |
| Example 108 | TAM001 Dye001 Dye005 | 2 parts by mass 0.4 parts by mass 0.2 parts by mass | 1.8 | 2.5 | 2.6 |
| Example 109 | TAM001 Dye002 PB15:6 | 2 parts by mass 0.4 parts by mass 0.2 parts by mass | 1.7 | 2.6 | 2.5 |
| Example 110 | TAM001 Dye002 SolventBlue70 | 2 parts by mass 0.4 parts by mass 0.2 parts by mass | 1.8 | 2.4 | 2.6 |

TABLE 4-continued

| Example or Comparative Example | Colorant | Amount of colorant (X parts by mass) | Heat resistance ΔEab | ITO resistance ΔEab | Light fastness ΔEab |
|---|---|---|---|---|---|
| Example 111 | TAM001 | 2 parts by mass | 1.8 | 2.5 | 2.7 |
|  | Dye002 | 0.4 parts by mass |  |  |  |
|  | Dye003 | 0.2 parts by mass |  |  |  |
| Example 112 | TAM001 | 2 parts by mass | 1.9 | 2.6 | 2.5 |
|  | Dye002 | 0.4 parts by mass |  |  |  |
|  | Dye004 | 0.2 parts by mass |  |  |  |
| Example 113 | TAM001 | 2 parts by mass | 1.6 | 2.5 | 3.4 |
|  | Dye005 | 0.4 parts by mass |  |  |  |
| Example 114 | TAM001 | 2 parts by mass | 1.6 | 2.5 | 3.3 |
|  | Dye006 | 0.4 parts by mass |  |  |  |
| Example 115 | TAM001 | 2 parts by mass | 1.7 | 2.4 | 2.5 |
|  | Dye005 | 0.4 parts by mass |  |  |  |
|  | PB15:6 | 0.2 parts by mass |  |  |  |
| Example 116 | TAM001 | 2 parts by mass | 1.7 | 2.5 | 2.5 |
|  | Dye006 | 0.4 parts by mass |  |  |  |
|  | PB15:6 | 0.2 parts by mass |  |  |  |

In the table, Dye001 to Dye006 represent the following compounds. Further, PB15:6 represents C. I. Pigment Blue 15:6.

Dye001

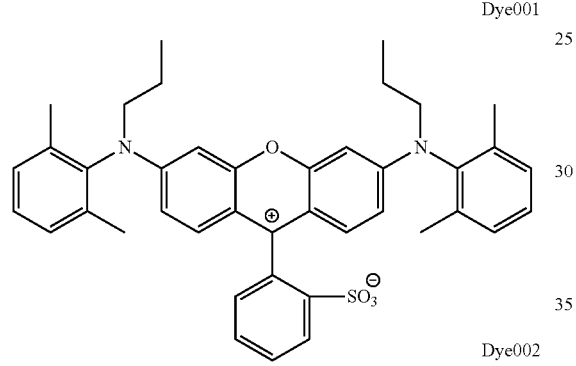

Dye002

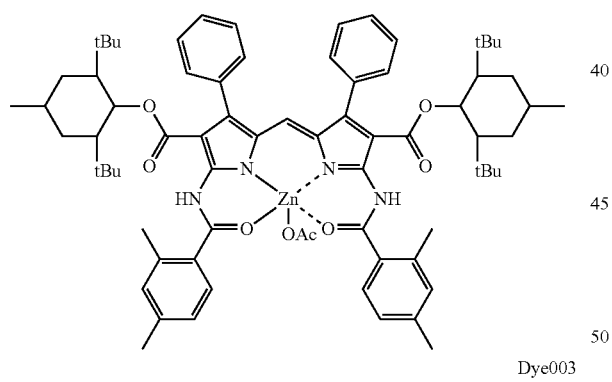

Dye003

Dye004

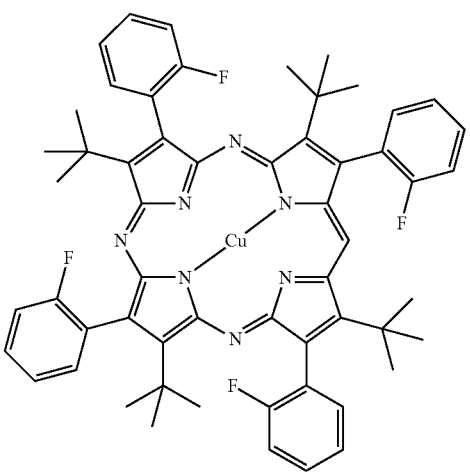

Dye005

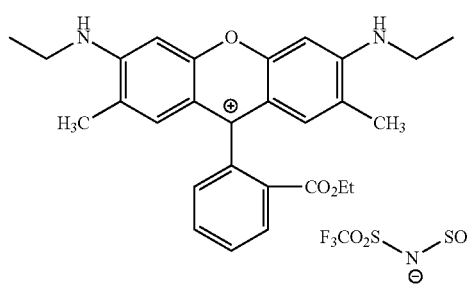

Dye006

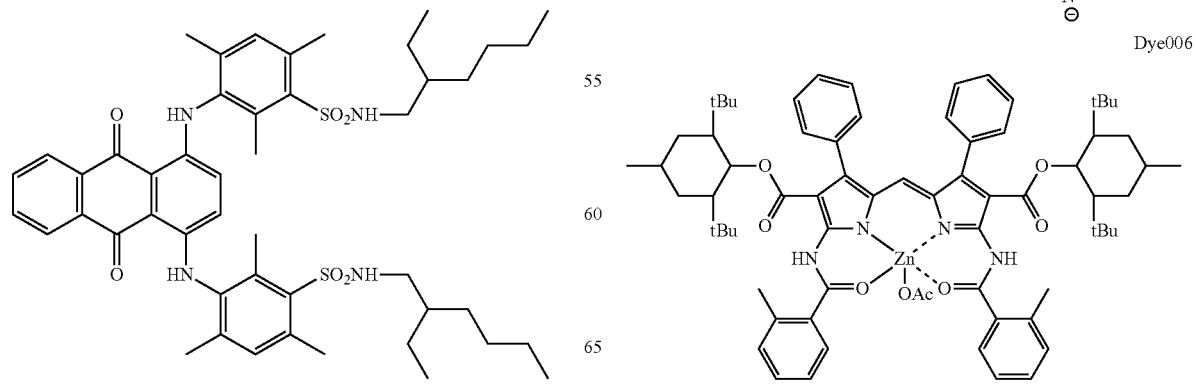

From the results of Example 101, Example 102, and Examples 105 to 116, it could be seen that by using a combination of at least one of a xanthene colorant or a dipyrromethene metal complex compound, the heat resistance and the ITO resistance could further be improved. Further, from the results of Examples 103 to 116, it could be seen that by using a combination of dyes having longer wavelength, the light fastness could be improved.

TABLE 5

|  | Colorant | Amount of colorant (X parts by mass) | Heat resistance ΔEab | ITO resistance ΔEab | Light Fastness ΔEab | Electrical properties | Solvent resistance ΔEab |
|---|---|---|---|---|---|---|---|
| Example 6 | TAM006 | 3 parts by mass | 3.1 | 5.4 | 2.8 | C | 7.0 |
| Example 201 | TAM101 | 3 parts by mass | 3.1 | 5.3 | 3.0 | B | 3.3 |
| Example 202 | TAM102 | 3 parts by mass | 3.2 | 5.4 | 3.1 | B | 3.2 |
| Example 203 | TAM103 | 3 parts by mass | 3.1 | 5.2 | 2.9 | A | 3.1 |
| Example 204 | TAM104 | 3 parts by mass | 1.7 | 2.6 | 2.9 | A | 3.3 |
| Example 205 | TAM105 | 3 parts by mass | 3.2 | 5.3 | 2.8 | A | 3.2 |
| Example 206 | TAM201 | 3 parts by mass | 3.1 | 5.1 | 3.0 | B | 2.4 |
| Example 207 | TAM202 | 3 parts by mass | 3.2 | 5.2 | 3.1 | A | 2.4 |
| Example 208 | TAM203 | 3 parts by mass | 3.2 | 5.2 | 2.9 | A | 2.5 |
| Example 209 | TAM204 | 3 parts by mass | 1.8 | 2.6 | 2.9 | B | 2.1 |
| Example 210 | TAM205 | 3 parts by mass | 1.9 | 2.7 | 2.8 | A | 2.4 |
| Example 211 | TAM206 | 3 parts by mass | 1.9 | 2.8 | 2.9 | A | 2.3 |
| Example 212 | TAM251 | 3 parts by mass | 1.9 | 2.9 | 2.8 | A | 3.2 |
| Example 213 | TAM252 | 3 parts by mass | 1.8 | 2.8 | 2.9 | A | 2.4 |
| Example 214 | TAM253 | 3 parts by mass | 3.1 | 5.4 | 2.9 | A | 2.1 |

TABLE 6

|  | Colorant | Amount of colorant (X parts by mass) | Heat resistance ΔEab | ITO resistance ΔEab | Light Fastness ΔEab | Electrical properties | Solvent resistance ΔEab |
|---|---|---|---|---|---|---|---|
| Example 306 | TAM106 | 3 parts by mass | 3.2 | 5.3 | 2.7 | B | 3.1 |
| Example 307 | TAM107 | 3 parts by mass | 1.7 | 2.5 | 2.6 | B | 3.1 |
| Example 308 | TAM108 | 3 parts by mass | 1.6 | 2.4 | 2.6 | B | 3.2 |
| Example 309 | TAM109 | 3 parts by mass | 1.6 | 2.6 | 2.7 | B | 3 |
| Example 310 | TAM110 | 3 parts by mass | 1.6 | 2.5 | 2.7 | B | 2.9 |
| Example 311 | TAM111 | 3 parts by mass | 3.1 | 5.1 | 2.8 | A | 3.1 |
| Example 312 | TAM112 | 3 parts by mass | 3.0 | 5.1 | 2.7 | B | 2.9 |
| Example 313 | TAM113 | 3 parts by mass | 3.1 | 5.2 | 2.7 | B | 3.1 |
| Example 314 | TAM114 | 3 parts by mass | 1.7 | 2.6 | 2.7 | A | 3.1 |
| Example 315 | TAM115 | 3 parts by mass | 1.7 | 2.7 | 1.8 | B | 3.2 |
| Example 316 | TAM116 | 3 parts by mass | 1.6 | 2.5 | 2.6 | B | 3.0 |
| Example 317 | TAM117 | 3 parts by mass | 1.7 | 2.6 | 2.5 | B | 3.0 |
| Example 318 | TAM118 | 3 parts by mass | 1.6 | 2.6 | 2.5 | B | 3.0 |
| Example 319 | TAM119 | 3 parts by mass | 1.6 | 2.5 | 2.6 | B | 2.9 |
| Example 320 | TAM120 | 3 parts by mass | 1.8 | 2.6 | 2.6 | B | 2.9 |
| Example 321 | TAM121 | 3 parts by mass | 1.7 | 2.6 | 2.5 | B | 3.0 |
| Example 322 | TAM122 | 3 parts by mass | 1.6 | 2.5 | 2.6 | B | 3.0 |

TABLE 6-continued

| | Colorant | Amount of colorant (X parts by mass) | Heat resistance ΔEab | ITO resistance ΔEab | Light Fastness ΔEab | Electrical properties | Solvent resistance ΔEab |
|---|---|---|---|---|---|---|---|
| Example 323 | TAM123 | 3 parts by mass | 2.5 | 2.8 | 3.0 | B | 3.0 |
| Example 324 | TAM124 | 3 parts by mass | 2.4 | 2.9 | 3.1 | B | 3.0 |
| Comparative Example 1 | Dye901 | 3 parts by mass | >10 | >10 | 3.6 | C | 7.5 |
| Comparative Example 2 | Dye902 | 3 parts by mass | >10 | >10 | 3.1 | C | 8.2 |
| Comparative Example 4 | Dye904 | 3 parts by mass | >10 | >10 | 3.2 | B | 5.6 |
| Comparative Example 8 | DYE908 | 3 parts by mass | >10 | >10 | 3.6 | C | 6.8 |
| Comparative Example 10 | Dye910 | 3 parts by mass | >10 | >10 | 3.5 | C | 7.5 |

In the table, TAM006 and TAM101 to TAM124 represent the compounds mentioned as examples of the compound represented by Formula (1), Formula (2), or Formula (3) of a low-molecular type. Further, TAM201 to TAM206 and TAM251 to TAM253 represent TAM201 to TAM206 and TAM251 to TAM253 mentioned as examples of the compound represented by Formula (1), Formula (2), or Formula (3) of a high-molecular type.

From the results of Examples 6, 201 to 214 and 306 to 324, it could be seen that since the colorant used in the present invention has a polymerizable group and/or a multimer structure, the electrical properties and the solvent resistance could further be improved.

In addition, it could be seen that even in the case where the oxime compound used in Example 1 was changed to IRGACURE OXE 01 (manufactured by BASF) or IRGACURE OXE 02 (manufactured by BASF), the same good results as in Example 1 were obtained.

From the table, it could be seen that with the coloring curable compositions of Examples, the heat resistance, the ITO resistance (durability in a sputtering process), the electrical properties, and the solvent resistance could be remarkably improved. On the other hand, it could be seen that with the coloring curable compositions of Comparative Examples, it was difficult to satisfy both of the heat resistance and the ITO resistance, and in addition, the electrical properties and the solvent resistance were also low.

What is claimed is:

1. A coloring curable resin composition comprising:
   a colorant represented by Formula (1A);
   a resin;
   a polymerizable compound; and
   a polymerization initiator:

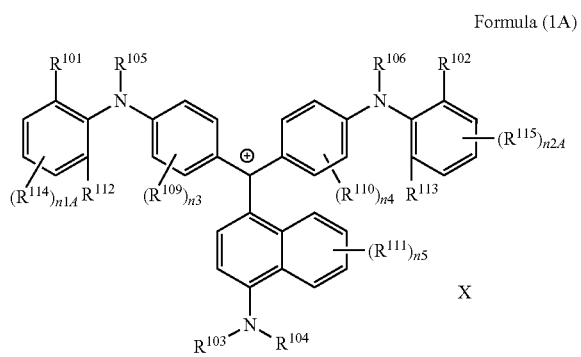

Formula (1A)

wherein $R^{101}$, $R^{102}$, $R^{112}$, and $R^{113}$ each independently represent an alkyl group, $R^{103}$ to $R^{106}$ each independently represent a hydrogen atom, an alkyl group, an aryl group, or a heteroaryl group, $R^{109}$ to $R^{111}$, $R^{114}$, and $R^{115}$ each independently represent a hydrogen atom or a substituent, n1A to n2A each independently represent an integer of 0 to n3, and n4 each independently represents an integer of 0 to 4, n5 represent an integer of 0 to 6, and X represents an anion or is not present, provided that when X is not present, at least one of $R^{101}$ to $R^{115}$ includes an anion.

2. The coloring curable resin composition according to claim 1, wherein in Formula (1A), $R^{105}$ and $R^{106}$ represent a hydrogen atom.

3. The coloring curable resin composition according to claim 1, wherein the colorant represented by Formula (1A) is represented by Formula (1C):

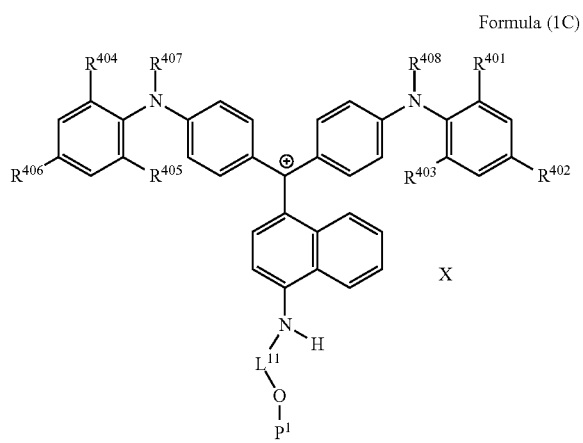

Formula (1C)

wherein $R^{401}$, $R^{403}$, $R^{404}$ and $R^{406}$ each independently represent an alkyl group, and $R^{402}$, $R^{405}$, $R^{407}$ and $R^{408}$ each independently represent a hydrogen atom or an alkyl group, $L^{11}$ represents a divalent linking group having 2 to 30 carbon atoms, $P^1$ represents a polymerizable group, and X represents an anion.

4. The coloring curable resin composition according to claim 3, wherein in Formula (1C), $R^{401}$ to $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, and $P^1$ represents an acryloyl group, a methacryloyl group, or a $-CH_2C_6H_4CH=CH_2$ group.

5. The coloring curable resin composition according to claim 1, wherein the colorant represented by Formula (1A) is represented by Formula (1B):

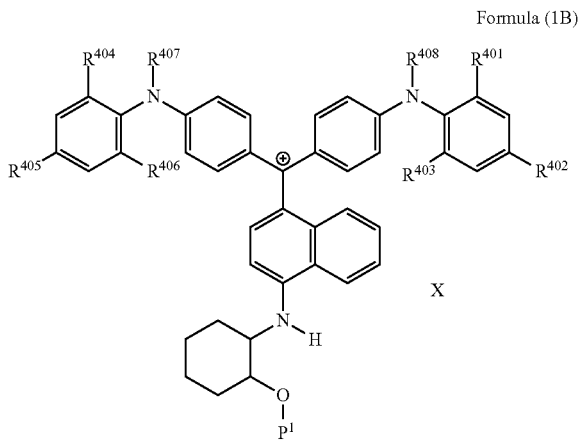

Formula (1B)

wherein $R^{401}$, $R^{403}$, $R^{404}$ and $R^{406}$ each independently represent an alkyl group, and $R^{402}$, $R^{405}$, $R^{407}$ and $R^{408}$ each independently represent a hydrogen atom or an alkyl group, $P^1$ represents a polymerizable group, and X represent an anion.

6. The coloring curable resin composition according to claim 5, wherein in Formula (1B), $R^{407}$ and $R^{408}$ represent an alkyl group having 1 to 6 carbon atoms.

7. The coloring curable resin composition according to claim 5, wherein in Formula (1B), $R^{401}$ to $R^{406}$ represent an alkyl group having 1 to 3 carbon atoms.

8. The coloring curable resin composition according to claim 5, wherein in Formula (1B), X represents a bistrifluoromethanesulfonylimide anion, a tristrifluoromethanesulfonylmethide anion, or a perfluoromethanesulfonic acid anion.

9. The coloring curable resin composition according claim 1, further comprising at least one of a xanthene colorant or a dipyrromethene-based metal complex compound.

10. The coloring curable resin composition according to claim 1, further comprising a pigment.

11. The coloring curable resin composition according to claim 1, wherein the colorant includes at least one of a polymerizable group or a multimer structure.

12. The coloring curable resin composition according to claim 1, wherein the coloring curable resin composition contains an oxime-based compound as a polymerization initiator.

13. A colored cured film formed by curing the coloring curable resin composition according to claim 1.

14. A color filter comprising the colored cured film according to claim 13.

15. A solid-state imaging device comprising the color filter according to claim 14.

16. An image display device comprising the color filter according to claim 14.

17. A color filter using the coloring curable resin composition according to claim 1.

18. A method for manufacturing a color filter, comprising:
applying the coloring curable resin composition according to claim 1 onto a support to form a coloring curable resin composition layer;
patternwise exposing the coloring curable resin composition layer; and
removing an unexposed area by development to form a colored pattern.

19. An image display device comprising a color filter in at least three colors of red, green, and blue, wherein the coloring curable resin composition according to claim 1 is used in the color filter in blue.

20. A compound represented by by Formula (14):

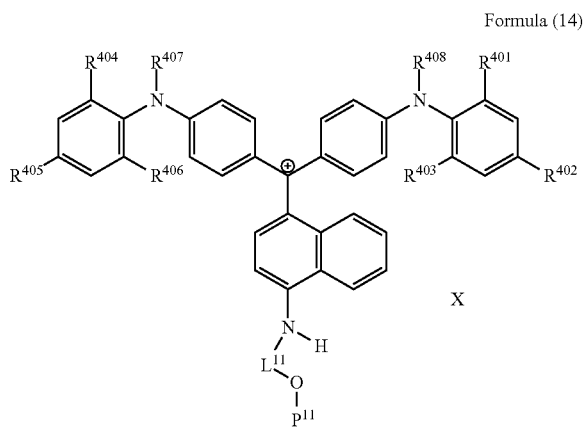

Formula (14)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, $P^{11}$ represents an acryloyl group, a methacryloyl group, or a —$CH_2C_6H_4CH$=$CH_2$ group, and X represents a bistrifluoromethanesulfonylimide anion, a tristrifluoromethanesulfonylmethide anion, or a perfluoromethanesulfonic acid anion.

21. The compound according to claim 20, wherein in Formula (14), $L^{11}$ represents an alkylene group having 2 to 10 carbon atoms, and $P^{11}$ represents an acryloyl group or a methacryloyl group.

22. The compound according to claim 20, represented by Formula (17):

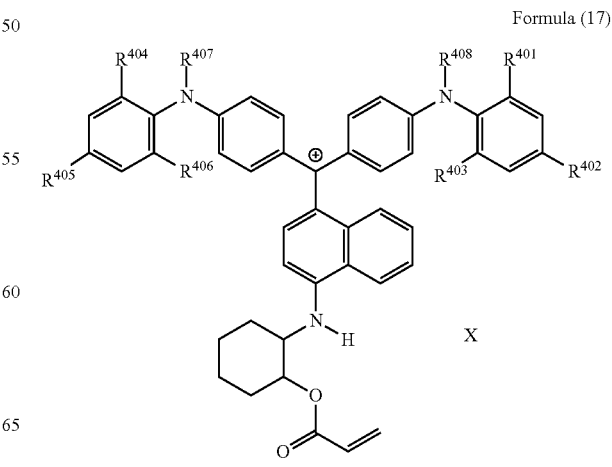

Formula (17)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and X represents a bistrifluoromethanesulfonylimide anion, a tristrifluoromethanesulfonylmethide anion, or a perfluoromethanesulfonic acid anion.

23. A compound represented by Formula (15):

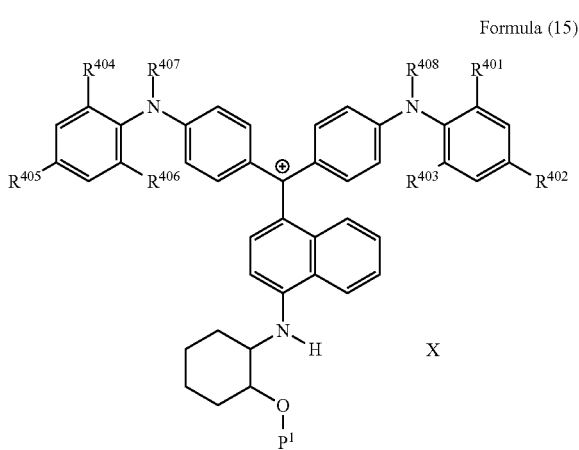

Formula (15)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $P^1$ represents a polymerizable group, and X represents a bistrifluoromethanesulfonylimide anion, a tristrifluoromethanesulfonylmethide anion, or a perfluoromethanesulfonic acid anion.

24. The compound according to claim 23, represented by Formula (16):

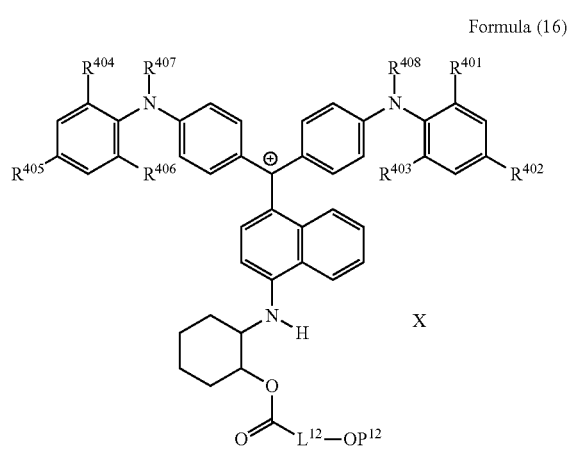

Formula (16)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents an alkylene group having 2 to 12 carbon atoms, a cycloalkylene group, a phenylene group, or a group formed by combination of these groups, $P^{12}$ represents an acryloyl group or a methacryloyl group, and X represents a bistrifluoromethanesulfonylimide anion, a tristrifluoromethanesulfonylmethide anion, or a perfluoromethanesulfonic acid anion.

25. A cation represented by Formula (4):

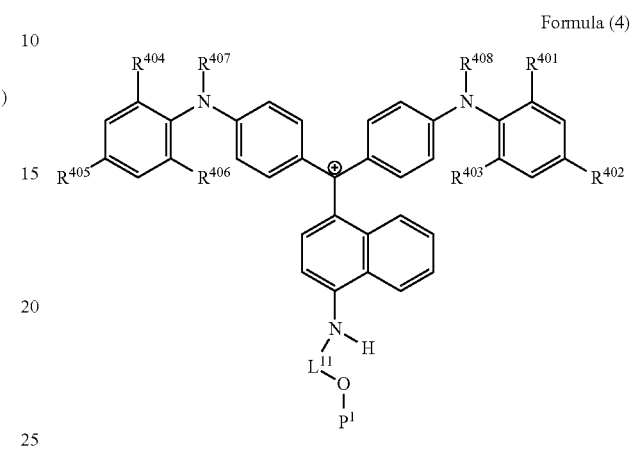

Formula (4)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{11}$ represents an alkylene group having 2 to 30 carbon atoms, a cycloalkylene group, a phenylene group, or a group formed by combination of these groups, and $P^1$ represents a polymerizable group.

26. The cation according to claim 25, wherein in Formula (4), $P^1$ represents an acryloyl group, a methacryloyl group, or a —CH$_2$C$_6$H$_4$CH=CH$_2$ group.

27. The cation according to claim 25, represented by Formula (5):

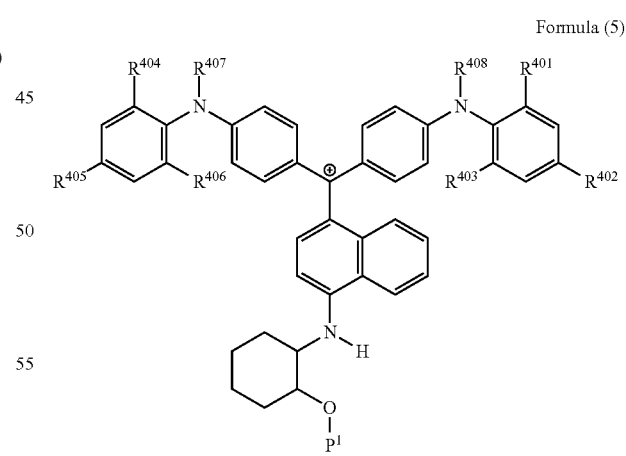

Formula (5)

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, and $P^1$ represents a polymerizable group.

28. The cation according to claim 25, represented by Formula (6):

Formula (6)

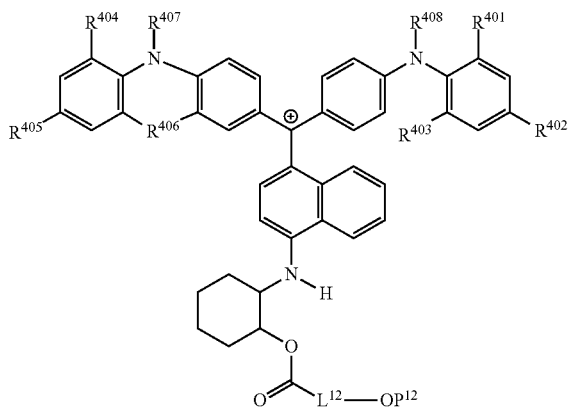

wherein $R^{401}$ to $R^{406}$ each independently represent a hydrogen atom or an alkyl group having 1 to 3 carbon atoms, $R^{407}$ and $R^{408}$ each independently represent an alkyl group having 1 to 6 carbon atoms, $L^{12}$ represents an alkylene group having 2 to 12 carbon atoms, a cycloalkylene group, a phenylene group, or a group formed by combination of these groups, and $P^{12}$ represents an acryloyl group or a methacryloyl group.

29. The cation according to claim 25, represented by Formula (7):

Formula (7)

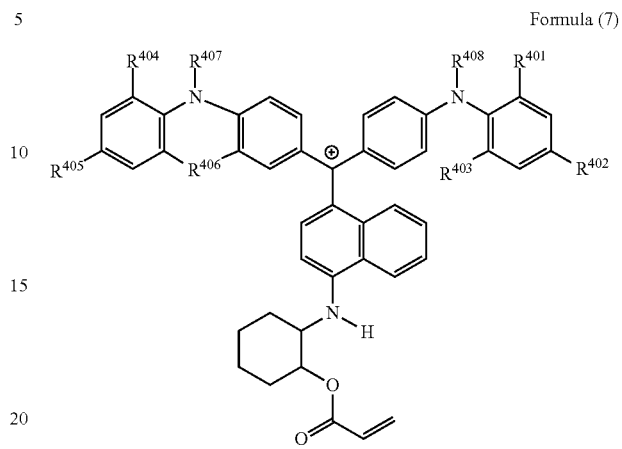

wherein, $R^{401}$ to $R^{406}$ each independently represent a hydrogen atom or an alkyl group having 1 to 3 carbon atoms, and $R^{407}$ and $R^{408}$ each independently represent an alkyl group having 1 to 6 carbon atoms.

* * * * *